United States Patent
Chatzistavrou et al.

(10) Patent No.: US 11,896,612 B2
(45) Date of Patent: Feb. 13, 2024

(54) RESURRECTION OF ANTIBIOTICS THAT MRSA RESISTS BY SILVER-DOPED BIOACTIVE GLASS-CERAMIC PARTICLES

(71) Applicant: Board of Trustees of Michigan State University, East Lansing, MI (US)

(72) Inventors: Xanthippi Chatzistavrou, Okemos, MI (US); Neal D. Hammer, Okemos, MI (US); Aljoscha Roch, Holt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 77 days.

(21) Appl. No.: 16/833,092

(22) Filed: Mar. 27, 2020

(65) Prior Publication Data
US 2020/0330510 A1 Oct. 22, 2020

Related U.S. Application Data

(60) Provisional application No. 62/826,672, filed on Mar. 29, 2019.

(51) Int. Cl.
| | |
|---|---|
| A61K 33/38 | (2006.01) |
| A61K 31/785 | (2006.01) |
| A61K 31/78 | (2006.01) |
| A61K 31/745 | (2006.01) |
| A61L 27/54 | (2006.01) |
| A61L 27/10 | (2006.01) |
| A61L 27/42 | (2006.01) |
| A61K 33/08 | (2006.01) |
| A61K 45/06 | (2006.01) |

(52) U.S. Cl.
CPC ............ *A61K 33/38* (2013.01); *A61K 31/745* (2013.01); *A61K 31/78* (2013.01); *A61K 31/785* (2013.01); *A61K 33/08* (2013.01); *A61L 27/105* (2013.01); *A61L 27/427* (2013.01); *A61L 27/54* (2013.01); *A61K 45/06* (2013.01)

(58) Field of Classification Search
CPC ........ A61L 27/10; A61L 27/105; A61L 27/54; A61L 27/56; A61L 2300/406; A61L 2400/08; A61L 27/427; A61K 33/38; A61K 9/70; A61K 31/745; A61K 31/785; A61K 31/78; A61K 33/08; A61K 2300/00; A61K 45/06; A61P 31/04; B33Y 80/00
See application file for complete search history.

(56) References Cited

U.S. PATENT DOCUMENTS

| | | | | |
|---|---|---|---|---|
| 5,762,950 A | * | 6/1998 | Yli-Urpo | A61K 9/0024 501/63 |
| 6,482,444 B1 | * | 11/2002 | Bellantone | A61L 17/005 424/618 |
| 6,756,060 B1 | * | 6/2004 | Greenspan | A61K 8/25 424/400 |
| 2005/0058673 A1 | | 3/2005 | Scholz et al. | |
| 2008/0242794 A1 | | 10/2008 | Sandford et al. | |
| 2009/0137622 A1 | | 5/2009 | Beck et al. | |
| 2010/0310665 A1 | | 12/2010 | Watson et al. | |
| 2011/0262556 A1 | | 10/2011 | Holladay et al. | |
| 2012/0082711 A1 | | 4/2012 | Goranov | |
| 2013/0108702 A1 | | 5/2013 | Santra | |
| 2014/0120168 A1 | | 5/2014 | Oldenburg et al. | |
| 2015/0064279 A1 | | 3/2015 | Lovetinska-Slamborova et al. | |
| 2015/0313912 A1 | | 11/2015 | Karandikar | |
| 2016/0287741 A1 | | 10/2016 | Harris et al. | |
| 2017/0119814 A1 | | 5/2017 | Friedman et al. | |
| 2018/0235232 A1 | | 8/2018 | Moeller et al. | |
| 2018/0303873 A1 | | 10/2018 | Been et al. | |

FOREIGN PATENT DOCUMENTS

| | | |
|---|---|---|
| WO | WO-2000076486 A1 | 12/2000 |
| WO | WO-2002004606 A1 | 1/2002 |
| WO | WO-2007072065 A2 | 6/2007 |
| WO | WO-2012123924 A2 | 9/2012 |
| WO | WO-2016004168 A1 | 1/2016 |
| WO | WO-2017215552 A1 | 12/2017 |

OTHER PUBLICATIONS

Bento et al., "Sol-Gel Synthesis and Characterization of a Quaternary Bioglass for Bone Regeneration and Tissue Engineering", Materials, 14, 4515, pp. 1-11, 2021. (Year: 2021).*
Chatzistavrou, Xanthippi, et al. "Development of new sol-gel derived Ag-doped biomaterials for dental applications." MRS Online Proceedings Library (OPL) 1417 (2012).
Chatzistavrou, Xanthippi, et al. "Fabrication and characterization of bioactive and antibacterial composites for dental applications." Acta biomaterialia 10.8 (2014): 3723-3732.
Wang, Y. Y., et al. "Biological and bactericidal properties of Ag-doped bioactive glass in a natural extracellular matrix hydrogel with potential application in dentistry." Eur Cell Mater 29 (2015): 342-355.

* cited by examiner

*Primary Examiner* — Lezah Roberts
(74) *Attorney, Agent, or Firm* — Harness, Dickey & Pierce, PLC

(57) ABSTRACT

A method of treating a bacterial infection including bacteria that have become resistant to an antibiotic in a subject in need thereof is provided. The method includes administering to the subject a safe and therapeutically effective amount of the antibiotic and a reviving agent selected from the group consisting of glass-ceramic particles, silver ions, and combinations thereof. The reviving agent restores antibiotic activity to the antibiotic against the bacteria.

18 Claims, 76 Drawing Sheets
Specification includes a Sequence Listing.

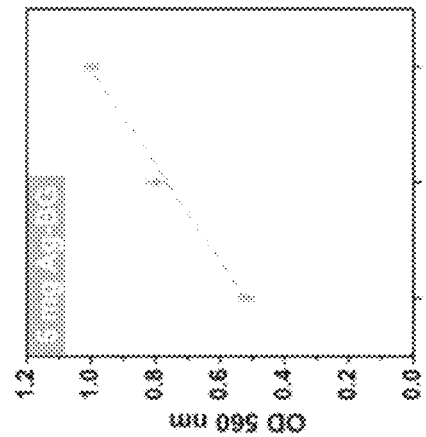
Fig. 14D
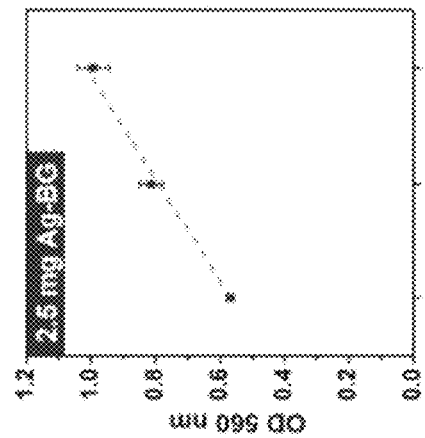
Fig. 14C
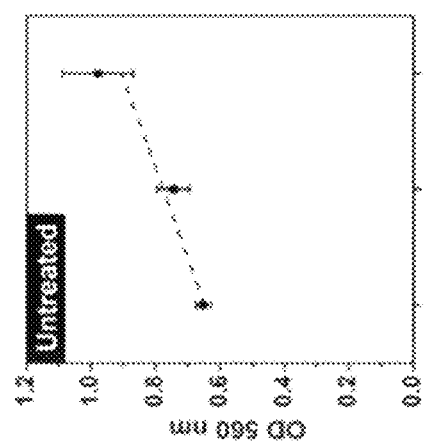
Fig. 14B
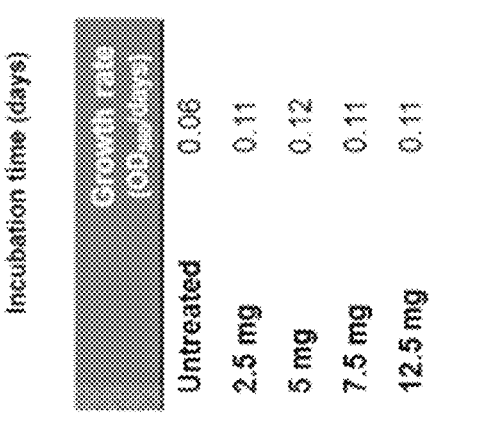
Fig. 14G
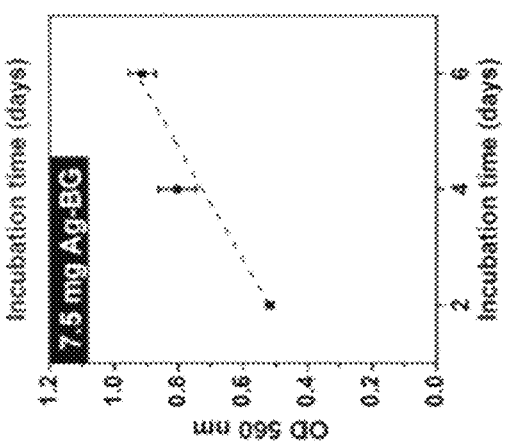
Fig. 14F
Fig. 14E

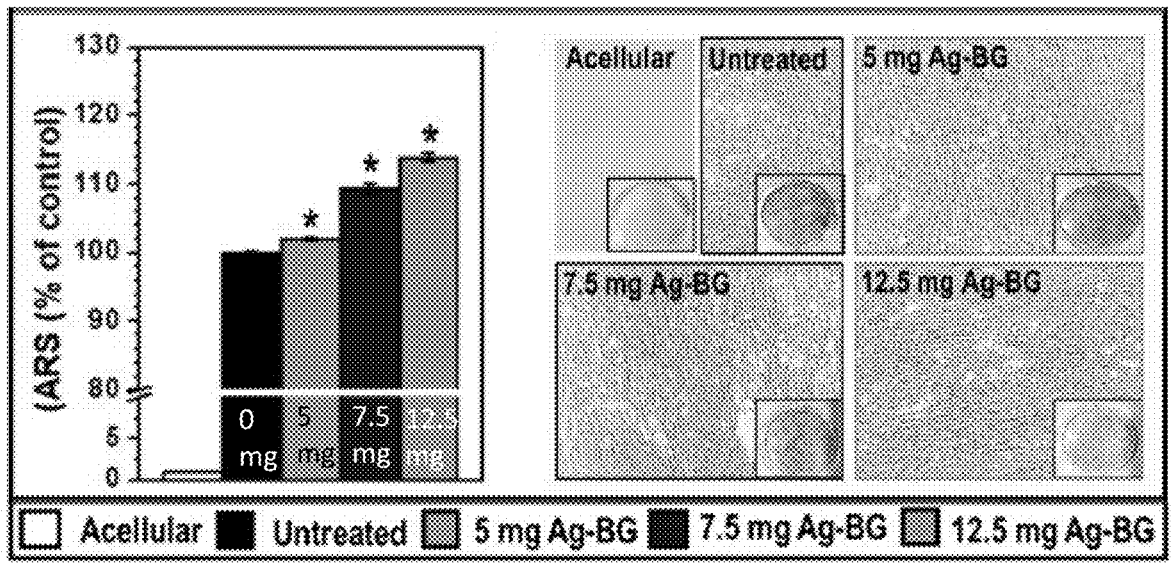
Fig. 16A      Fig. 16B
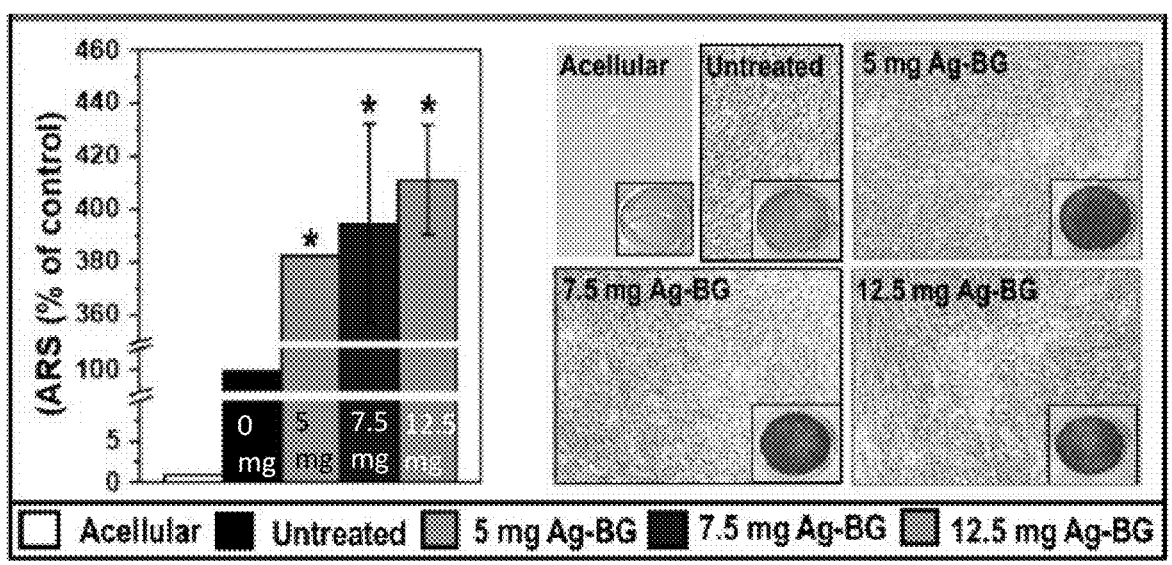
Fig. 16C      Fig. 16D

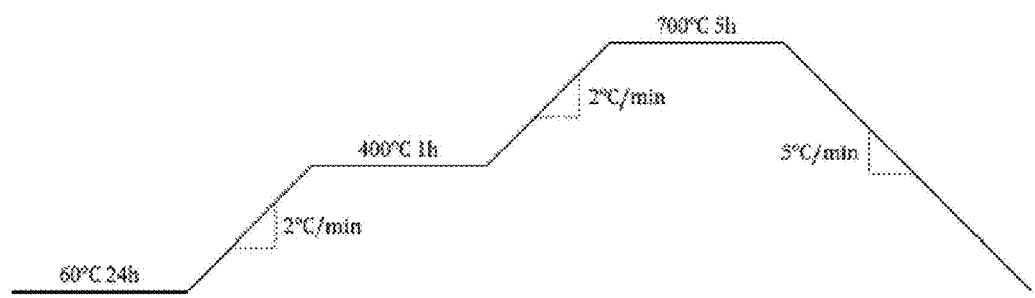
Fig. 25
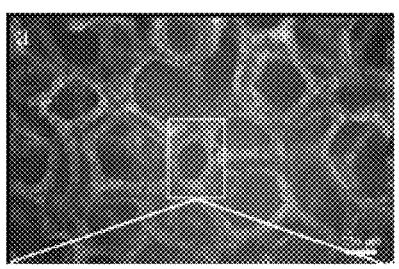 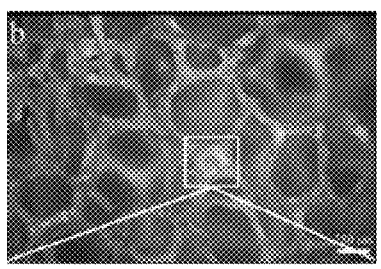 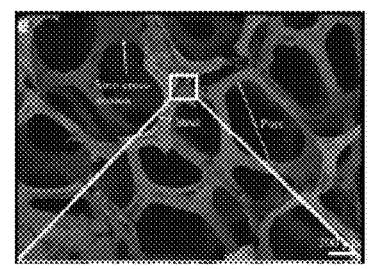
Fig. 26A  Fig. 26B  Fig. 26E
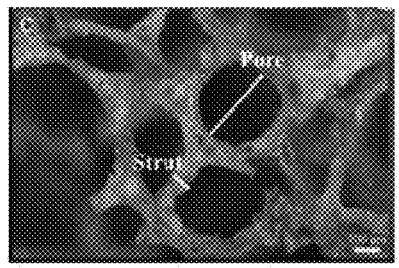 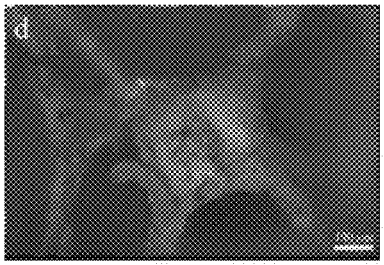 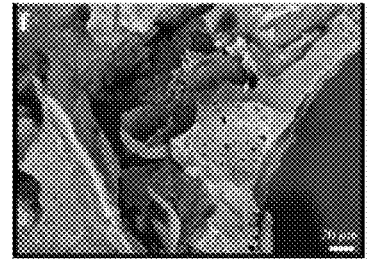
Fig. 26C  Fig. 26D  Fig. 26F

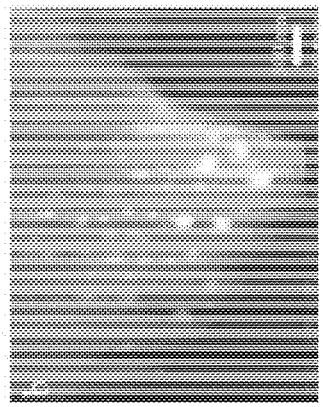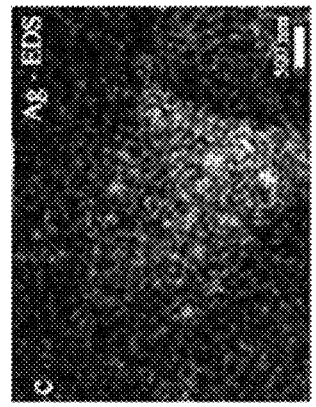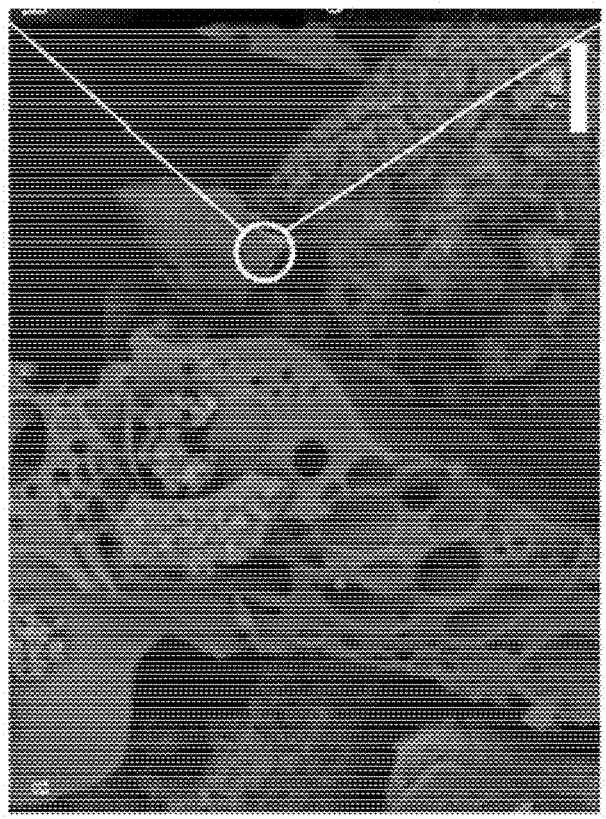

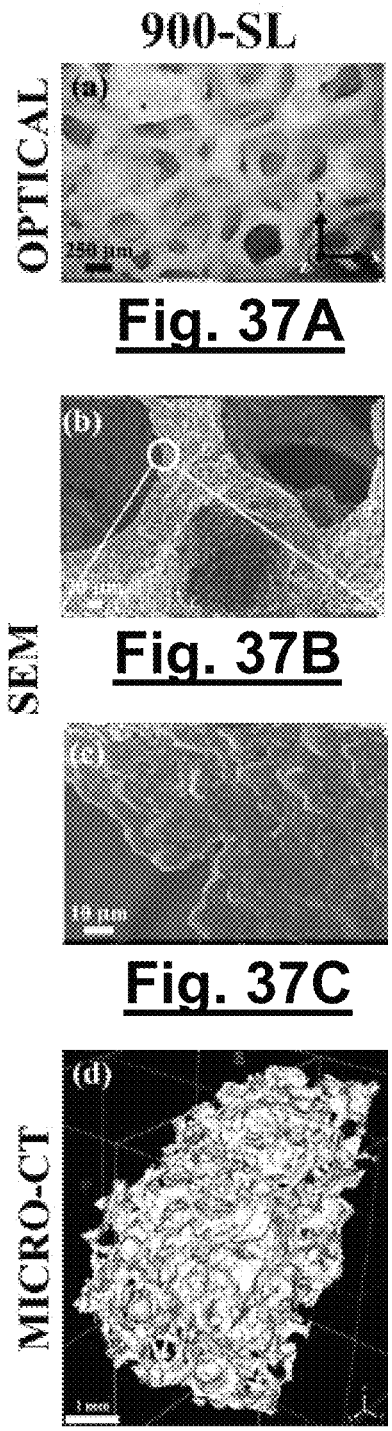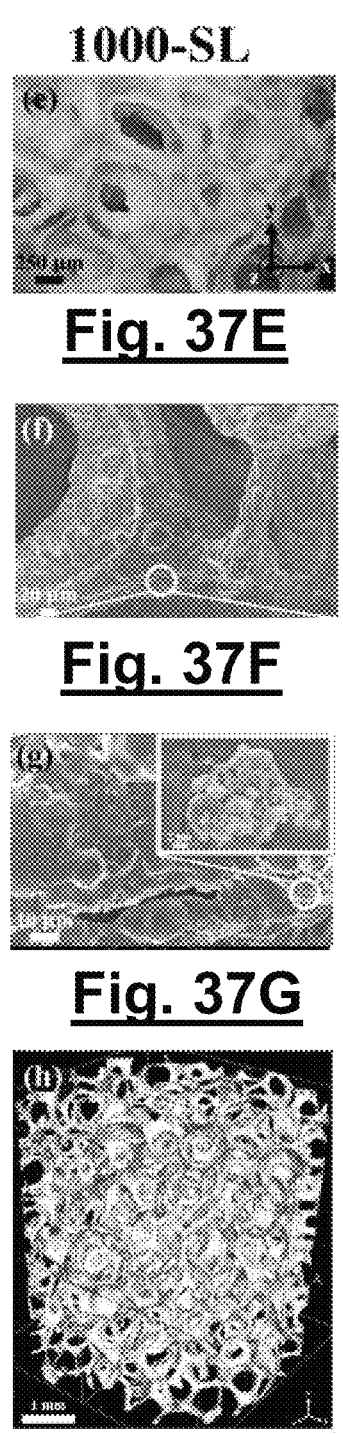
Fig. 37A  Fig. 37E
Fig. 37B  Fig. 37F
Fig. 37C  Fig. 37G
Fig. 37D  Fig. 37H

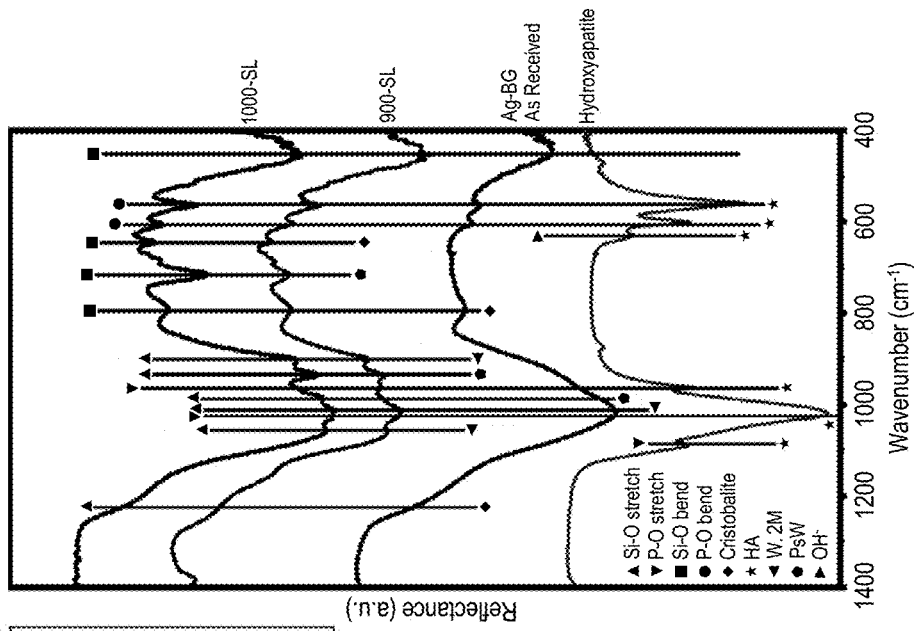
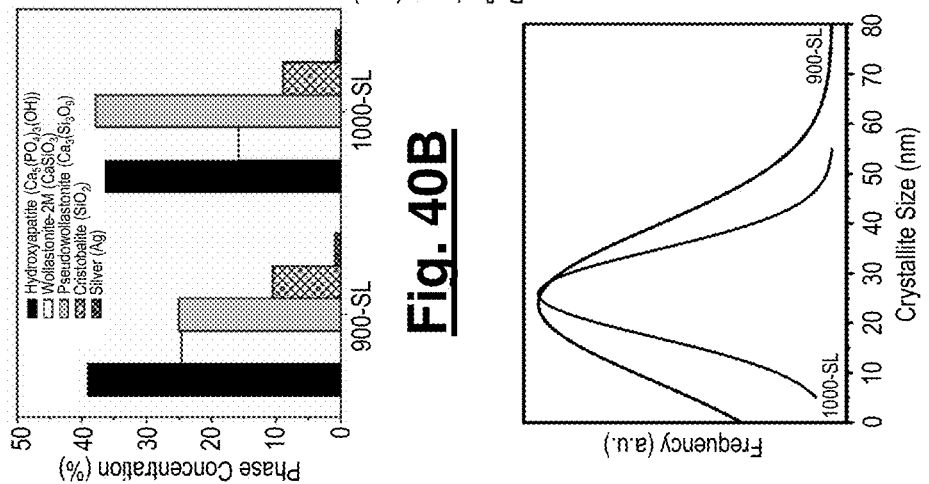
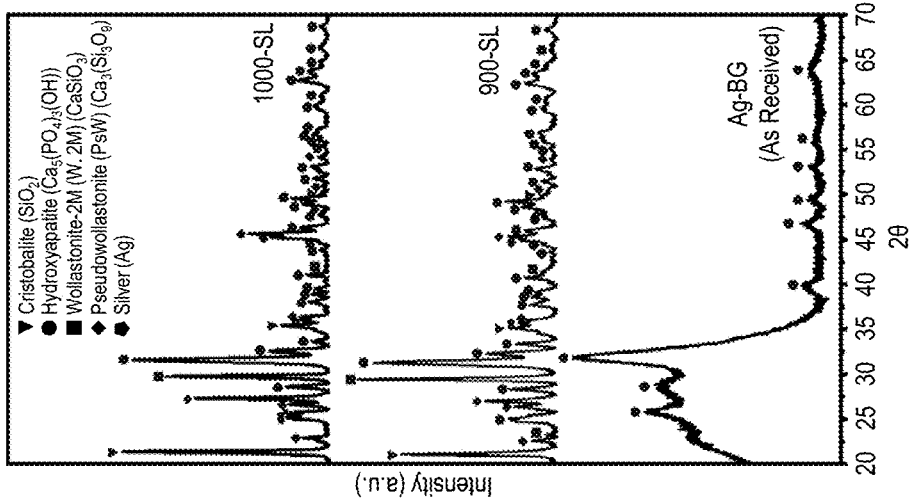
Fig. 40A, Fig. 40B, Fig. 40C, Fig. 40D

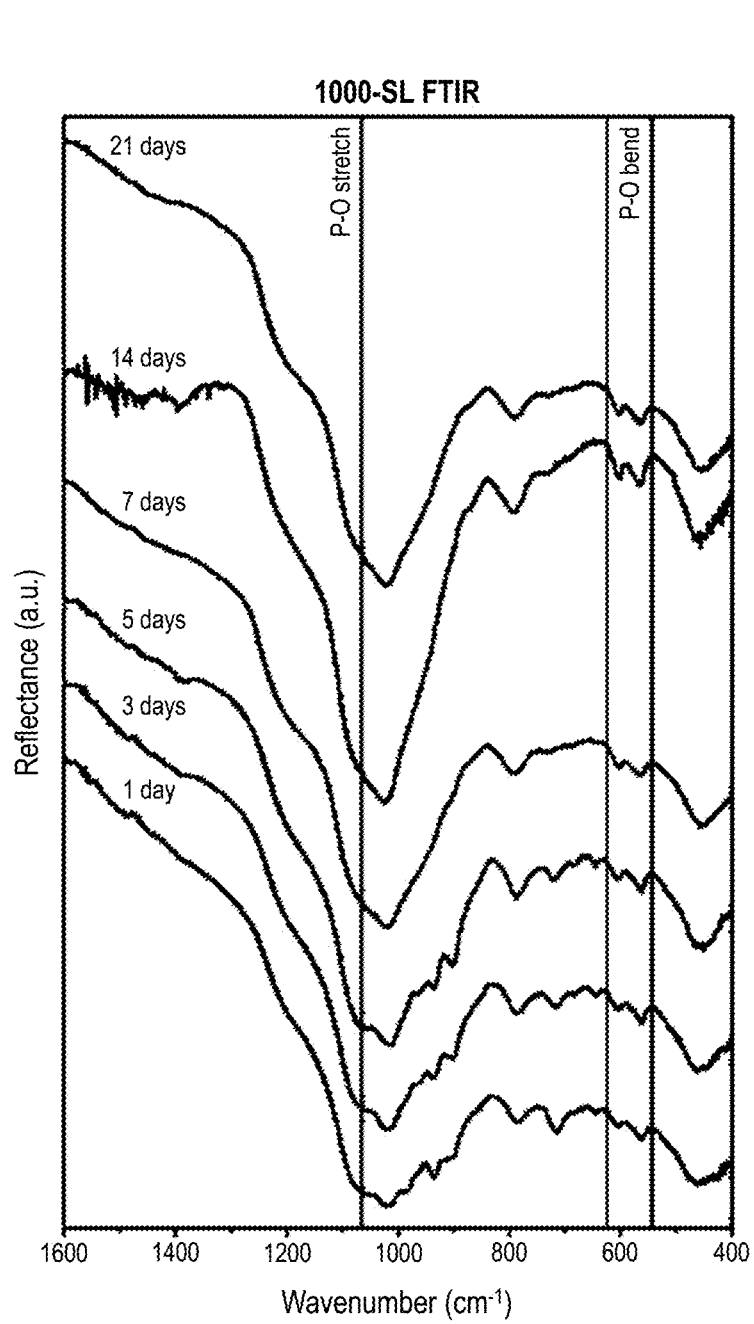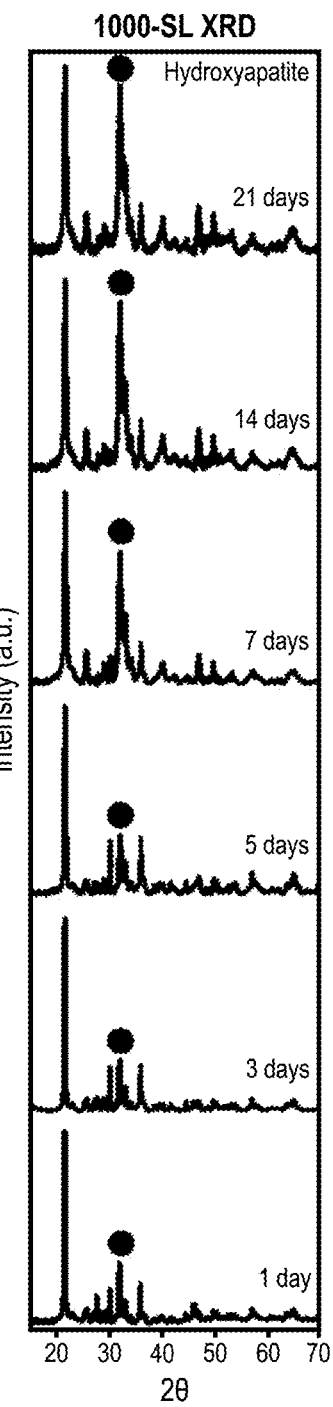
Fig. 45I
Fig. 45J

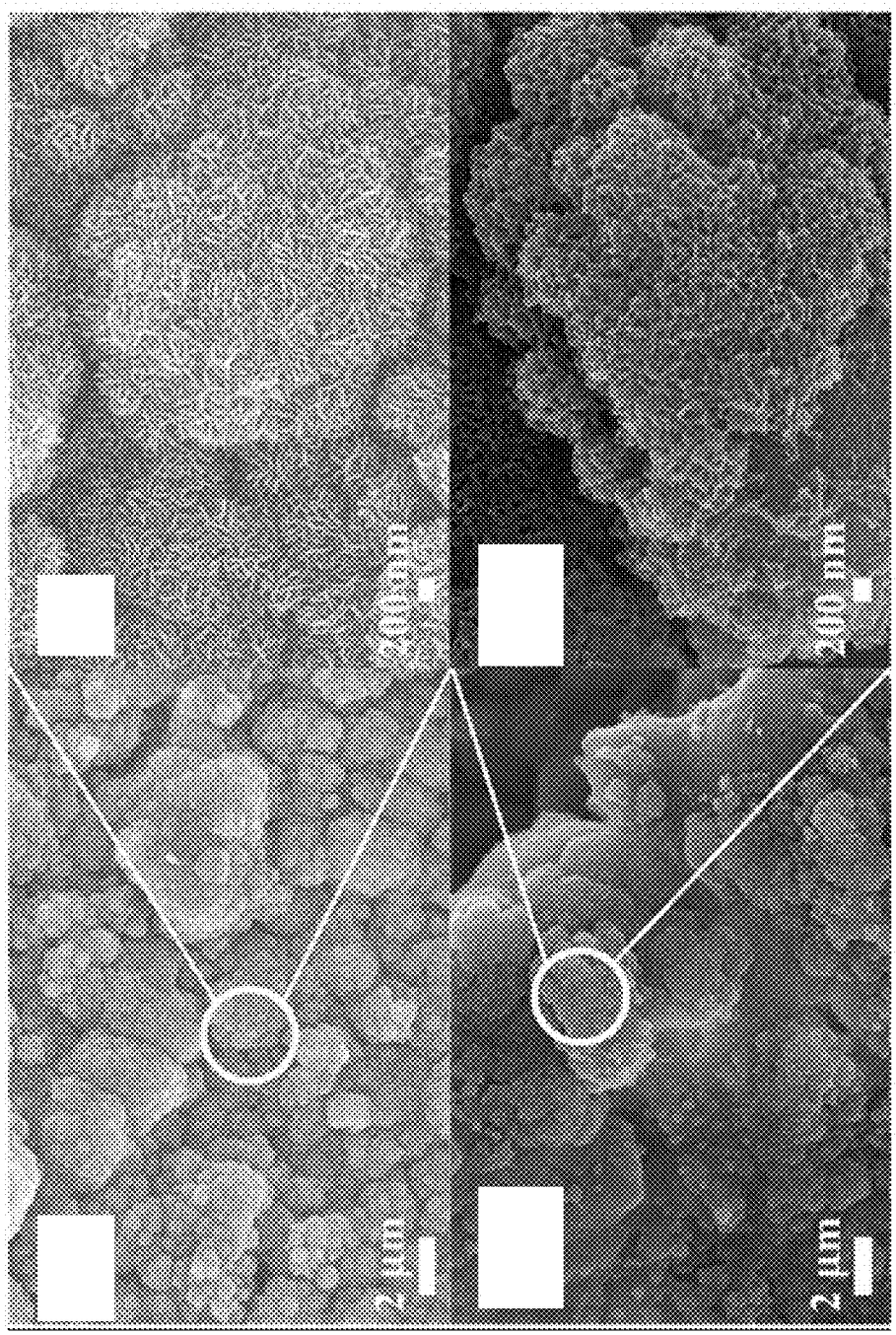

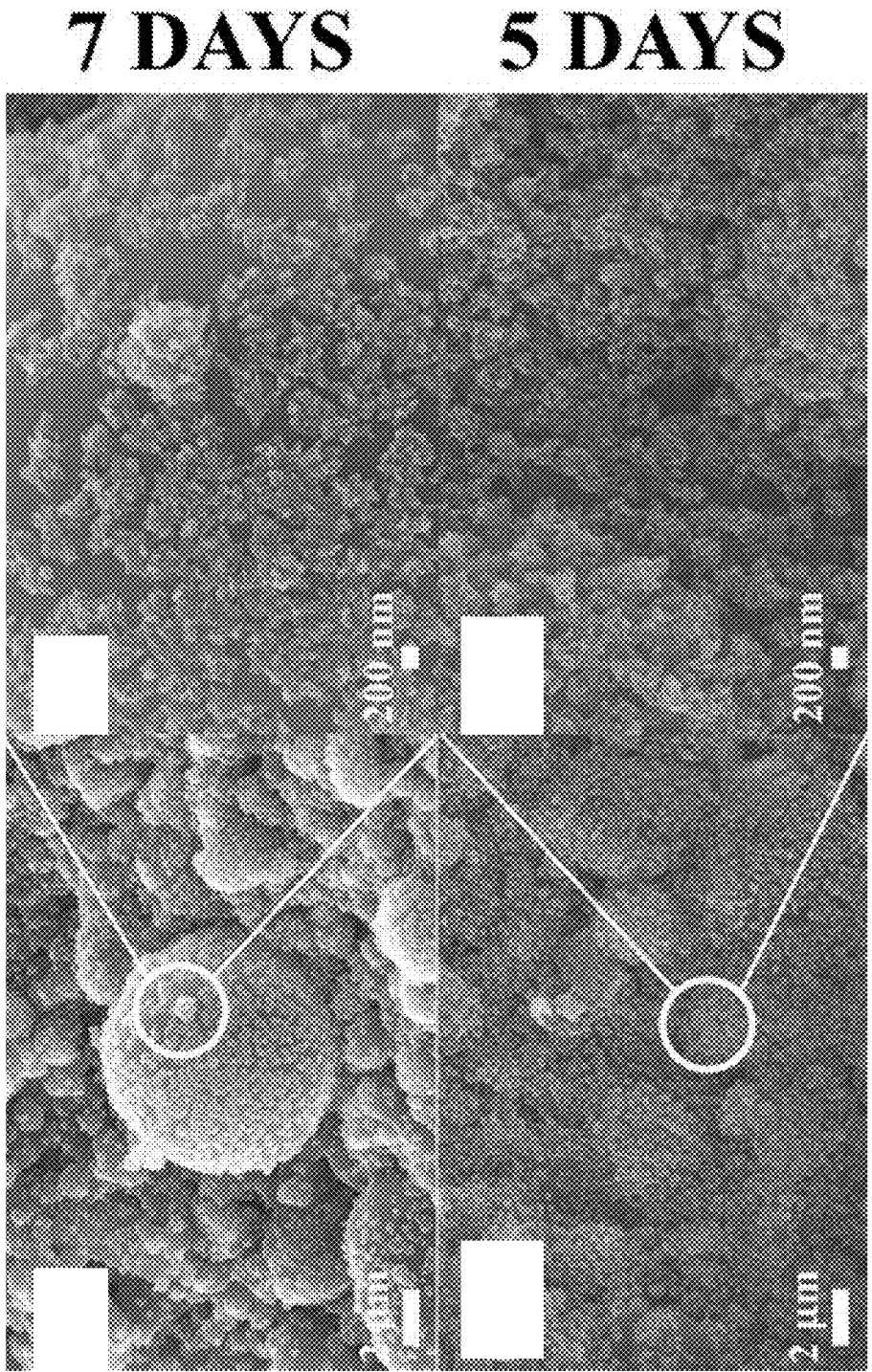

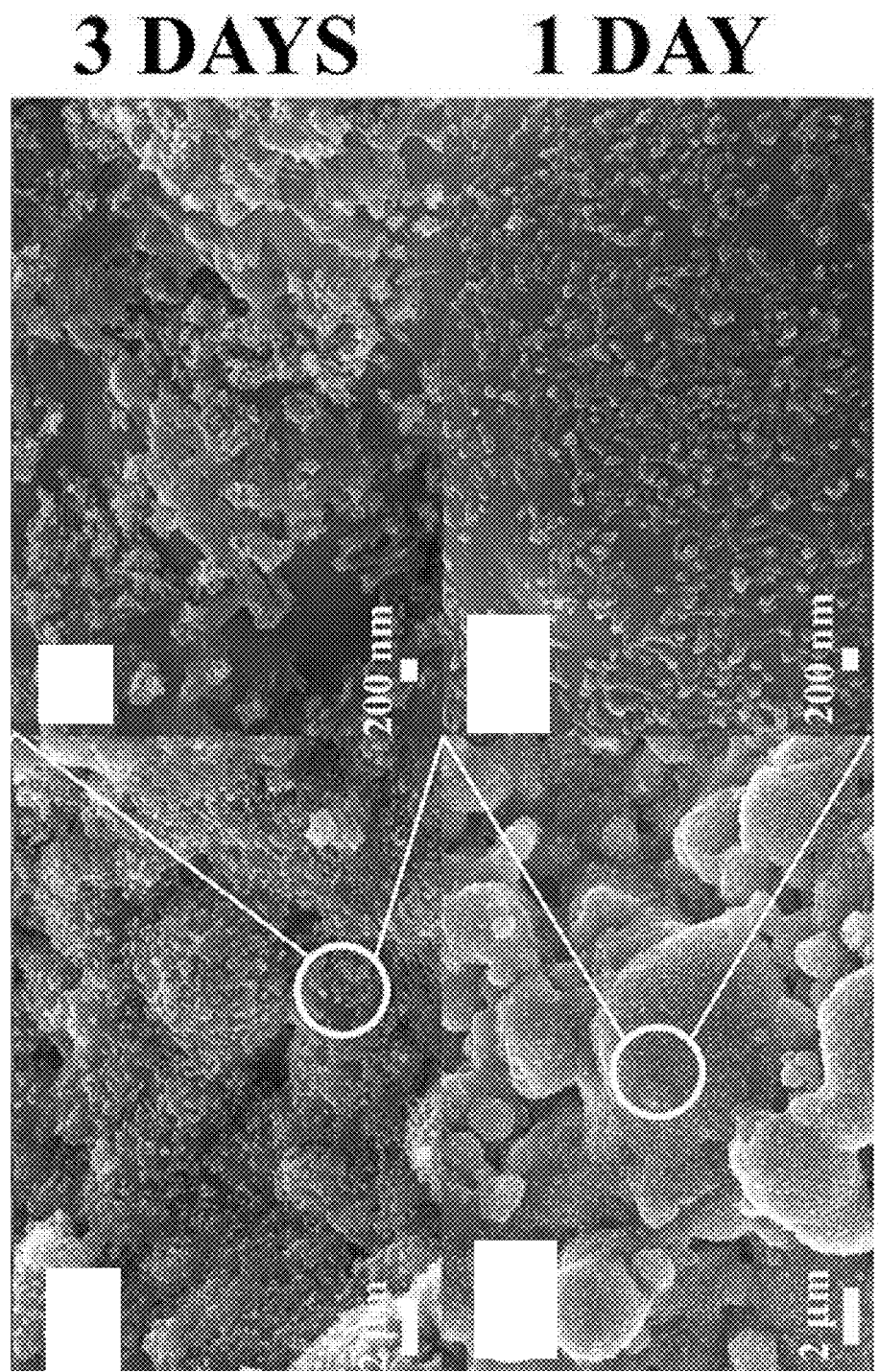

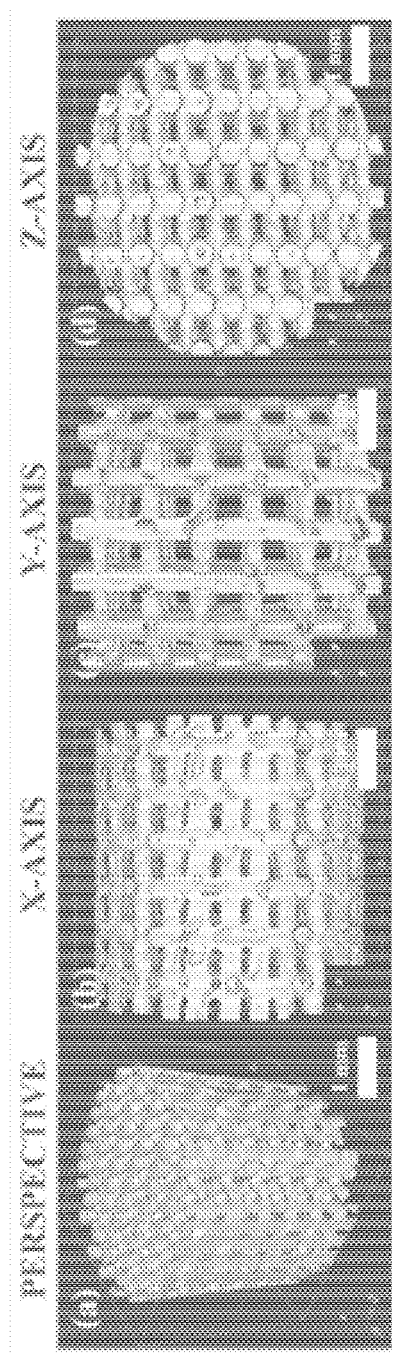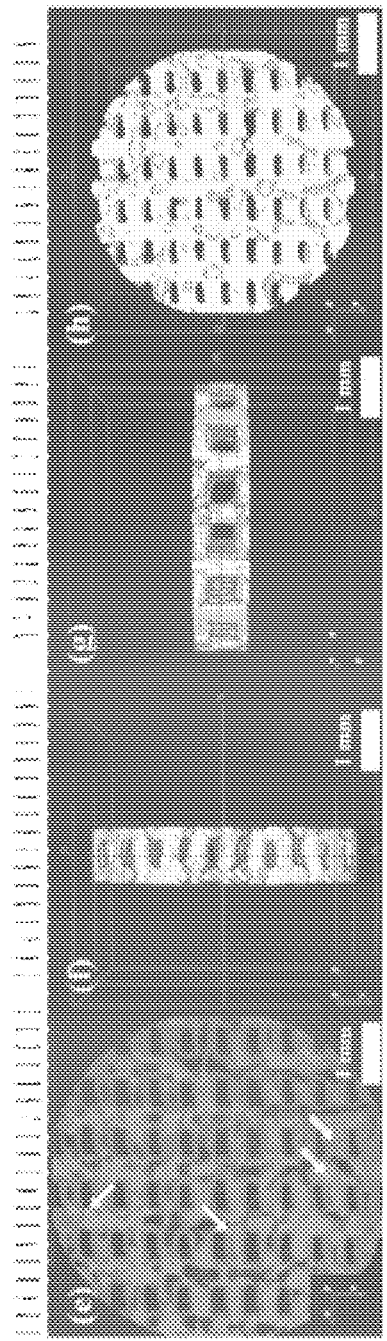

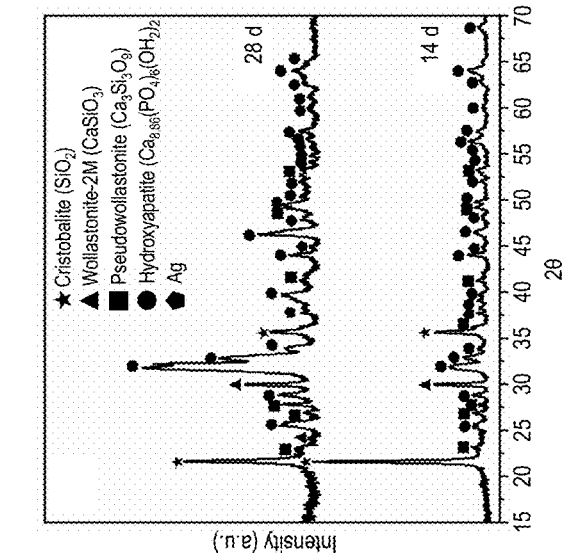
Fig. 54F
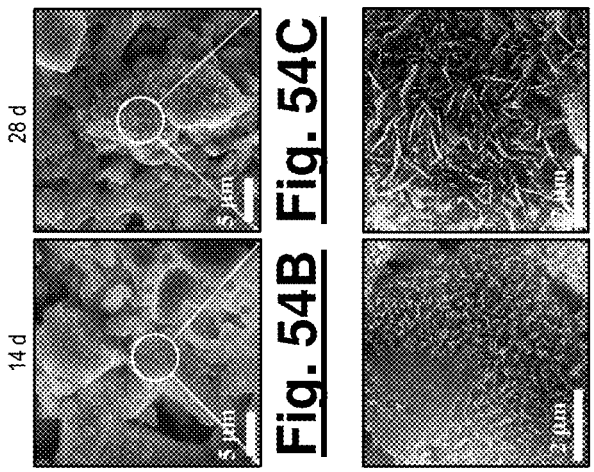
Fig. 54C
Fig. 54E
Fig. 54B
Fig. 54D
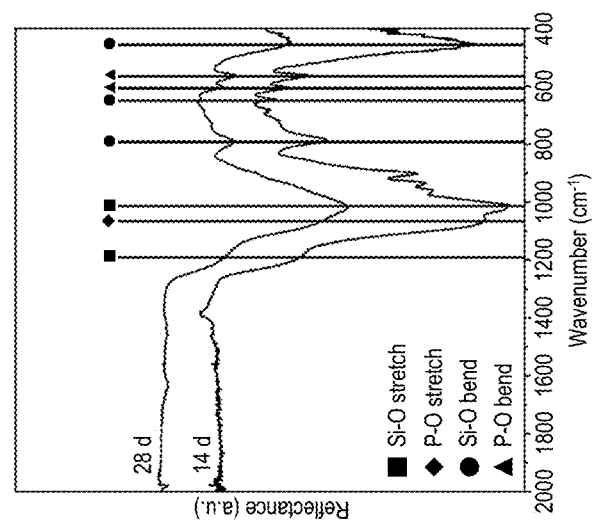
Fig. 54A

RESURRECTION OF ANTIBIOTICS THAT MRSA RESISTS BY SILVER-DOPED BIOACTIVE GLASS-CERAMIC PARTICLES

CROSS-REFERENCE TO RELATED APPLICATIONS

This application claims the benefit of U.S. Provisional Application No. 62/826,672, filed on Mar. 29, 2019. The entire disclosure of the above application is incorporated herein by reference.

FIELD

The present disclosure relates to methods of resurrecting antibiotic activity in an antibiotic directed against a bacteria strain has developed resistance to the antibiotic and methods of regenerating bone tissue using materials that include bioactive glass-ceramic and/or bioactive glass.

BACKGROUND

This section provides background information related to the present disclosure which is not necessarily prior art.

Healing infected tissue and combating resistant bacteria are significant clinical challenges. Antibiotic-based therapies are increasingly unsuccessful due to the ability of pathogens to develop resistance. For example, methicillin resistant *Staphylococcus aureus* (MRSA) is a leading cause of many infections, including skin and soft tissue infections, endocarditis, and osteomyelitis. Disease typically presents in the 30% of the population that are asymptotic carriers of MRSA. Mortality associated with MRSA results in a tremendous socioeconomic burden. In 2009, the European Union (EU) reported approximately 1% mortality in 4.1 million patients that developed MRSA infections, which led to an additional cost of 380 million euros to the EU healthcare system. Additionally, in 2016, the Australian government invested approximately $3.5 billion in the fight against MRSA infections. Thus, there is an urgent need to develop approaches to combat MRSA.

Systematic administration of antibiotics is the traditional therapeutic approach against MRSA. However, the ability of MRSA to develop resistance has rendered this approach increasingly ineffective. Often, prolonged dosage of antibiotics is required to combat MRSA. However, this strategy increases the risk of side effects that negatively affect vital organs. Moreover, the extensive use of different antibiotics enables bacteria to develop resistance. In fact, it has been demonstrated that during the administration of drugs, bacteria develop new pathways for antibiotic inactivation. The most effective resistance mechanisms are enzymatic hydrolysis or modification of the antibiotic, efflux pumps that expel the antibiotic, and altering the target of the antibiotic.

To combat antibiotic resistant pathogens, attempts have been made to expand the action of the drug. There are two main strategies of antibiotic combinations that have been explored—those that target different processes in the cell and those that attempt to inhibit or bypass the resistant mechanism. An example of the former is based on the administration of several antibiotics to treat MRSA infections. In this case, each of the antibiotics presents different mechanisms of action, increasing the probability of synergy and complementary action between them. Another approach to combat antibiotic resistant bacteria is administering a combination of antimicrobial agents. In this approach, an antibiotic aims to inactivate the defense mechanism that bacteria develop to block the activity of another antimicrobial agent that is also delivered. A key feature of the combinatorial methodology is the selection of the antibiotics, as well as the timing of the provided amounts.

Unfortunately, combinatorial antibiotic strategies are not always successful. It has been demonstrated that despite the initial in vitro inhibition, vancomycin supplementation with rifampin does not eliminate bacterial biofilms in a mouse model of *Staphylococcus aureus* spinal implant infection. The combined use of antibiotics in prolonged treatments does not eliminate the risk of developing resistance towards each of the delivered antibiotics. On the contrary, it has been shown that bacteria resistant to an antibiotic tend to rapidly develop resistance against other antibiotics. For example, fluoroquinolone-resistance emerged from a *Neisseria gonorrhoeae* strain resistant to penicillin and tetracycline.

Heavy metal ions (e.g., Ag, Au, and Cu) have been explored as antimicrobial agents due to multiple mechanisms of action that minimize the development of resistance. In particular, Ag ions damage the bacterial cell envelope and nucleic acids and inhibit the activity of specific proteins. A considerable flaw of heavy metal-based strategies is that the therapeutic dose and the toxic dose are comparable. Therefore, heavy metal treatments are not viable therapeutic strategies. However, incorporation of heavy metal ions into bioactive glass-ceramic microparticles controls the release of ions, leading to localized concentrations that are lethal to bacteria but not to the host. In addition to containing heavy metals, particles can also serve as a vehicle for the delivery of antibiotics, improving their efficacy. Moreover, it has been reported that supplementation of antibiotics with heavy metals is synergistic. The delivery process can be applied by different loading methods, such as ion-doped mesoporous bioactive glasses or surface functionalized vehicles with antibiotics and therapeutic ions. However, methods of resurrecting or reactivating antibiotics that target bacteria that are resistant to the antibiotics are still needed.

SUMMARY

This section provides a general summary of the disclosure, and is not a comprehensive disclosure of its full scope or all of its features.

In various aspects, the current technology provides a method of restoring antibiotic activity to an antibiotic against a bacteria strain that has developed resistance to the antibiotic, the method including combining the antibiotic with a reviving agent, wherein the reviving agent is a source of silver ions.

In one aspect, the antibiotic is a molecule that disrupts the ability of a bacterium to assemble a cell wall or replicate DNA.

In one aspect, the antibiotic includes a β-lactam ring.

In one aspect, the antibiotic is selected from the group consisting of penicillin, oxacillin, methicillin, nafcillin, cloxacillin, diclosacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, fosfomycin, vancomycin, daptomycin, gentamicin, ciprofloxacin, and combinations thereof.

In one aspect, the bacteria strain is methicillin-resistant *Staphylococcus aureus* (MRSA).

In one aspect, the source of silver ions is a plurality of silver-doped bioactive glass particles (Ag-BG).

In various aspects, the current technology provides a method of treating or inhibiting the growth of a bacterial infection in a subject in need thereof with an antibiotic, wherein the bacterial infection includes bacteria that are resistant to the antibiotic. The method includes administering to the subject the antibiotic and a source of silver ions.

In one aspect, the subject has an infection that includes the bacteria.

In one aspect, the subject is at risk of developing an infection that includes the bacteria.

In one aspect, the source of silver ions is a plurality of silver-doped bioactive glass particles (Ag-BG).

In one aspect, the Ag-doped bioactive glass particles are Ag-doped bioactive glass-ceramic microparticles or Ag-doped bioactive glass nanoparticles.

In one aspect, the antibiotic and the source of silver ions are combined in a single composition.

In one aspect, the administering includes administering a first composition that includes the antibiotic and separately administering a second composition that includes the source of silver ions.

In one aspect, the administering is performed by administering the antibiotic and source of silver ions directly to tissue having the bacterial infection.

In one aspect, the method further includes administering an adjunct composition that includes a β-lactamase inhibitor.

In one aspect, the β-lactamase inhibitor is clavulanic acid, sulbactam, tazobactam, or a combination thereof.

In one aspect, the bacteria are methicillin-resistant *Staphylococcus aureus* (MRSA).

In one aspect, the antibiotic is selected from the group consisting of penicillin, oxacillin, methicillin, nafcillin, cloxacillin, diclosacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, fosfomycin, vancomycin, daptomycin, gentamicin, ciprofloxacin, and combinations thereof.

In various aspects, the current technology provides a composition that includes a synergistic combination of an antibiotic and a reviving agent including a source of silver ions.

In one aspect, the antibiotic is selected from the group consisting of penicillin, oxacillin, methicillin, nafcillin, cloxacillin, diclosacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, fosfomycin, vancomycin, daptomycin, gentamicin, ciprofloxacin, and combinations thereof, and the source of silver ions is a plurality of silver-doped bioactive glass particles (Ag-BG).

In various aspects, the current technology also provides a method of restoring antibiotic activity to an antibiotic against a bacteria strain that has developed resistance to the antibiotic, the method including combining the antibiotic with a reviving agent including a material including bioactive glass (BG).

In one aspect, the material has a form selected from the group consisting of particles, a scaffold, a thin film, a porous matrix, a coating, and combinations thereof.

In one aspect, the material is substantially free of silver ions.

In one aspect, the material is free of silver ions.

In one aspect, the material includes silver ions.

In one aspect, at least a portion of the silver ions are completely embedded within the material.

In one aspect, at least a portion of the silver ions are partially embedded in an outer surface of the material.

In various aspects, the current technology also provides a composition that includes a synergistic combination of an antibiotic and bioactive glass (BG).

In one aspect, the BG is optionally Ag-doped bioactive glass-ceramic particles, Ag-doped bioactive glass particles, or a combination thereof.

In various aspects, the current technology yet further provides a method of treating or inhibiting the growth of a bacterial infection in a subject in need thereof, wherein the bacterial infections includes bacteria that have developed resistance to an antibiotic, the method include administering to the subject the antibiotic and a reviving agent, the reviving agent being a material that includes bioactive glass (BG).

In one aspect, the material has a form selected from the group consisting of particles, a scaffold, a thin film, a porous matrix, a coating, and combinations thereof.

In one aspect, the material is substantially free of silver ions.

In one aspect, the material is free of silver ions.

In one aspect, the material includes silver ions.

In one aspect, the material includes optionally Ag-doped glass-ceramic microparticles, optionally Ag-doped glass nanoparticles, an optionally Ag-doped bioactive glass scaffold, an optionally Ag-doped bioactive glass-ceramic scaffold, an optionally Ag-doped glass-ceramic film, or a combination thereof.

In one aspect, the administering includes separately administering the antibiotic and the material.

In one aspect, the administering includes administering a single composition that includes the antibiotic and the material.

In one aspect, the composition further includes a pharmaceutically acceptable carrier.

In one aspect, the administering includes administering the antibiotic and the material directly to tissue having the bacterial infection.

In one aspect, the subject has the bacterial infection.

In one aspect, the subject is at risk of developing the bacterial infection.

In various aspects, the current technology provides a method of treating a bacterial infection including bacteria that have become resistant to an antibiotic in a subject in need thereof, the method including administering to the subject a safe and therapeutically effective amount of the antibiotic and a reviving agent selected from the group consisting of glass-ceramic particles, silver ions, and combinations thereof, wherein the reviving agent restores antibiotic activity to the antibiotic against the bacteria.

In one aspect, the bacteria include methicillin-resistant *Staphylococcus aureus* (MRSA).

In one aspect, the antibiotic is selected from the group consisting of penicillin, oxacillin, methicillin, nafcillin, cloxacillin, diclosacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, fosfomycin, vancomycin, daptomycin, gentamicin, ciprofloxacin, and combinations thereof.

In one aspect, the reviving agent is the glass-ceramic particles, wherein the glass-ceramic microparticles are synthesized from $SiO_2$, $CaO$, $P_2O_5$, $Al_2O_3$, $Na_2O$, and $K_2O$, and are glass-ceramic microparticles having a diameter of greater than or equal to about 500 nm to less than or equal to about 100 μm or glass-ceramic nanoparticles having a diameter of greater than or equal to about 0.75 nm to less than or equal to about 100 nm, or a combination thereof.

In one aspect, the reviving agent is silver (Ag)-doped glass-ceramic particles, wherein the glass-ceramic microparticles are synthesized from $SiO_2$, CaO, $P_2O_5$, $Al_2O_3$, $Na_2O$, $K_2O$, and $Ag_2O$, and are Ag-doped glass-ceramic microparticles having a diameter of greater than or equal to about 500 nm to less than or equal to about 100 µm or Ag-doped glass-ceramic nanoparticles having a diameter of greater than or equal to about 0.75 nm to less than or equal to about 100 nm, or a combination thereof.

In one aspect, the Ag-doped glass-ceramic microparticles or the Ag-doped glass-ceramic nanoparticles also regenerate bone tissue in the subject.

In various aspects, the current technology provides a bioactive glass-ceramic scaffold including an interconnected web of struts that define a three dimensional porous structure, the struts including a glass-ceramic material system synthesized from $SiO_2$, CaO, $P_2O_5$, $Al_2O_3$, $Na_2O$, $K_2O$, and optionally $Ag_2O$, wherein the bioactive glass-ceramic scaffold has antibiotic activity, and wherein the bioactive glass-ceramic scaffold promotes proliferation and differentiation of cells that are in contact with the bioactive glass-ceramic scaffold.

In one aspect, the bioactive glass-ceramic scaffold has as porosity of greater than or equal to about 60% to less than or equal to about 99% and an average pore size of greater than or equal to about 250 µm to less than or equal to about 750 µm.

In various aspects, the current technology provides a method of fabricating the bioactive glass-ceramic scaffold, the method including preparing a bioactive glass solution including water and greater than or equal to about 50 wt. % to less than or equal to about 70 wt. % $SiO_2$, greater than or equal to about 25 wt. % to less than or equal to about 40 wt. % CaO, and greater than or equal to about 5 wt. % to less than or equal to about 15 wt. % $P_2O_5$; preparing a sol-gel porcelain solution including water and greater than or equal to about 50 wt. % to less than or equal to about 70 wt. % $SiO_2$, greater than or equal to about 1 wt. % to less than or equal to about 10 wt. % CaO, greater than or equal to about 1 wt. % to less than or equal to about 15 wt. % $P_2O_5$, greater than or equal to about 10 wt. % to less than or equal to about 20 wt. % $Al_2O_3$, greater than or equal to about 0 wt. % to less than or equal to about 15 wt. % $Na_2O$, greater than or equal to about 0 wt. % to less than or equal to about 15 wt. % $K_2O$, and greater than or equal to about 0 wt. % to less than or equal to about 10 wt. % $Ag_2O$; combining the bioactive glass solution and the sol-gel porcelain solution to form a composite solution; submerging a porous foam having a predetermined three-dimensional shape into the composite solution; drying the composite solution in the porous foam to generate a coated foam; burning out the coated foam to form a scaffold precursor; and sintering the scaffold precursor to form the bioactive glass-ceramic scaffold, the bioactive glass-ceramic scaffold having a three-dimensional shape.

In various aspects, the current technology provides a method of fabricating the bioactive glass-ceramic scaffold, the method including obtaining glass-ceramic microparticles particles comprising crystalline and amorphous phases, the glass-ceramic microparticles optionally doped with Ag; preparing a polymer slurry by combining and mixing water, a polymer, and the glass-ceramic microparticles particles; submerging a porous foam having a predetermined three-dimensional shape into the composite solution; drying the composite solution in the porous foam to generate a coated foam burning out the coated foam to form a scaffold precursor; and sintering the scaffold precursor to form the bioactive glass-ceramic scaffold.

In various aspects, the current technology provides a method of fabricating the bioactive glass-ceramic scaffold, the method including generating a computer model of a scaffold having a predetermined three-dimensional (3D) structure; obtaining glass-ceramic microparticles particles including crystalline and amorphous phases, the glass-ceramic microparticles optionally doped with Ag; adding the glass-ceramic microparticles particles into a binder system comprising a polyolefin, an elastomer, and a fatty acid comprising a polyolefin, an elastomer, and a fatty acid, introducing the binder system to an extruder and mixing the glass-ceramic microparticles particles, the polyolefin, and the elastomer in the extruding to form a binder system comprising microparticles; extruding the binder system as a filament; and 3D printing the computer model from the filament to form the bioactive glass-ceramic scaffold.

In one aspect, the polyolefin is selected from the group consisting of poly(methyl methacrylate) (PMMA), polyethylene, polypropylene, acrylonitrile butadiene styrene (ABS), polycarbonate (PC), polylactic acid (PLA), PC/ABS, polyethylene terephthalate (PET), polyphenylsulfone (PPSF), polystyrene, polyether ether ketone (PEEK), polytetrafluoroethylene (PTFE), and combinations thereof; the elastomer is selected from the group consisting of thermoplastic polyurethanes (TPU), ethylene propylene diene monomer (EPDM), thermoplastic polyolefin (TPO), and combinations thereof; and the fatty is a saturated fatty acid, an unsaturated fatty acid, or a combination thereof.

In various aspects, the current technology provides a method of treating a subject having or at risk of having a bacterial infection, the method including implanting the bioactive glass-ceramic scaffold in the subject at a location of the bacterial infection or at a location at risk of developing the bacterial infection.

In one aspect, the bioactive glass-ceramic scaffold is doped with Ag.

In one aspect, the bioactive glass ceramic scaffold releases a safe and therapeutically effective amount of Ag ions over a time period of from about 10 days to about 20 days.

In various aspects, the current technology provides a bioactive glass-ceramic film including a material including a glass-ceramic material system synthesized from $SiO_2$, CaO, $P_2O_5$, $Al_2O_3$, at least one of $Na_2O$ or $K_2O$, and optionally $Ag_2O$, wherein the bioactive glass-ceramic film has antibiotic activity, and wherein the bioactive glass-ceramic film promotes proliferation and differentiation of cells that are in contact with the bioactive glass-ceramic film.

In one aspect, the bioactive glass-ceramic film has a thickness of greater than or equal to about 0.1 µm to less than or equal to about 50 µm.

In various aspects, the current technology provides a medical implant having a surface including steel, a metal, a metal alloy, a ceramic, a glass, or a polymer, wherein the surface is coated with the bioactive glass-ceramic film.

In various aspects, the current technology provides a method of synthesizing the bioactive glass-ceramic film, the method including preparing a first solution comprising water and greater than or equal to about 50 wt. % to less than or equal to about 70 wt. % $SiO_2$, greater than or equal to about 25 wt. % to less than or equal to about 40 wt. % CaO, and greater than or equal to about 5 wt. % to less than or equal to about 15 wt. % $P_2O_5$; preparing a second solution including water and greater than or equal to about 50 wt. % to less than or equal to about 70 wt. % $SiO_2$, greater than or equal to about 1 wt. % to less than or equal to about 10 wt. % CaO, greater than or equal to about 1 wt. % to less than or equal to about 15 wt. % $P_2O_5$, greater than or equal to about 10 wt. % to less than or equal to about 20 wt. % $Al_2O_3$, greater than or equal to about 0 wt. % to less than or equal to about 15 wt. % $Na_2O$, greater than or equal to about 0 wt. % to less than or equal to about 15 wt. % $K_2O$, and greater than or equal to about 0 wt. % to less than or equal to about 10 wt. % $Ag_2O$; combining the first solution and the second solution to form a composite solution comprising greater than or equal to about 60 vol. % to less than or equal to about 80 vol. % of the first solution and greater than or equal to about 20 vol. % to less than or equal to about 40 vol. % of the second solution; applying the composite solution to a substrate to form a coated substrate; performing a first heat treatment by heating the coated substrate to a heating temperature of greater than or equal to about 100° C. to less than or equal to about 150° C. and maintaining the heating temperature for greater than or equal to about 1 hour to less than or equal to about 24 hours; performing a second heat treatment by heating the coated substrate to a heating temperature of greater than or equal to about 300° C. to less than or equal to about 700° C. and maintaining the heating temperature for greater than or equal to about 1 hour to less than or equal to about 10 hours; and cooling the coated substrate to form the bioactive glass-ceramic film on the substrate.

In one aspect, the substrate is a surface of medical implant.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-1B show that particles of Ag-BG exhibit antibacterial activity against MRSA. In FIG. 1A, a suspension of MRSA was mixed with increasing concentrations of Ag-BG for 24 hours before enumerating CFUs. In FIG. 1B, Ag-BG bactericidal activity was measured over time using the MIC (2.5 mg). Black columns denote CFUs for the untreated control (0 mg). Error bars represent standard deviation. (*) indicates the significant difference between the untreated versus the Ag-BG treatment, and (#) indicates the significant difference for the Ag-BG treatment at 0 hours versus at the marked time points (p<0.05).

FIGS. 2A-2I show that AF-BG synergizes with oxacillin (oxa), fosfomycin (fosfo), and vancomycin (vanc) to reduce the viability of MRSA. FIGS. 2A, 2D, and 2G show the effects of oxacillin alone, fosfomycin alone, and vancomycin alone, respectively, at different concentrations after 24 hours. MRSA was exposed to oxacillin (oxa, 0.1 µg/ml—white bars), fosfomycin (fosfo, 0.05 µg/ml—white bars), vancomycin (vanc, 0.5 mg/ml—white bars), Ag-BG (2.5 mg/ml—gray bar), or a combination of the substances (Ag-BG/oxa; Ag-BG/fosfo; Ag-BG/vanc—bar with light gray stripe pattern) for 12 hours (FIGS. 2B, 2E, and 2H, respectively) and 24 hours (FIGS. 2C, 2F, and 2I, respectively) prior to enumeration of CFU. The black bar indicates the CFU for the untreated control (0 mg/ml). Error bars represent standard deviation. (*) indicates the significant difference between the combination versus the substances alone, and (#) indicates the significant difference for the combination at the two different time points (p<0.05).

FIG. 3 is a graph showing neutral values for the pH for both Ag-BG and Ag-BG/vanc when immersed in PBS solution for up to 48 hours.

FIG. 4A-4C show that Ag-BG does not synergize with gentamicin (gent) to reduce viability of MRSA. FIG. 4A shows the effect of gentamicin alone at different concentrations after 24 hours. MRSA was exposed to gentamicin (gent, 0.01 µg/ml—white bars), Ag-BG (2.5 mg/ml—gray bar), or a combination of the substances (Ag-BG/gent—bar with light gray stripe pattern) for 12 hours (FIG. 4B) and 24 hours (FIG. 4C) prior to enumeration of CFU. The black bar indicates the CFU for the untreated control (0 mg/ml). Error bars represent standard deviation. (*) indicates the significant difference between untreated and different concentrations of gentamycin (p<0.05).

FIG. 5 shows that BG displays antibacterial properties and synergizes with fosfomycin (fosfo) to reduce MRSA viability. MRSA was exposed to fosfomycin (fosfo, 0.05 µg/ml—white bar), Ag-BG (2.5 mg/ml—light gray bar), or a combination of the substances (Ag-BG/fosfo—bar with light gray stripe pattern), and also to BG (2.5 mg/ml—dark gray bar) and a combination of the substances (BG/fosfo—bar with dark gray stripe pattern) for 24 hours prior to enumeration of CFU. The black bar indicates the CFU for the untreated control (0 mg/ml). Error bars represent standard deviation. (•) indicates the significant difference between BG and the combination BG/fosfo, (*) indicates the significant difference between BG and Ag-BG, and (#) indicates the significant difference between the combinations BG/fosfo and Ag-BG/fosfo (p<0.05).

FIGS. 6A-6X show bacterial cells imaged using TEM after 24 hours exposure to different antibiotic and/or Ag-BG combinations. Shown are TEM images of bacteria untreated (FIGS. 6A, 6B, 6C), after being exposed for 24 hours to oxacillin alone (FIGS. 6D, 6E, 6F), fosfomycin alone (FIGS. 6G, 6H, 6I), vancomycin alone (FIGS. 6J, 6K, 6L), Ag-BG particles alone (FIGS. 6M, 6N, 6O), or to the following combinations: Ag-BG/oxa (FIGS. 6P, 6Q, 6R), Ag-BG/fosfo (FIGS. 6S, 6T, 6U), and Ag-BG/vanc (FIGS. 6V, 6W, 6X). Ag-BG microsize and nanosize particles are marked with white lines. Black arrows point to damaged cells, gray arrows indicate the void formation between the cell envelope and cytoplasm, and the white arrow marks a nanotunnel/channel.

FIGS. 7A-7F are SEM images of untreated MRSA cultured for 12 hours in PBS (FIGS. 7A, 7B, 7C) and exposed to Ag-BG particles alone (FIGS. 7D, 7E, 7F). In FIG. 7D, the arrows indicate the cytoplasmic contents. In FIG. 7F, the arrow shows cell-wall fragments.

Figures 13A, 13B:
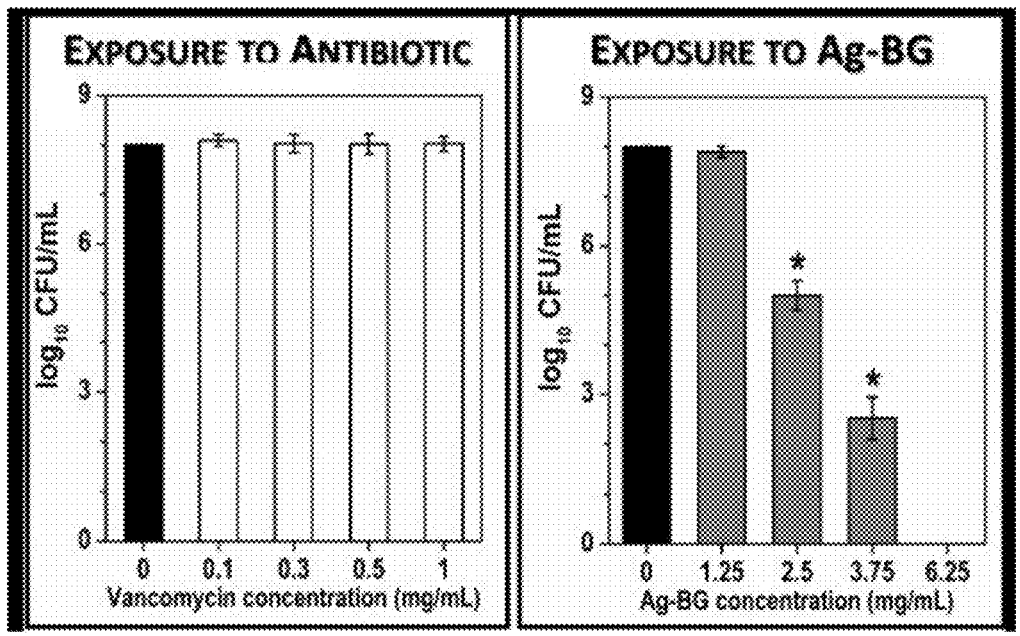
Figures 13C, 13D:
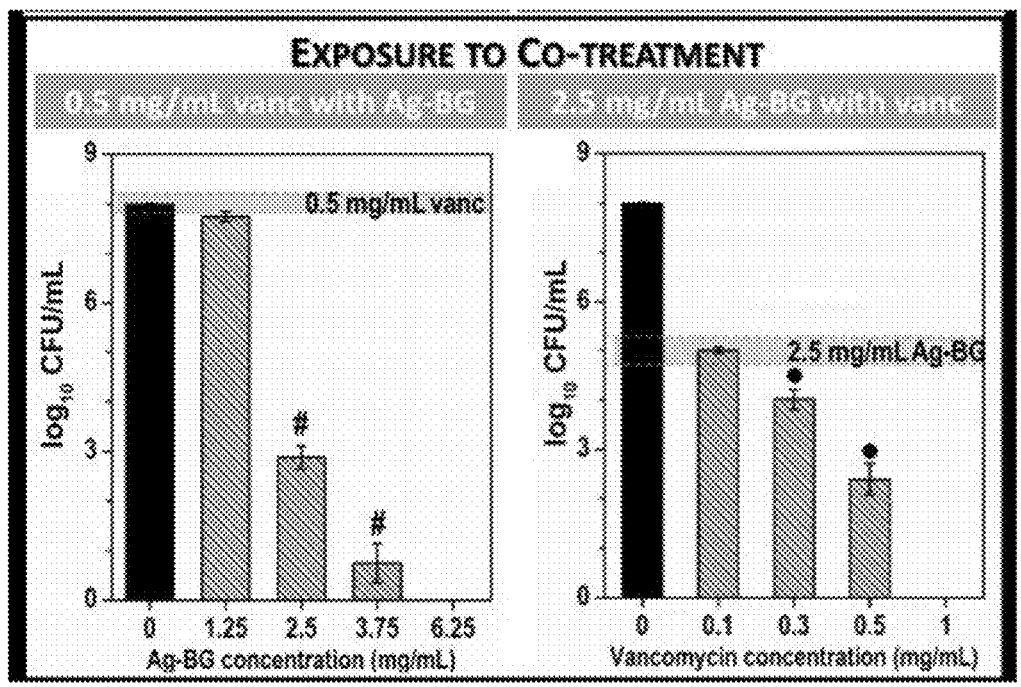

FIG. 13A-13D are bar graphs showing that Ag-BG synergizes with vancomycin against MRSA in PBS. The minimum inhibitory concentration of vancomycin (FIG. 13A) and Ag-BG (FIG. 13B), are reproduced from FIGS. 2G and 1A, respectively. Statistical significance (p<0.05) between Ag-BG and untreated marked with (*). FIG. 13C shows MRSA exposed to 0.5 mg/mL vancomycin with increasing concentration of Ag-BG, where (#) indicates statistical significance (p<0.05) between 0.5 mg/mL of vancomycin and Ag-BG/vanc. FIG. 13D shows MRSA exposed to 2.5 mg/mL Ag-BG with increasing concentration of vancomycin where (•) indicates statistical significance between 2.5 mg/mL of Ag-BG and Ag-BG/vanc.

Figure 14A:
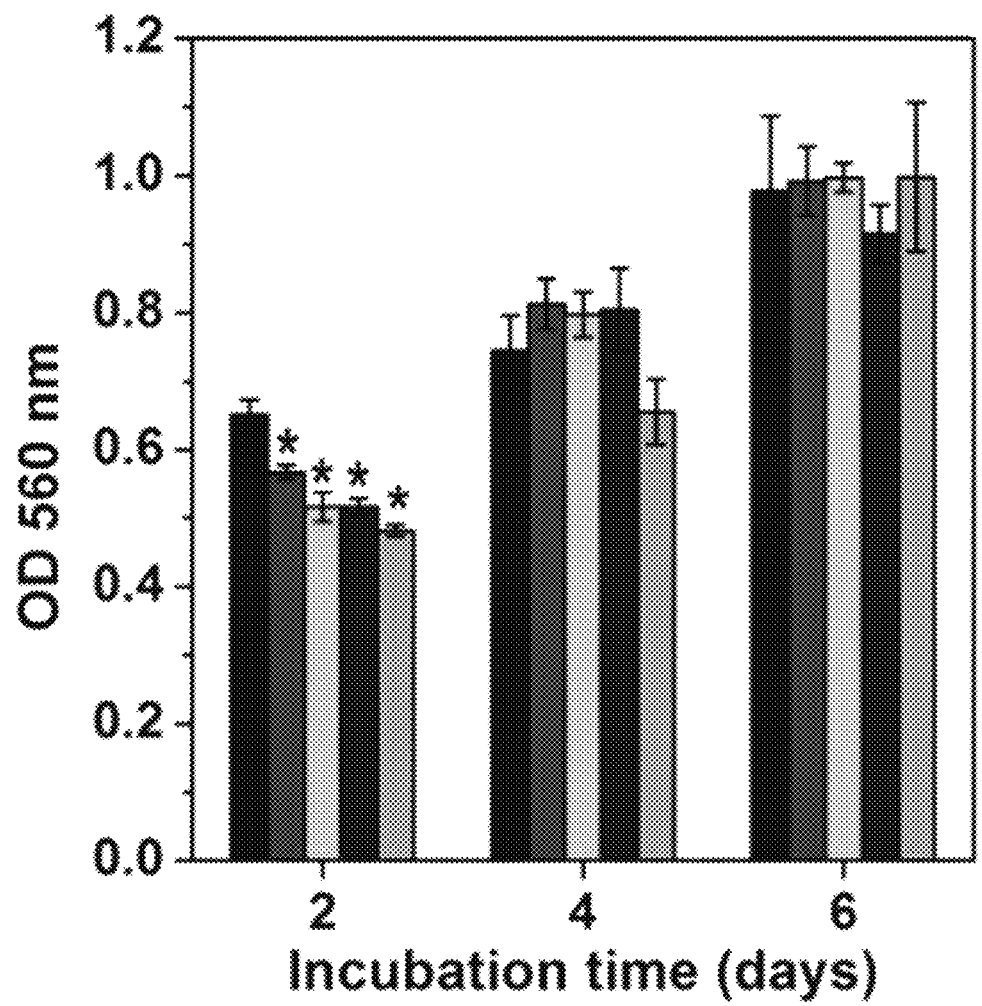

FIG. 14A-14G are a bar graph and individual line graphs, respectively, showing the proliferation rate of hBMSC cells when co-cultured with different concentrations of Ag-BG. The line graphs of FIGS. 14B-14F correspond to the bars of the bar graph of FIG. 14A. In the bar graph of FIG. 14A, each group of 5 bars sequentially represents untreated hBMSC cells, hBMSC cells treated with 2.5 mg Ag-BG, hBMSC cells treated with 5 mg Ag-BG, hBMSC cells treated with 7.5 mg Ag-BG, and hBMSC cells treated with 12.5 mg Ag-BG. The significant difference (P<0.05) between untreated and Ag-BG treated cells is indicated with (*) FIG. 14B is a line graph represented untreated hBMSC cells. FIG. 14C is a line graph representing hBMSC cells treated with 2.5 mg Ag-BG. FIG. 14D is a line graph representing hBMSC cells treated with 5 mg Ag-BG. FIG. 14E is a line graph representing hBMSC cells treated with 7.5 mg Ag-BG. FIG. 14F is a line graph representing hBMSC cells treated with 12.5 mg Ag-BG. FIG. 14G is a table showing growth rate ($OD_{560}$/days).

Figure 15:
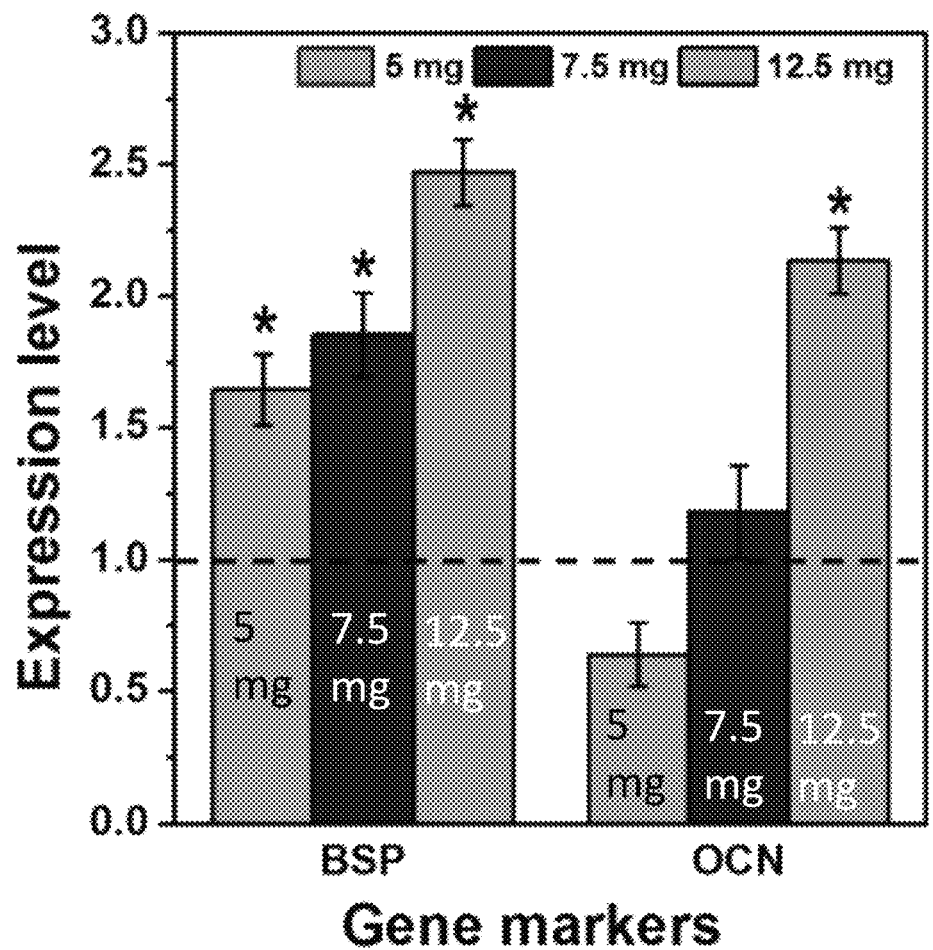

FIG. 15 is a bar graph showing the expression level for bone sialoprotein (BSP) and osteocalcin (OCN) gene markers after 10 days in osteogenic media with 5, 7.5 and 12.5 mg of Ag-BG. A gene expression level of untreated cells was normalized to 1 (dashed line). The significant difference (p<0.05) between untreated and Ag-BG treated cells is indicated with (*).

FIGS. 16A-16D show hBMSC differentiation with Alizarin Red Staining (ARS) in growth (FIGS. 16A-16B) and osteogenic medium (FIGS. 16C-16D). Optical density (FIGS. 16A and 16C) was normalized utilizing untreated cells as 100%. Fibroblast optical images (FIGS. 16B and 16D) with ARS wells as inserts. (*) Statistical difference between untreated and Ag-BG treated cell for p<0.05.

Figure 17A:
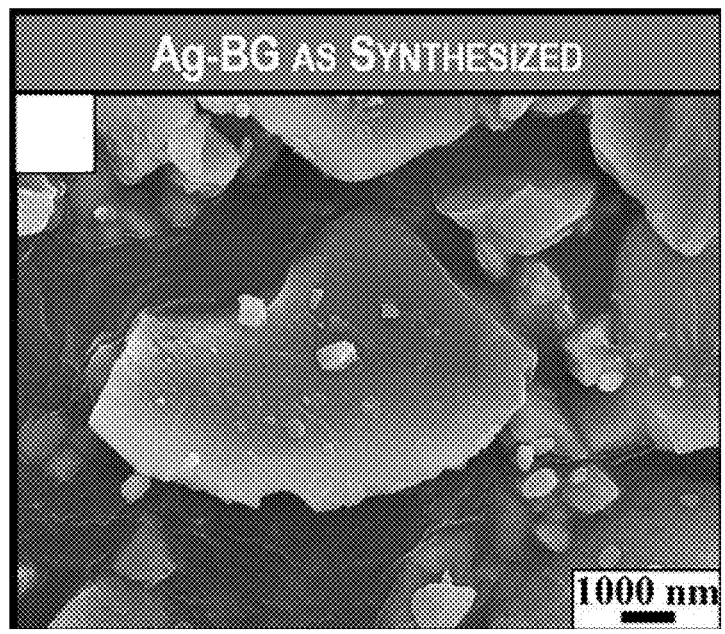
Figure 17B:
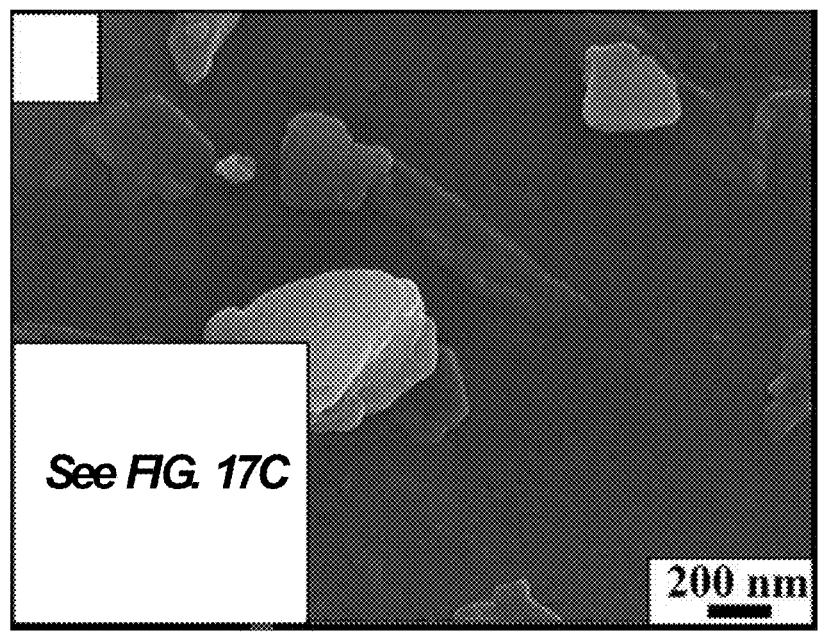
Figure 17C:
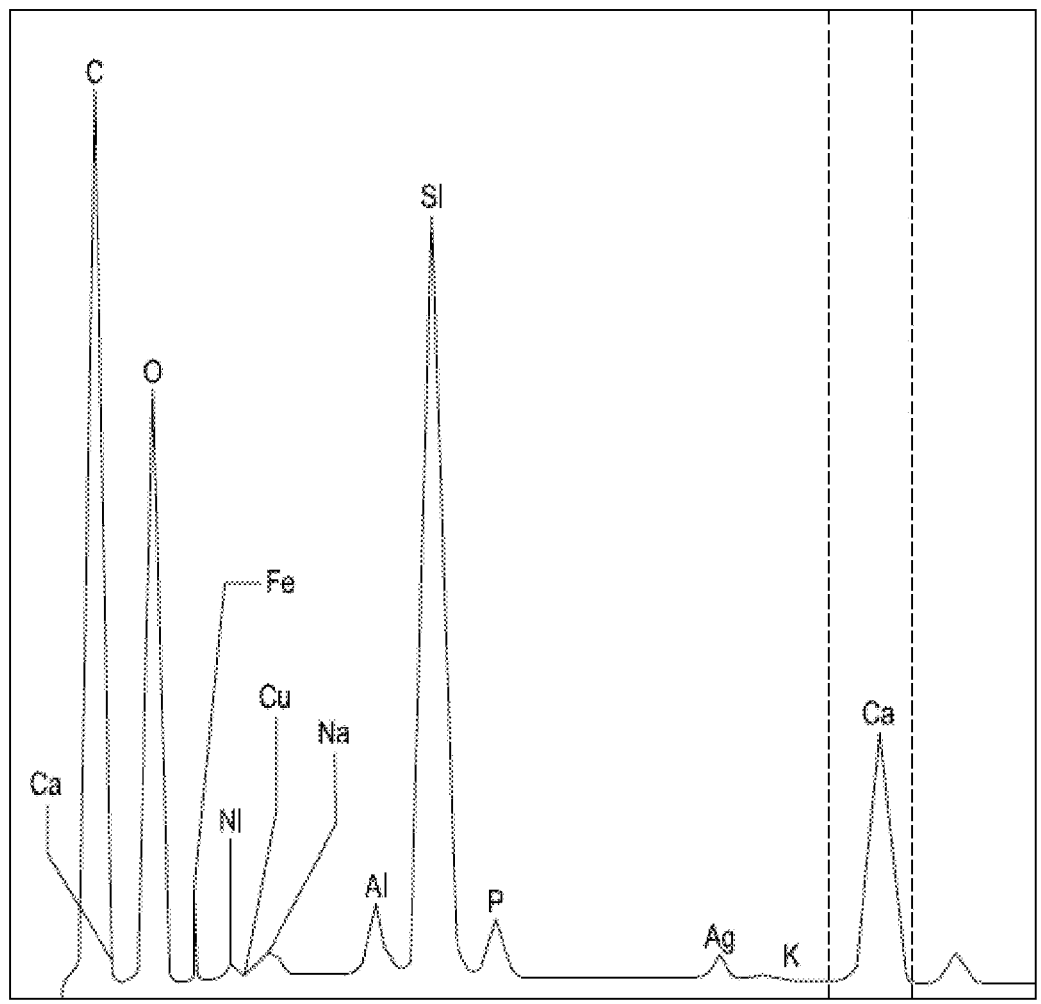
Figure 17D:
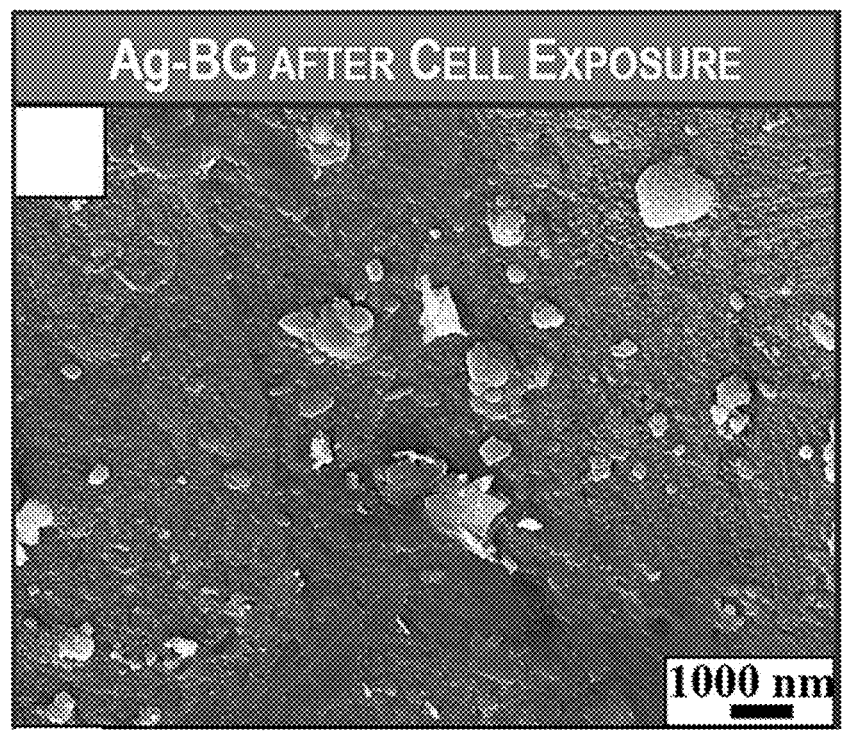
Figure 17E:
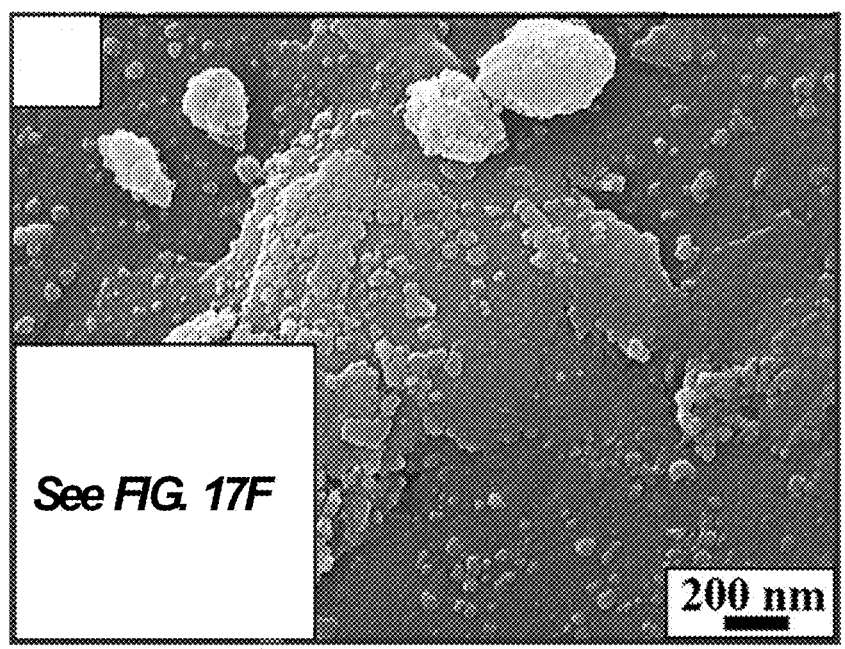
Figure 17F:
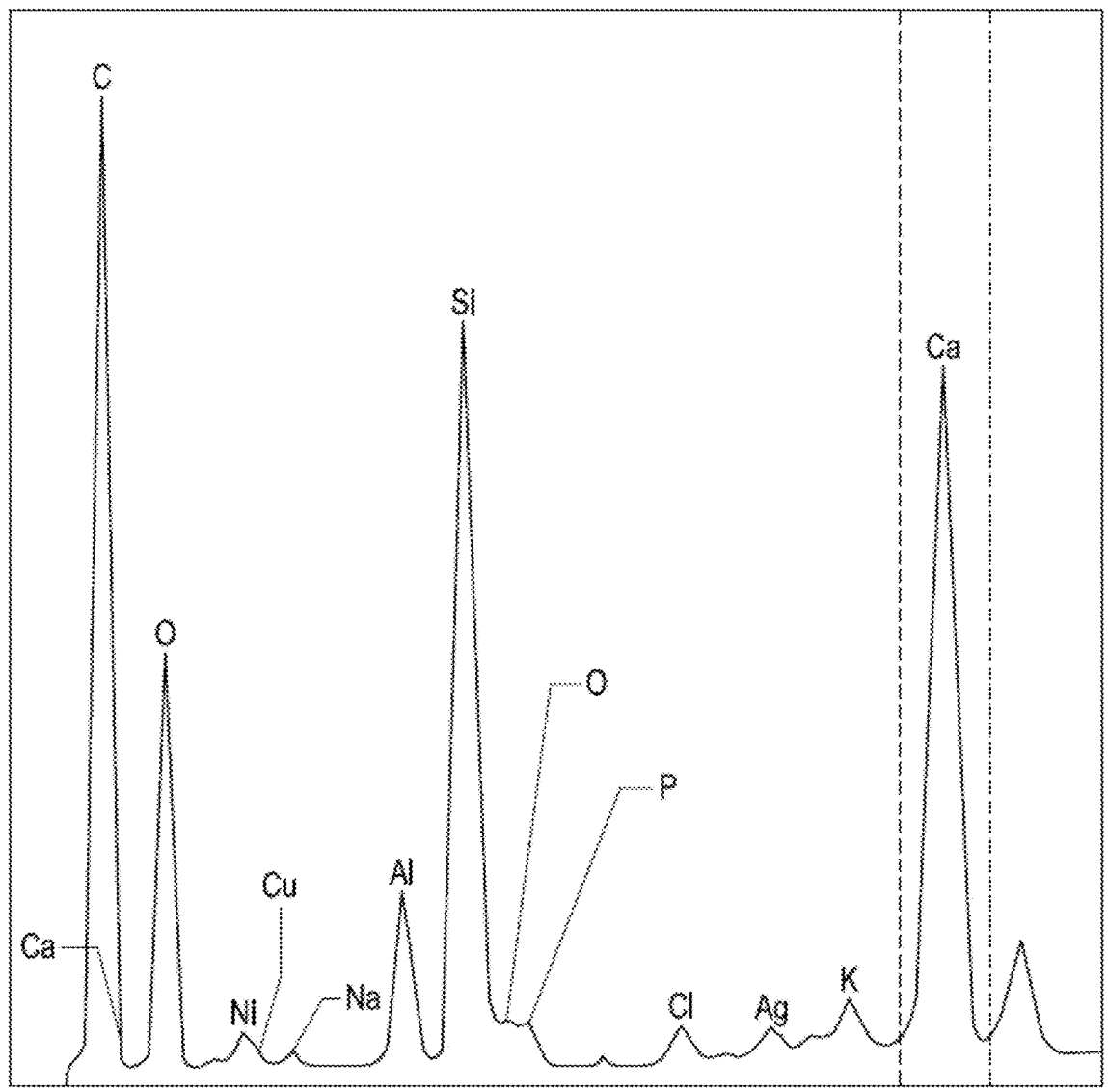
Figure 17G:
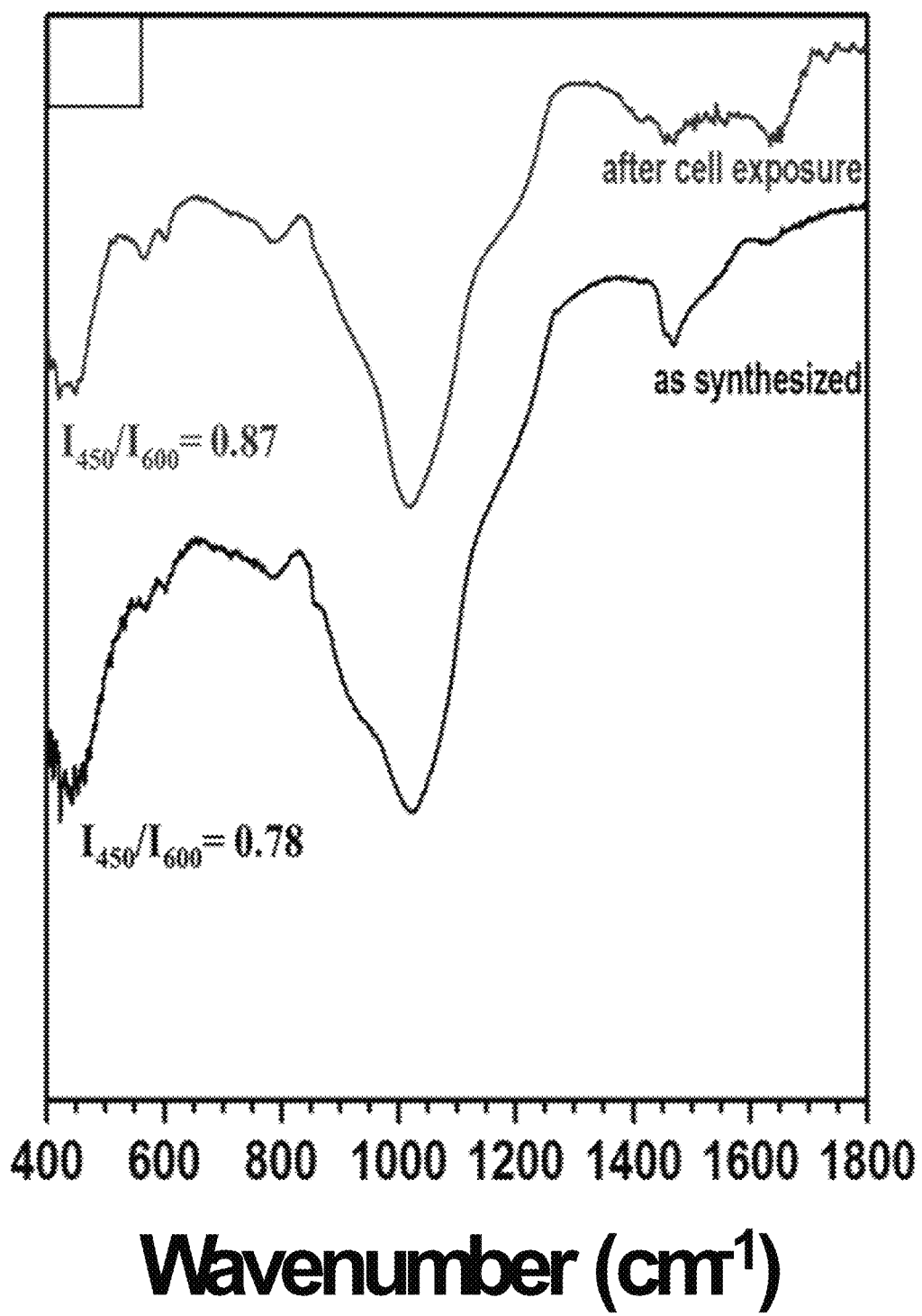

FIGS. 17A-17G show apatite forming ability of Ag-BG. The surface of the microparticles as-synthesized are shown in FIGS. 17A-17C and after 10 days in cell culture are shown in FIGS. 17D-17F. EDS spectra of Ag-BG surface as-synthesized and after cell-culture appear as inserts in FIGS. 17C and 17F, respectively. FTIR spectra of Ag-BG particles before (bottom line) and after (top line) exposure to cells are shown in FIG. 17G.

Figure 18A:
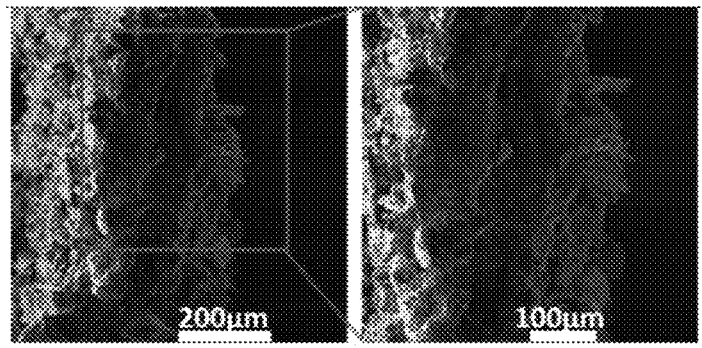
Figure 18B:
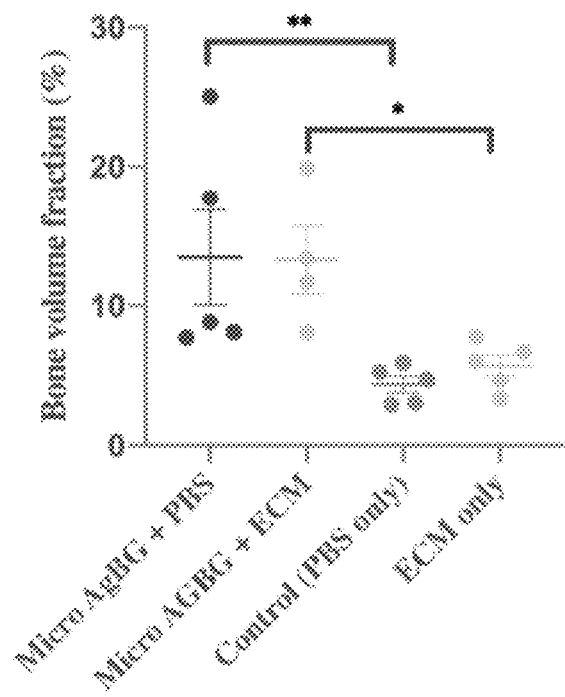
Figure 18C:
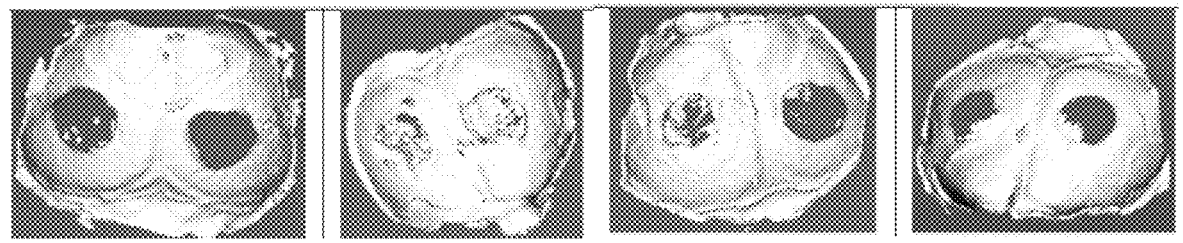

FIGS. 18A-18C show bone regeneration results. FIG. 18A shows SEM images from the cross-section of representative collagen sponge loaded with Ag-BG particles. FIG. 18B shows the bone volume fraction of the new bone being formed in the defects under different treatments, as calculated by microCT analysis. Representative microCT images are shown in FIG. 18C (from left to right, PBS only, Ag-BG+PBS, Ag-BG+ECM and ECM only). Histology images for defects treated with (1) collagen sponges alone, (2) sponge loaded with Ag-BG particles in PBS, (3) sponge loaded with Ag-BG particles in ECM, and (4) sponge loaded with ECM alone.

Figure 19A:
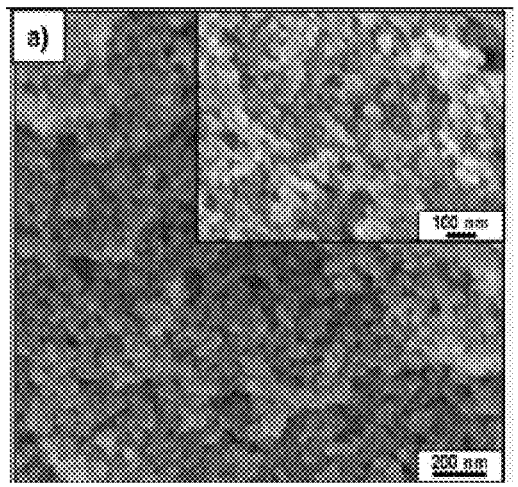
Figure 19B:
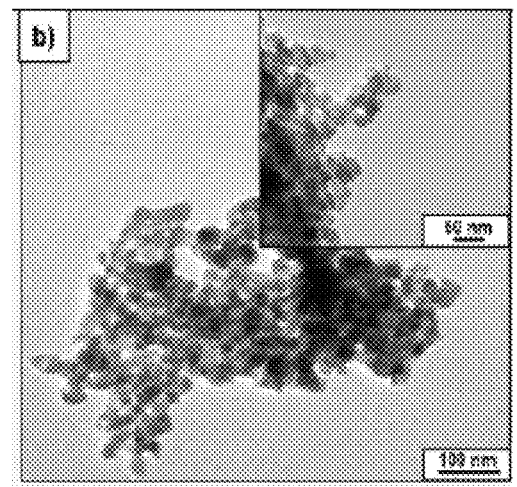
Figure 19C:
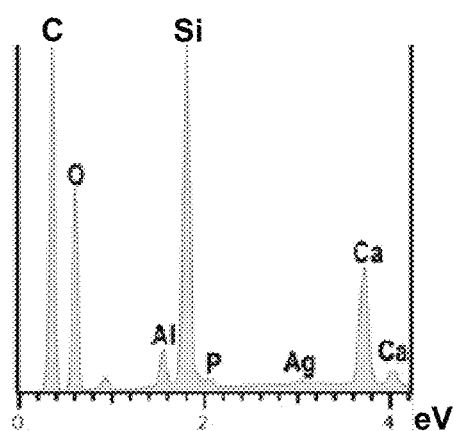

FIGS. 19A-19C show morphology, size, and dispersity by SEM (FIG. 19A) and TEM (FIG. 19B) and elemental analysis by SEM-EDS spectra (FIG. 19C).

Figure 20A:
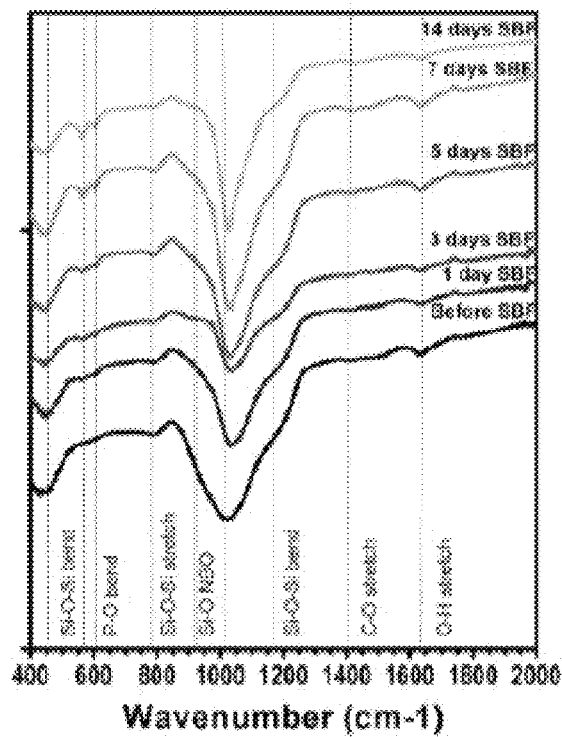
Figure 20B:
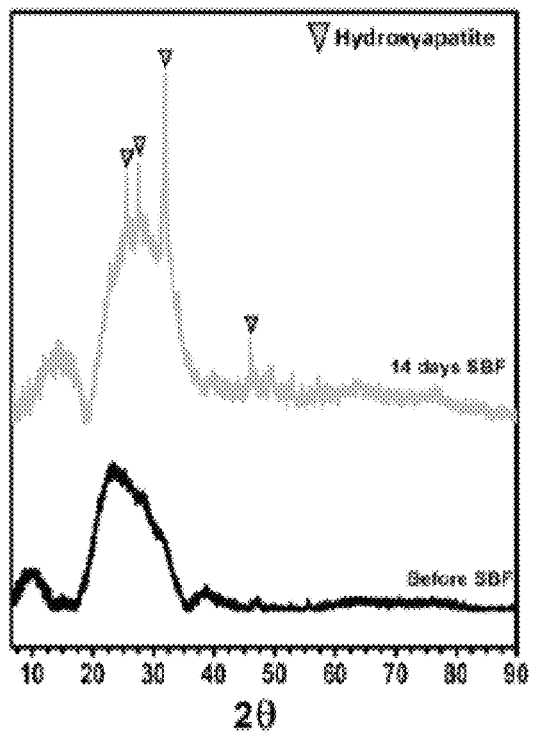

FIGS. 20A-20B show a structural evolution of Ag-BGN after apatite deposition by FIR-ATR (FIG. 20A) and XRD (FIG. 20B).

Figure 21A:
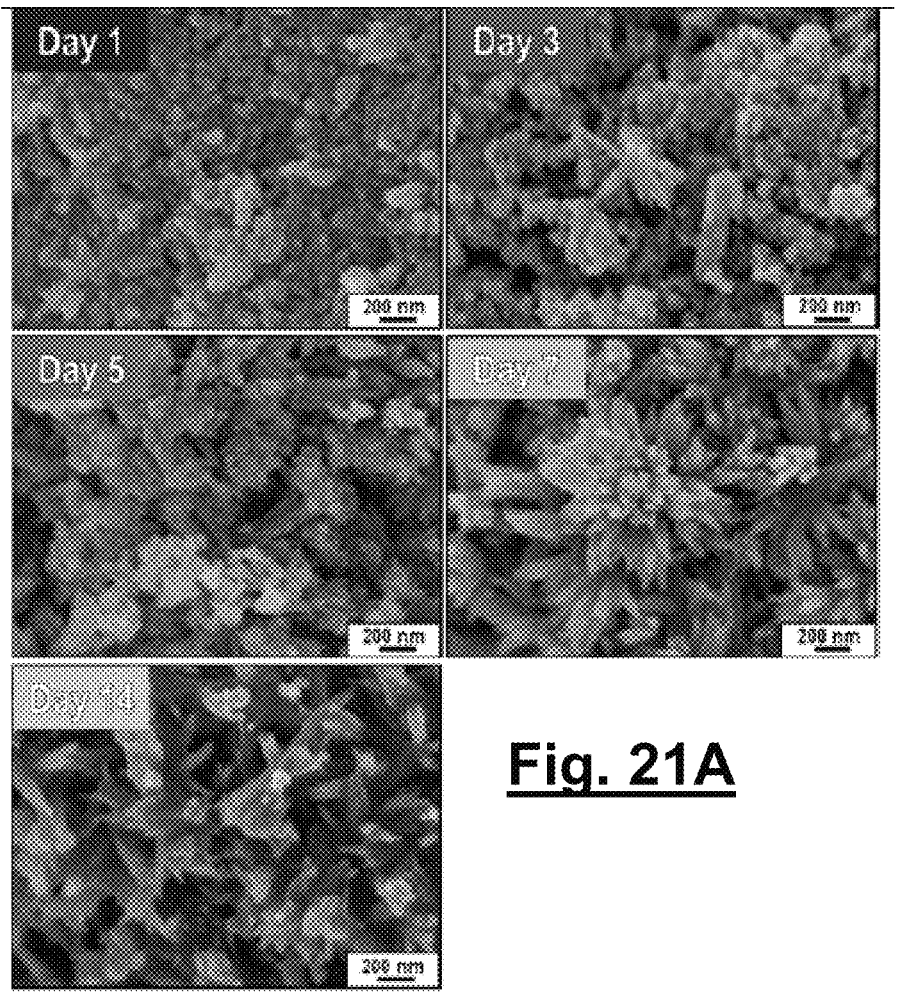
Figure 21B:
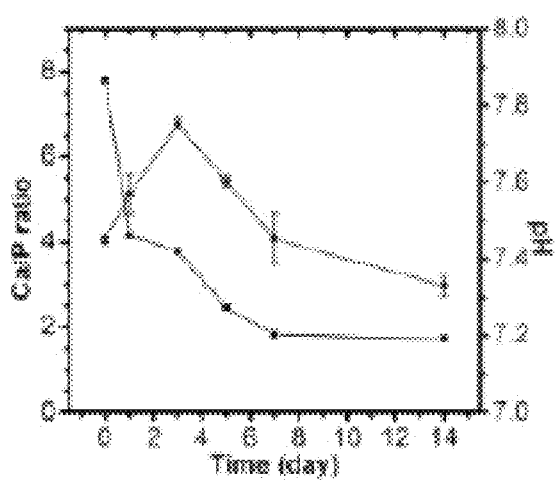

FIGS. 21A-21B show a morphological progress of Ag-BGN due to apatite deposition is shown by SEM (FIG. 21A) and a ratio of Ca/P from SEM-EDS and pH evolution in SBF (FIG. 21B).

Figure 22A:
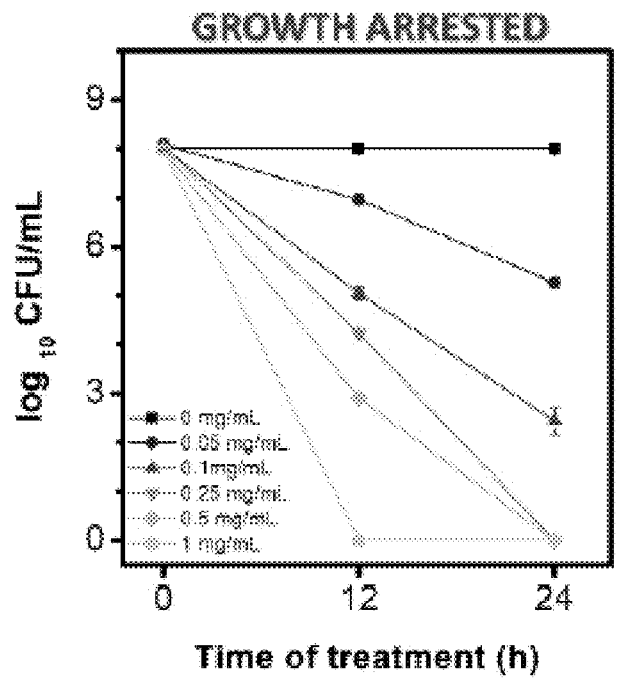
Figure 22B:
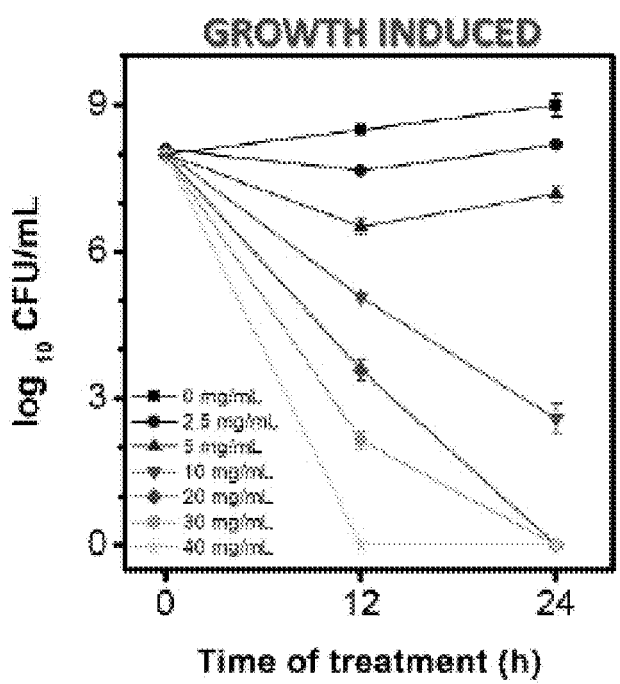

FIGS. 22A-22B show MRSA inhibition after Ag-BGN treatment under growth arrested conditions in PBS (FIG. 22A) and growth induce conditions in TSB (FIG. 22B).

Figure 23:
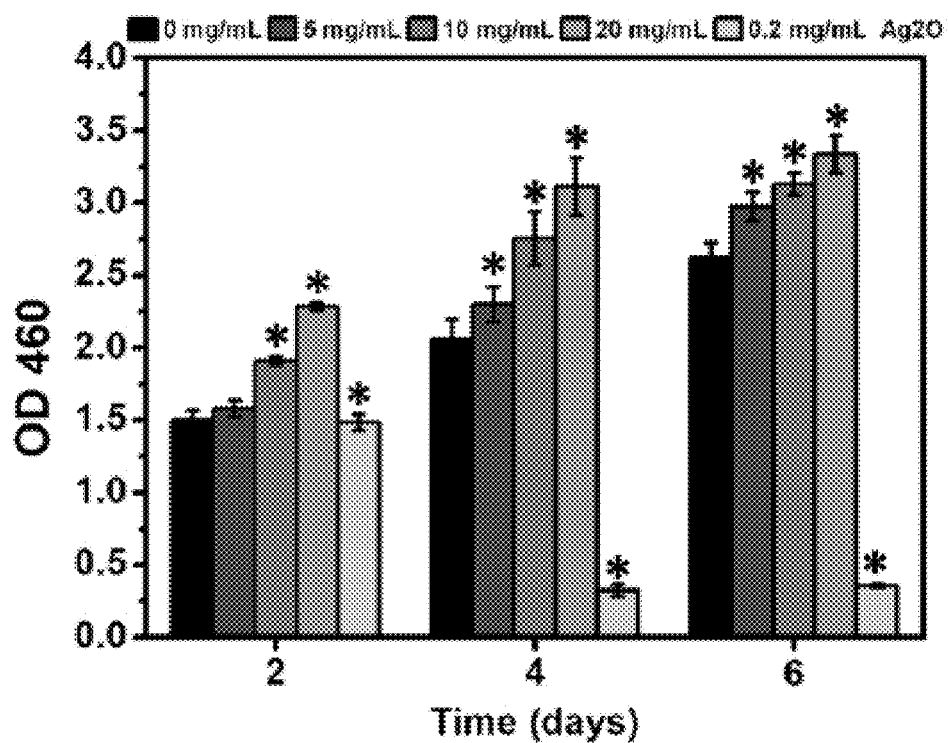

FIG. 23 shows cell viability of human mesenchymal stem cells when co-cultured with different concentrations of Ag-BGN. Significant difference (p<0.05) between untreated (0 mg/mL) and Ag-BGN treated cell at each time point. The bars in each group of five bars sequentially represent (from left to right) 0 mg/mL, 5 mg/mL, 10 mg/mL, 20 mg/mL, and 0.2 mg/mL $Ag_2O$.

Figure 24A:
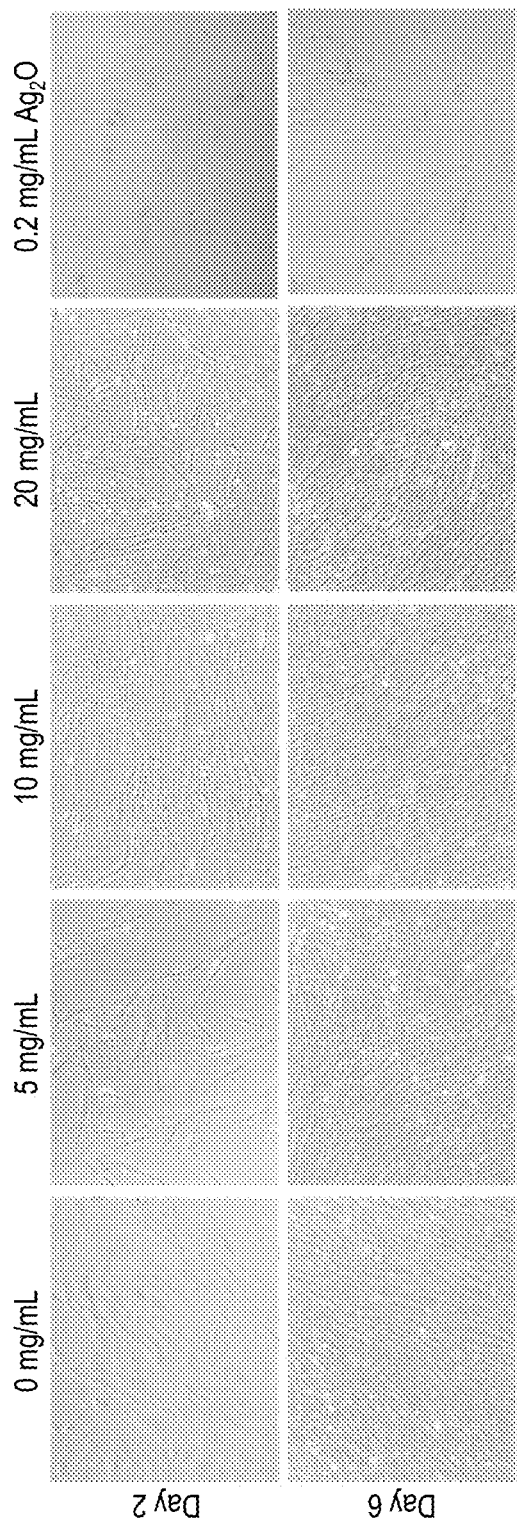
Figure 24B:
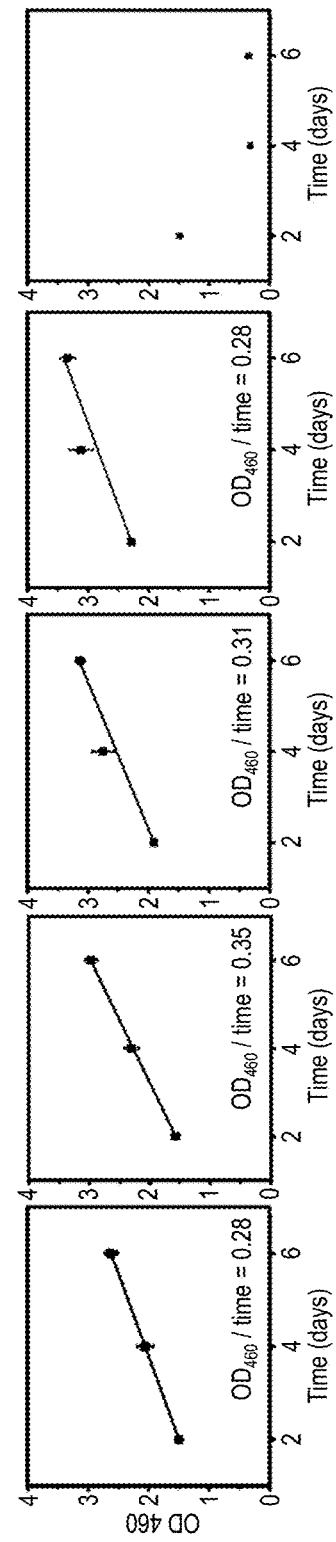

FIGS. 24A-24B show a morphology of human mesenchymal stem cells when co-cultured with different concentrations of Ag-BGN (FIG. 24A) and their proliferation rate according to CCK-8 results (FIG. 24B).

FIG. 25 shows a heat treatment profile for method of fabricating Ag-BG scaffolds.

FIGS. 26A-26F show optical images of a fracture surface of an exemplary Ag-BG scaffold at 100× (FIGS. 26A-26B), 300× (FIG. 26C), and 500× (FIG. 26D) and back-scattered SEM images of the fracture surface of an Ag-BG scaffold at low magnification (FIG. 26E) and high magnification (FIG. 26F).

Figure 27:
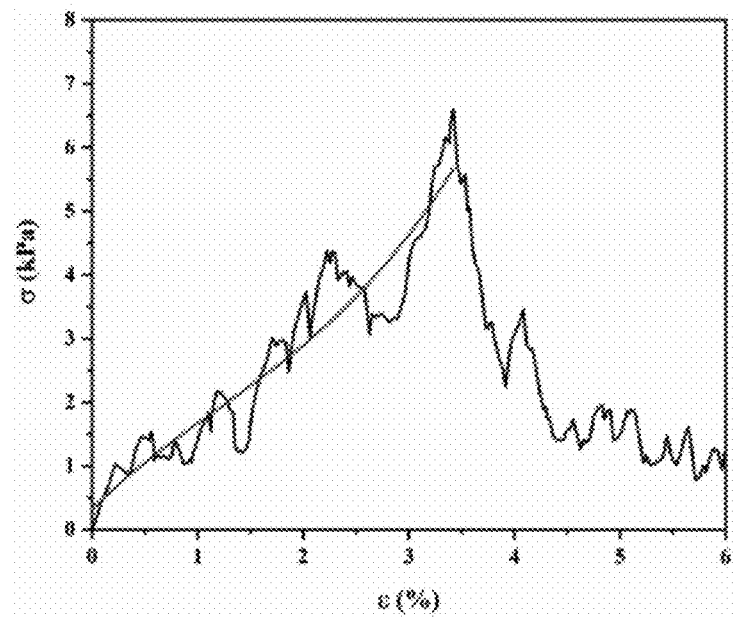

FIG. 27 is a stress-strain curve of an exemplary Ag-BG scaffold representative of the compressive strength of the Ag-BG scaffolds (the line is a guide to the eye).

Figure 28:
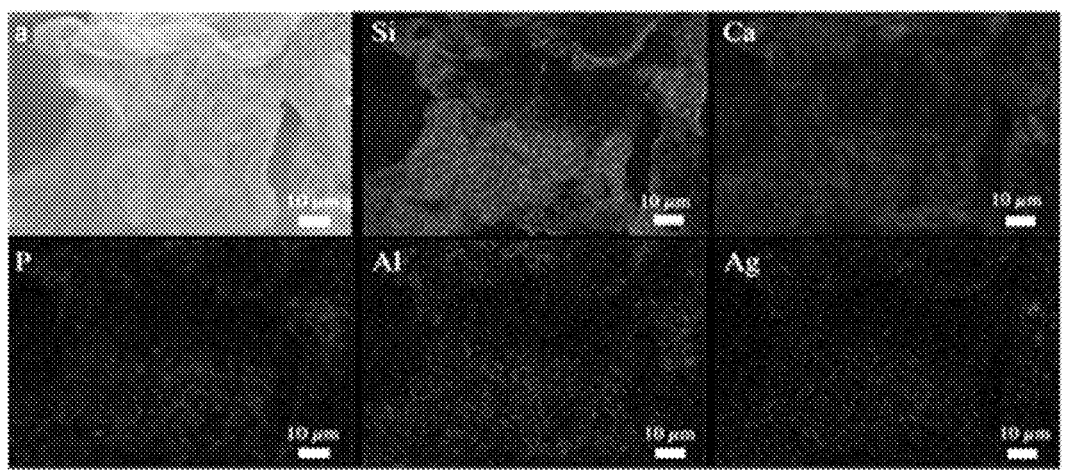

FIG. 28 is a representative secondary electron image and corresponding EDS x-ray maps of a fracture surface of an Ag-BG scaffold.

FIGS. 29A-29C show high-resolution back-scattered electron images of a fracture surface of an exemplary Ag-BG scaffold at 3700× low magnification (FIG. 29A) and 30,000× high magnification (FIG. 29B) and corresponding EDS x-ray maps of Ag of the Ag-BG scaffold fracture surface (FIG. 29C).

Figure 30:
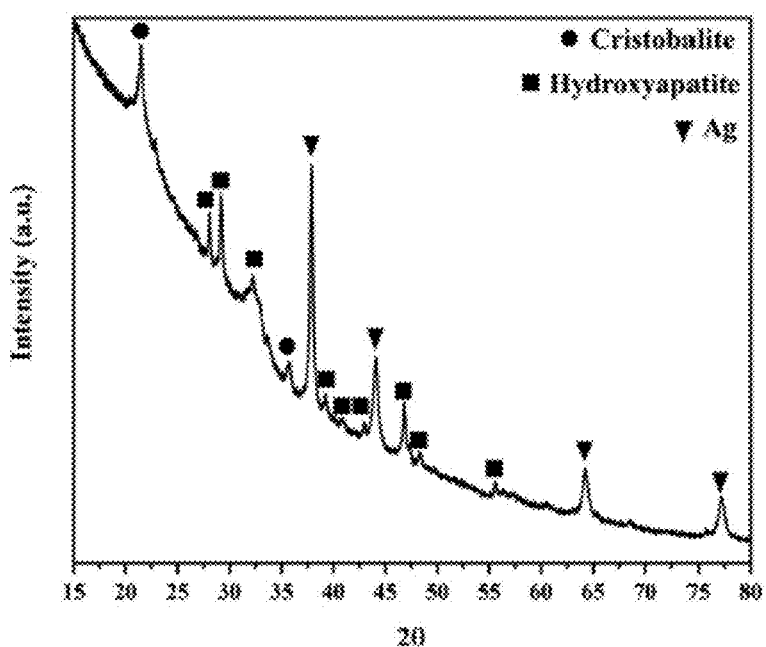

FIG. 30 is an XRD pattern of powdered exemplary Ag-BG scaffolds.

Figures 31A, 31B:
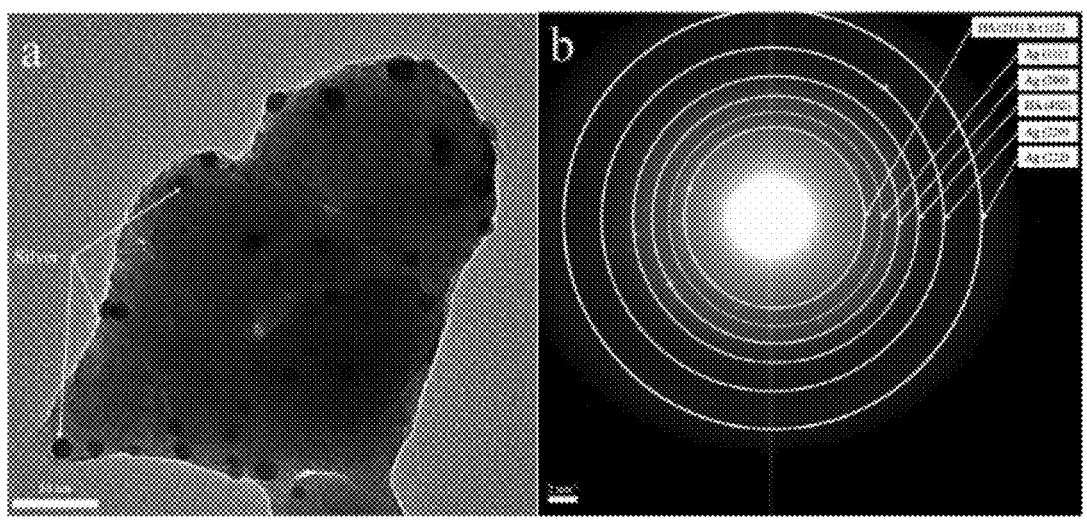

FIGS. 31A-31B provide a TEM bright field image (FIG. 31A) of an exemplary Ag-BG scaffold and a diffraction pattern (FIG. 31B) showing the microstructure at the nanoscale.

Figure 32:
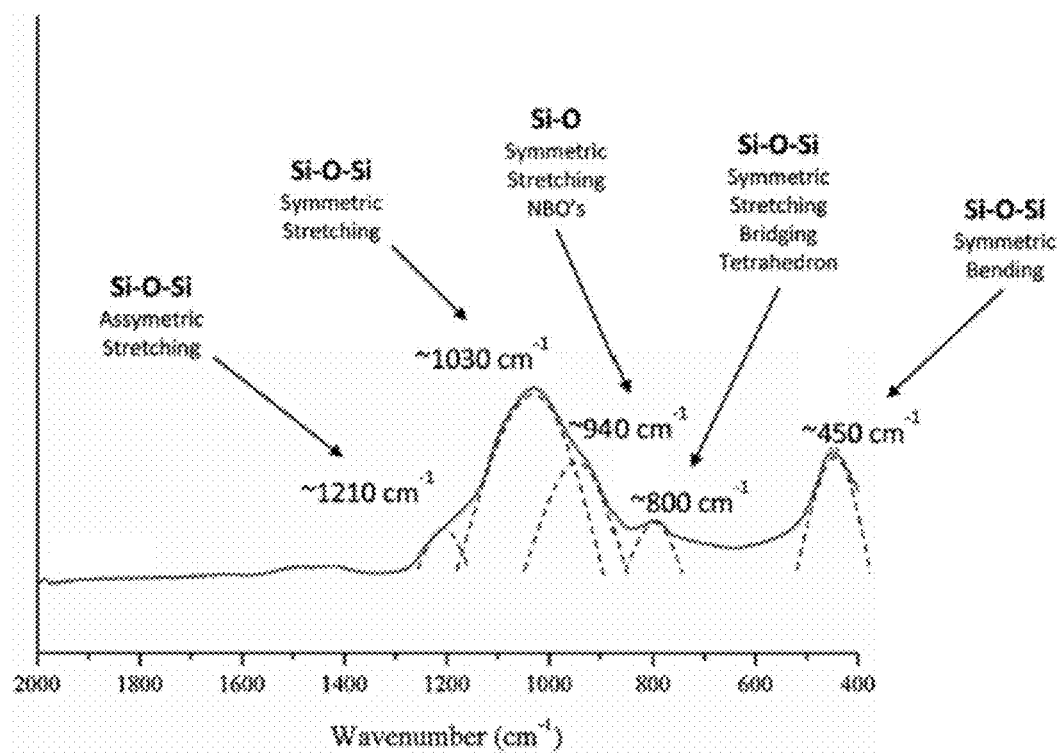

FIG. 32 shows FTIR spectra of exemplary powdered Ag-BG scaffolds, where dashed lines are shown to guide the eye for qualitative peak deconvolution.

Figure 33A:
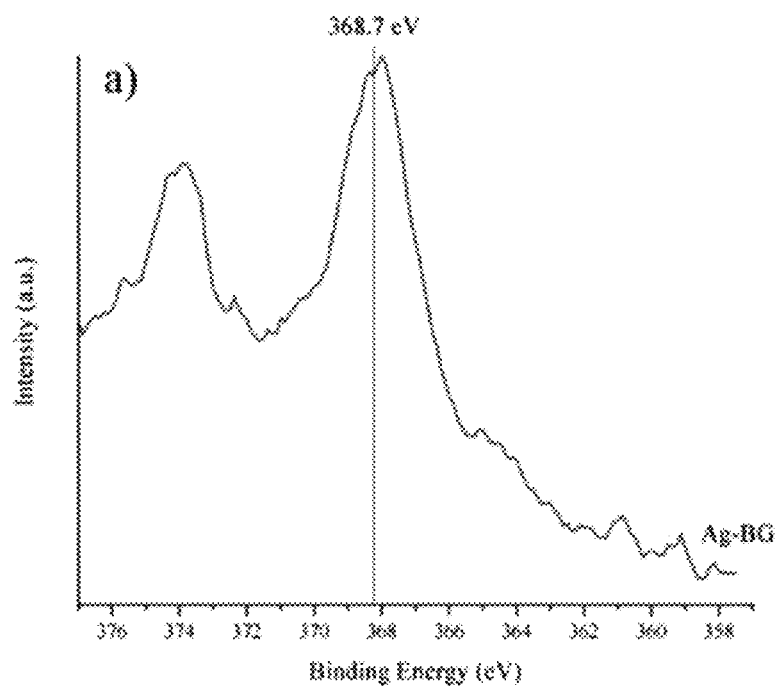
Figure 33B:
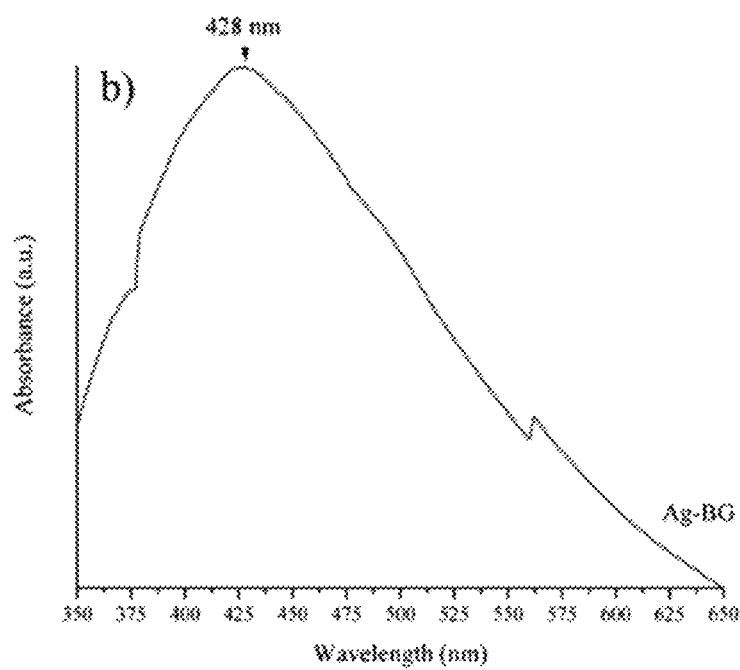

FIGS. 33A-33B show high-resolution XPS ($Ag_{3d}$) spectra of exemplary powdered Ag-BG scaffolds (FIG. 33A) and UV-VIS absorbance (FIG. 33B).

Figure 34A:
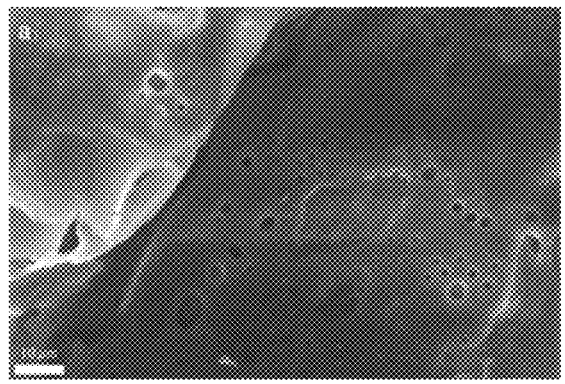
Figure 34B:
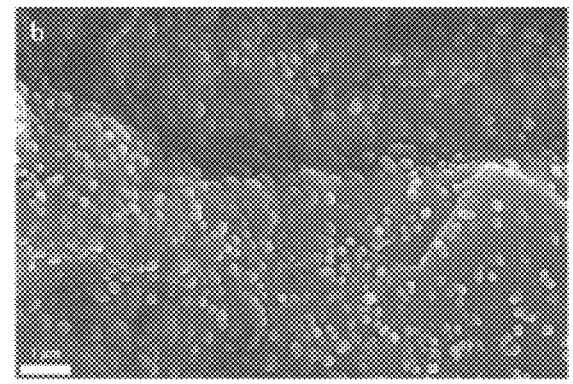
Figure 34C:
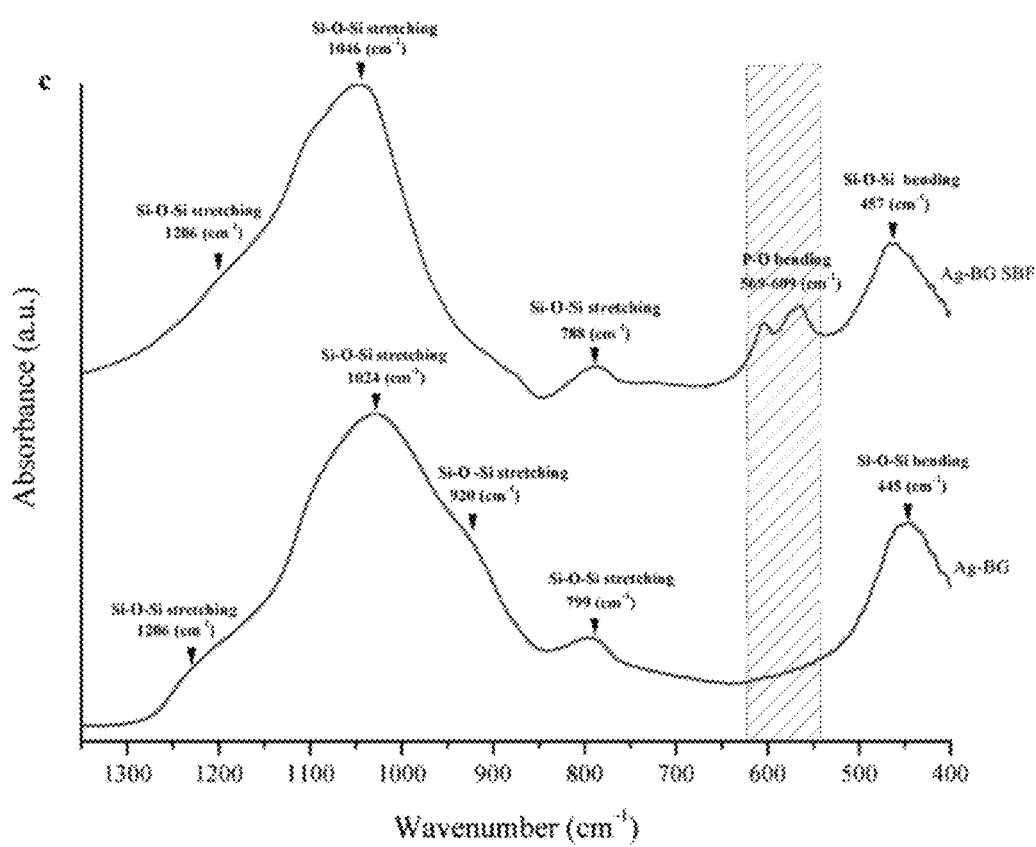

FIGS. 34A-34C show secondary electron images of a fracture surface of an exemplary Ag-BG scaffold prior to SBF immersion (FIG. 34A) and post SBF immersion for 14 days (FIG. 34B) and a FTIR spectra before (bottom line) and after (top line) the immersion in SBF (FIG. 34C).

Figures 35A, 35B:
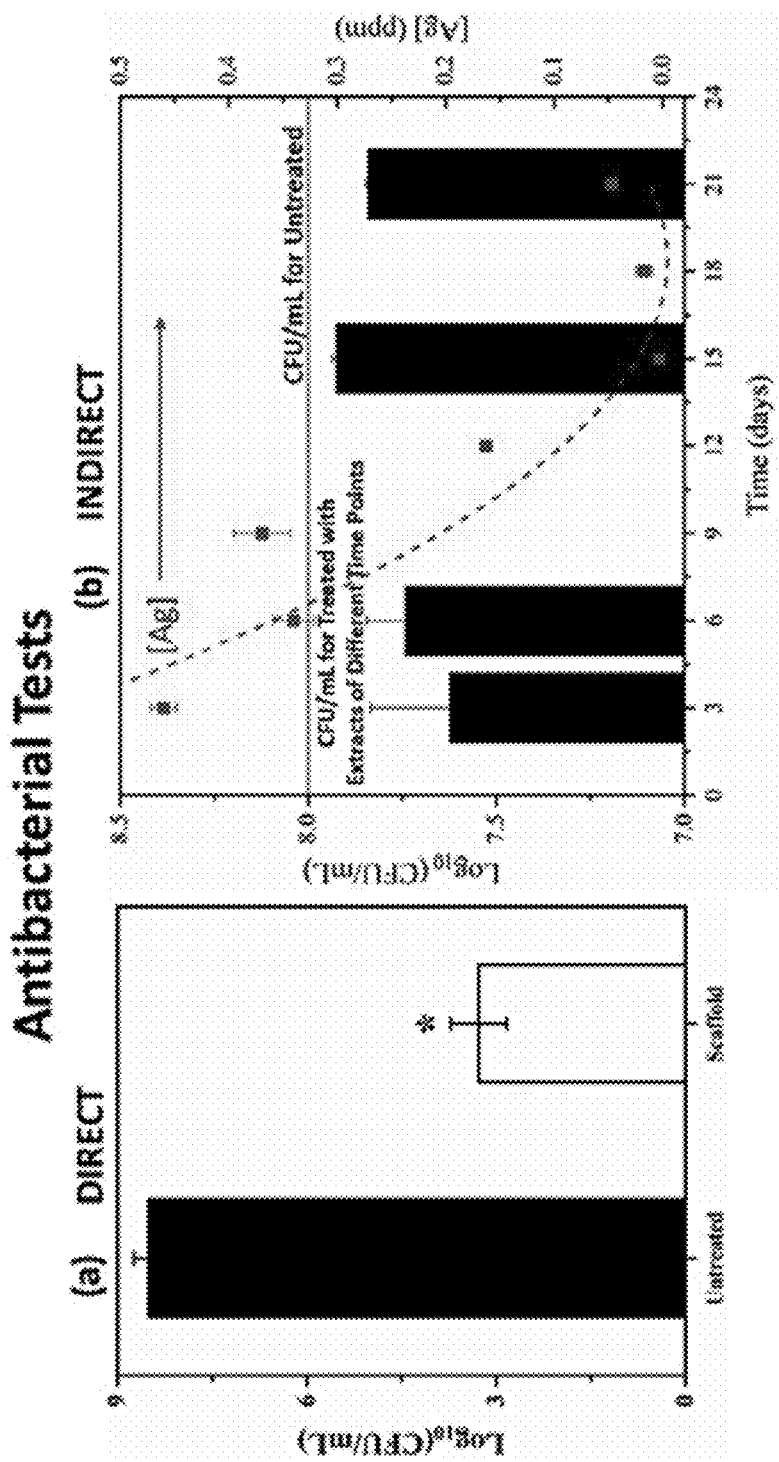

FIGS. 35A-35B show anti-MRSA characteristics of exemplary Ag-BG scaffolds under direct tests (FIG. 35A) and under indirect tests (FIG. 35B). The squares in FIG. 35B show the Ag concentration in extracts of the Ag-BG scaffolds that is decreased with time (where the slashed line is a guide to the eye).

Figure 36A:
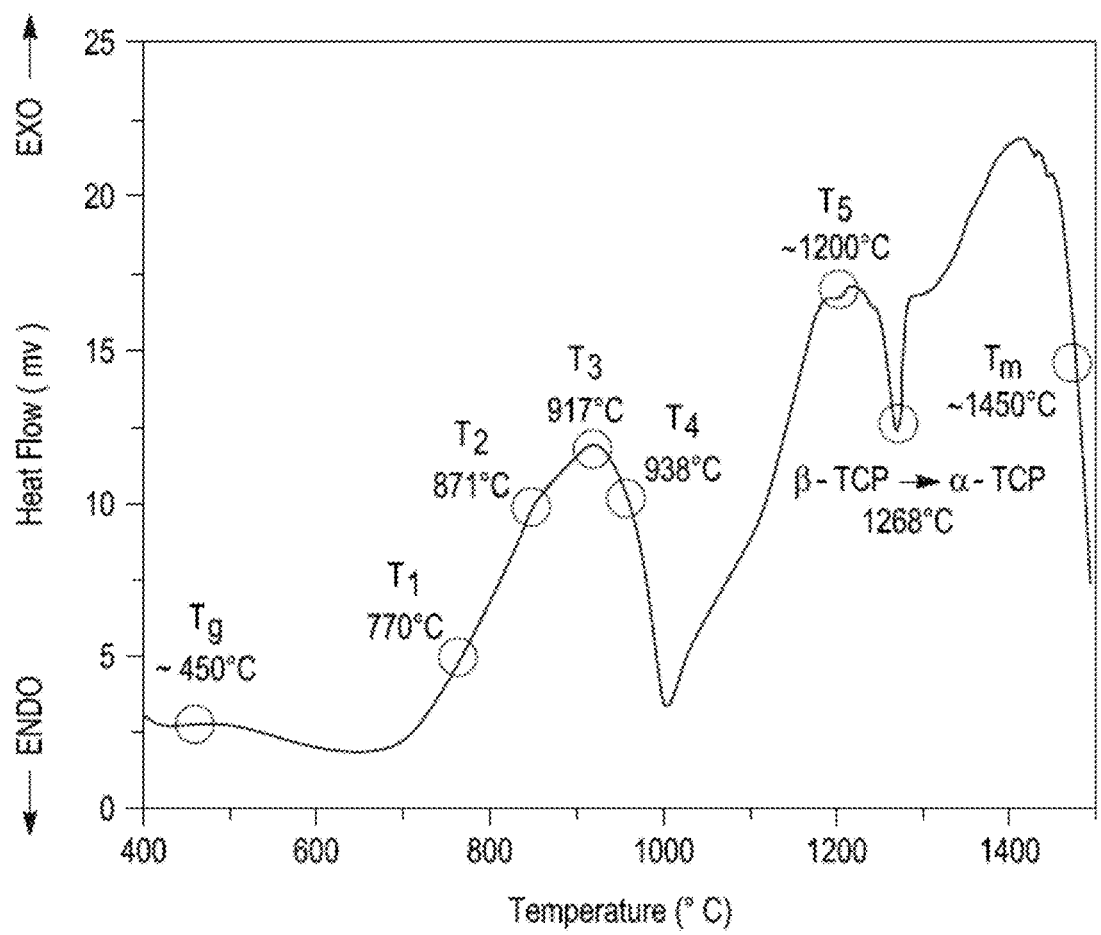
Figure 36B:
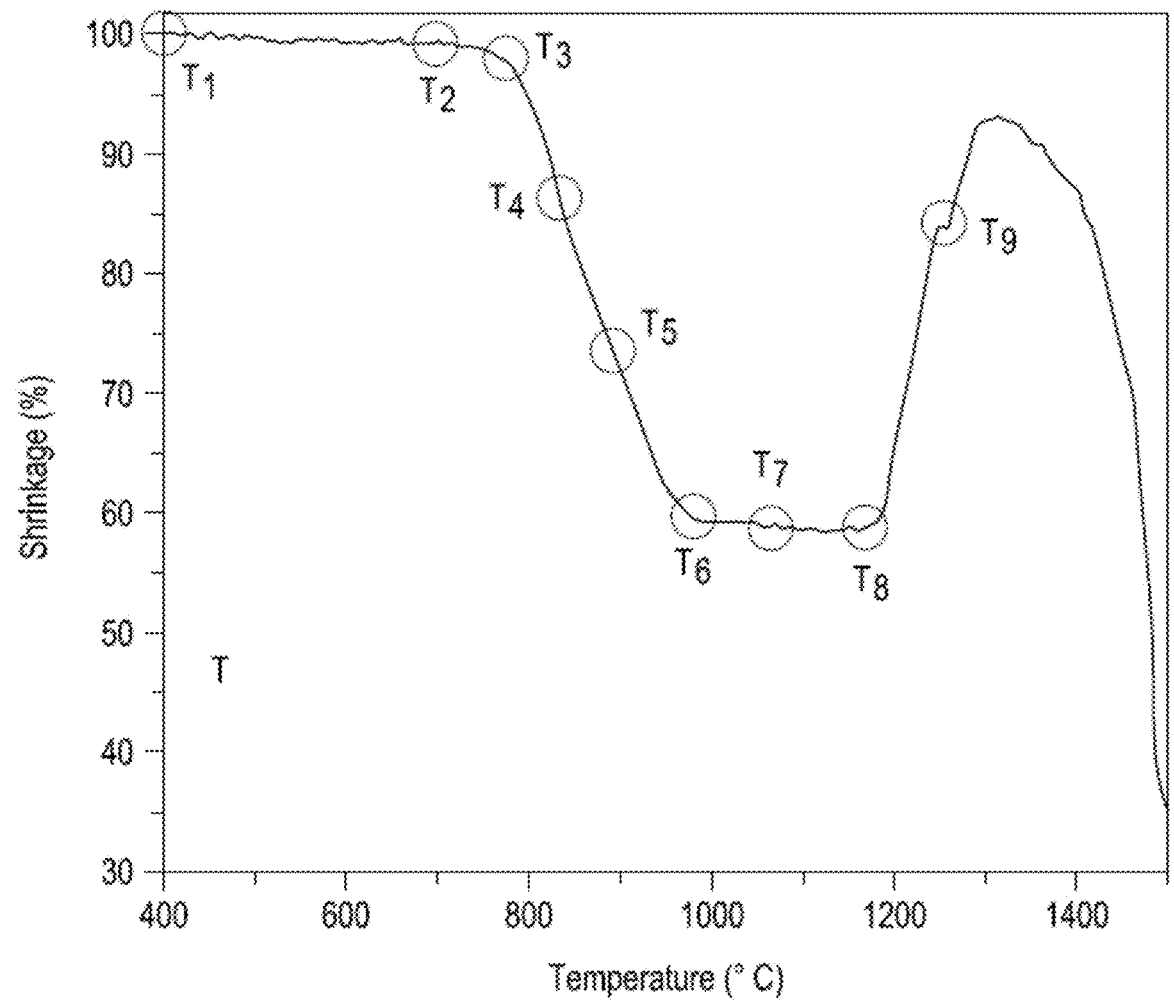
Figure 36C:
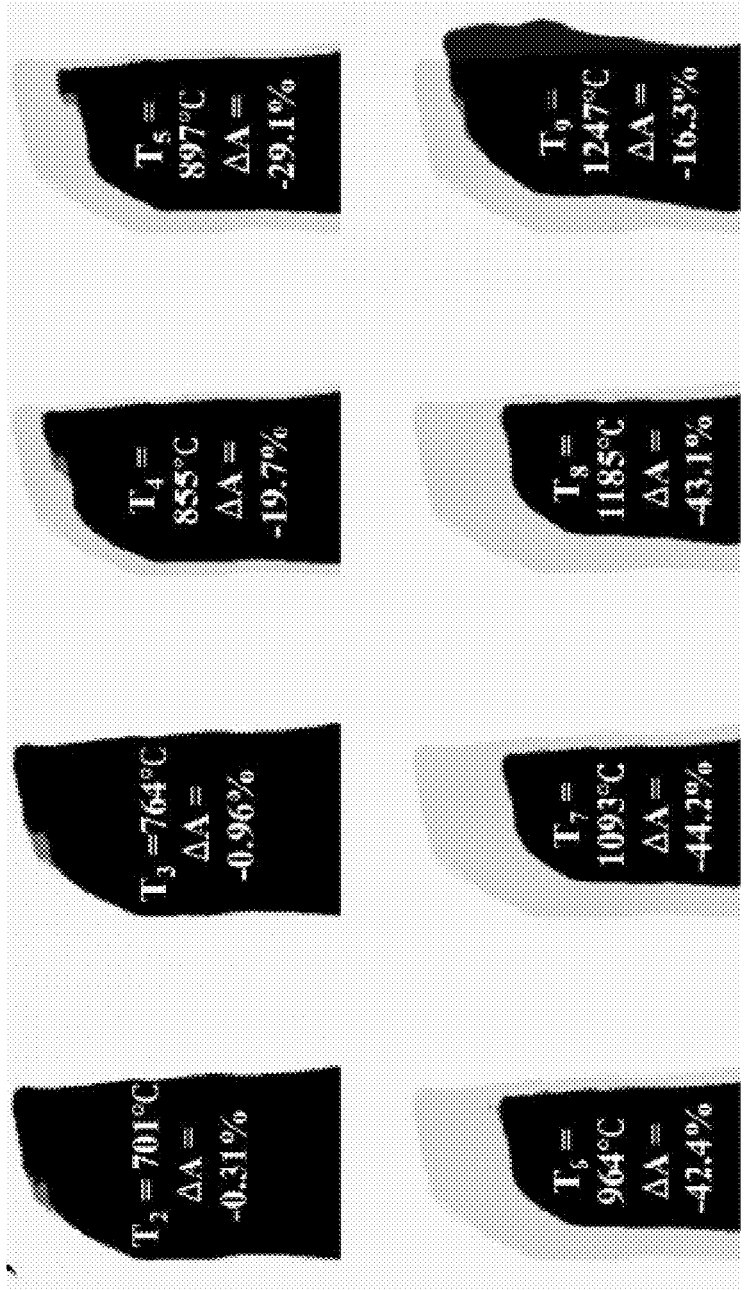

FIGS. 36A-36C provides a graph showing the DTA/TGA behavior of Ag-BG particles (FIG. 36A), a graph showing the shrinkage behavior of the Ag-BG particles as a function of temperature derived from HSM (FIG. 36B), and images of the Ag-BG at different temperatures during HSM (FIG. 36C).

FIGS. 37A-37H show a 900-SL optical image (FIG. 37A), SEM images (FIGS. 37B-37C), and a 3D reconstruction perspective (FIG. 37D) and a 1000-SL optical image (FIG. 37E), SEM images (FIGS. 37F-37G), and a 3D reconstruction perspective (FIG. 37H).

FIGS. 38A-38F show representative SEM images of the cross-section of a strut (FIGS. 38A-38B) and a micro-CT XY-plane image (FIG. 38C) for 910-SL and SEM images of the cross-section of a strut (FIGS. 38D-38E) and a micro-CT XY-plane image (FIG. 38F) for 1010-SL.

Figure 39:
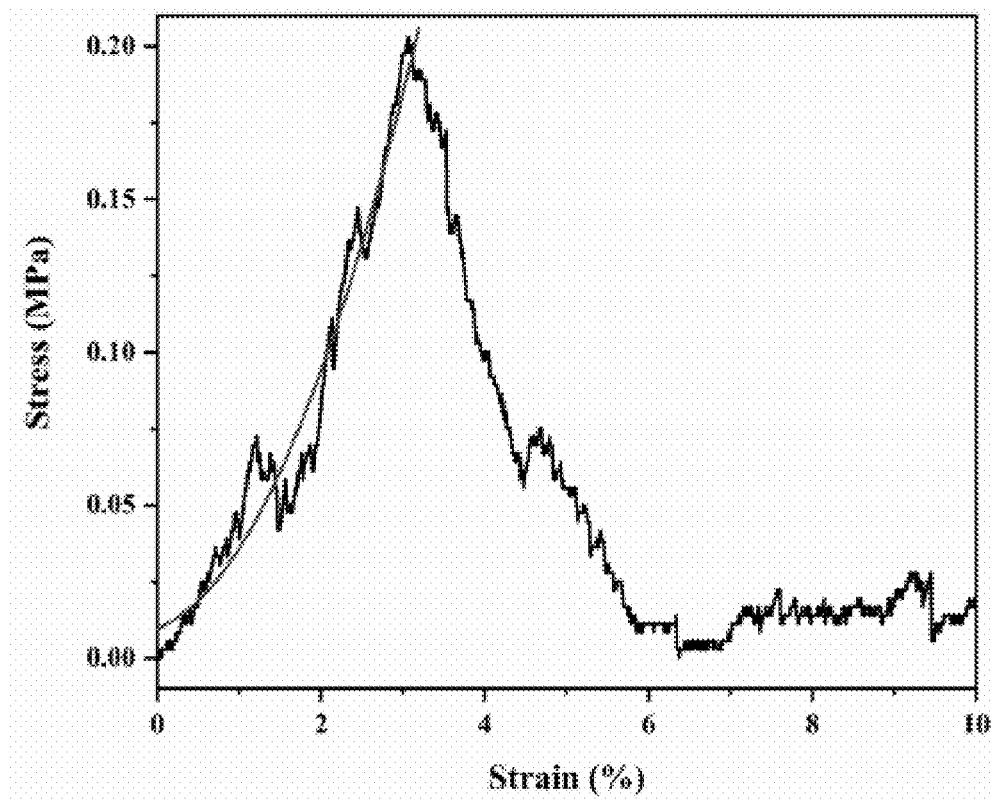

FIG. 39 shows a stress-strain curve of 1010-SL representative of the compressive strength (the smooth line is a guide to the eye).

FIGS. 40A-40D show XRD and FTIR-ATR spectra of all applied heat treatments for Ag-BG scaffolds in addition to the concentration of phases present for each distinct heat treatment as derived from Rietveld analysis.

Figure 41A:
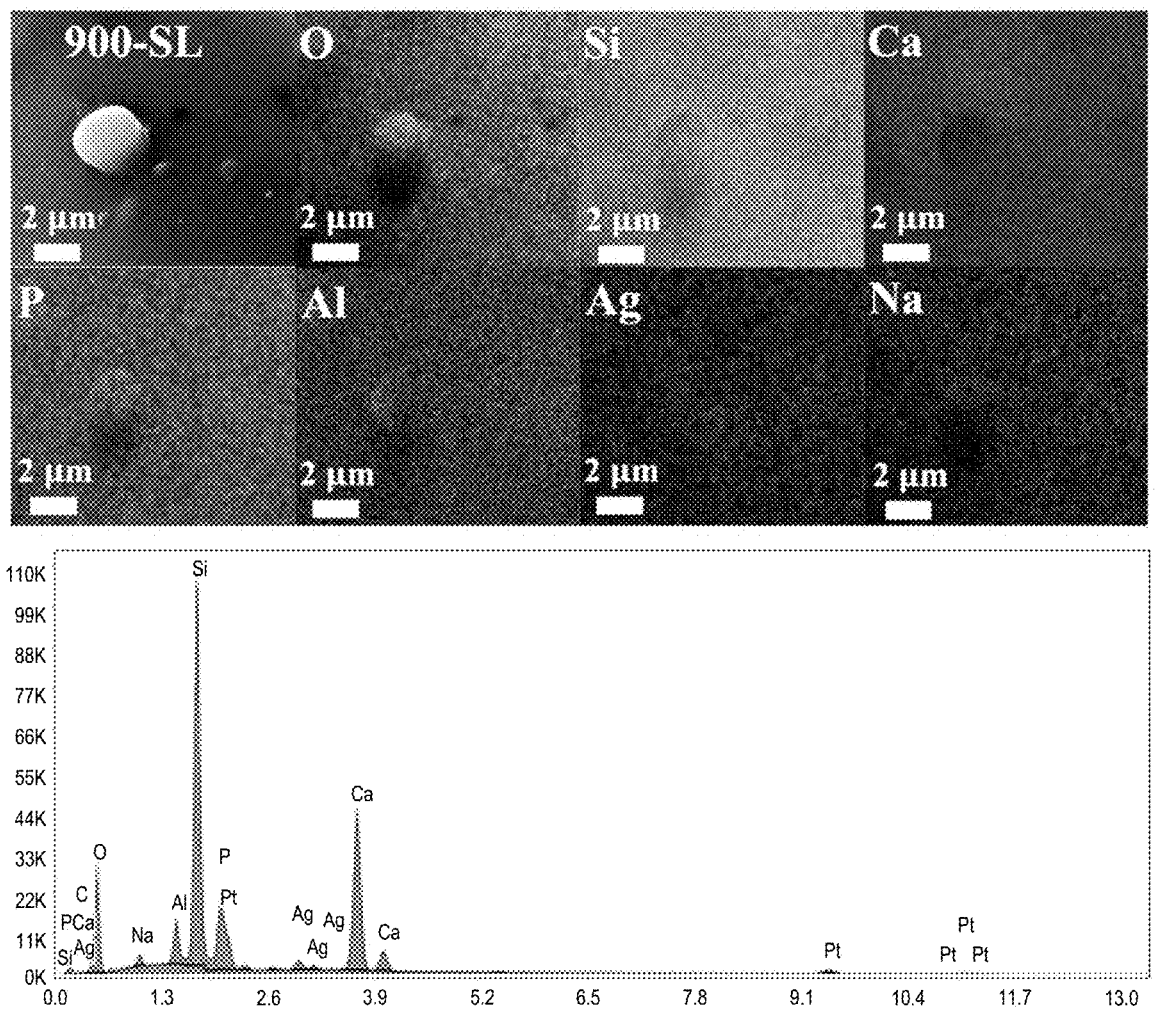
Figure 41B:
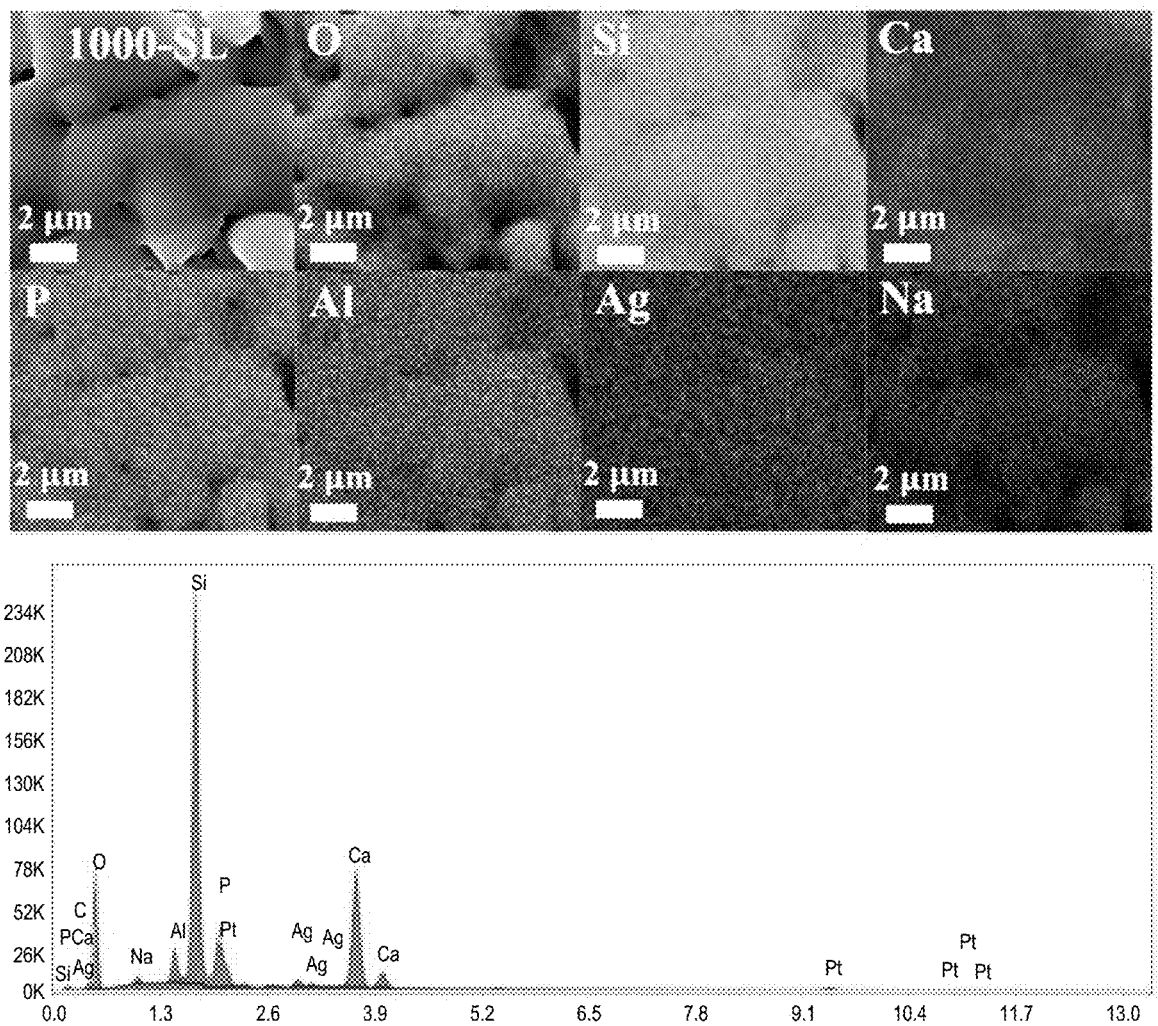

FIGS. 41A-41B provide representative EDS X-ray maps of 900-SL (FIG. 41A) and 1000-SL (FIG. 41B).

Figures 42A, 42B:
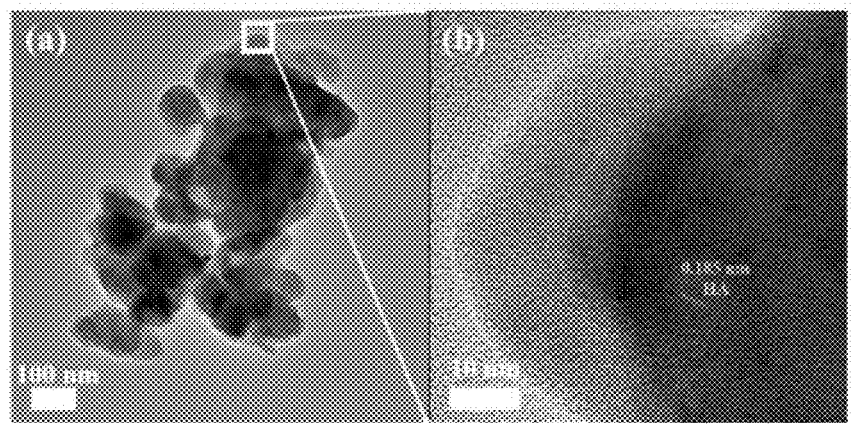
Figures 42C, 42D:
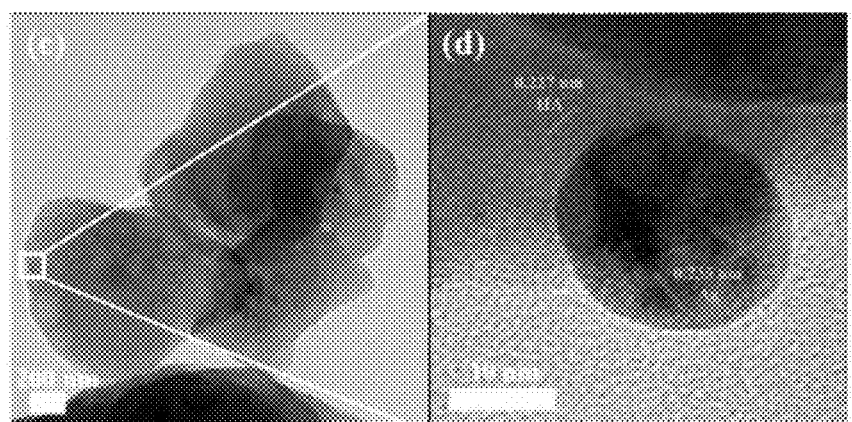
Figures 42E, 42F:
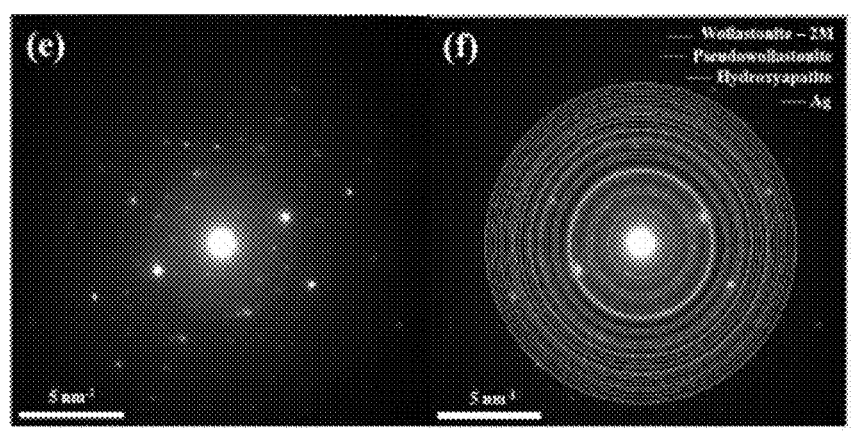

FIGS. 42A-42F show TEM micrographs of two different 1010-SL particles at low magnification (FIGS. 42A and 42C) and high magnification (FIGS. 42B and 42D) where lattice fringes are noticeable, a representative diffraction pattern of 1010-SL (FIG. 42E), and the attributed diffraction pattern where wollastonite-2M (orange), pseudowollastonite (blue), hydroxyapatite (green), and Ag (yellow) were identified (FIG. 42F).

Figure 43A:
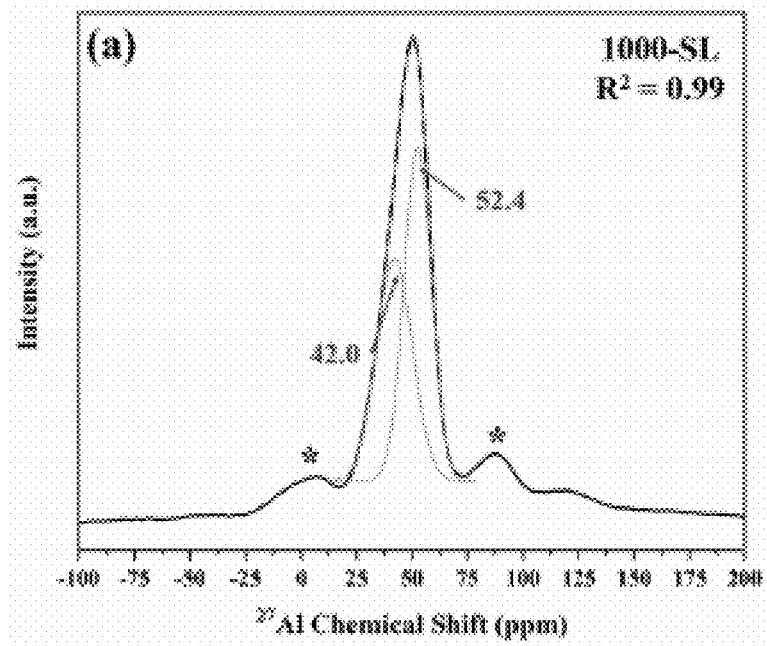
Figure 43B:
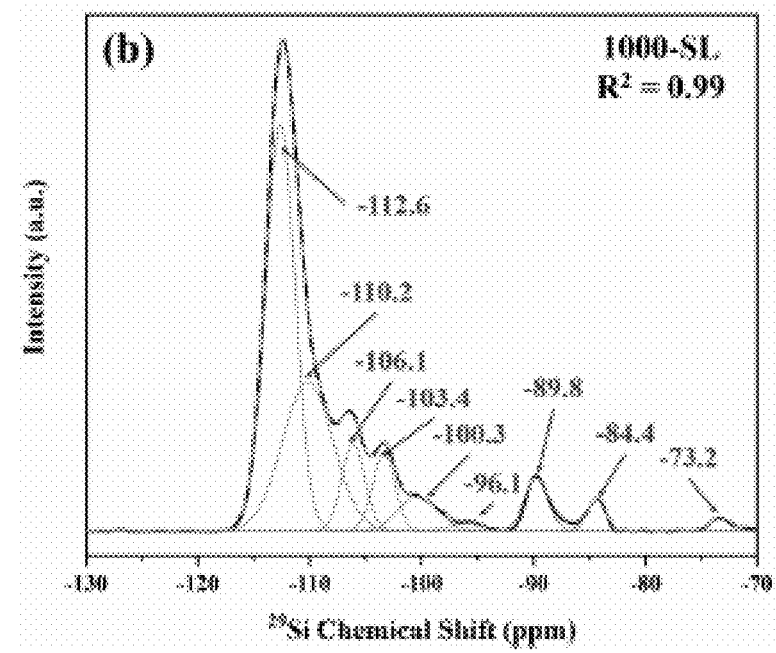

FIGS. 43A-43B show a $^{27}$Al NMR spectrum (FIG. 43A) and a $^{29}$Si spectrum (FIG. 43B) of 1000-SL where (*) denotes magic angle spinning sidebands (MASS) and the smooth curved line shows the cumulative fitting from peak deconvolution.

Figure 44A:
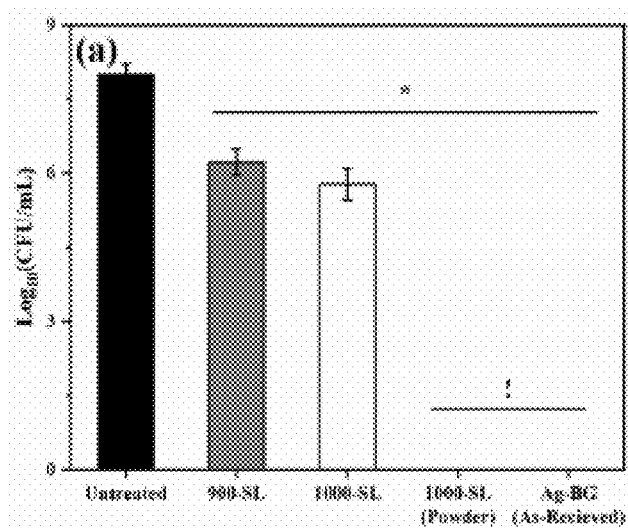
Figure 44B:
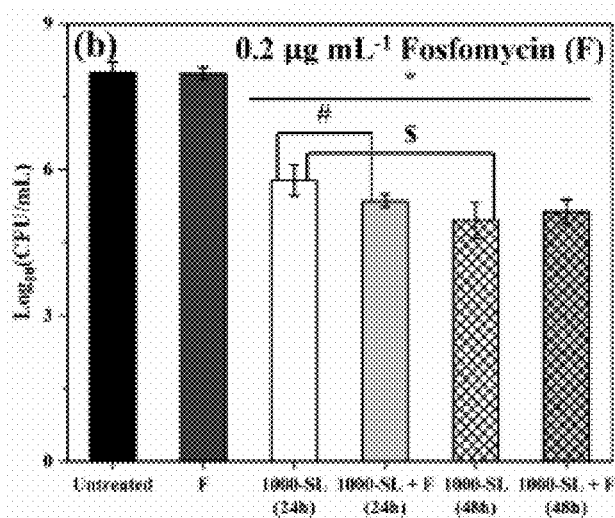
Figure 44C:
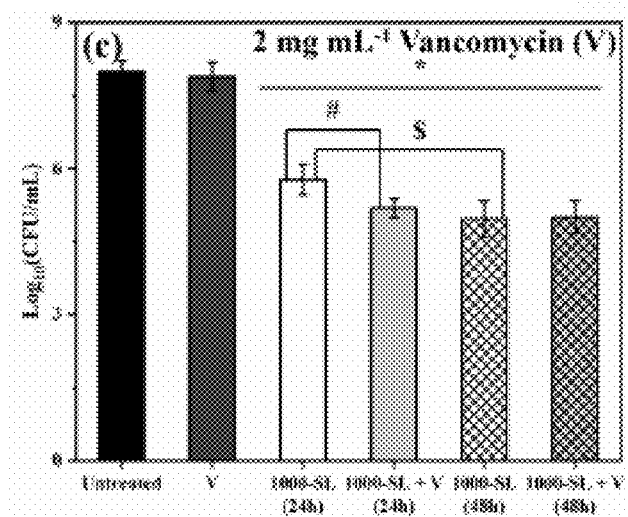

FIGS. 44A-44C show the anti-MRSA effect of the Ag-BG scaffolds, powderized 1000-SL, and Ag-BG as-received after 11 mg were exposed to planktonic MRSA for 24 hours (FIG. 44A); the anti-MRSA effect of 1000-SL alone and in combination with 0.2 μg mL$^{-1}$ of Fosfomycin (F) after 24 and 48 hours of exposure (FIG. 44B); and the anti-MRSA effect of 1000-SL alone and in combination with 2 mg mL-1 of vancomycin (V) (FIG. 44C), where (*) indicates p<0.05 against the untreated and antibiotic controls, (!) represents p<0.05 of powderized 1000-SL and Ag-BG as-received against 900-SL and 1000-SL, (#) denotes p<0.05 of the Ag-BG scaffold antibiotic combination against the Ag-BG scaffold alone after 24 hours of MRSA exposure, and ($) indicates p<0.05 of the anti-MRSA response of the Ag-BG scaffolds after 48 hours of exposure against 24 hours of exposure.

Figure 45A:
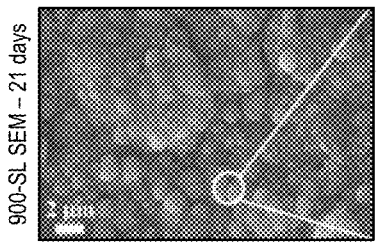
Figure 45B:
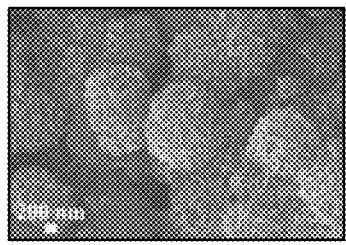
Figure 45C:
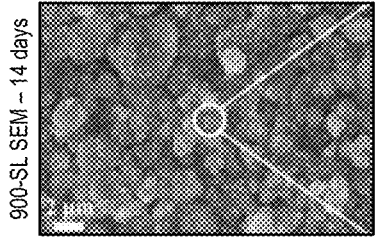
Figure 45D:
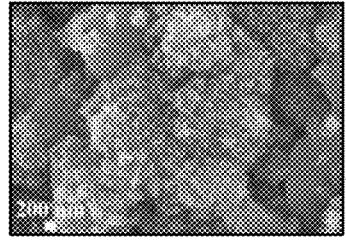
Figure 45E:
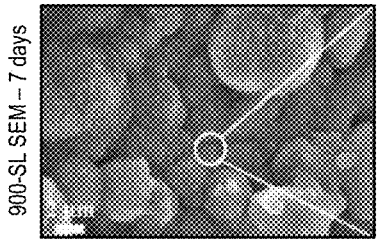
Figure 45F:
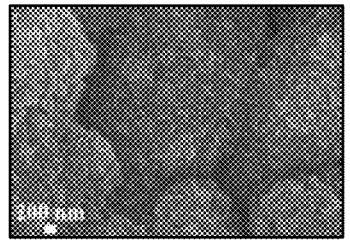

FIGS. 45A-45V show representative SEM images of 910-SL after soaking in SBF for 21 days (FIGS. 45A-45B), 14 days (FIGS. 45C-45D), and 7 days (FIGS. 45E-45F); respective FTIR-ATR spectra and XRD patterns for 910-SL after immersion in SBF (FIGS. 45A-45B, respectively); FTIR-ATR spectra of 1010-SL after immersion in SBF for 1, 3, 5, 7, 14, and 21 days (FIGS. 45I-45J); and SEM images representative of the surface morphology for 1010-SL after soaking in SBF for 21 days (FIGS. 45K-45L), 14 days (FIGS. 45M-45N), 7 days (FIGS. 45O-45P), 5 days (FIGS. 45Q-45R), 3 days (FIGS. 45S-45T), and 1 day (FIGS. 45U-45V).

Figure 46A:
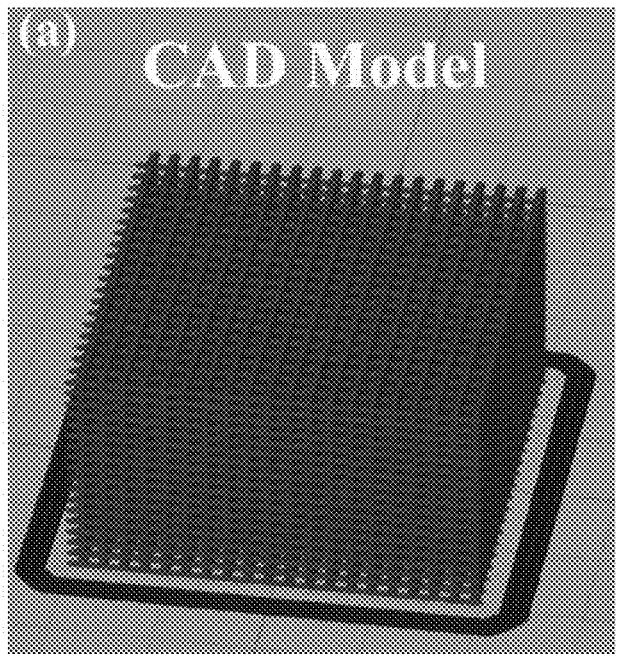
Figure 46B:
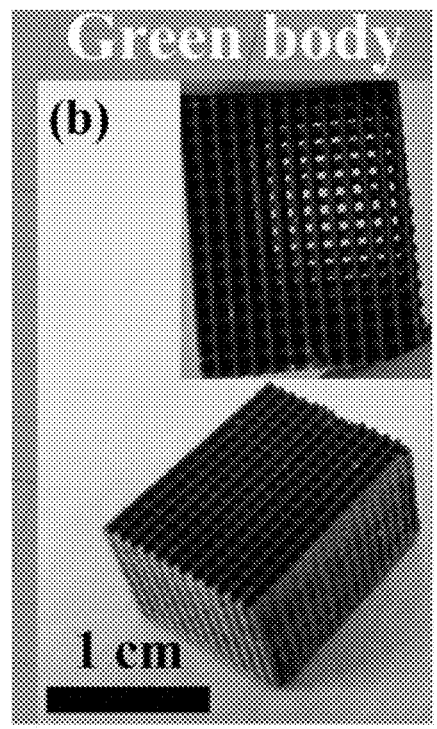

FIGS. 46A-46B show a CAD model used for 3D printing (FIG. 46A) and green body Ag-BG scaffolds (FIG. 46B).

Figure 47:
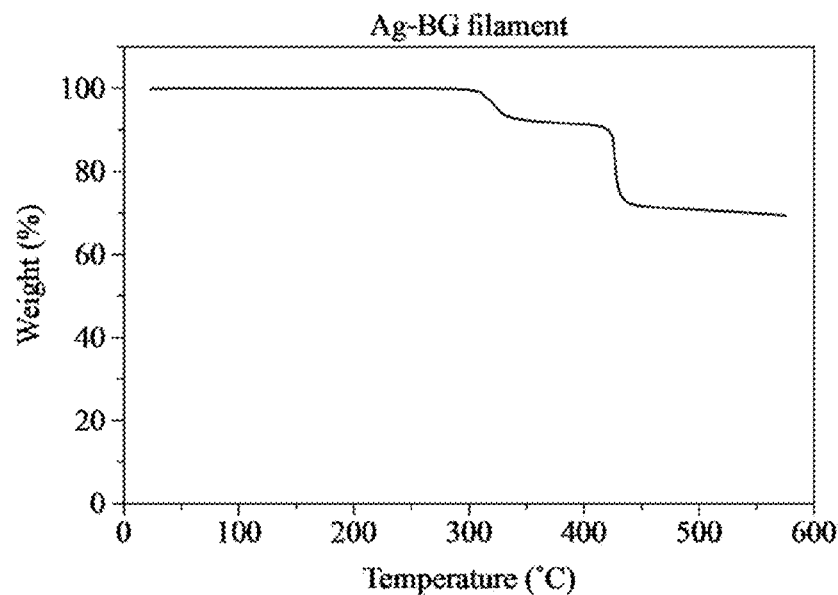

FIG. 47 shows a thermogravimetric analysis (TGA) of an Ag-BG filament.

Figures 48A, 48B:
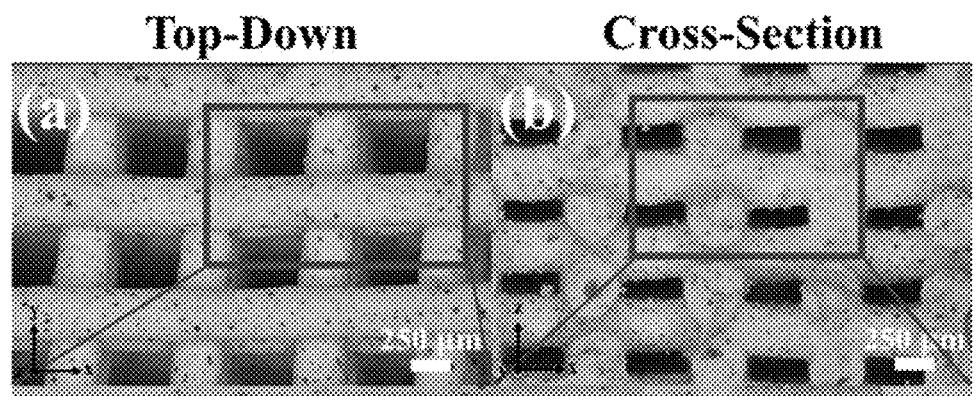
Figures 48C, 48D:
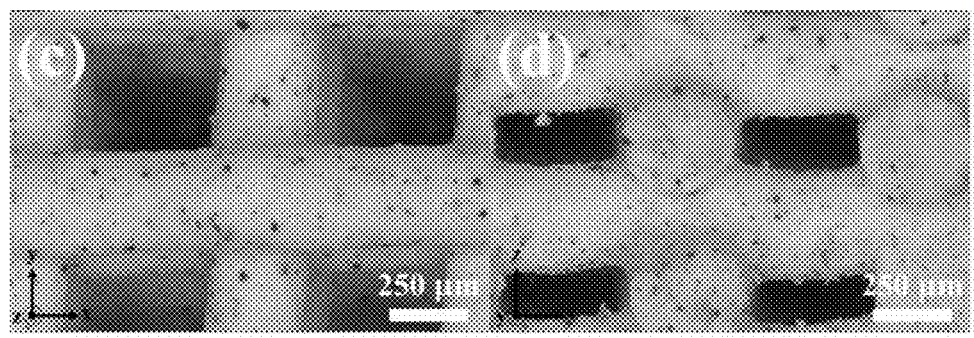

FIGS. 48A-48D show optical images of a 3D printed Ag-BG glass-ceramic scaffold showing top-down views (FIGS. 48A and 48C) and cross-sectional views (FIGS. 48B and 48D).

FIGS. 49A-49H show 3D reconstructions from micro-CT imaging applied to an Ag-BG scaffold, where FIG. 49A presents a perspective view of the Ag-BG scaffold and FIGS. 49B-49D show the macrostructure of the Ag-BG scaffold from the x- y-, and z-axis, respectively. FIG. 49E displays a representative cross-section of the Ag-BG scaffold where the internal structure appeared tortured with the white arrows denoting regions of locally high x-ray attenuation. FIGS. 49F-49H present 3D reconstructions of two print layers of the Ag-BG scaffold viewed along the x-, y-, and z-axis, respectively.

Figures 50A, 50B:
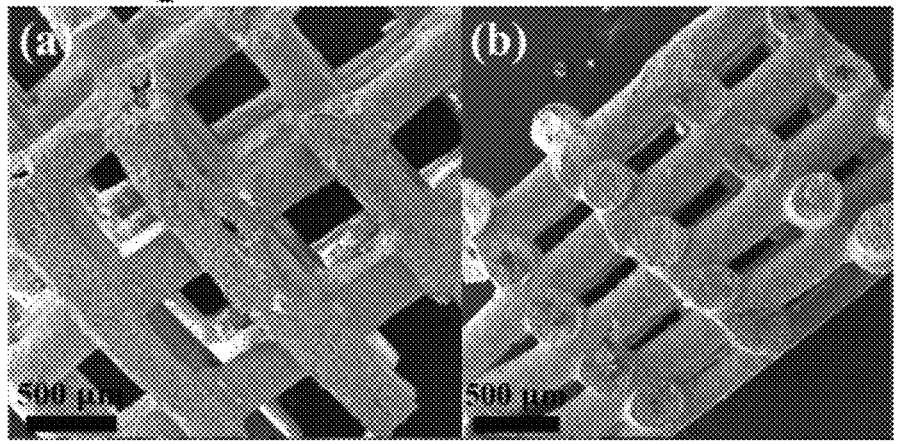
Figure 50C:
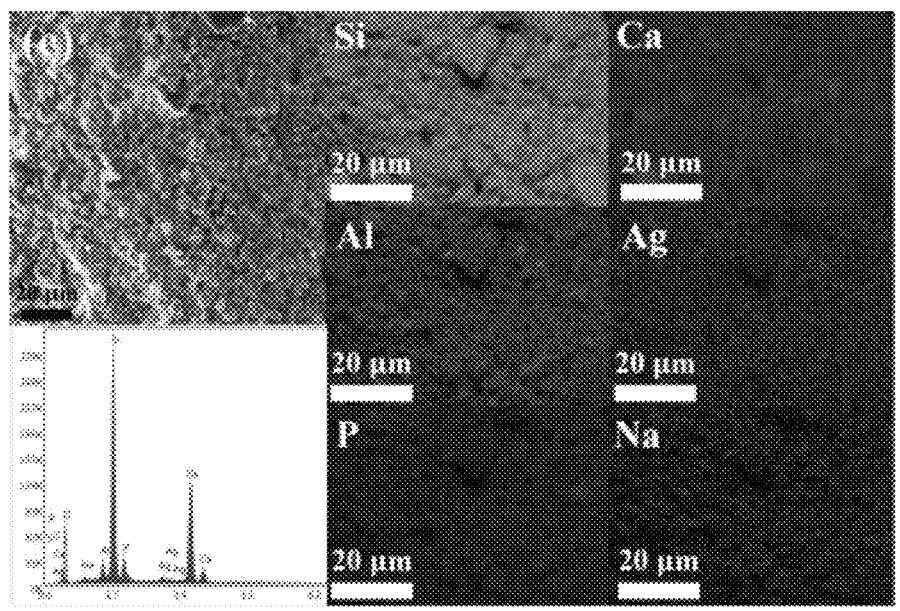

FIGS. 50A-50C show macroscopic SEM micrograph of an Ag-BG scaffold from a top-down perspective (FIG. 50A), a cross-sectional view (FIG. 50B), and the area where EDS X-ray mapping was performed with the distribution of the elements presented (FIG. 50C). The corresponding EDS spectrum is also shown.

Figure 51A:
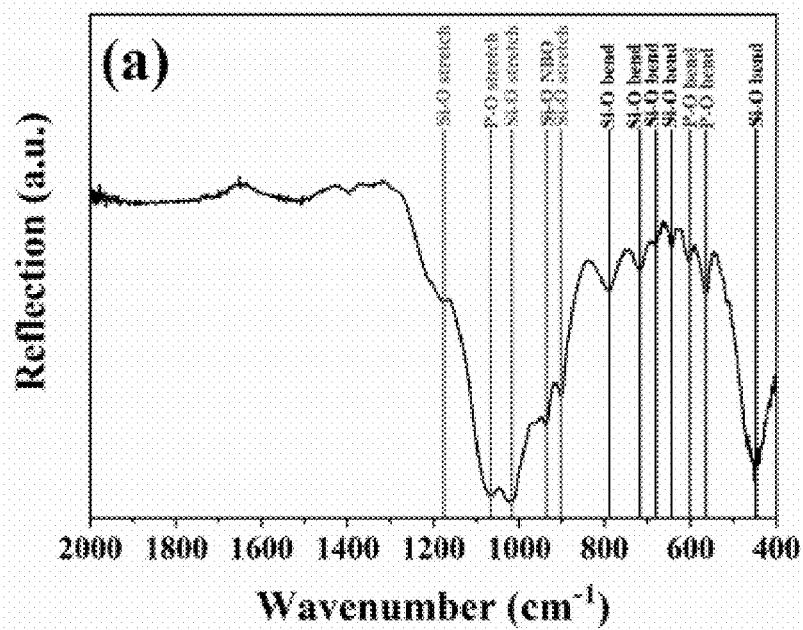
Figure 51B:
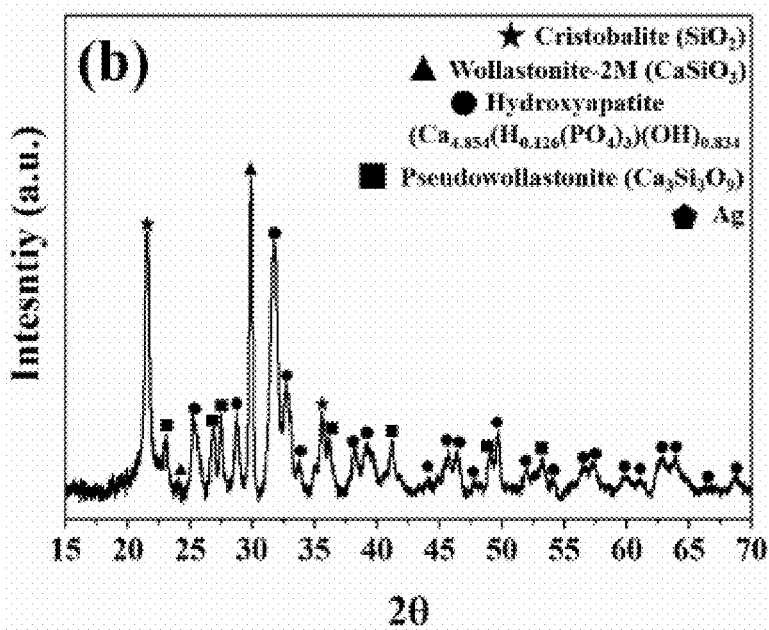

FIGS. 51A-51B show a FTIR-ATR spectrum (FIG. 51A) and an XRD pattern (FIG. 51B) of powdered Ag-BG scaffolds showing highly crystalline microstructures.

Figures 52A, 52B:
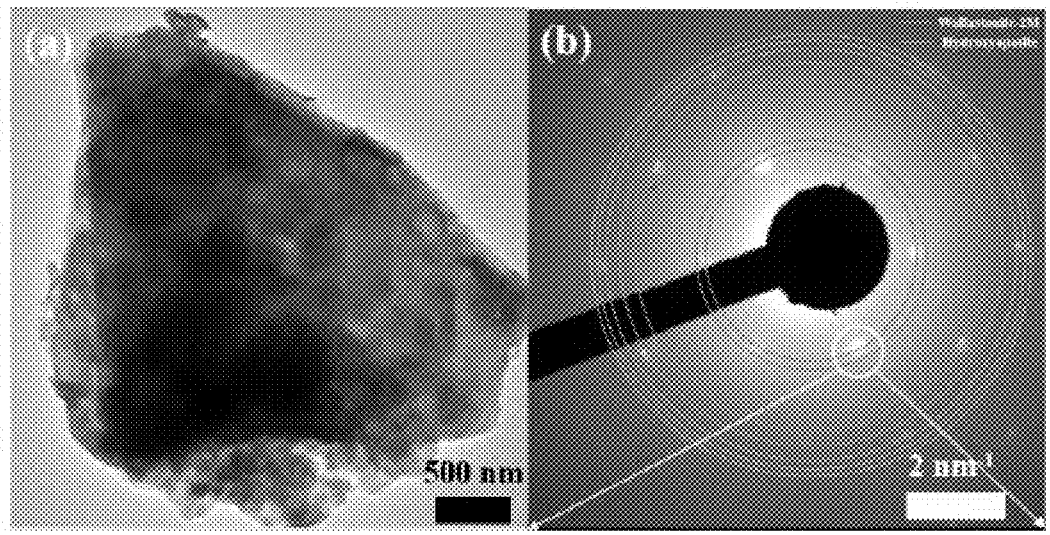
Figures 52C, 52D:
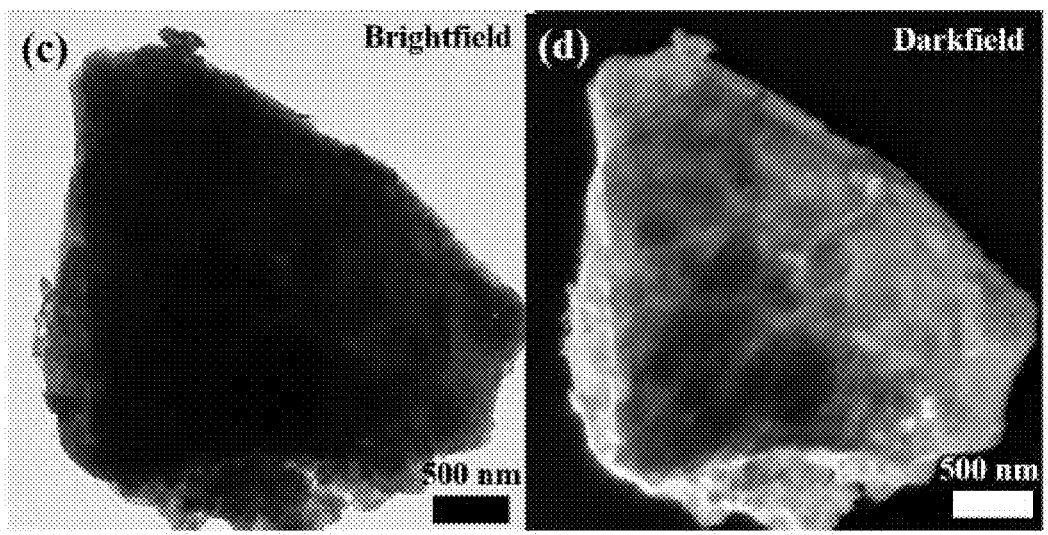

FIGS. 52A-52D show a phase-contrast TEM micrograph of an isolated 3D printed Ag-BG scaffold particle (FIG. 52A), a respective electron diffraction pattern where wollastonite-2M and hydroxyapatite were identified (FIG. 52B), a bright field micrograph showing minimal electron transmission (FIG. 52C), and corresponding axial dark field image established using a wollastonite-2M (200) electron diffraction spot (FIG. 52D).

Figure 53:
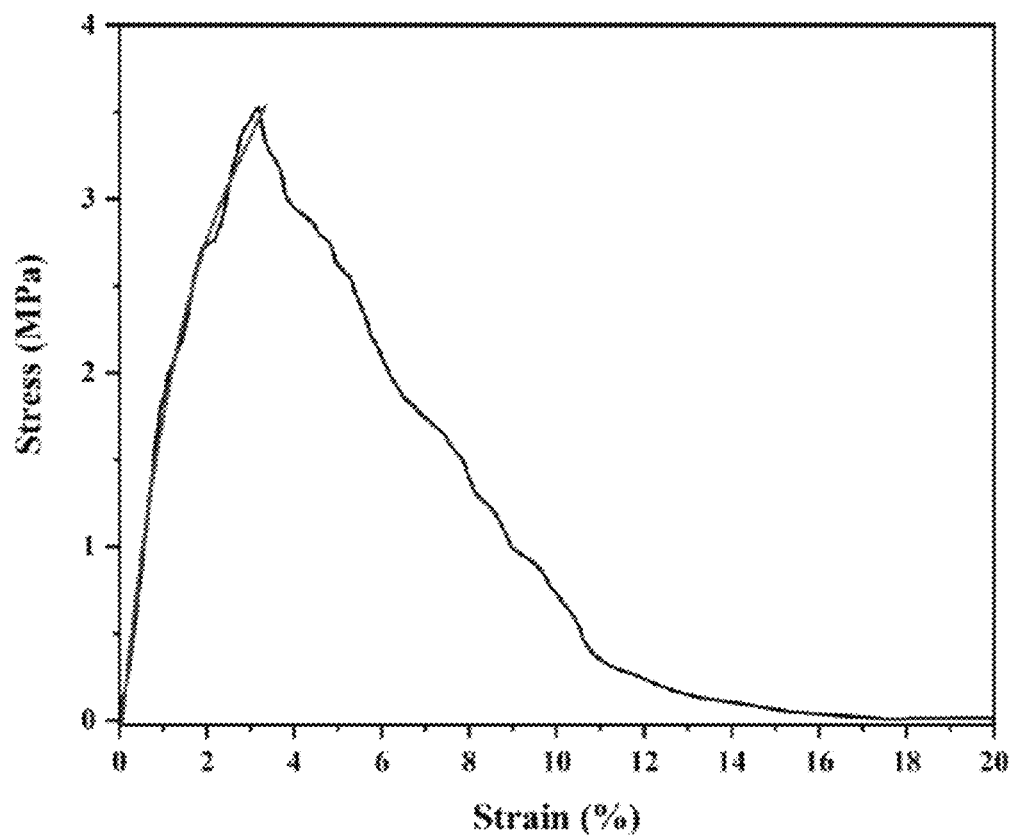

FIG. 53 shows a stress-strain curve representative of the compressive behavior of the 3D printed Ag-BG scaffolds. The smooth curved line is a guide to the eye.

FIGS. 54A-54F show FTIR-ATR spectra of powdered 3D printed Ag-BG scaffolds after immersion in SBF for 14 and 28 days (FIG. 54A); representative SEM micrographs of the surface morphology of the Ag-BG scaffolds after 14 days (FIGS. 54B and 54D) and 28 days (FIGS. 54C and 54E) of soaking in SBF, which showed needle-like features correlated to the deposition of an apatite-like layer; and XRD patterns of the powdered Ag-BG scaffolds after exposure to SBF for 14 and 28 days (FIG. 54F).

Figure 55:
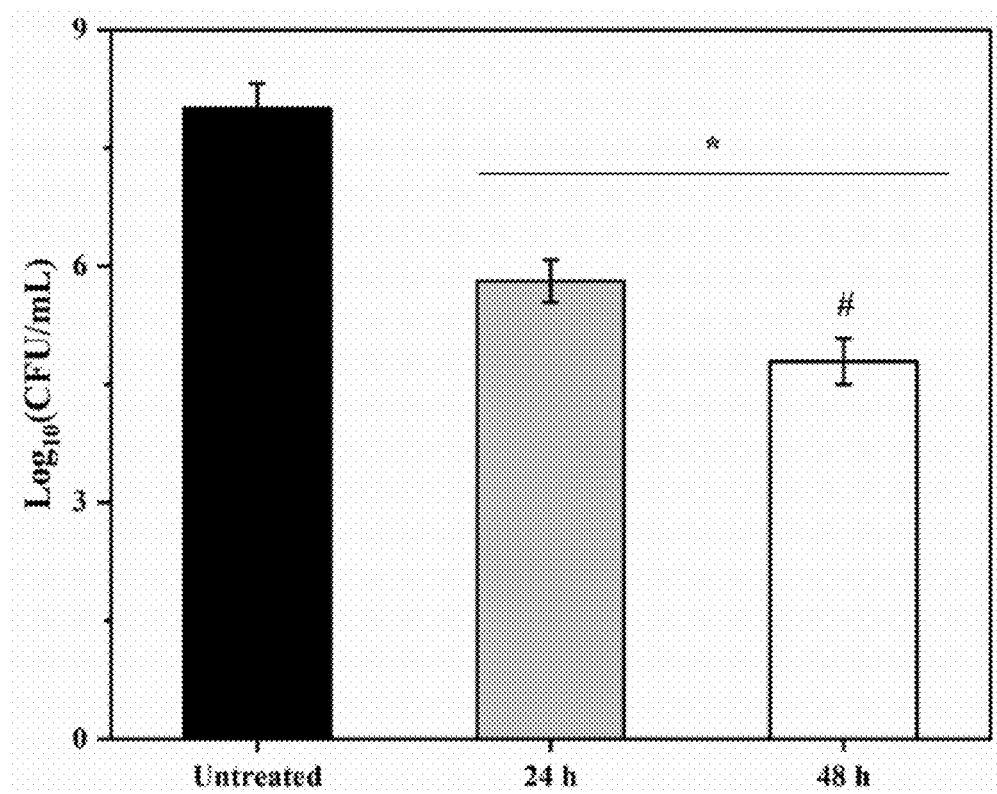

FIG. 55 is a bar graph showing anti-MRSA behavior of the Ag-BG scaffolds after being exposed to MRSA for 24 and 48 hours. (*) Statistical significant compared to untreated, (#) statistical significant between 24 hours and 48 hours of exposure.

Figure 56:
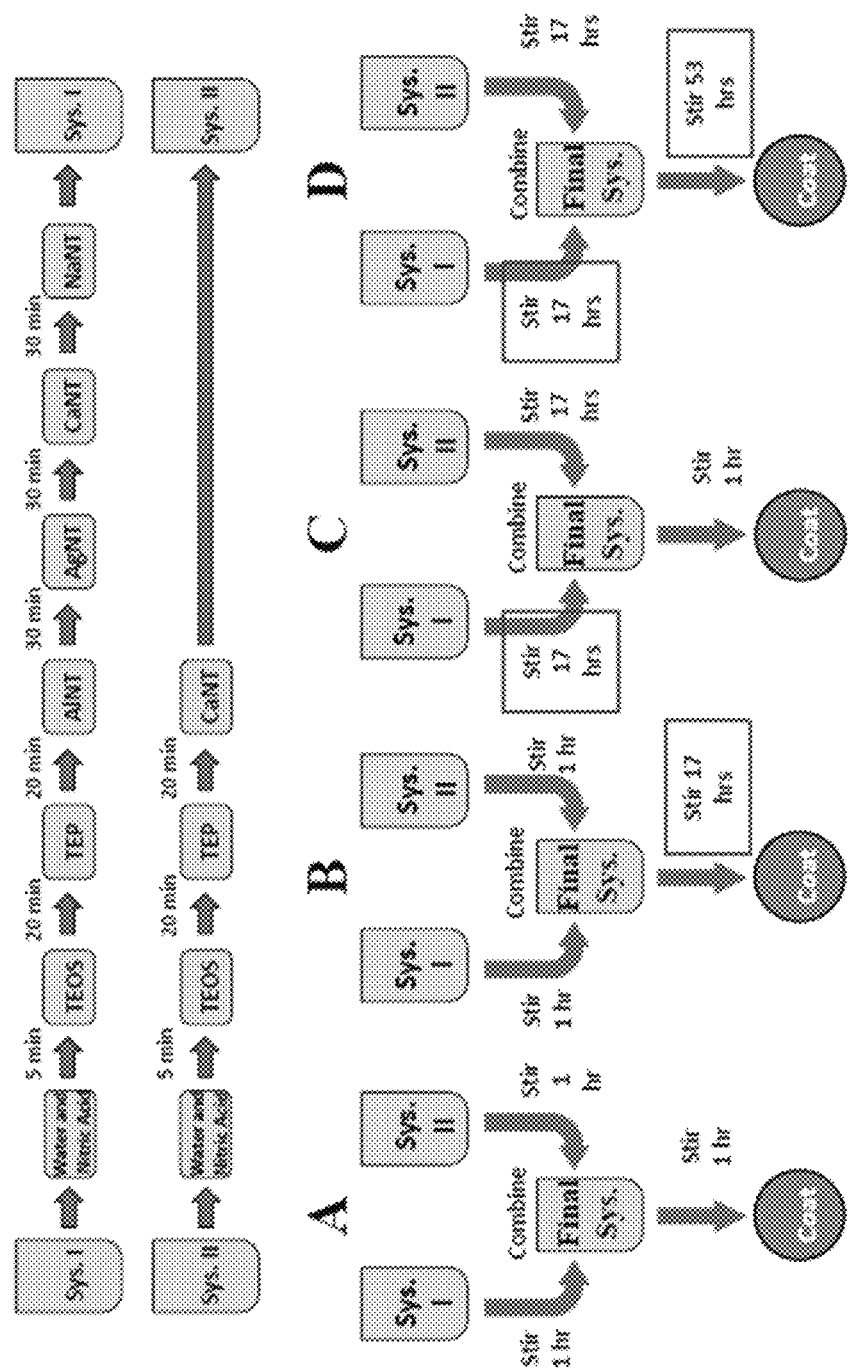

FIG. 56 shows four protocols with different stirring time durations as certain steps were applied to fabricate Ag-BG solutions for a spin coating method.

Figure 57:
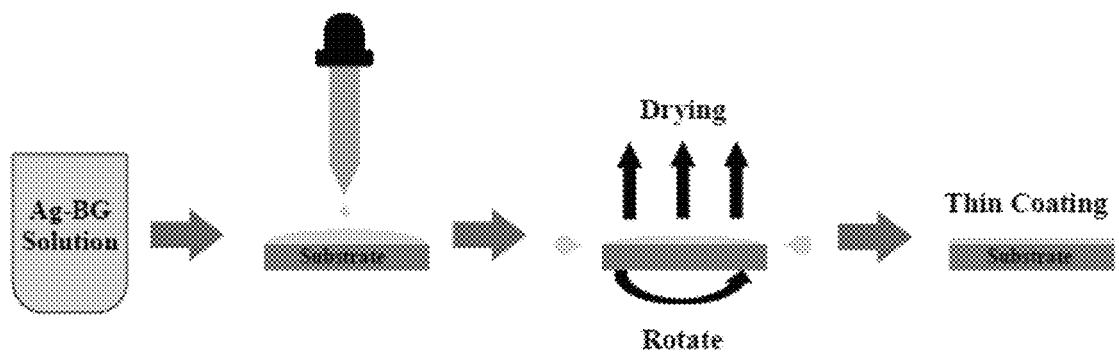

FIG. 57 is an illustration of a layout for a spin coating process using a silver-doped bioactive glass solution.

Figure 58:
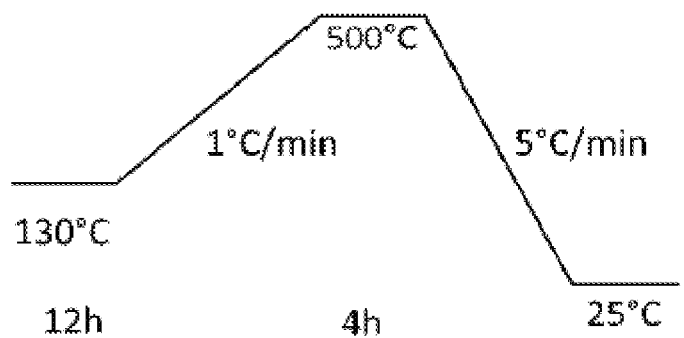

FIG. 58 shows a heat treatment profile performed during a film preparation.

Figure 59:
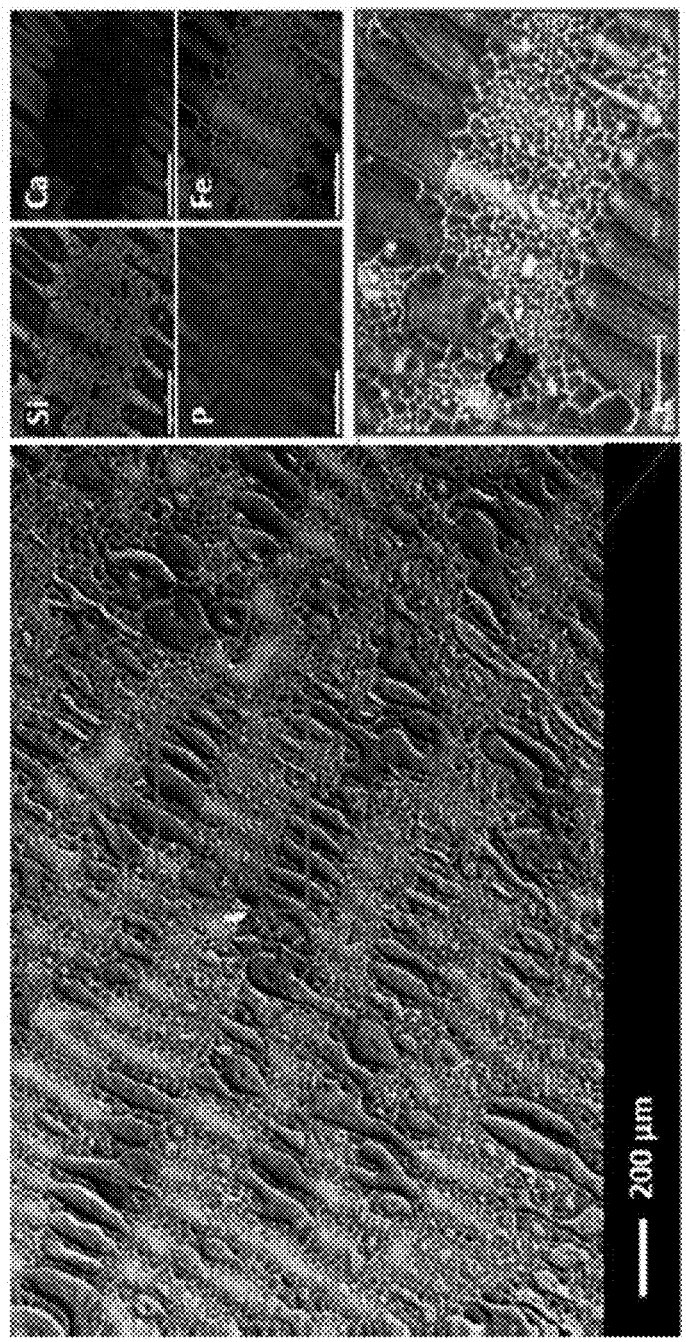

FIG. 59 shows SEM and EDS analysis of coated samples using a sol-gel derived bioactive glass 58S (Sys II).

Figure 60:
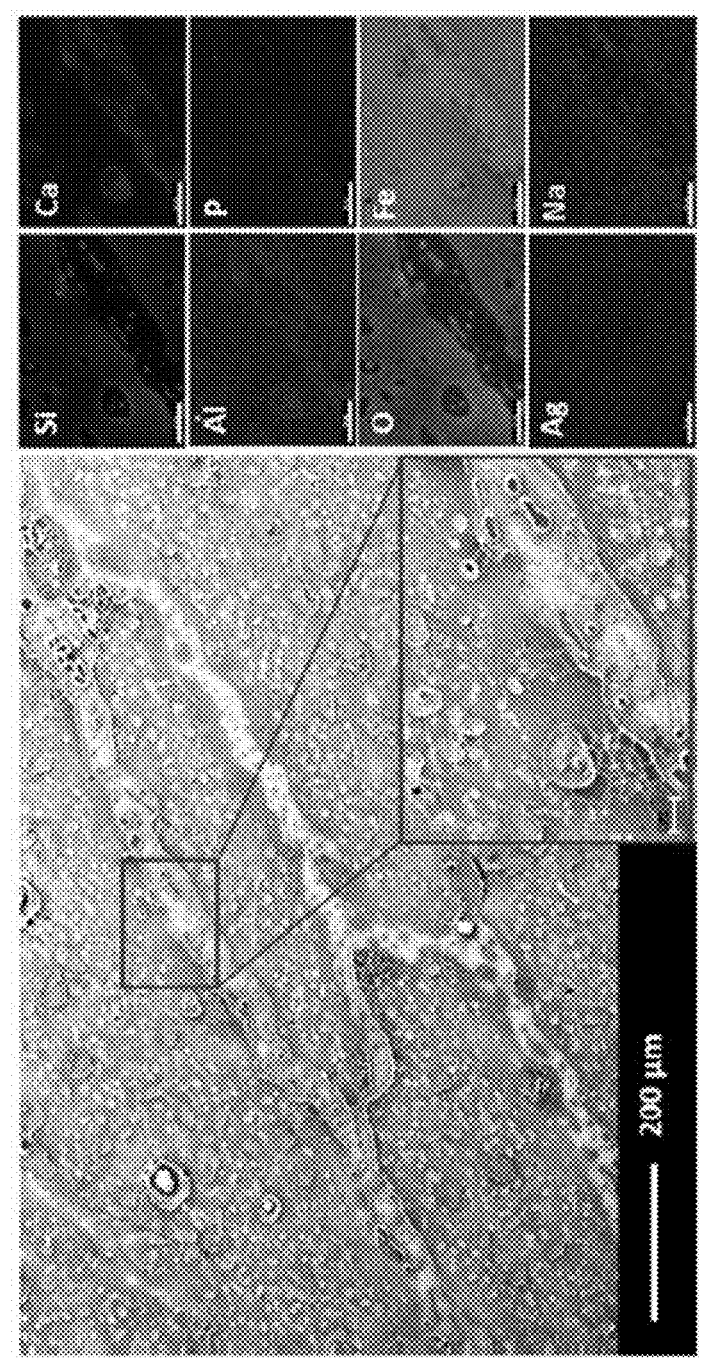

FIG. 60 shows SEM and EDS analysis of an Ag-BG bioactive glass system synthesized by protocol A.

Figure 61A:
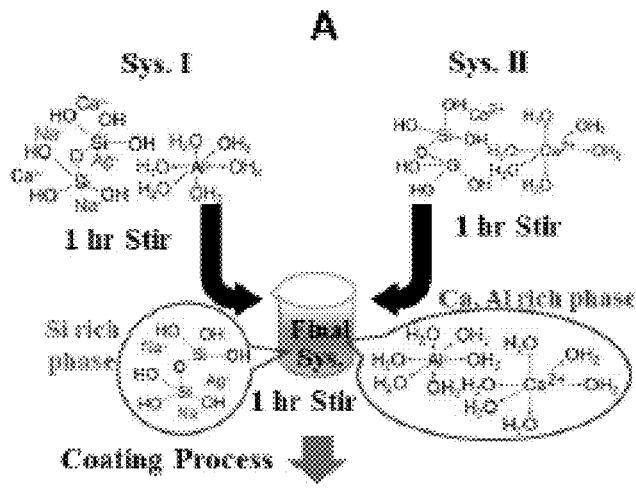
Figure 61B:
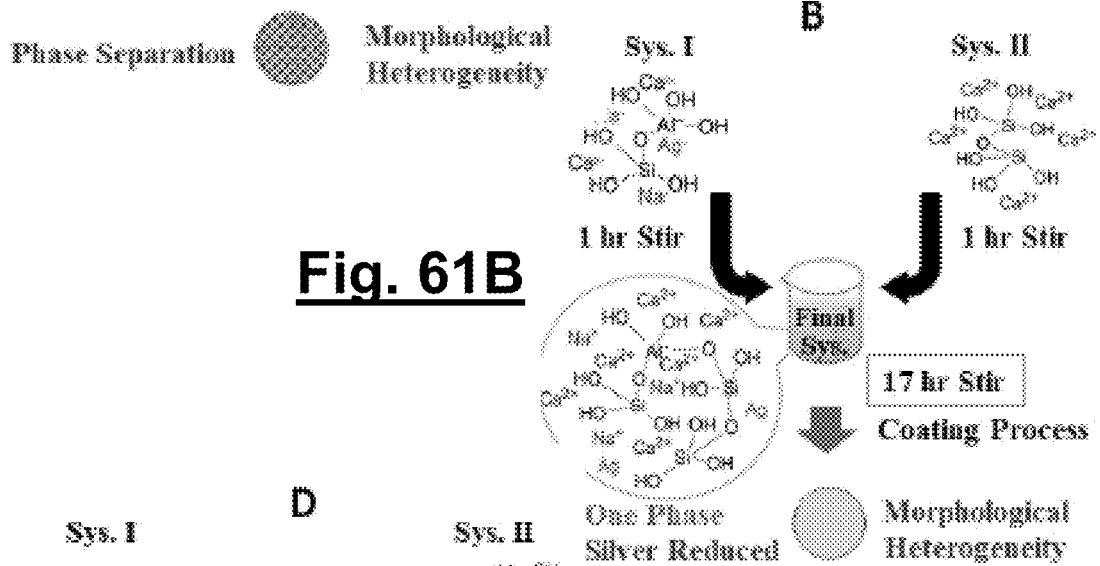
Figure 61C:
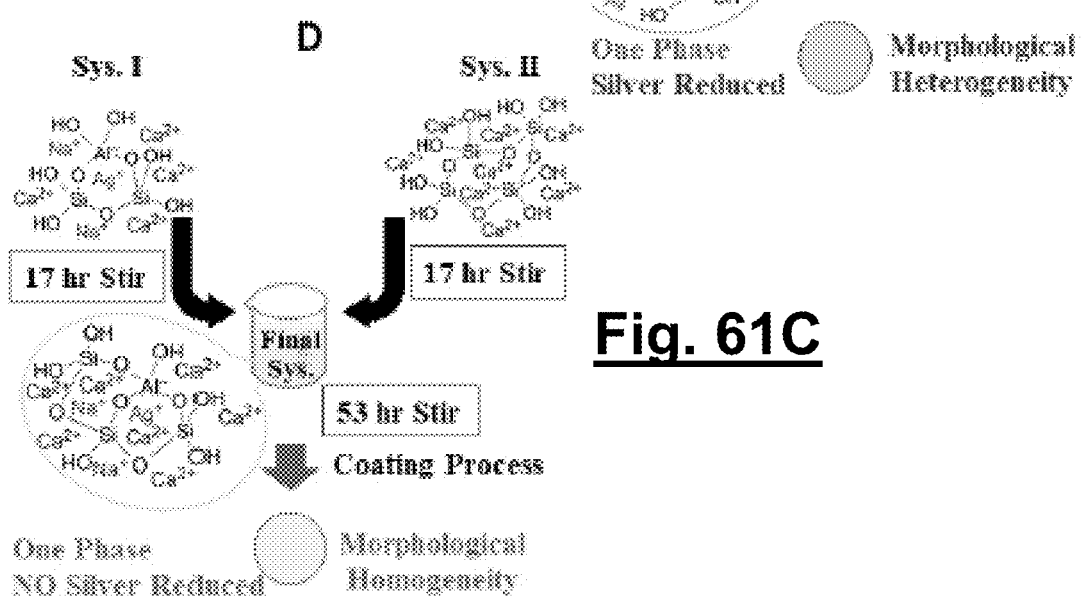

FIGS. 61A-61C shows mechanisms involved in the solution chemistry of protocol A (FIG. 61A), protocol B (FIG. 61B), and protocol C (FIG. 61C).

Figure 62:
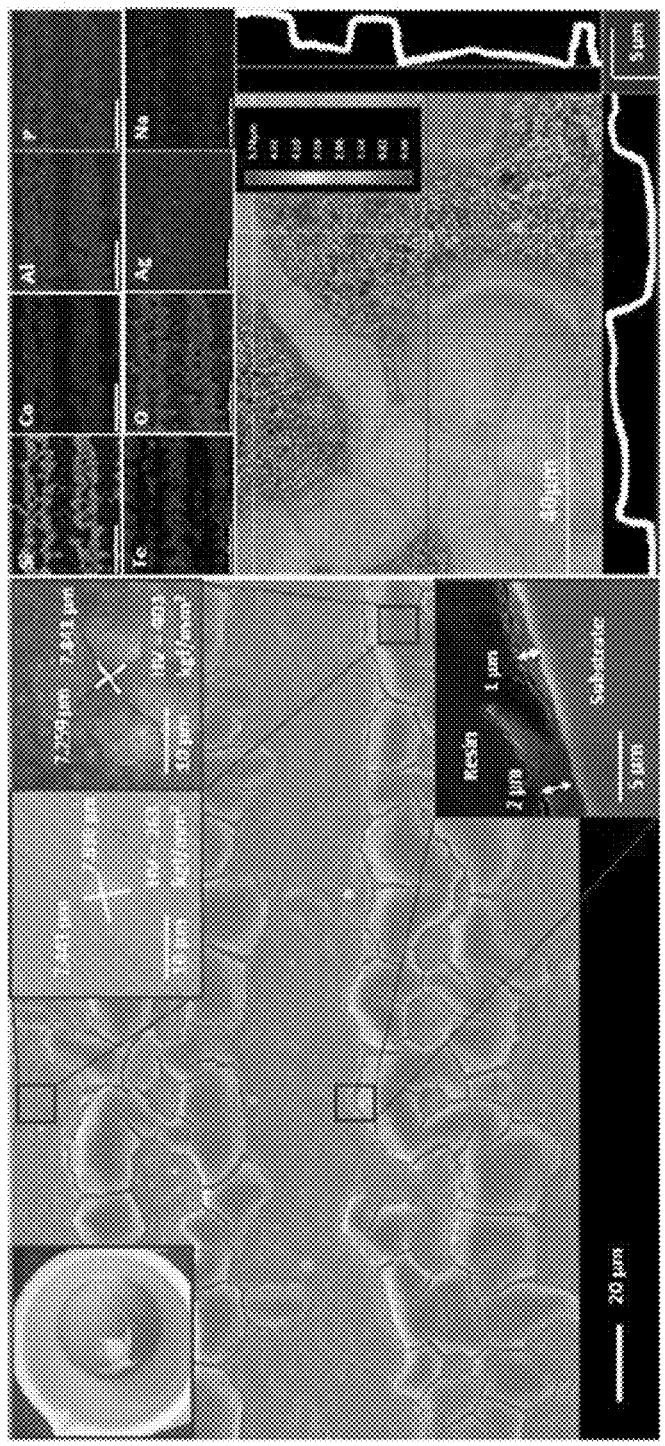

FIG. 62 shows SEM and EDS analysis of the Ag-BG bioactive glass coatings synthesized using protocol B. Top left insert of optical image presents final system prior to coating having a grey discoloration indicative of silver reduction. Top right insert SEM images present micro hardness indentation of both thin (left) and thicker (right) morphologies. Bottom right insert SEM image presents the cross section and the thickness of the coating. Bottom right optical image presents the surface roughness of the Ag-BG coatings fabricated by protocol B.

Figure 63:
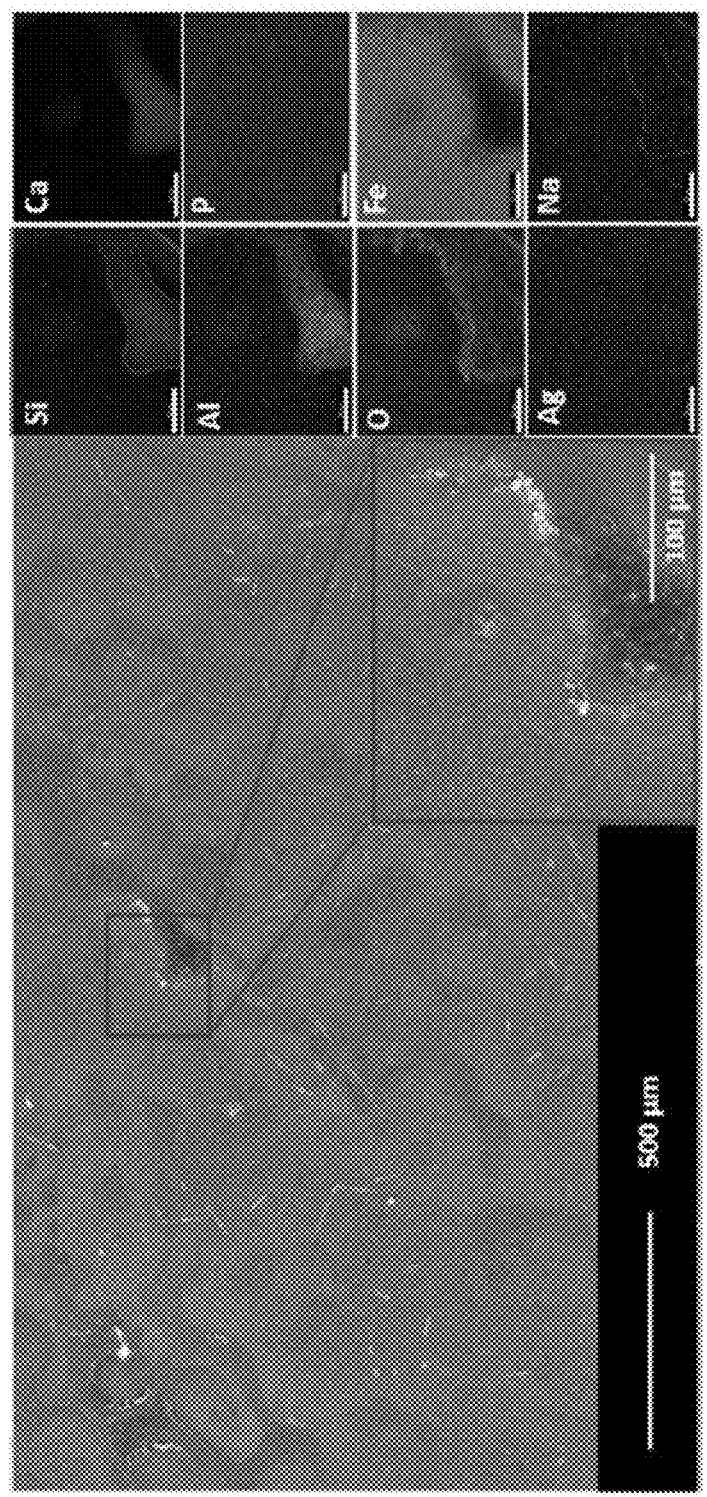

FIG. 63 shows SEM and EDS analysis of Ag-BG bioactive glass coatings synthesized protocol C. Elemental homogeneity and no silver reduction but morphologically heterogeneous surface were observed.

Figure 64:
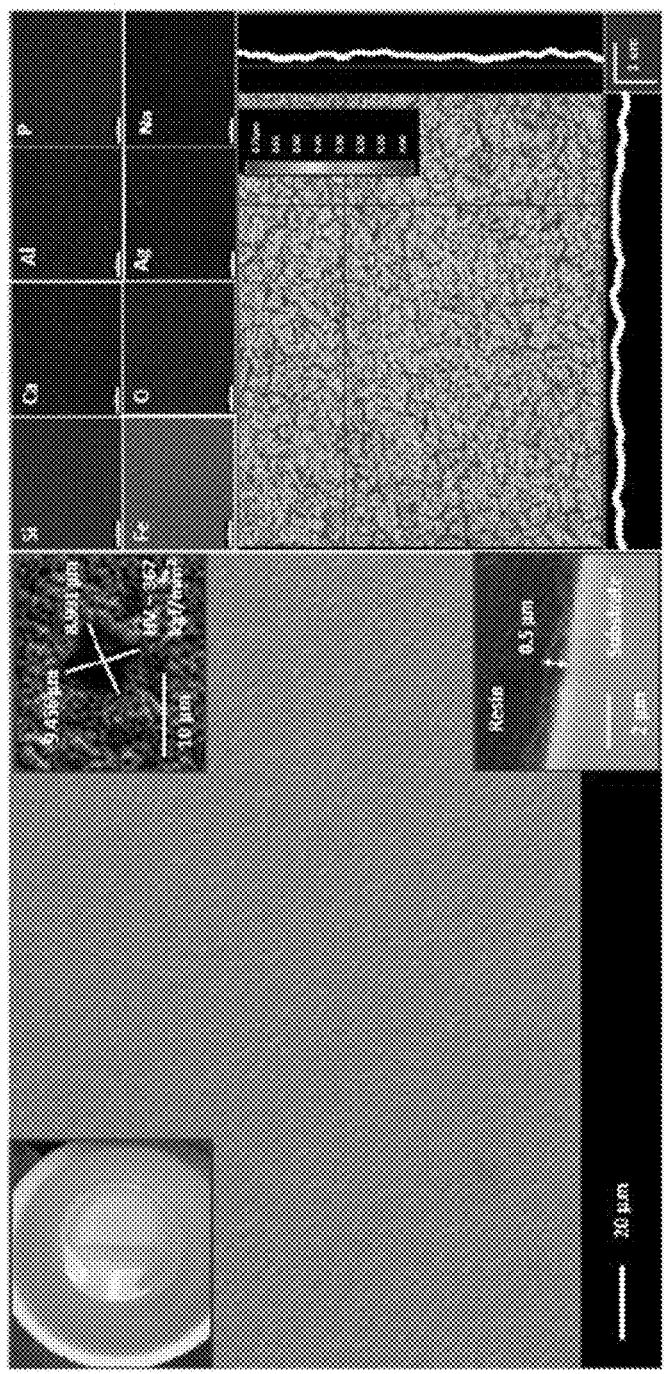

FIG. 64 shows SEM and EDS analysis of the Ag-BG bioactive glass coatings synthesized using protocol D. Morphologically and elementally homogeneous coatings have been fabricated. Top left insert of optical image presents final system prior to coating being clear without signs of silver reduction and discoloration. Top right insert SEM image presents micro hardness indentation. Bottom right insert SEM image presents the cross section and the thickness of the coating. Bottom right optical image presents the surface roughness of the Ag-BG coatings fabricated by protocol D.

Figure 65:
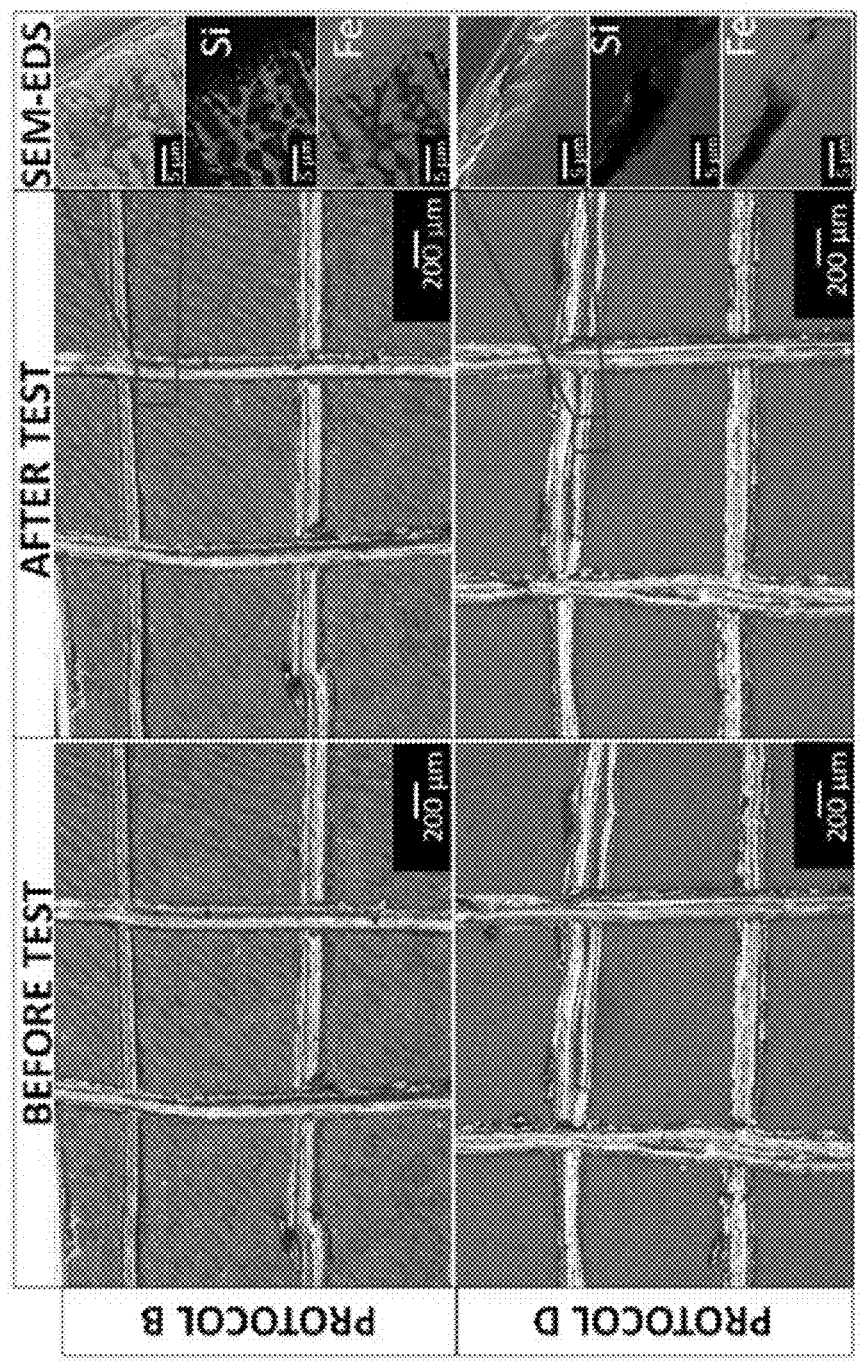

FIG. 65 provides images showing tight adhesion of the Ag-BG coatings on the substrates for samples synthesized by protocols B and D as the representative optical images before and after the test present, as well as the SEM-EDS analysis show by micro-observation throughout the coatings.

Figure 66A:
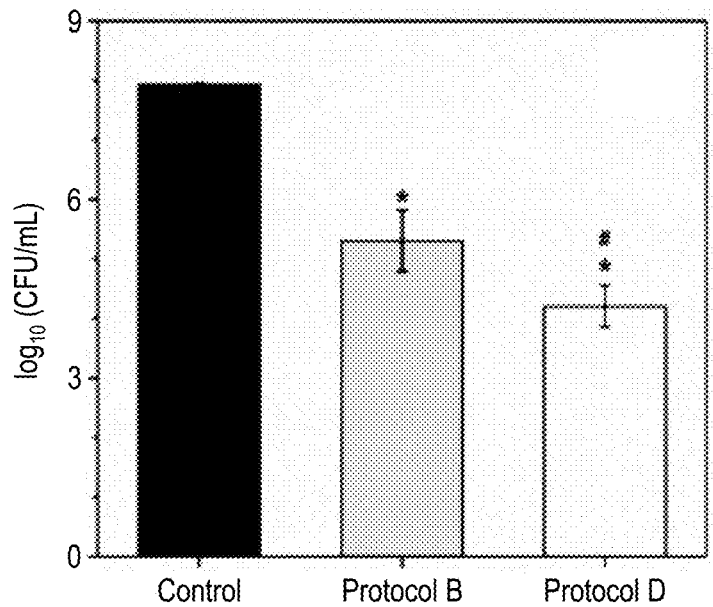
Figure 66B:
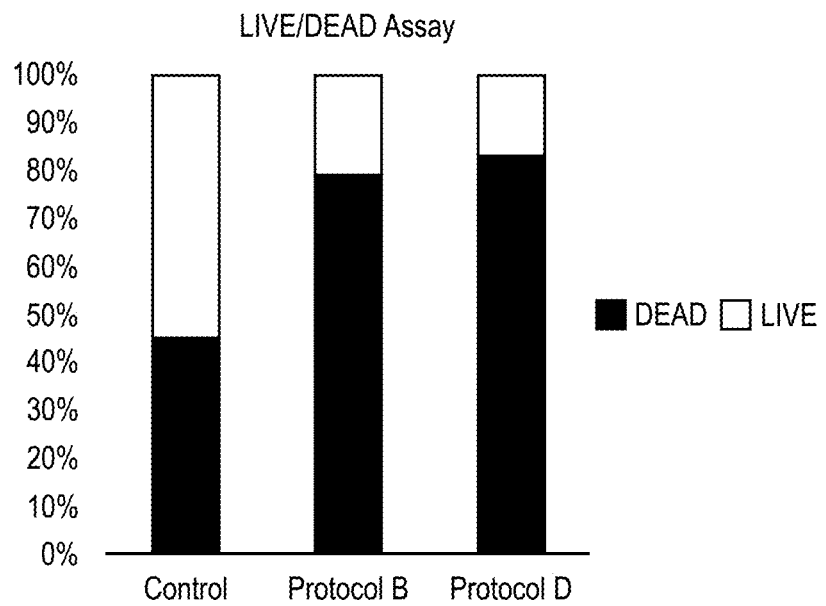
Figure 66C:
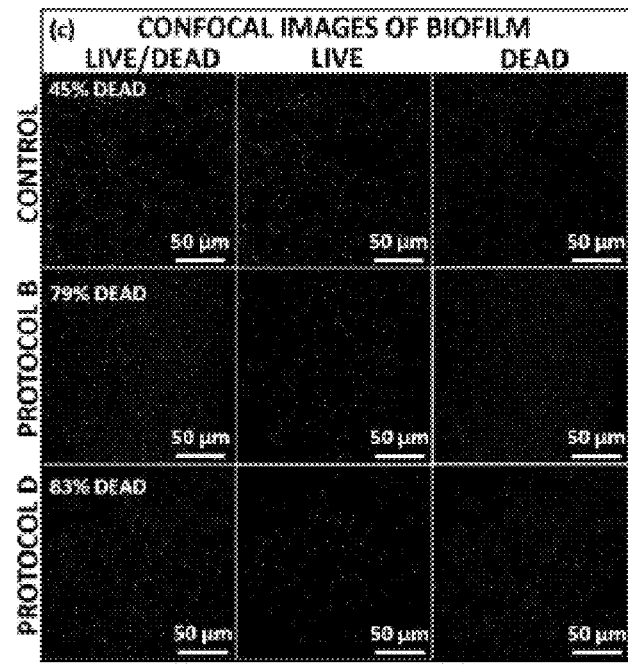
Figure 66D:
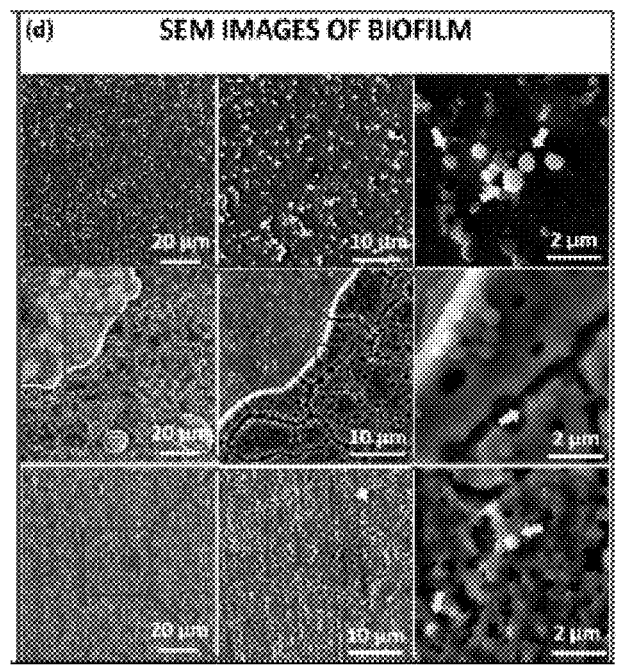

FIGS. 66A-66D show Antibacterial activity against planktonic MRSA by Ag-BG fabricated by protocol B and protocol D (FIG. 66A). Antibacterial activity against MRSA biofilm studied by Live/Dead staining (FIG. 66B). Confocal microscopy images of biofilm (FIG. 66C) and SEM images (FIG. 66D).

Figure 67A:
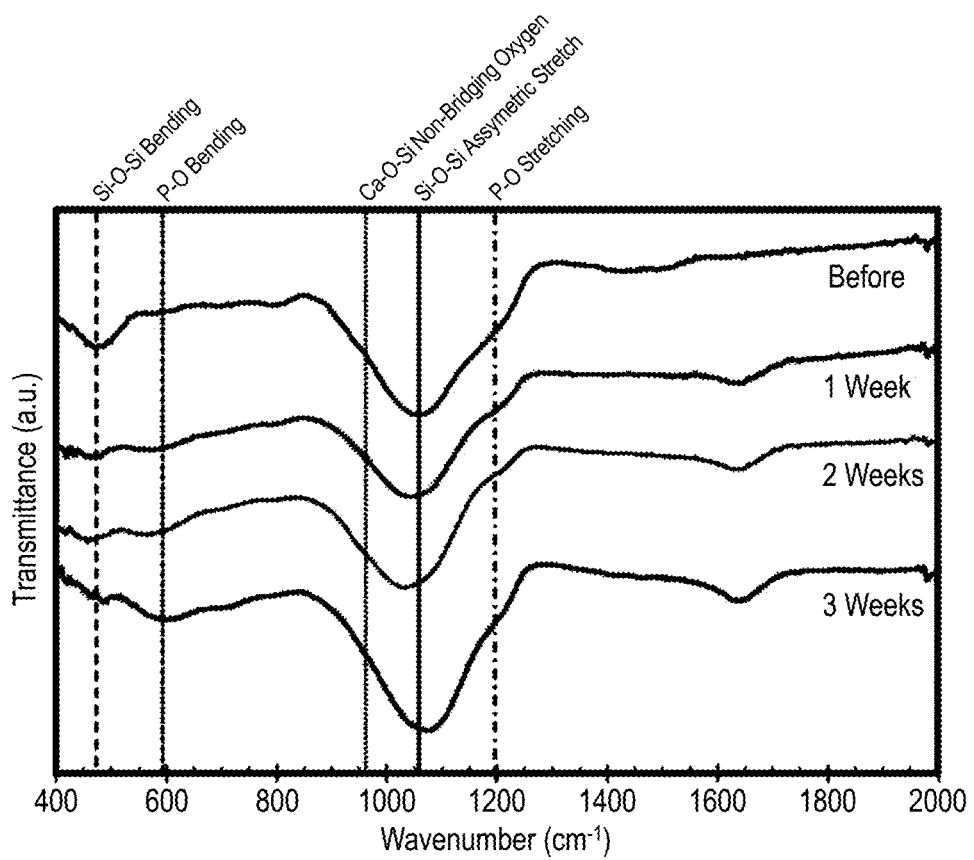
Figure 67B:
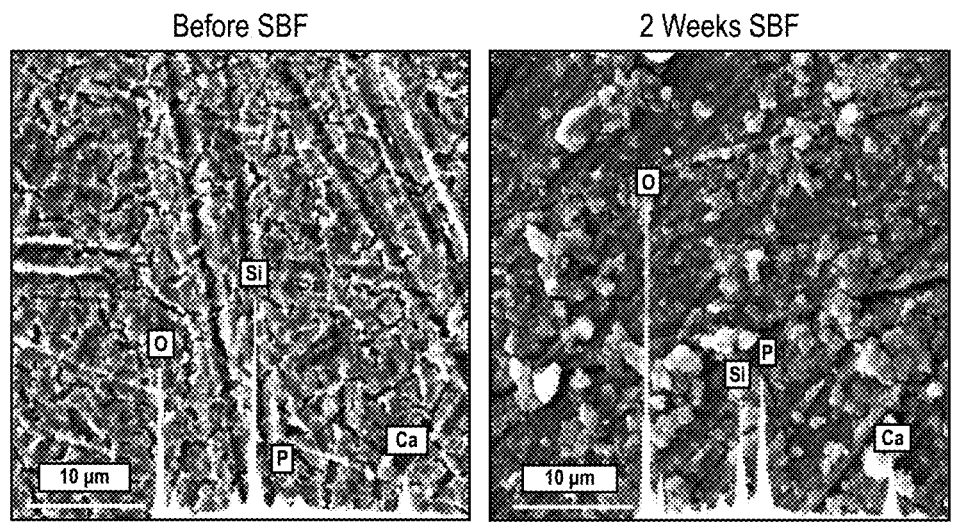

FIGS. 67A-67B show Samples coated with Ag-BG fabricated by protocol D are able to induce the deposition of a calcium-phosphate phase after immersion in SBF as it is confirmed by FTIR spectra (FIG. 67A), and SEM-EDS analysis (FIG. 67B) taken from the surfaces of the samples.

Figure 68:
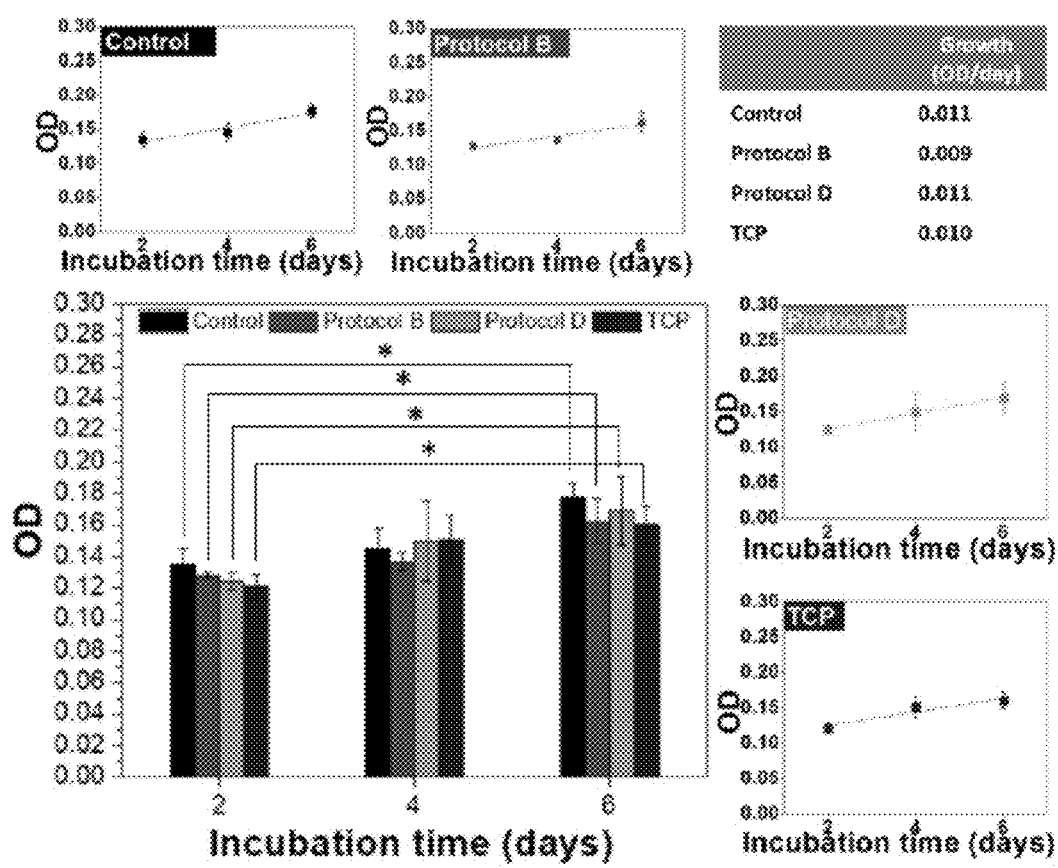

FIG. 68 shows cell viability and proliferation of hFOB 1.19 cells on the surface of different samples with culture times 2, 4, and 6 days. The optical density (450 nm) between the tested groups at each time point does not show any significant difference in cell response to different surfaces. Each sample condition at each time point was done in triplicate (n=3) with * representing significance with $p<0.05$.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower,"

"above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges. As referred to herein, ranges are, unless specified otherwise, inclusive of endpoints and include disclosure of all distinct values and further divided ranges within the entire range. Thus, for example, a range of "from A to B" or "from about A to about B" is inclusive of A and B.

Example embodiments will now be described more fully with reference to the accompanying drawings.

The current technology provides methods for treating bacterial infections and biofilms, including bacterial infections and biofilms that have become resistant to an antibiotic, by administering a safe and therapeutically effective amount of a material comprising a bioactive glass, which can be a bioactive glass, bioactive glass-ceramic or a combination thereof. Where the bacteria or biofilm is resistant to an antibiotic, the antibiotic is also administered to the subject because the material comprising the bioactive glass acts as a reviving agent that restores, revives, or resurrects the antibiotic activity of the antibiotic against the bacteria or biofilm. Thus, in certain aspects, the material comprising the bioactive glass is a reviving agent. As used herein, the term "therapeutically effective amount" means an amount of a compound that, when administered to a subject having a bacterial infection or biofilm, suspected of having a bacterial infection or biofilm, or at risk of developing a bacterial infection or biofilm, is sufficient, either alone or in combination with additional therapies, to effect treatment for the bacterial infection or biofilm. The "therapeutically effective amount" will vary depending on, for example, the material form (e.g., particles, scaffold, film, or combination thereof), composition (e.g., optionally Ag-doped bioactive glass, optionally Ag-doped bioactive glass-ceramic, or combination thereof) pharmaceutical dosage form, the condition treated and its severity, and the age and weight of the patient to be treated. When the subject has an infection or biofilm that is resistant to an antibiotic, there is no safe and therapeutically effective amount of the antibiotic by itself that is useful for treating the infection or biofilm. Therefore, the safe and effective amount of the antibiotic is considered in combination with a reviving agent, especially because the reviving agent and antibiotic may interact synergistically. In various aspects, the therapeutically effective amount of the doped or unhoped bioactive glass provides a dose greater than or equal to about 1 mg to less than or equal to about 100 mg to a cite of infection. As used herein, the "subject" is a human or non-human mammal.

The current technology provides a method for combatting methicillin-resistant *Staphylococcus aureus* (MRSA) and other bacteria strains via reactivation of inert antibiotics by expanding their spectrum of action. The method exploits multifunctional, bioactive glass-ceramic particles with antibacterial properties in combination with various antibiotics to kill MRSA. Specifically, sol-gel derived Ag-doped bioactive glass particles (Ag-BG), which can be Ag-doped bioactive glass particles or Ag-doped bioactive glass-ceramic particles, combined with antibiotics that MRSA resists, such as oxacillin or fosfomycin, significantly decreases the viability of MRSA cells. Ag-BG also potentiates the activity of vancomycin on static bacteria, which are typically resistant to this antibiotic. Notably, synergistic activity is found in cell-envelope acting antibiotics. Bacteria viability and electron microscopy demonstrate that Ag-BG synergize to restore antibacterial activity to antibiotics that MRSA resists. The known regenerative properties of the Ag-BG together with the unique antibacterial properties that occur when they are combined with antibiotics make this multifunctional system practical for healing infected tissue.

Unless specifically described otherwise, the term bioactive glass (BG) refers to both bioactive glass (optionally Ag-doped) and bioactive glass-ceramic (optionally Ag-doped).

Accordingly, the current technology provides a method of restoring antibiotic activity to an antibiotic against a bacteria strain that has developed resistance to the antibiotic. The method comprises combining the antibiotic with a source of silver ions.

In some embodiments, the antibiotic is a molecule that disrupts the ability of a bacterium to assemble a cell wall, such as antibiotics that comprise a β-lactam ring. In other embodiments, the antibiotic targets bacterial DNA (synthesis or transcription) and/or RNA (synthesis or translation). However, the antibiotics are not limited and can be selected from the group consisting of penicillin, oxacillin, methicillin, nafcillin, cloxacillin, diclosacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, fosfomycin, vancomycin, daptomycin, gentamicin, ciprofloxacin, and combinations thereof.

The bacteria strain can be any Gram-positive or Gram-negative strain of bacteria that has developed a resistance to an antibiotic. Non-limiting examples of gram-positive bacteria include methicillin-resistant *Staphylococcus aureus* (MRSA), *Streptococcus pneumoniae, Streptococcus mutans, Streptococcus sanguinis, Enterococcus faecalis*, and *Lactobacillus casei*. Non-limiting examples of gram-negative bacteria include *Escherichia coli, Pseudomonas aeruginosa, Salmonella* spp., *Klebsiella pneumonia, Neisseria gonorrhoeae, Neisseria meningitidis, Acinetobacter baumanii, Enterobacter* spp., and *Yersinia pestis*. It is understood that infections associated with additional strains of Gram-positive and Gram-negative bacteria, including additional species of the above recited genera can be treated by the method.

The source of silver ions can be any source known in the art, including silver nanoparticles. However, in some embodiments, the source of silver ions is a plurality of silver-doped bioactive glass particles (Ag-BG), which can be Ag-doped bioactive glass particles or Ag-doped bioactive glass-ceramic particles. The Ag-BG can be sol-gel derived.

The current technology also provides a method of treating or inhibiting the growth of a bacterial infection in a subject in need thereof with an antibiotic, wherein the bacterial infection includes bacteria that are resistant to the antibiotic. The subject can be, for example, a subject having an infection that includes the bacteria or a subject that is at risk of developing an infection that includes the bacteria. The method comprises administering to the subject the antibiotic and a reviving agent, such as a source of silver ions. The antibiotic and source of silver ions can be any combination of those described above.

In one embodiment, the antibiotic and the source of silver ions are combined in a single composition. In another embodiment, the administering comprises administering a first composition that comprises the antibiotic and separately administering a second composition that comprises the source of silver ions. The administering can be performed by administering the antibiotic and the source of silver ions directly to tissue having the bacterial infection.

In one aspect, the method further includes administering an adjunct composition that includes a β-lactamase inhibitor. Non-limiting examples of β-lactamase inhibitors include clavulanic acid, sulbactam, tazobactam, and combinations thereof.

The current technology also provides a composition that includes a synergistic combination of an antibiotic and a source of silver ions. The antibiotic and source of silver ions can be any of those described above. In one embodiment, the antibiotic is selected from the group consisting of penicillin, oxacillin, methicillin, nafcillin, cloxacillin, diclosacillin, flucloxacillin, ampicillin, amoxicillin, pivampicillin, hetacillin, bacampicillin, metampicillin, talampicillin, epicillin, carbenicillin, ticarcillin, temocillin, mezlocillin, piperacillin, azlocillin, fosfomycin, vancomycin, gentamycin, ciprofloxacin, and combinations thereof and the source of silver ions comprises a plurality of silver-doped bioactive glass particles (Ag-BG).

The current technology also provides a method of restoring antibiotic activity to an antibiotic against a bacteria strain that has developed resistance to the antibiotic. The bacteria strain and antibiotic can be any of those described above. The method includes combining the antibiotic with a reviving agent. The reviving agent is a material comprising bioactive glass (BG). The BG can be bioactive glass (optionally Ag-doped), or a bioactive glass-ceramic (optionally Ag-doped).

The material is not limited and, in various embodiments, has a form selected from the group consisting of particles, a scaffold, a thin film, a porous matrix, a coating, and combinations thereof. The particles have an average diameter of greater than or equal to about 500 µm to less than or equal to about 500 µm, such as nanoparticles having an average diameter of greater than or equal to about 0.5 nm to less than or equal to about 500 nm or microparticles having an average diameter of greater than or equal to about 0.5 µm to less than or equal to about 500 µm. The scaffold is a material system comprising a plurality of interconnected branches or arms, i.e., struts, that define a three-dimensional web-like pattern. The thin film is a film having an average thickness of greater than or equal to about 500 µm to less than or equal to about 500 µm, or greater than or equal to about 0.1 µm to less than or equal to about 50 µm. The porous matrix is a material comprising a plurality of pores, similar to a sponge. The porous matrix can have a porosity of greater than or equal to about 10% to less than or equal to about 90%. The coating can be a layer that coats a particle, such as any particle described herein, a layer that coats a medical implant (including stents) or prosthesis, or a layer that coat a medical device, such as, for example, a catheter.

In various embodiments, the material comprising BG is free or substantially free of silver and/or silver ions. By "substantially free" of silver ions it is meant that the material comprises less than or equal to about 10 wt. % or less than or equal to about 5 wt. % of silver and/or silver ions.

In various other embodiments, the material comprises silver and/or silver ions. The silver and/or silver ions can be completed embedded within the material, partially embedded within the material, or partially embedded in an outer surface of the material. In some embodiments, the material is porous and the silver and/or silver ions are disposed within the pores.

The current technology also provides a composition that includes a synergistic combination of an antibiotic and a material that comprises, consists essentially of, or consists of BG. As discussed above, the BG can be optionally Ag-doped glass or optionally Ag-doped glass-ceramic.

The current technology yet further provides a method of treating or inhibiting the growth of a bacterial infection in a subject in need thereof, wherein the bacterial infections comprises bacteria that have developed resistance to an antibiotic. The bacteria and antibiotic can be any of the described herein. The subject in need thereof can actively have the bacterial infection or be at risk of developing the bacterial infection. A subject at risk of developing the bacterial infection can be, for example, a subject who had undergone a medical procedure in which a medical instrument contacts the subject's skin, tissue, or blood. An exemplary procedure is surgery, in which case the current method is performed during the surgery and before a surgical wound is closed.

The method comprises administering to the subject the antibiotic and a material that comprises BG. As discussed above, the material has a form selected from the group consisting of particles, a scaffold, a thin film, a porous matrix, a coating, and combinations thereof. In some embodiments, the material is free or substantially free of silver and/or silver ions. In other embodiments, the material comprises silver and/or silver ions. Also as discussed above, the BG can be optionally Ag-doped glass or optionally Ag-doped glass-ceramic.

In some embodiments, the administering comprises separately administering the antibiotic and the material. In other embodiments, the administering includes administering a single composition that comprises both the antibiotic and the material. The single composition can further comprise a pharmaceutically acceptable carrier. In various embodiments, the administering comprises administering the antibiotic and the material directly to tissue having the bacterial infection or being at risk of having the bacterial infection.

Accordingly, the current technology provides a material that comprises bioactive glass (BG), In certain aspects, the material comprises optionally Ag-doped glass-ceramic microparticles, optionally Ag-doped glass nanoparticles, an optionally Ag-doped bioactive glass scaffold, an optionally Ag-doped bioactive glass-ceramic scaffold, an optionally Ag-doped glass-ceramic film, or combinations thereof. The material comprising BG has antibiotic activity, but is also functional as a reviving agent, including a synergistic reviving agent, that restores or resurrects antibiotic activity to an antibiotic to which a bacteria strain or biofilm has become resistant. The material comprising BG prevents or inhibits, slows, or minimizes peri-implantitis and osteomyelitis. The material comprising BG is active under aerobic and anaerobic conditions and is additionally functional to enhance cell-proliferation and differentiation in cells to which it contacts. The cells can be in soft tissue, such as cartilage as a non-limiting example, or in hard tissue, such as bone as a non-limiting example.

As discussed above, in some aspects the material comprising BG is bioactive glass-ceramic microparticles that are optionally doped with silver. A method of forming glass-ceramic microparticles is described by Chatzistavrou et al., *MRS Proceedings* 2012, 1417, Mrsf11-1417-kk06-09. doi: 10.1557/op1.2012.743, which is incorporated herein by reference in its entirety. The method comprises forming a bioactive glass solution by combining greater than or equal to about 50 wt. % to less than or equal to about 70 wt. % $SiO_2$, greater than or equal to about 25 wt. % to less than or equal to about 40 wt. % CaO, and greater than or equal to about 5 wt. % to less than or equal to about 15 wt. % $P_2O_5$ in a solvent, such as water (from about 15 mL to about 30 mL in certain aspects); and a sol-gel porcelain solution stage by combining greater than or equal to about 50 wt. % to less than or equal to about 70 wt. % $SiO_2$, greater than or equal to about 1 wt. % to less than or equal to about 10 wt. % CaO, greater than or equal to about 1 wt. % to less than or equal to about 15 wt. % $P_2O_5$, greater than or equal to about 10 wt. % to less than or equal to about 20 wt. % $Al_2O_3$, greater than or equal to about 0 wt. % to less than or equal to about 15 wt. % $Na_2O$, greater than or equal to about 0 wt. % to less than or equal to about 15 wt. % $K_2O$, and greater than or equal to about 0 wt. % to less than or equal to about 10 wt. % $Ag_2O$ in a solvent, such as water (from about 10 mL to about 20 mL in certain aspects). The $Ag_2O$ is optionally included for the reasons discussed below. The method then comprises combining the bioactive glass solution with the sol-gel porcelain solution to form a composite solution.

The method then comprises aging the composite solution at a temperature of greater than or equal to about 50° C. to less than or equal to about 75° C., such as a temperature of about 50° C., about 55° C., about 60° C., about 65° C., about 70° C., or about 75° C., for a time period of from greater than or equal to about 10 minutes to less than or equal to about 120 minutes, such as for a time of about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 70 minutes, about 80 minutes, about 90 minutes, about 100 minutes, about 110 minutes, or about 120 minutes, to form an aged solution.

The method then comprises drying the aged solution at a temperature of greater than or equal to about 150° C. to less than or equal to about 200° C., such as a temperature of about 150° C., about 160° C., about 170° C., about 180° C., about 190° C., or about 200° C., for a time period of from greater than or equal to about 1 hour to less than or equal to about 48 hours, such as for a time of about 1 hour, about 6 hours, about 12 hours, about 18 hours, about 24 hours, about 30 hours, about 36 hours, about 42 hours, or about 48 hours, to form a glass-ceramic material.

The method then comprises stabilizing the glass-ceramic material by calcining the glass-ceramic material at a temperature of greater than or equal to about 600° C. to less than or equal to about 800° C., such as a temperature of about 600° C., about 625° C., about 675° C., about 700° C., about 725° C., about 750° C., about 775° C., or about 800° C., for a time period of from greater than or equal to about 1 hour to less than or equal to about 96 hours, such as for a time of about 1 hour, about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours, or about 96 hours to form solid glass-ceramic coarse-size particles. The method then comprises mechanically milling, such as by ball milling using, e.g., a zirconia or alumina jar using zirconia balls to form the glass-ceramic is microparticles.

It is understood that the time periods for the aging, drying, and stabilizing can be conducted for longer than the times provided herein. However, the benefits of each step will not substantially increase during such extended periods of time.

The glass-ceramic microparticles comprise composite compositions resulting from combining the bio-active glass solution and the sol-gel porcelain solution to form the composite solution comprising greater than or equal to about 60 vol. % to less than or equal to about 80 vol. % of the bio-active glass solution and greater than or equal to about 20 vol. % to less than or equal to about 40 vol. % of the sol-gel porcelain solution. For example, when the bio-active glass solution comprises 58 wt. % $SiO_2$, 33 wt. % CaO, and 9 wt. % $P_2O_5$ and the sol-gel porcelain solution comprises 60 wt. % $SiO_2$, 6 wt. % CaO, 3 wt. % $P_2O_5$, 14 wt. % $Al_2O_3$, 7 wt. % $Na_2O$, and 10 wt. % $K_2O$, and the resulting combined composite solution comprises 70% of the bioactive glass solution and 30 vol. % of the sol-gel porcelain solution, the resulting bio-active glass-ceramic microparticles comprise 58.6 wt. % $SiO_2$, 24.9 wt. % CaO, 7.2 wt. % $P_2O_5$, 4.2 wt. % $Al_2O_3$, 2.1 wt. % $Na_2O$, and 3 wt. % $K_2O$.

The bio-active glass-ceramic microparticles have at least one crystalline phase and a non-crystalline phase, i.e., an amorphous phase. In certain aspects, the crystalline phase comprises wollastonite, hydroxylapatite, or combinations thereof, among other possible crystalline phases.

The bio-active glass-ceramic microparticles have a diameter (at a widest location, i.e., a longest diameter) of greater than or equal to about 0.5 µm to less than or equal to about 500 µm, greater than or equal to about 0.8 µm to less than or equal to about 100 µm, or greater than or equal to about 0.9 µm to less than or equal to about 20 µm, such a diameter of about 0.5 µm, 0.75 µm, about 0.8 µm, about 0.85 µm about 0.9 µm, about 0.95 µm, about 1 µm, about 2 µm, about 3 µm, about 4 µm, about 5 µm, about 6 µm, about 7 µm, about 8 µm, about 9 µm, about 10 µm, about 20 µm, about 30 µm, about 40 µm, about 50 µm, about 60 µm, about 70 µm, about 80 µm, about 90 µm, about 100 µm, about 150 µm, about 200 µm, about 250 µm, about 300 µm, about 350 µm, about 400 µm, about 450 µm, or about 500 µm.

As discussed above, in some aspects the material comprising BG is bioactive glass microparticles that are optionally doped with silver. A method of forming the bioactive glass nanoparticles is provided by the current technology. The method comprises preparing a first solution (also referred to herein as "Solution A") and a second solution (also referred to herein as "Solution B").

A method for preparing the first solution comprises stirring an organic solvent, such as methanol, at room temperature. The stirring is performed mechanically at about greater than or equal to about 400 rpm to less than or equal to about 500 rpm, such as at about 400 rpm, about 450 rpm, about 500 rpm, about 550 rpm, or about 600 rpm. The method then comprises adding glass precursors to the methanol. The glass precursors can include $SiO_2$, CaO, $P_2O_5$, $Al_2O_3$, and optionally $Ag_2O$, $Na_2O$, $K_2O$, and combinations thereof. The $Ag_2O$ is added when it is desired to form silver-doped bioactive glass nanoparticles. The precursors are added in stoichiometric amounts relative to their desired final concentrations (wt. %).

The method then comprises adding tetraethyl orthosilicate (TEOS) and triethyl phosphate (TEP) to the methanol/precursor solution and mixing the solution for greater than or equal to about 0.5 hours to less than or equal to about 48 hours, such as for about 0.5 hours, about 1 hour, about 6 hours, about 12 hours, about 18 hours, about 24 hours, about 30 hours, about 36 hours, about 42 hours, or about 48 hours.

The method then comprises sequentially adding $Al(NO_3)_3$, $AgNO_3$ (preferably mortar-pulverized into a fine powder), and $Ca(NO_3)_2$. The solution is stirred for after each sequential addition of the $Al(NO_3)_3$, $AgNO_3$, and $Ca(NO_3)_2$ for greater than or equal to about 0.5 hours to less than or equal to about 48 hours, such as for about 0.5 hours, about 1 hour, about 6 hours, about 12 hours, about 18 hours, about 24 hours, about 30 hours, about 36 hours, about 42 hours, or about 48 hours. During this method, the reaction is covered, for example with film and/or foil, to prevent methanol evaporation. The solution is then homogenized by stirring for from about 12 hours to about 48 hours to form the first solution.

A method for preparing the second solution comprises mixing together distilled water, ammonium hydroxide ($NH_4OH$), and ethanol (EtOH).

The method of forming the bioactive glass nanoparticles then comprises pouring the second solution into the first solution, which forms a reaction solution that induces condensation reactions for nanoparticle nucleation. The concentration of TEOS in the reaction solution is greater than or equal to about 0.2 M to less than or equal to about 0.25 M. The methanol in the reaction solution is provided as a MeOH:TEOS ratio of greater than or equal to about 0.005 to less than or equal to about 0.04. The distilled water in the reaction solution is provided as a $H_2O$:TEOS ratio of greater than or equal to about 50 to less than or equal to about 60. The $NH_4OH$ in the reaction solution is provided as a $NH_4OH$:TEOS ratio of greater than or equal to about 2 to less than or equal to about 8. The ethanol in the reaction solution is provided as a EtOH:TEOS ratio of greater than or equal to about 40 to less than or equal to about 60.

After reacting for greater than or equal to about 5 minutes to less than or equal to about 48 hours, nanoparticle precursors are collected by centrifuging at greater than or equal to about 1000 rpm to less than or equal to about 5000 rpm for greater than or equal to about 1 minute to less than or equal to about 5 minutes. It is understood that the centrifugation time is shorter for faster speeds and longer for relatively slower speeds.

Next, the method comprises heat treating the nanoparticle precursors at a temperature of greater than or equal to about 50° C. to less than or equal to about 75° C., such as a temperature of about 50° C., about 55° C., about 60° C., about 65° C., about 70° C., or about 75° C., for a time period of from greater than or equal to about 10 minutes to less than or equal to about 12 hours, such as for a time of about 10 minutes, about 1 hour, about 2 hours, about 3 hours, about 4 hours, about 5 hours, or about 6 hours, to form heat treated nanoparticle precursors.

The method then comprises calcining the heated treated nanoparticle precursors to form calcined bioactive glass nanoparticles. The calcining comprises heating the heat treated nanoparticle precursors to a temperature of greater than or equal to about 600° C. to less than or equal to about 800° C., such as a temperature of about 600° C., about 625° C., about 675° C., about 700° C., about 725° C., about 750° C., about 775° C., or about 800° C., for a time period of from greater than or equal to about 10 minutes to less than or equal to about 6 hours, such as for a time of about 10 minutes, about 0.5 hour, about 1 hour, about 2 hours, about 3 hours, about 4 hours, about 5 hours, or about 6 hours. The heating is performed by heating the heat treated nanoparticles at a rate of greater than or equal to about 1° C./min to less than or equal to about 3° C./min until; the calcining temperature is reached. After calcining, the temperature is decreased to about room temperature at a rate of greater than or equal to about 4° C./min to less than or equal to about 10° C./min.

The method then comprises mortar pulverizing the calcined bioactive glass nanoparticles to form pulverized bioactive glass nanoparticles and washing the pulverized bioactive glass nanoparticles 1 to 5 times with ethanol to form the bioactive glass nanoparticles.

It is understood that the time periods for the centrifuging, heat treating, and calcining can be conducted for longer than the times provided herein. However, the benefits of each step will not substantially increase during such extended periods of time.

The glass nanoparticles are amorphous and comprise compositions resulting from the glass precursors. Exemplary glass nanoparticles comprise 59.6 wt. % $SiO_2$, 25.5 wt. % CaO, 5.1 wt. % $P_2O_5$, 7.2 wt. % $Al_2O_3$, and 2.2 wt. % $Ag_2O$.

The glass nanoparticles have a diameter (at a widest location, i.e., a longest diameter) of greater than or equal to about 0.5 nm to less than or equal to about 500 nm, greater than or equal to about 0.8 nm to less than or equal to about 100 nm, or greater than or equal to about 0.9 nm to less than or equal to about 20 nm, such a diameter of about 0.5 nm, 0.75 nm, about 0.8 nm, about 0.85 nm, about 0.9 nm, about 0.95 nm, about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 60 nm, about 70 nm, about 80 nm, about 90 nm, about 100 nm, about 150 nm, about 200 nm, about 250 nm, about 300 nm, about 350 nm, about 400 nm, about 450 nm, or about 500 nm.

As discussed above, in some aspects the material comprising BG is a bioactive glass-ceramic scaffold that is optionally doped with silver. The current technology provides a method (i.e., a sacrificial template method) of forming the bioactive glass-ceramic scaffold that is three dimensional and that is optionally doped with silver. The method comprises forming the composite solution as described above (with or without the $Ag_2O$) in reference to the method of forming glass-ceramic microparticles. The method then optionally comprises stirring the composite solution (sol gel) for greater than or equal to 10 minutes to less than or equal to about 24 hours to ensure homogeneity.

The method also comprises cutting polyurethane foam into a desired predetermined three-dimensional shape. In various aspects, the polyurethane foam comprises greater than or equal to about 10 pores per inch (ppi) to less than or equal to about 100 ppi, such as about 10 ppi, about 15 ppi, about 20 ppi, about 25 ppi, about 30 ppi, about 35 ppi, about 45 ppi, about 50 ppi, about 55 ppi, about 60 ppi, about 65 ppi, about 70 ppi, about 75 ppi, about 80 ppi, about 85 ppi, about 90 ppi, about 95 ppi, or about 100 ppi. The average pore size is greater than or equal to about 200 μm to less than or equal to about 1000 μm. Optimally, but advantageously, the polyurethane foam is cleaned by immersing the polyurethane foam in an alcohol, such as 200 proof ethanol, followed by ultrasonic cleaning and drying, such as at from greater than or equal to about 30° C. to less than or equal to about 70° C. for greater than or equal to about 2 minutes to less than or equal to about 20 minutes, or until the cleaned polyurethane foam is sufficiently dry.

The method then comprises soaking, such as by dipping or submerging, the polyurethane foam into the composite solution for greater than or equal to about 30 seconds to less than or equal to about 5 minutes. After removing the soaked polyurethane foam from the composite solution, the method comprises compressing the soaked polyurethane foam by greater than or equal to about 25% to less than or equal to about 75% in each principal axis for greater than or equal to about 1 second to less than or equal to about 10 seconds to release excess composite solution and heating the soaked polyurethane foam in an oven set at greater than or equal to about 30° C. to less than or equal to about 75° C. for greater than or equal to about 30 seconds to less than or equal to about 5 minutes or at about ambient or room temperature for greater than or equal to about 12 hours to less than or equal to about 48 hours. The soaking and drying is then repeated at least one additional time and up to about 10 additional times to form a coated substrate. The coated substrate is optionally dried at greater than or equal to about 30° C. to less than or equal to about 75° C. for greater than or equal to about 1 hour to less than or equal to about 48 hours to ensure proper gelling of the composite solution.

The method then comprises burning out the polyurethane foam by heat treating the coated substrate. The heat treating comprises elevating the temperature at a rate of greater than or equal to about 0.5° C./min to less than or equal to about 5° C./min to a heating temperature of greater than or equal to about 300° C. to less than or equal to about 500° C. and maintaining the heating temperature for greater than or equal to about 10 minutes to less than or equal to about 2 hours, or until the polyurethane foam is completely burned out and a scaffold precursor is formed. Optionally without any prior cooling, the method then comprises elevating the temperature at a rate of greater than or equal to about 0.5° C./min to less than or equal to about 5° C./min to a temperature of greater than or equal to about 600° C. to less than or equal to about 800° C. and maintaining the heating temperature for greater than or equal to about 1 hour to less than or equal to about 12 hours to sinter the scaffold precursor and form the bioactive glass-ceramic scaffold or Ag-doped bioactive glass-ceramic scaffold.

The optionally Ag-doped bioactive glass-ceramic scaffold is an interconnected network of struts that define a porous material, such as a mesh. The struts comprise an amorphous, non-crystalline phase and crystalline phases, such as hydroxyapatite, cristobalite, metallic silver phases, and combinations thereof. Additionally, the struts have an average width of greater than or equal to about 50 μm to less than or equal to about 100 μm. The optionally Ag-doped bioactive glass-ceramic scaffold has a porosity (defined as a fraction of the total volume of pores over the total volume of the optionally Ag-doped bioactive glass-ceramic scaffold) of greater than or equal to about 60% to less than or equal to about 99% with an average pore size of greater than or equal to about 250 μm to less than or equal to about 750 μm or greater than or equal to about 400 μm to less than or equal to about 600 μm. The optionally Ag-doped bioactive glass-ceramic scaffold has a compressive strength of greater than or equal to about 3.5 kPa to less than or equal to about 6 kPa (or higher). When doped with Ag, the bioactive glass-ceramic scaffold releases greater than or equal to about 0.1 ppm to less than or equal to about 1.6 ppm $Ag^+$ over a course of from about 10 days to 20 days. Accordingly, the Ag-doped bioactive glass-ceramic scaffold is effective for treating bacteria, including MRSA, without being cytotoxic to human subjects and to non-human mammalian subjects.

The current technology also provides a method, i.e., a fused filament fabrication (FFF) method, of forming a bioactive scaffold that is three dimensional and that is optionally doped with silver as the material comprising BG. The bioactive scaffold is an optionally Ag-doped glass-ceramic scaffold or an optionally Ag-doped glass scaffold. The method comprises obtaining particles, the being the optionally Ag-doped glass-ceramic microparticles prepared by the above method, the optionally Ag-doped glass nanoparticles prepared by the above method, or a combination thereof, and introducing the particles and a binder system into an extruder, such as a modified twin-screw extruder, to form a filament composition. The extruder comprises a barrel kept at a temperature of greater than or equal to about 150° C. to less than or equal to about 250° C. The binder system comprises a polyolefin, an elastomer, and a surfactant. The surfactant has a concentration of greater than or equal to about 3 vol. % to less than or equal to about 10 vol. % in the binder system and the particles have a concentration of greater than or equal to about 30 vol. % to less than or equal to about 70 vol. % in the filament composition. Non-limiting examples of polyolefins include poly(methyl methacrylate) (PMMA), polyethylene (e.g., high density polyethylene (HDPE)), polypropylene, acrylonitrile butadiene styrene (ABS), polycarbonate (PC), polylactic acid (PLA), PC/ABS, polyethylene terephthalate (PET), polyphenylsulfone (PPSF), polystyrene (such as high impact polystyrene (HIPS)), polyether ether ketone (PEEK), polytetrafluoroethylene (PTFE), and combinations thereof. Non-limiting examples of elastomers include thermoplastic polyurethanes (TPU), ethylene propylene diene monomer (EPDM), thermoplastic polyolefin (TPO), and combinations thereof. The polyolefin and elastomer are provided in a polyolefin:elastomer ratio of from about 90:10 to about 50:50. However, the polyolefin:elastomer ratio may be extended beyond this range. Non-limiting examples of surfactants include saturated fatty acids, such as stearic acid, arachidic acid, and combinations thereof (as non-limiting examples), unsaturated fatty acids, such as oleic acid, palmitoleic acid, and combinations thereof (as non-limiting examples), and combinations thereof. The extruder has a mixing speed of greater than or equal to about 25 rpm to less than or equal to about 100 rpm (or higher). The method then comprises extruding the filament composition as a filament having a diameter of greater than or equal to about 1 mm to less than or equal to about 3 mm and spooling the filament in preparation of three-dimensional (3D) printing.

The method further comprises generating a computerized model, i.e., a computer-aided design (CAD) model, of a scaffold having a predetermined 3D shape defined by a network or interconnected struts and having a predetermined porosity and average pore size. In certain aspects, the porosity can be greater than or equal to about 60% to less than or equal to about 90%, and the average pore size can be greater than or equal to about 300 μm to less than or equal to about 800 μm. Next, the method comprises printing a green scaffold having the predetermined 3D shape using a 3D printer and the spooled filament using a nozzle temperature of greater than or equal to about 150° C. to less than or equal to about 200° C. The method also comprises transferring the green scaffolds to a heating chamber, such as a furnace, for debindering (pyrolyzing) at greater than or equal to about 450° C. to less than or equal to about 600° C. and sintering, at greater than or equal to about 800° C. to less than or equal to about 1200° C., thus forming the optionally Ag-doped bioactive glass-ceramic scaffold or the optionally Ag-doped bioactive glass scaffold. In various aspects, a scaffold is formed that comprises, consists essentially of, or consists of the optionally Ag-doped bioactive glass-ceramic. In other words, the optionally Ag-doped bioactive glass scaffold may include only the Ag-doped glass-ceramic, and be substantially free of any other components, such as polyolefin, elastomer, and/or fatty acid. As used here, "substantially free" means that the other components are present in a concentration of less than or equal to about 20 wt. %, less than or equal to about 15 wt. %, less than or equal to about 10 wt. %, less than or equal to about 5 wt. %, or less than or equal to about 1 wt. %, The characteristics of the bioactive scaffold are dependent on the predetermined 3D shape. However, the bioactive scaffold can have the porosity and average pore diameter of any scaffold described herein.

The current technology also provides a method, i.e., a solution method, of forming a bioactive scaffold as the material comprising BG. The bioactive scaffold is three dimensional and is optionally doped with silver as the bioactive material. The bioactive scaffold is an optionally Ag-doped glass-ceramic scaffold or an optionally Ag-doped glass scaffold The method comprises obtaining particles, the particles being the optionally Ag-doped glass-ceramic microparticles prepared by the above method, the optionally Ag-doped glass nanoparticles prepared by the above method, or a combination thereof. The method then optionally comprises stirring the composite solution (sol gel) for greater than or equal to 10 minutes to less than or equal to about 24 hours to ensure homogeneity.

The method also comprises cutting polyurethane foam into a desired predetermined three-dimensional shape. In various aspects, the polyurethane foam comprises greater than or equal to about 10 pores per inch (ppi) to less than or equal to about 100 ppi, such as about 10 ppi, about 15 ppi, about 20 ppi, about 25 ppi, about 30 ppi, about 35 ppi, about 45 ppi, about 50 ppi, about 55 ppi, about 60 ppi, about 65 ppi, about 70 ppi, about 75 ppi, about 80 ppi, about 85 ppi, about 90 ppi, about 95 ppi, or about 100 ppi. The average pore size is greater than or equal to about 200 μm to less than or equal to about 1000 μm. Optionally, but advantageously, the polyurethane foam is cleaned by immersing the polyurethane foam in an alcohol, such as 200 proof ethanol, followed by ultrasonic cleaning and drying, such as at from greater than or equal to about 30° C. to less than or equal to about 70° C. for greater than or equal to about 2 minutes to less than or equal to about 20 minutes, or until the cleaned polyurethane foam is sufficiently dry.

The method also comprises preparing a particle slurry by combining water, a polymer, and the particles at a water:polymer:particles ratio of 1.5-2:1.5-2:1. As a non-limiting example, the polymer can be poly(vinyl) alcohol (PVA).

The method then comprises soaking, such as by dipping or submerging, the polyurethane foam into the particle slurry for greater than or equal to about 20 seconds to less than or equal to about 2 minutes. After removing the soaked polyurethane foam from the particle slurry, the method comprises compressing the soaked polyurethane foam by greater than or equal to about 25% to less than or equal to about 75% in each principal axis for greater than or equal to about 1 second to less than or equal to about 10 seconds to release excess particle slurry and maintaining the soaked polyurethane foam at greater than or equal to about 30° C. to less than or equal to about 75° C. for greater than or equal to about 30 seconds to less than or equal to about 5 minutes or at about ambient or room temperature for greater than or equal to about 12 hours to less than or equal to about 48 hours to form a coated foam.

The method then comprises burning out the polyurethane foam by heat treating the coated substrate. The heat treating comprises elevating the temperature at a rate of greater than or equal to about 0.5° C./min to less than or equal to about 5° C./min to a heating temperature of greater than or equal to about 300° C. to less than or equal to about 500° C. and maintaining the heating temperature for greater than or equal to about 10 minutes to less than or equal to about 2 hours, or until the polyurethane foam is completely burned out and a scaffold precursor is formed. Optionally without any prior cooling, the method then comprises elevating the temperature at a rate of greater than or equal to about 0.5° C./min to less than or equal to about 15° C./min to a temperature of greater than or equal to about 800° C. to less than or equal to about 1200° C. and maintaining the heating temperature for greater than or equal to about 1 hour to less than or equal to about 12 hours to sinter the scaffold precursor and form the bioactive scaffold.

The optionally bioactive scaffold is an interconnected network of struts that define a porous material, such as a mesh. When the bioactive scaffold is the optionally Ag-doped glass-ceramic scaffold, the struts comprise an amorphous, non-crystalline phase and crystalline phases, such as hydroxyapatite, cristobalite, metallic silver, pseudowollastonite, wollastonite, phases, and combinations thereof. When the bioactive scaffold is the optionally Ag-doped glass scaffold, the struts comprise an amorphous, non-crystalline phase. The struts have an average width of greater than or equal to about 50 μm to less than or equal to about 150 μm. The bioactive scaffold has a porosity (defined as a fraction of the total volume of pores over the total volume of the bioactive scaffold) of greater than or equal to about 60% to less than or equal to about 99% with an average pore size of greater than or equal to about 250 μm to less than or equal to about 750 μm. The bioactive scaffold has a compressive strength of greater than or equal to about 0.1 MPa to less than or equal to about 2 MPa (or higher).

As discussed above, in some aspects the material comprising BG is a bioactive glass-ceramic film that is optionally doped with silver. The current technology also provides a method of synthesizing the bioactive glass-ceramic film that is optionally doped with silver. The method comprises preparing a first solution and a second solution. The first solution and the second solution are equivalent to the bioactive glass solution and porcelain solution, respectively, described above in regard to the method of forming glass-ceramic microparticles.

The method then comprises consecutively adding to the first solution from about 1.5 N or about 2.5 N nitric acid (in water), tetraethyl orthosilicate (TEOS), triethyl phosphate (TEP), aluminum nitrate nonahydrate ($Al(NO_3)_3 \cdot 9H_2O$), silver nitrate ($AgNO_3$), calcium nitrate tetrahydrate ($Ca(NO_3)_2 \cdot 4H_2O$), and sodium nitrate ($NaNO_3$) at a respective total molar ratio of 7-8:0.02-0.06:1:0.05-0.15:0.05-0.1:0.01-0.03:0.25-0.75:0.025-0.075 for a total water:TEOS ratio of 5-30:1 with greater than or equal to about 1 minute to less than or equal to about 120 minutes of stirring after each individual and sequential addition.

The method then comprises consecutively adding to the second solution from about 1.5 N or about 2.5 N nitric acid (in water), tetraethyl orthosilicate (TEOS), triethyl phosphate (TEP), and calcium nitrate tetrahydrate ($Ca(NO_3)_2 \cdot 4H_2O$) at a respective total molar ratio of 7-8:0.02-0.06: 1:0.25-0.75 with greater than or equal to about 1 minute to less than or equal to about 120 minutes of stirring after each individual and sequential addition.

After the final addition to the first and second solutions, the first and second solutions are stirred for greater than or equal to about 30 minutes to less than or equal to about 24 hours. The method then comprises combining the first solution with the second solution to form a precursor solution, and stirring the precursor solution for greater than or equal to about 30 minutes to less than or equal to about 24 hours. The precursor solution comprises greater than or equal to about 60 vol. % to less than or equal to about 80 vol. % of the first solution and greater than or equal to about 20 vol. % to less than or equal to about 40 vol. % of the second solution.

Next, the method comprises coating a surface of a substrate with the precursor solution. The surface can comprise steel, stainless steel, a metal, a metal alloy, or a polymer (i.e., plastic, rubber, or a combination thereof). Also, the surface can be flat and planar, flat and curved, or irregularly shaped. The substrate can be a medical prosthesis or implant, such a knee implant, a hip implant, a shoulder implant, a dental implant, a stent, a catheter, or hardware for implanting as non-limiting examples. The coating is performed by applying the precursor solution to the implant by spin coating, doctor blading, pouring, spreading, brushing, dipping, spraying, or pipetting, as non-limiting examples.

Next, the process comprises performing heat treatment on the coated substrate. The heat treatment comprises elevating a temperature from room or ambient temperature at a rate of greater than or equal to about 1° C./min to less than or equal to about 10° C./min to a first heating temperature of greater than or equal to about 100° C. to less than or equal to about 150° C. and maintaining the first heating temperature for greater than or equal to about 1 hour to less than or equal to about 24 hours. Optimally without any prior cooling, the heat treatment then comprises elevating the temperature at a rate of greater than or equal to about 0.25° C./min to less than or equal to about 3° C./min to a second heating temperature of greater than or equal to about 400° C. to less than or equal to about 600° C. and maintaining the second heating temperature for greater than or equal to about 1 hour to less than or equal to about 10 hours. Then the method comprises cooling the heated substrate to room or ambient temperature at a rate of greater than or equal to about 1° C./min to less than or equal to about 10° C./min to form the optionally Ag-doped bioactive glass-ceramic film on the substrate.

The optionally Ag-doped bioactive glass-ceramic film has a thickness that depends on the amount of precursor solution applied to the substrate. In various aspects, the thickness, which may be an average thickness, is greater than or equal to about 0.1 µm to less than or equal to about 50 µm. The film can be substantially uniform, having a thickness that varies by less than or equal to about 20%, less than or equal to about 15%, or less than or equal to about 10% of an average thickness of the optionally Ag-doped bioactive glass-ceramic film, non-uniform, having a thickness that varies by greater than or equal to about 20% of an average thickness of the optionally Ag-doped bioactive glass-ceramic film, it the film can have at least one uniform portion and at least one non-uniform portion.

Embodiments of the present technology are further illustrated through the following non-limiting examples.

Example 1

Summary

Here, a strategy to combat methicillin-resistant *Staphylococcus aureus* (MRSA) via the reactivation of inert antibiotics by expanding their spectrum of action is described. This strategy utilizes multifunctional, bioactive glass-ceramic particles with antibacterial properties in conjunction with various antibiotics to kill MRSA. Specifically, sol-gel derived silver-doped bioactive glass particles (Ag-BG) combined with antibiotics that MRSA resists, such as oxacillin or fosfomycin, significantly decrease the viability of the MRSA. Ag-BG also potentiates the activity of vancomycin on static bacteria, which are typically resistant to this antibiotic. Notably, the synergistic activity is restricted to cell-envelope acting antibiotics, as Ag-BG supplementation did not increase the efficacy of gentamicin. Bacteria viability assays and electron microscopy images demonstrate that Ag-BG synergize to restore antibacterial activity to antibiotics that MRSA resists. Null cytotoxicity, together with the known regenerative properties of the glass-ceramic and the unique antibacterial properties that are observed when they are combined with antibiotics, make this multifunctional system a promising approach for healing infected tissue.

Introduction

Here, the capacity of solution-gelation (sol-gel) derived, silver doped bioactive glass-ceramic microparticles (Ag-BG) to restore the sensitivity of antibiotics that MRSA resists is investigated. Silver ions incorporated within the glass-ceramic structure are selected because of the broad spectrum of their action that allows for multiple inhibition mechanisms. Additionally, silver has a very broad spectrum of action. Bioactive glasses with different compositions have been studied in vivo before for their anti-MRSA properties. For example, the ability of a bioactive glass to treat osteomyelitis on human patients has been explored. Additionally, borate bioactive glass with silver has been used as a coating for titanium plates to eradicate a MRSA infection in tibial bone fracture on rabbits. Although there is a broad background on the antimicrobial properties of different bioactive glasses and glass-ceramics, the capability of a biomaterial to restore the sensitivity of antibiotics that bacteria resist has yet to be explored.

Here, cell wall active antibiotics, each with a unique mechanism of action are assessed including the methicillin derivative oxacillin, fosfomycin, and vancomycin. MRSA encodes oxacillin and fosfomycin resistance mechanisms that are corrupted and overcome by Ag-BG supplementation. Vancomycin requires cell growth for its activity; however, it is observed that Ag-BG particles induce vancomycin killing in non-replicating cells. Gentamicin that acts on the ribosomes of the bacteria and inhibits translation is also considered. Interestingly, Ag-BG supplementation did not enhance the antimicrobial activity of gentamicin. The synergy between Ag-BG particles and each antibiotic is different in terms of the degree of bactericidal activity and bacteria morphology. This demonstrates that the mechanism of the synergistic action is dependent on the combination. This strategy of antibiotic administration that overcomes antibiotic resistance of MRSA and other multi-drug resistant bacteria is described further below.

Materials and Methods

Synthesis of the silver-doped bioactive-glass ceramic particles (Ag-BG). The fabrication of the Ag-BG microsize particles (less than 20 μm) with a composition of $SiO_2$ 58.6-CaO 24.9-$P_2O_5$ 7.2-$Al_2O_3$ 4.2-$Na_2O$ 1.5-$K_2O$ 1.5-$Ag_2O$ 2.1 wt. % is performed by the solution-gelation (sol-gel) technique applying an acid catalysis. Briefly, the fabrication protocol is based on mixing the solution stage of the 58S sol-gel bioactive glass (in the system $SiO_2$ 58-CaO 33-$P_2O_5$ 9 wt. %) with the respective solution stage of another sol-gel glass in the system $SiO_2$ 60-CaO 6-$P_2O_5$ 3-$Al_2O_3$ 14-$Na_2O$ 5-$K_2O$ 5-$Ag_2O$ 7 wt. %. After extended stirring, the final homogeneous solution follows a specific heat treatment comprising aging at 60° C., drying at 180° C., and stabilization up to 700° C. Finally, the fabricated material is received in powder form with a particle size of less than 20 μm. The same fabrication process is applied for the fabrication of Ag-free bioactive glass (BG) having the same composition as Ag-BG but without incorporating $Ag_2O$. In particular, BG is fabricated in the system: $SiO_2$ 58.6-CaO 24.9-$P_2O_5$ 7.2-$Al_2O_3$ 4.2-$Na_2O$ 2.1-$K_2O$ 3 wt. %. The powder is disinfected via UV radiation prior to the co-culture with MRSA.

Antibiotics.

Oxacillin (molecular formula: $C_{19}H_{18}N_3O_5SNa \cdot H_2O$, Oxacillin sodium) and Fosfomycin (molecular formula: $C_7H_{18}NO_7P$, Fosfomycin tromethamine) are selected based on the high degree of resistance demonstrated by MRSA. Oxacillin and fosfomycin are used at 0.1 and 0.05 μg/ml, respectively—a concentration that is considerably lower than their MIC. Vancomycin (molecular formula: $C_{66}H_{75}C_{12}N_9O_{24} \cdot HCl$, Vancomycin hydrochloride) is selected due to a mechanism of action that is dependent on cell growth. MRSA is susceptible to 0.47 μg/ml of vancomycin when cultured in tryptic soy broth (TSB). However, exposure to vancomycin in growth arrested conditions, such as suspension in phosphate buffered saline (PBS), enhances tolerance to the antibiotic. Cells are exposed to 0.5 mg/ml vancomycin in PBS. Thus, the selected concentrations of all three antibiotics do not reduce viability of MRSA suspended in PBS. Gentamicin (molecular formula: $C_{21}H_{43}N_5O_7$, Gentamycin Sulfate) is used at 0.01 μg/ml, which, under the experimental conditions, does not inhibit significantly bacterial viability. All antibiotics are purchased from Sigma Aldrich in powder USP Reference Standard and are used without further purification.

Antibacterial Test.

All experiments are conducted using the laboratory derived methicillin-resistant S. aureus USA300 JE2. Cells are streaked for isolation on tryptic soy agar (TSA) and cultured at 37° C. overnight. An isolated colony is then grown in broth (TSB), shaking at 225 rpm at 37° C. overnight. Next, 1 mL solution of MRSA in PBS, normalized to an optical density ($OD_{600\ nm}$) equal to 1 (equivalent to $10^8$ CFU/mL) is prepared. The bacterial suspension is mixed in a 1:1 volume ratio, with each of the solutions containing twofold the final concentration of Ag-BG, antibiotic, or the indicated Ag-BG/antibiotic combination. An untreated control is also prepared by mixing the bacterial suspension in a 1:1 volume ratio with PBS.

Bacterial suspensions are placed in a 37° C. incubator for the indicated time. At each time point, an aliquot of the bacterial suspension is removed to enumerate colony forming units (CFU) of the bacteria via serial dilution and plating on TSA. All plates are incubated at 37° C. Quantification of CFU are performed in biological and technical triplicate. Measurements are repeated three times. Standard deviation is indicated as error bars. Statistical analysis is performed using the paired Student's t-test, two tailed, n=9 and p<0.05.

The measurements of the pH values for the Ag-BG and Ag-BG/vanc particles are performed in PBS and monitored up to 48 hours. Samples are prepared containing 2.5 mg of Ag-BG with 0.5 mg of vancomycin for the Ag-BG/vanc in 1 mL of PBS pH=7.4 and are placed under 37° C. to simulate the conditions of the antibacterial assays.

Transmission Electron Microscopy (TEM).

After 24 hours of incubation, solutions are prepared for studies with TEM to observe the morphology and ultrastructural properties of bacteria in each of the tested groups. The cultures are centrifuged and fixed using Karnovsky fixative, consisting of 2.5% glutaraldehyde, 2.5% paraformaldehyde and 0.1 M cacodylate buffer dissolved in deionized water. In the cases of the tested groups with Ag-BG particles, the particles are removed by allowing them to settle to the bottom of the Eppendorf microcentrifuge tubes before centrifugation and fixation. Bacteria pellets are suspended and incubated in fixative for 2 hours at room temperature. Next, the suspensions are centrifuged to remove the fixative. To capture bacteria in a solid matrix, a drop of a 2% agarose deionized water solution is added to the cell pellet. After the agarose solidifies, the matrix is washed three times at room temperature for 15 minutes with 0.1 M cacodylate buffer. A solution of 2% osmium tetroxide is used to stain the bacterial cells for 1 hour at the post-fixation stage. Subsequently, the cubes are washed with deionized water. Dehydration is done by a series of different concentrations of acetone: 25%, 50%, 75%, and 100%. Next, Spurr resin is infiltrated in a series of dilutions in acetone (acetone: resin): 3:1, 1:1, and 100% resin for two days. The cells are embedded in 100% Spurr resin at 60° C. for 24 hours and then, thin sections of less than 100 nm thickness are obtained by ultramicrotome (RMC MYX ultramicrotome) with glass knives and are mounted in bare copper grids. Positive staining is done with 2% uranyl acetate for 7 minutes and lead citrate for 3 minutes. Finally, samples are observed at 100 kV in a JEOL 100CX microscope.

Scanning Electron Microscopy (SEM).

Bacterial morphology upon exposure to Ag-BG particles is studied using SEM. Cells are prepared after 12 hours of exposure. In this case, the Ag-BG particles remain in the solution with the cells and are fixed using 2.5% glutaraldehyde, 2.5% paraformaldehyde, and 0.1 M cacodylate buffer dissolved in deionized water. Cover slips are prepared with one drop of 1% poly-L-Lysine to capture the cells. One drop of the fixed culture suspension is placed on the cover slip and washed after 5 minutes of incubation with water. Subsequently, the samples are dehydrated with a dilution series of ethanol (25%, 50%, 75%, and 95%), followed by three washes in 100% ethanol. Incubations of 5 minutes are performed between each step. Samples are critical point dried (Leica Microsystem model EM CPD300) using liquid carbon dioxide as transitional fluid. Samples are mounted in aluminum stubs using an epoxy glue (System Three Quick Cure 5 purchased from Systems Three Resins, Inc.). Finally, they are coated with 10 nm of osmium gas and examined at 5 kV using the SEM microscope (JEOL JSM-7500F).

Results

Ag-BG Elicit Antimicrobial Activity.

Figure 1A:
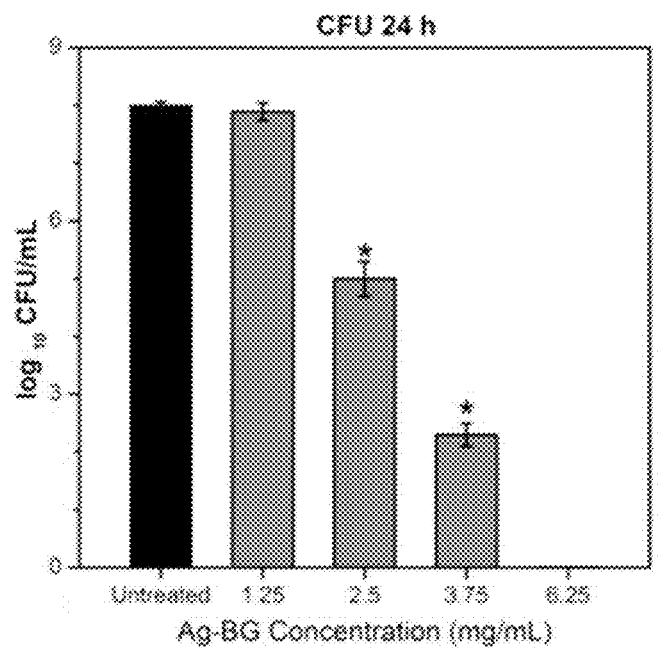
Figure 1B:
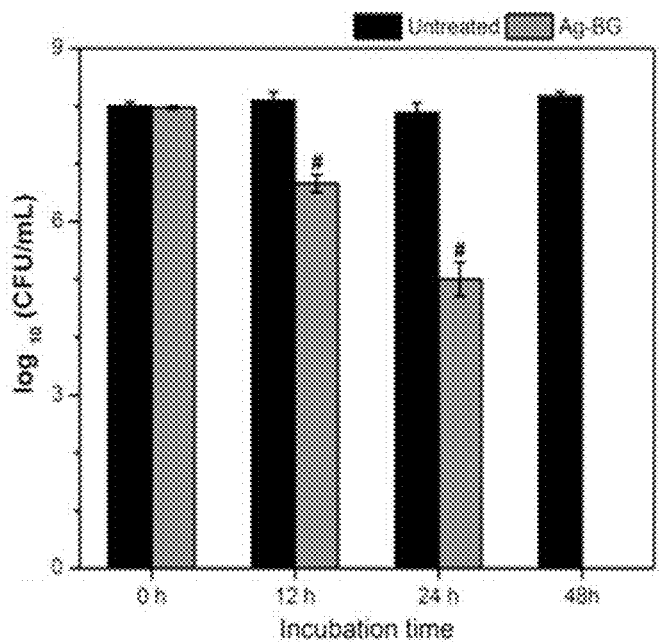

To determine the basal level of Ag-BG antibacterial activity, increasing concentrations of particles are incubated with bacteria as shown in FIG. 1A. The minimum inhibitory concentration (MIC) after 24 hours of incubation is 2.5 mg/ml, and the number of CFUs are below the limit of detection upon exposure to 6.25 mg/ml Ag-BG (FIG. 1A, limit of detection 100 CFU). Ag-BG antibacterial effect is also time dependent, as the viability of cells in presence of the MIC (2.5 mg/ml) of Ag-BG significantly decrease after an additional 24 hours of exposure as shown in FIG. 1B. Notably, 48 hours of incubation is sufficient to reduce CFUs below the limit of detection (FIG. 1B, limit of detection 100 CFU), indicating that Ag-BG is bactericidal to MRSA. Based on these results, 2.5 mg/ml of Ag-BG is used for the remainder of the example.

Antibiotics Targeting the Cell Envelope.

Ag-BG Restores Antibacterial Activity of Oxacillin Against MRSA.

Figures 2A, 2B, 2C, 2D, 2E, 2F, 2G, 2H, 2I:
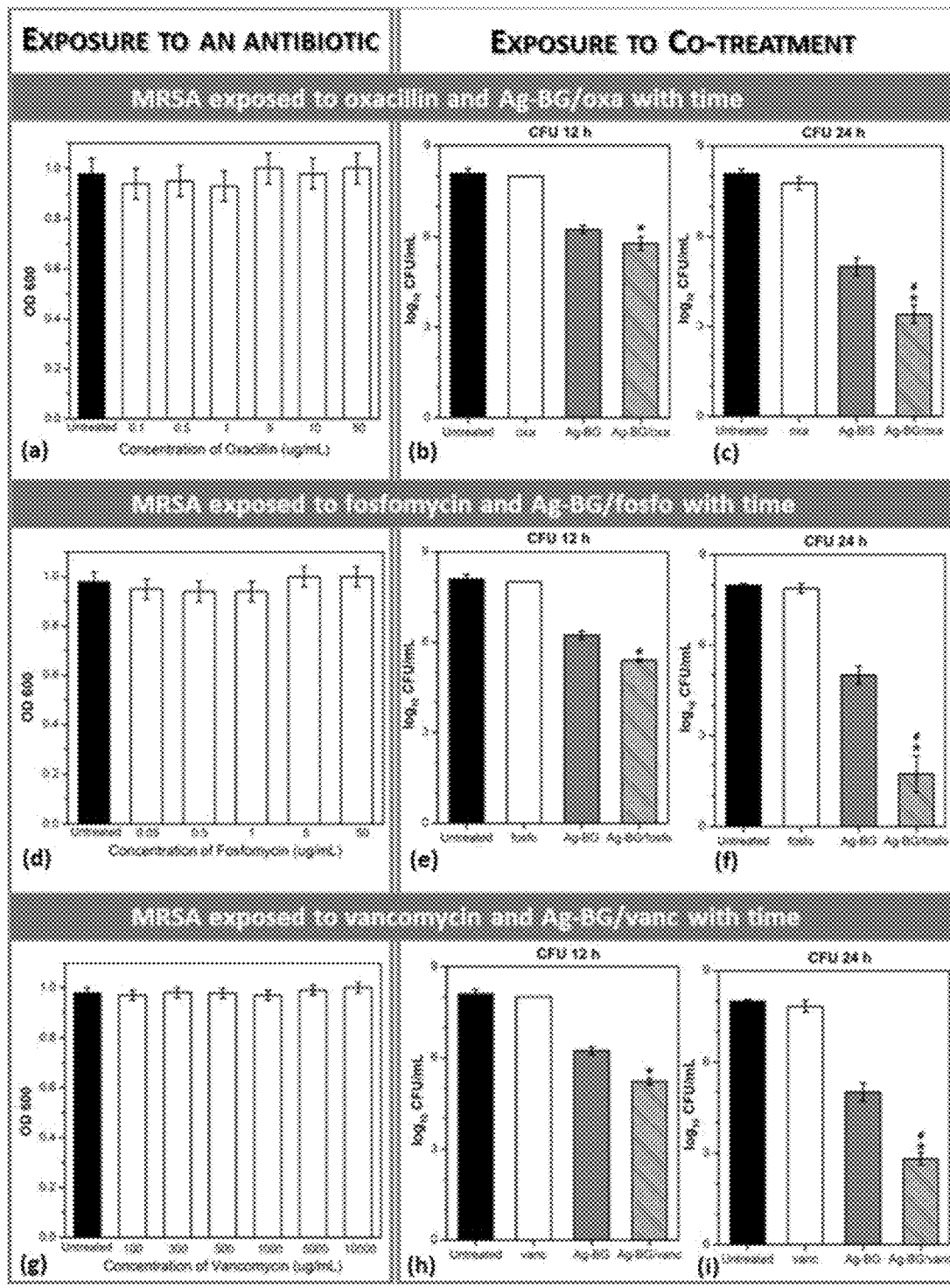

Oxacillin is a β-lactam antibiotic that acts by blocking the action of the penicillin-binding proteins (PBPs) that assemble the cell wall. MRSA strains, such as the one used here, are resistant to oxacillin. Consistent with this, no demonstrable bacterial inhibition is observed upon exposure to 0.1, 0.5, 1, 5, 10, or 50 µg/ml of oxacillin after 24 hours as shown in FIG. 2A. However, concomitant exposure to 0.1 µg/ml oxacillin and 2.5 mg/ml Ag-BG (Ag-BG/oxa) enhances bactericidal activity over time (FIGS. 2B and 2C). The Ag-BG/oxa combination inhibits bacteria at 12 hours and 24 hours significantly better than untreated cells or cells exposed to oxacillin or Ag-BG alone for both time points. There is also a significant increase of MRSA inhibition for Ag-BG/oxa after 24 hours versus 12 hours.

Ag-BG Restores Antibacterial Activity of Fosfomycin Against MRSA.

Fosfomycin inhibits the UDP-N-acetylglucosamine-3-enolpyruvyltransferase, MurA, an essential enzyme required for peptidoglycan and cell wall synthesis. Most strains of $S.$ $aureus$ resist fosfomycin by inactivating the drug. In keeping with this, the strain here exposed in the presence of 0.05, 0.5, 1, 5, and 50 µg/ml of fosfomycin for 24 hours as shown in FIG. 2D. However, despite the resistance, inhibition of MRSA is achieved after 12 hours of administrating the antibiotic with Ag-BG (Ag-BG/fosfo) as shown in FIG. 2E. The combination consists of 0.05 µg/ml of fosfomycin and 2.5 mg of Ag-BG. Additionally, the bactericidal activity of Ag-BG/fosfo shows time dependent efficacy (FIG. 2F) and significantly higher inhibition than the untreated controls and cells treated with only fosfomycin or Ag-BG.

Ag-BG Enhances Bactericidal Activity of Vancomycin by Reducing the Viability of Static MRSA.

The glycopeptide vancomycin blocks cell wall synthesis by binding and occluding access to the D-Ala-D-Ala termini of Lipid II. Thus, transport of new cell wall precursors from the cytoplasm to the peptidoglycan is inhibited. In static conditions where cells are not growing, vancomycin is not lethal to MRSA, even at concentrations as high as 10 mg/ml (FIG. 2G). However, when combined with 2.5 mg/ml Ag-BG particles, bacterial viability is significantly decreased upon exposure to 0.5 mg/ml of vancomycin (Ag-BG/vanc) for 12 hours (FIG. 2H). Similar to the other antibiotic combinations tested, Ag-BG/vanc shows higher bacteria inhibition compared to the other groups that improve with increasing culture time (FIG. 2I).

pH Values are not Cytotoxic.

Figure 3:
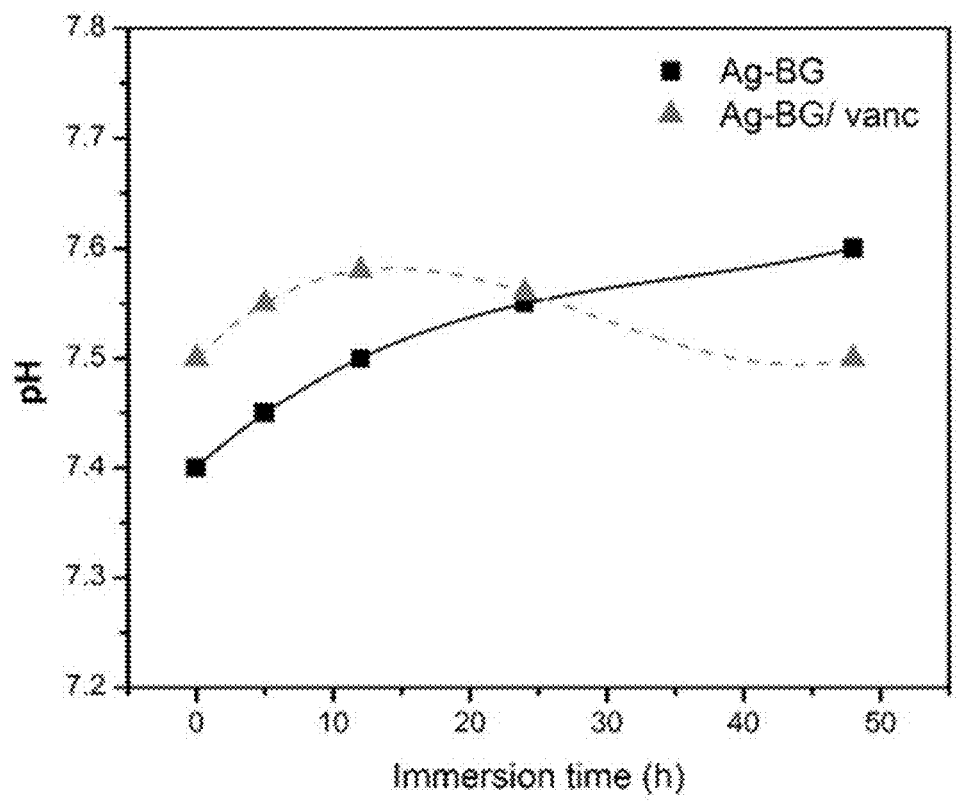

The changes in the pH values with the time are observed for Ag-BG particles alone and combined with an antibiotic (vancomycin). The pH for both cases remains constantly at neutral values (approximately 7.5) for up to 48 hours as shown in FIG. 3.

Antibiotic Targeting the Ribosomes.

Ag-BG does not Synergize with Gentamicin Against MRSA.

Figures 4A, 4B, 4C:
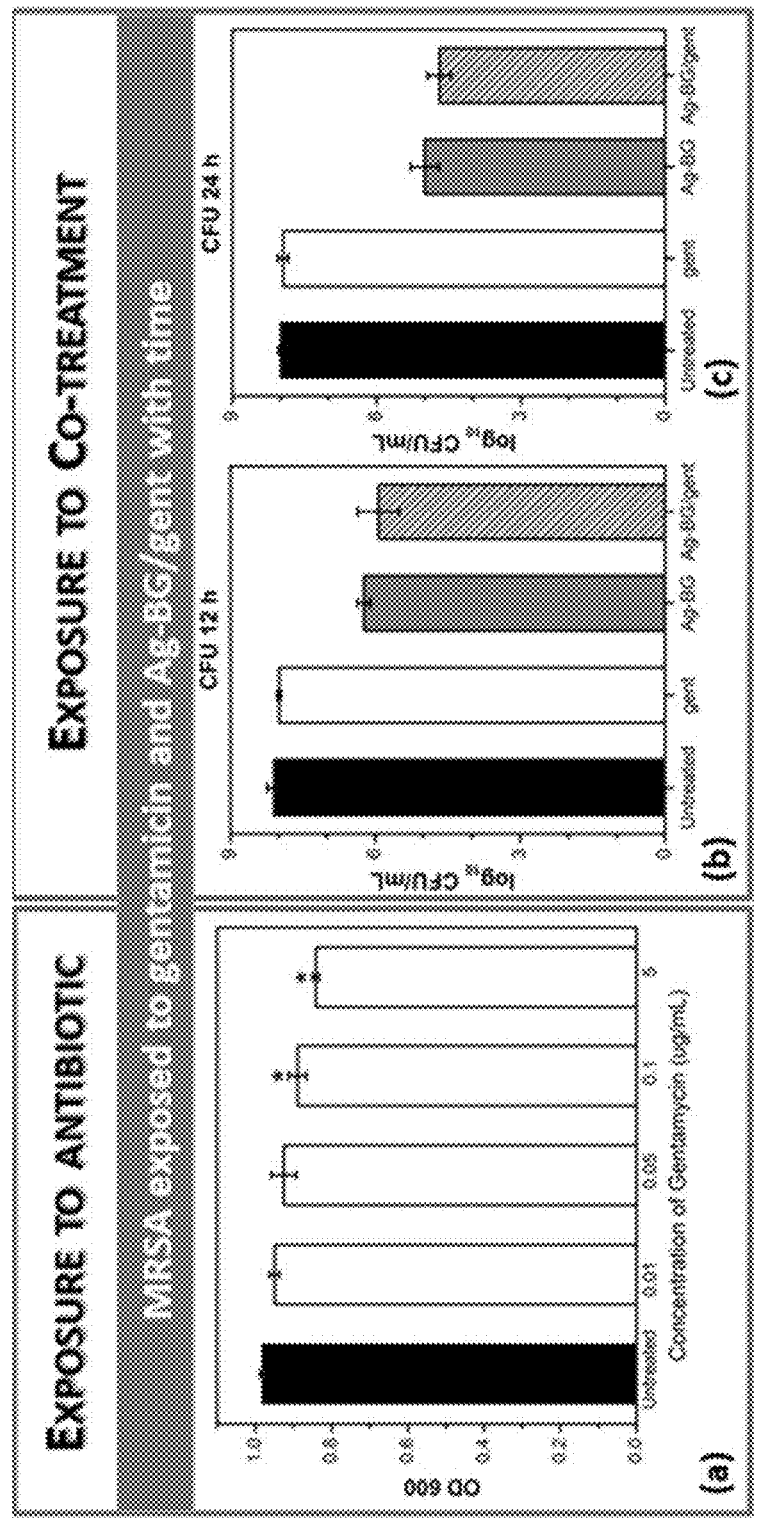

To determine whether Ag-BG synergizes with antibiotics that have targets beyond the cell envelope, the aminoglycoside gentamicin is tested. Gentamicin inhibits protein synthesis by binding the ribosomes. Gentamicin administrated in static conditions inhibits significant MRSA at concentrations higher than 0.1 µg/ml (FIG. 4A). Compared to the cell wall active antibiotics, no significant synergy between Ag-BG (2.5 mg/ml) and gentamicin (0.01 µg/ml) is observed after 12 hours and 24 hours as shown in FIGS. 4B and 4C.

Understanding the Effect of Ag Ions on the Antibacterial Properties of Ag-BG and on the Synergism with Fosfomycin.

Figure 5:
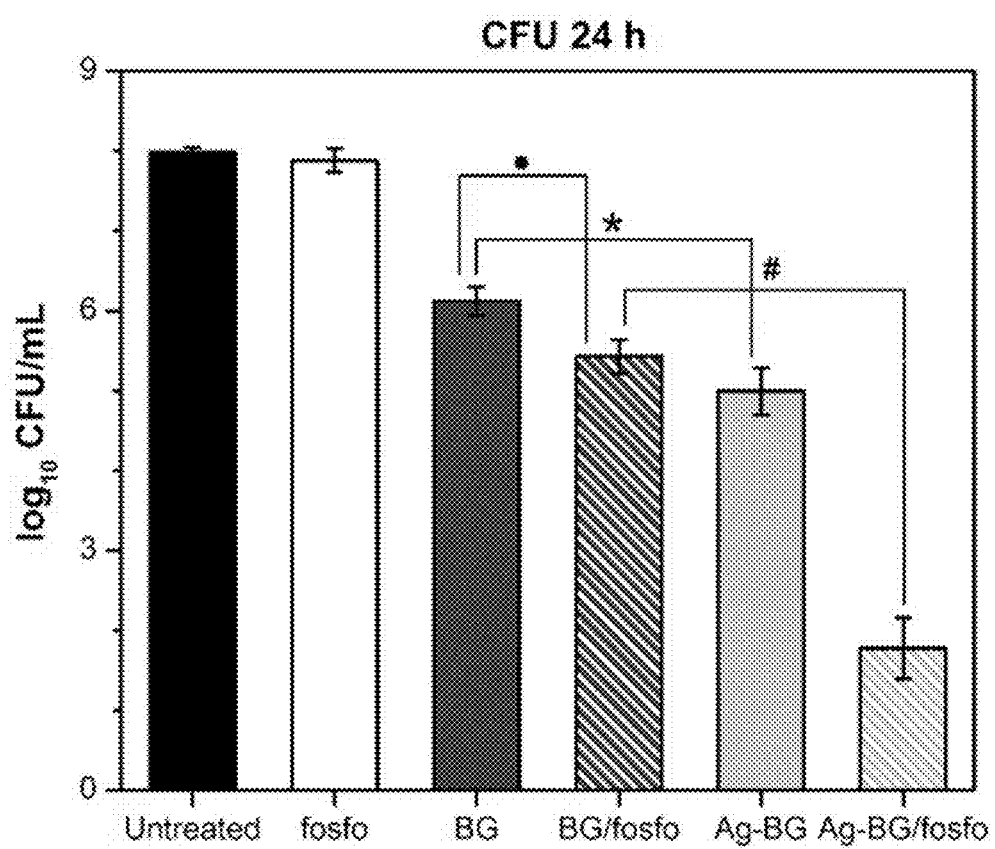

The antibacterial activity of the bioactive glass-ceramic without Ag ions (BG) is assessed by exposing MRSA to 2.5 mg/ml of BG. After 24 hours of exposure, BG effectively inhibits MRSA. However, Ag-BG is considerably more lethal to bacterial cells than BG alone (as shown in FIG. 5, where the statistically significant difference is marked with *). Also, BG combined with 0.05 µg/ml of fosfomycin demonstrates synergy, leading to a statistically significant inhibition (as shown in FIG. 5, marked with •). However, Ag-BG/fosfo inhibits significantly better than BG/fosfo (as shown in FIG. 5, marked with #). These findings demonstrate that the antibacterial activity is not limited to Ag ions, but they hold an effective role to Ag-BG bactericidal action.

High Resolution Imaging of MRSA after Exposure to Different Groups.

Figures 6A, 6X:
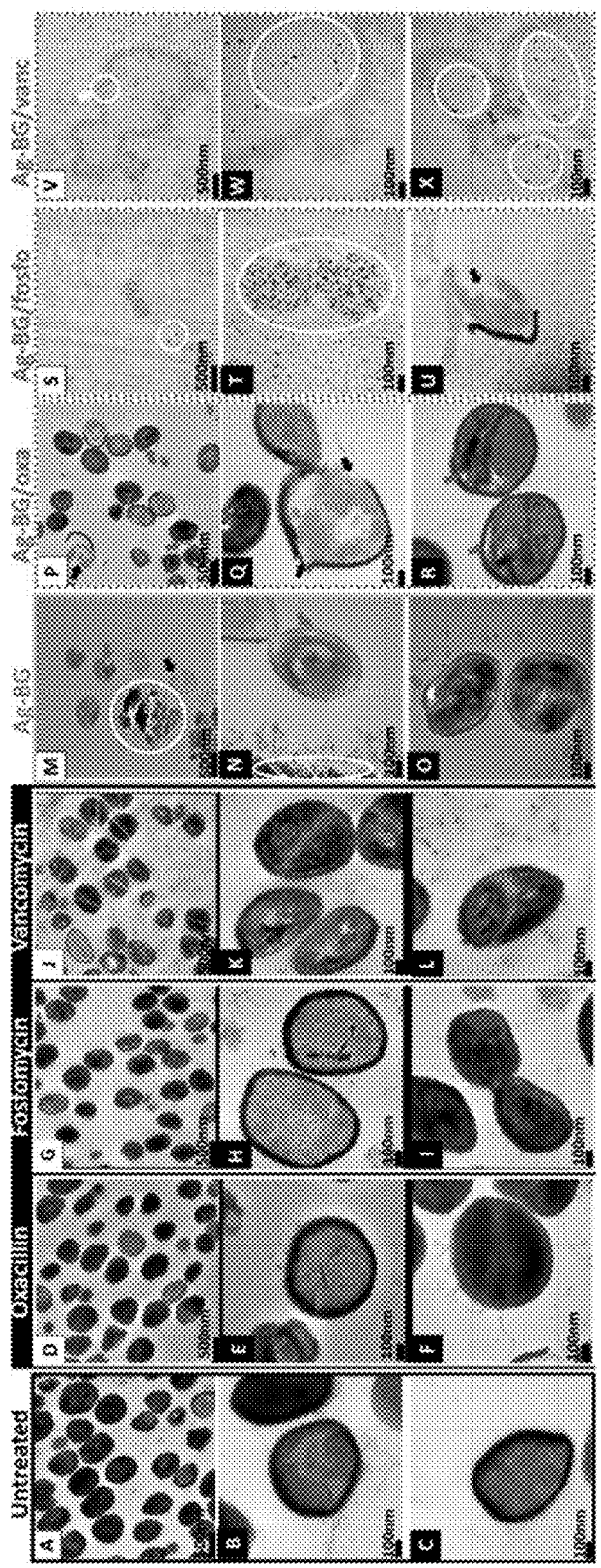

Bacterial cells are imaged using TEM after 24 hours exposure to the different antibiotic and/or Ag-BG combinations (FIGS. 6A-6X). MRSA is a cocci-shaped bacterium with diameter of approximately 500 nm. Cells demonstrate a uniformly thick cell wall well attached to the cytoplasm (FIGS. 6A, 6B, and 6C). The homogeneity of the electron-density of the cell wall, as well as the smooth transition from the wall to cytoplasm, highlights the intact cells. This is also the representative bacteria status observed for MRSA exposed to each of the antibiotics alone at a certain concentration. In particular, MRSA exposed to oxacillin alone (FIGS. 6D, 6E, and 6F), fosfomycin alone (FIGS. 6G, 6H, and 6I), and vancomycin alone (FIGS. 6J, 6K, and 6L) present intact cells with structural features similar to the untreated bacteria. This observation confirms that MRSA resists these antibiotics as it was presented in FIGS. 2A, 2D, and 2G.

However, bacteria exposed to Ag-BG (FIGS. 6M, 6N, and 6O) are concentrated in areas surrounding the particles (marked with white lines) and these cells appear to harbor damaged cell wall areas that are releasing cytoplasm (marked with black arrows). The damaged cell wall areas are underscored by a loss of electron-density contrast and irregular thickness. Released cytoplasmic contents can also be found near some of the cells. Additionally, the development of a clear void (gray arrows) between the cell envelope and cytoplasm is observed. Therefore, it is surmised that the void space increase over time, creating a localized separation prior to the breakdown of the cell wall and the release of the cellular content. These features are exacerbated in cells treated with both Ag-BG and oxacillin (Ag-BG/oxa, FIGS. 6P, 6Q, and 6R). After 24 hours of culture, several bacteria are observed with clear cytoplasmic membrane disruption (FIG. 6Q) and a void space between the cell envelope and cytoplasm (FIG. 6R, gray arrows). In addition, a substantial number of cells appear to contain a damaged cell wall and separation of cytoplasmic contents from the membrane (indicated by black arrows).

Cells exposed to the Ag-BG and fosfomycin (Ag-BG/fosfo) show considerably different results compared to the Ag-BG/oxa-treated cells (FIGS. 6S, 6T, and 6U). In these samples, intact cells are rarely observed. Interestingly, nanosized Ag-BG pieces, created during the degradation of the microsized Ag-BG particles, appear as dark accumulations within the cellular material (areas highlighted with white lines). Damaged cells with fragmented cell walls and released cytoplasm are also observed (FIG. 6U).

Finally, the appearance of cells exposed to Ag-BG and vancomycin (Ag-BG/vanc, FIGS. 6V, 6W, and 6X) have some features similar to those observed to MRSA incubated with the Ag-BG/fosfo samples. Accumulations of Ag-BG pieces within cellular structures are also observed (FIGS. 6W and 6X, marked with white lines). Interestingly, the development of nanotunnels/channels created in the dark gray areas is observed (FIG. 6V, marked with white arrow), showing a penetration of particles through the cell wall. The silhouettes of cells are apparent but are larger in diameter than bacteria cells, indicating substantial ultrastructural changes.

MRSA Morphology Exposed to Ag-BG.

Figures 7A, 7B, 7C, 7D, 7E, 7F:
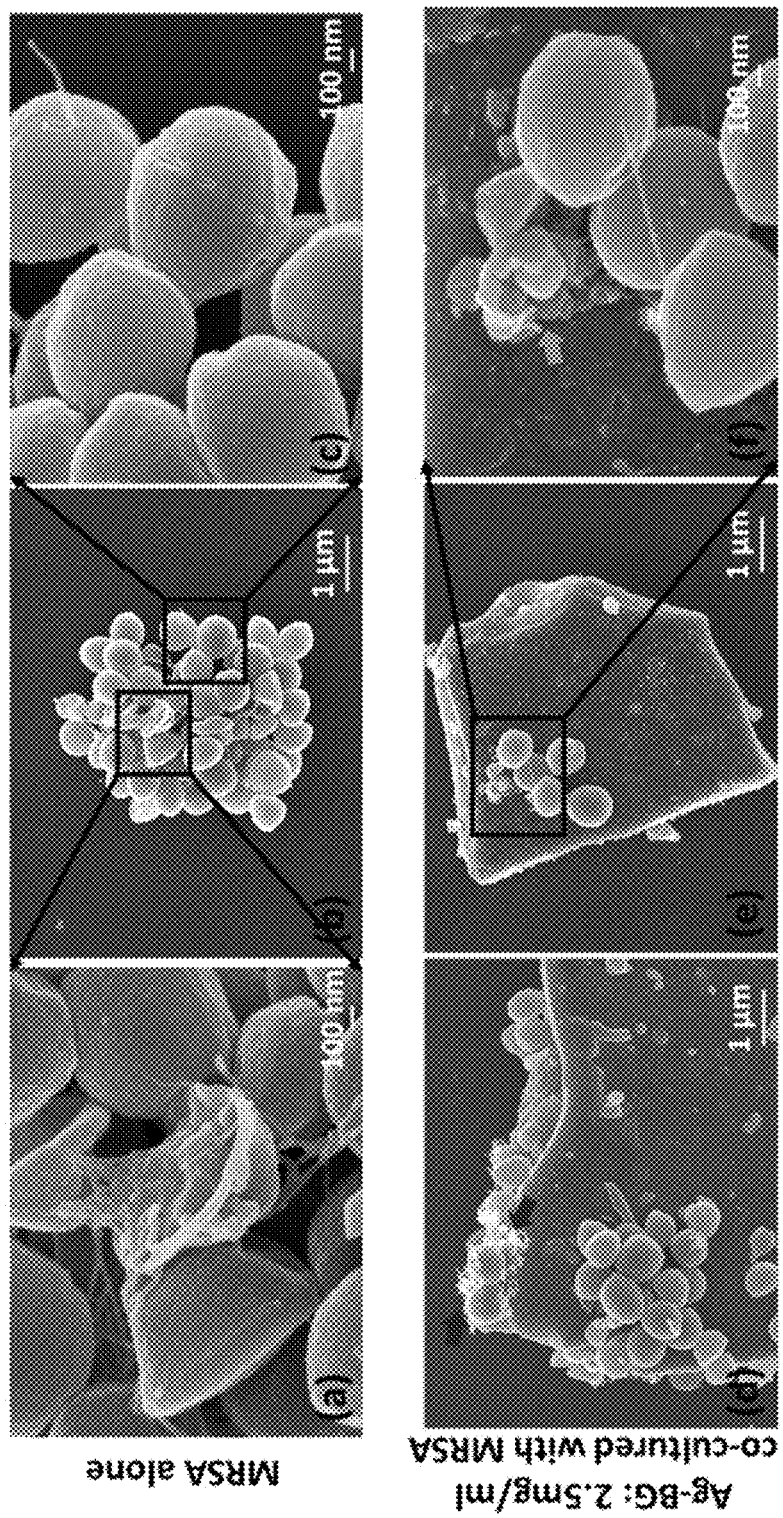

To elucidate how the cells are interacting with the particles, the morphology of bacteria cultured alone (FIGS. 7A, 7B, and 7C) and upon exposure to Ag-BG (FIGS. 7D, 7E, and 7F) is observed using Scanning Electron Microscopy (SEM). Bacteria cultured alone is aggregated without signs of dead or damaged cells. An extracellular matrix is also observed. However, exposure to Ag-BG alters the morphology of the cells. The cells appear to be attached to the Ag-BG particles. Cytoplasmic contents (arrows in FIG. 7D) are found between cells attached on the surface of particles. Cell-wall fragments are also found on the surface of the particles, as it is presented in FIG. 7F (indicated by arrow), confirming the antibacterial activity of Ag-BG particles.

Discussion

Ag-BG particles exhibit significant antibacterial activity against MRSA at an MIC of 2.5 mg/ml. Growth inhibition with time (FIG. 1B) is due to degradation of the bioactive glass network, which releases silver and other ions in amounts that are lethal to the bacteria. The concentration of the released silver ions from the Ag-BG particles was found previously to be approximately 0.4 ppm after four hours of incubation and increases up to 0.7 ppm for incubation time higher than eight days. The silver ion concentration reaches a plateau of 0.7 ppm that remains stable for up to a month. Notably, at this concentration, silver ions are innocuous to humans, as the lowest concentration that induces cytotoxicity is 1.6 ppm. In comparison, the reported minimum bactericidal concentration of silver is 0.1 ppm. The kinetics of silver ion release is a critical factor for the degree of antibacterial activity. As shown here, it is clear that over time Ag-BG elicits greater anti-MRSA activity. Simultaneously, the degradation of the bioactive glass network triggers a nontoxic response in host cell, underscored by findings demonstrating that Ag-BG particles regenerate hard and soft tissue in dental applications. In particular, it has been previously observed in vitro that viability and proliferation of pulp cells and dental pulp stem cells are enhanced with Ag-BG, while the differentiation of dental pulp stem cells to odontoblast is also enhanced. In vivo studies also show pulp regeneration and a significant increase on the amount of the regenerative dentine when Ag-BG particles have been incorporated into the implant compared to the control. Biological activities of Ag-BG are further displayed here, as the antibacterial properties of these particles and their capacity to restore activity to antibiotics that MRSA resists is shown. In keeping with this, Ag-BG expands the spectrum of action of antibiotics, holding great promise in the biomedical field.

Figure 8:
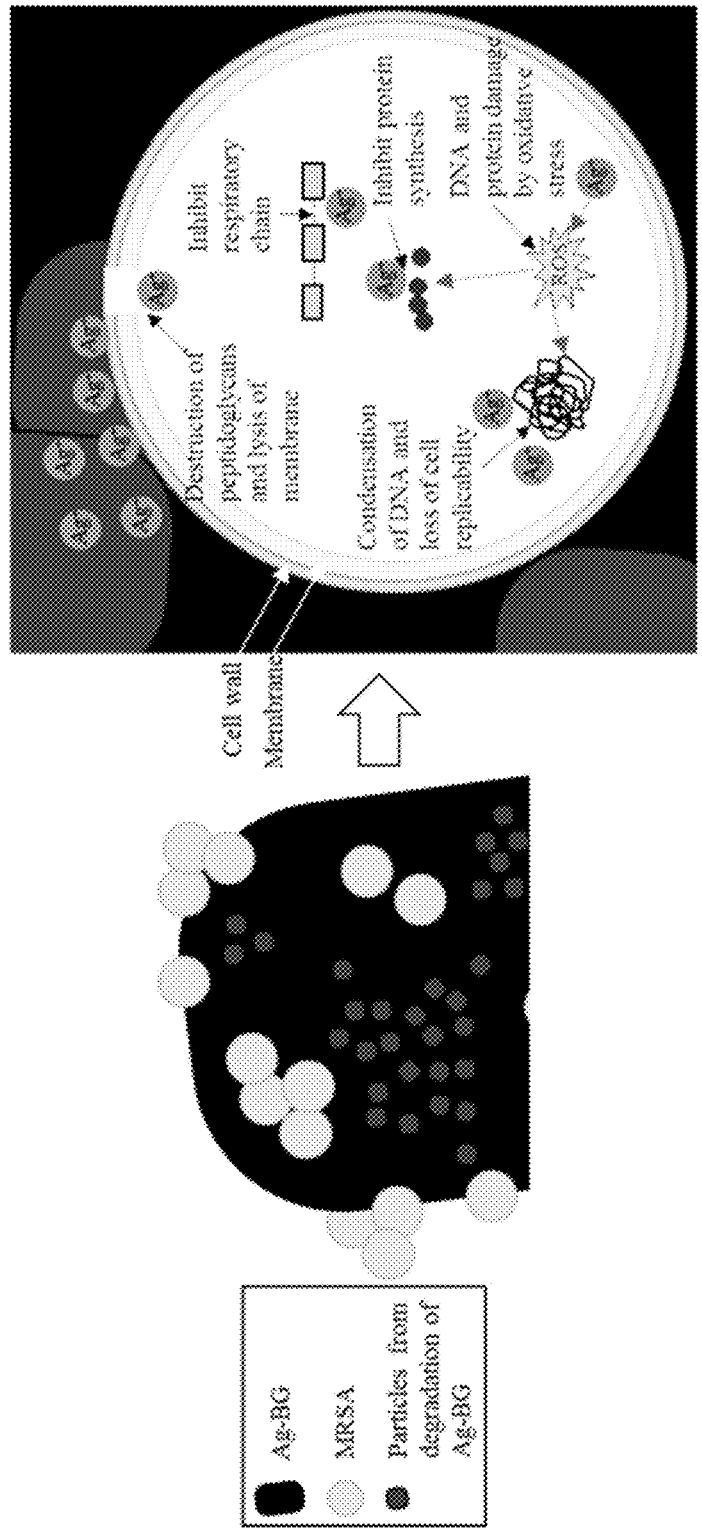
FIG. 8 is an illustration of the antibacterial mechanisms of silver ions.
Figure 9A:
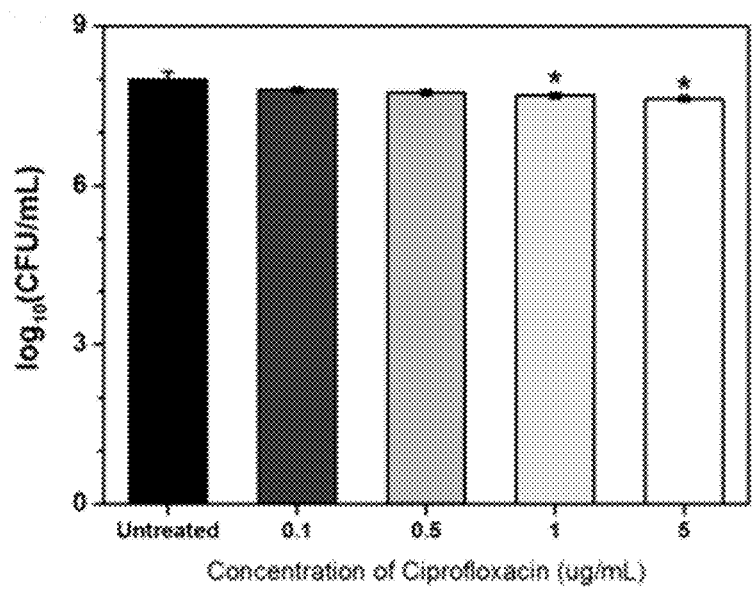
FIGS. 9A-9B are graphs showing synergy between ciprofloxacin and Ag-BG in resistant bacteria.
Figure 9B:
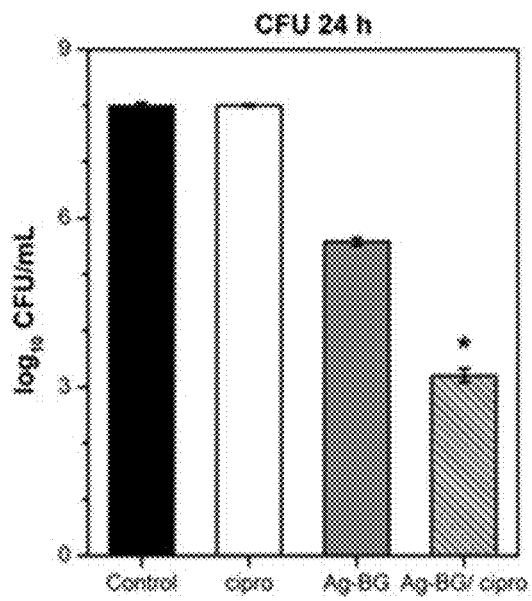
Figure 10A:
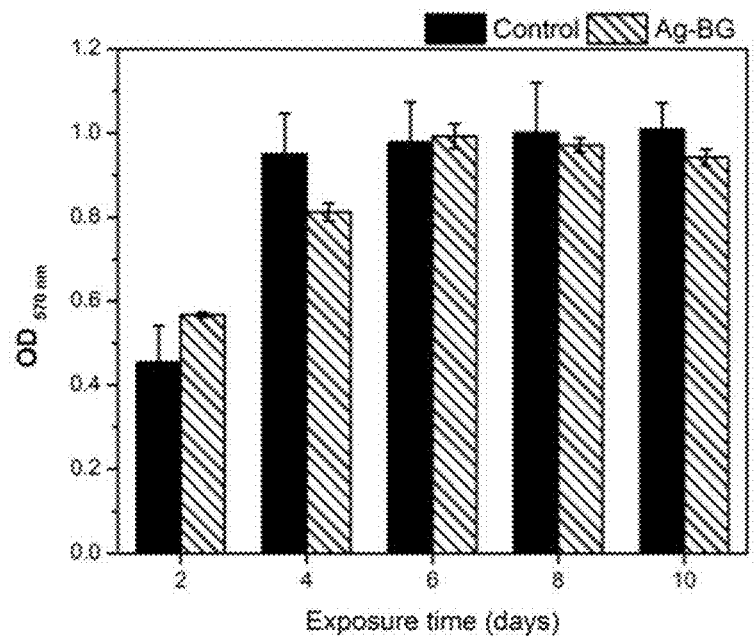
FIG. 10A-10B are a graph and micrographs, respectively, showing the effect of Ag-BG on bacteria growth over a 10-day period.
Figure 10B:
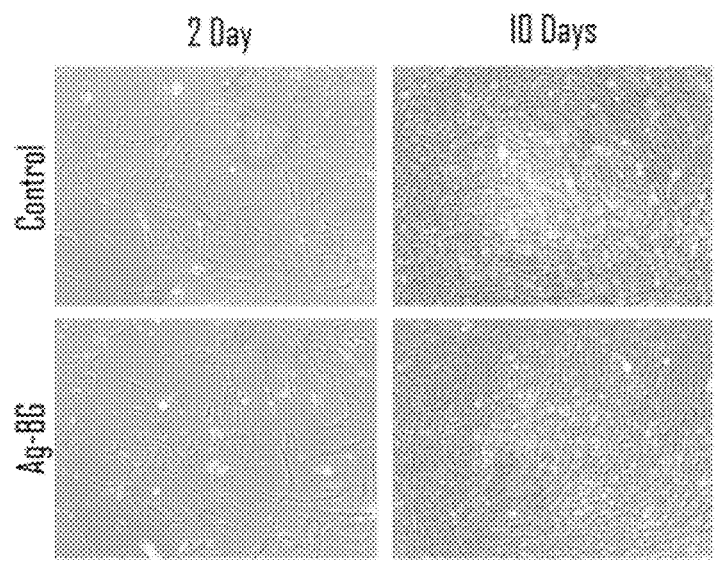

It is proposed that ions and nanosized pieces released from the Ag-BG particles corrupt the cell envelope, increasing the permeability of the bacterial cells and enhancing the exposure to the antibiotic. Consistent with this, the ultrastructural changes resulting from exposure to Ag-BG show distinct alterations in the cell envelope (FIGS. 6A-6X). Previous reports suggest that the antibacterial activity mostly occurs due to multiple mechanisms of silver action with the bacteria. However, the culture medium induces degradation of micro Ag-BG to nanosized pieces, followed by the release of ions from the structure. These nanosized pieces are observed to travel along nanotunnels/channels created in cells envelope and accumulate within the cytoplasm. This mechanism appears to contribute to the antibacterial activity of Ag-BG. In addition, the emission of Ag, Ca, Si, P, Na, and K ions is expected from the glass network. These ions contribute to a relatively small increase in the pH value and an osmotic effect. Although pH increases from 7.4 to 7.6 after 2 days (FIG. 3), this increase is significantly low to result from antibacterial activity. Thus, the osmotic effect could be a possible contributing factor to the bactericidal properties. However, an important contribution to the bactericidal activity is expected because of the silver ions (FIG. 5) due to a broad range of previously reported mechanisms (FIG. 8).

Silver ions demonstrate potent antibacterial activity due to their ability to interact with several major cellular constituents. Nearly every subcellular compartment is effected by silver ions. In the cell wall and membrane, the positively charged silver ions may interact with negatively charged teichoic acids or phospholipids, leading to the overt damage and increased permeability. Another mechanism that has been reported is destabilization and disruption of the outer membrane in *E. coli*. Other reports have explained that an interaction within the cytoplasm of Ag ions binding to enzymes and nucleic acids causes DNA condensation, resulting in decreased replication and subsequent cell death. Additionally, silver ions were found to be deleterious to Recombinase A (RecA) protein activity, which repairs DNA and triggers the SOS-response. Silver ions also obstruct metabolism as they inhibit respiratory enzymes. In this case, the ions may bind to thiol groups and induce hydroxyl and peroxide radicals in MRSA. It was also reported that silver induces oxidative stress in the cytoplasm via formation of free radicals such as reactive oxygen species (ROS). Production of ROS leads to further protein and DNA damage. Additionally, silver ions induce denaturalization of the 30S ribosomal subunit, which is essential for protein synthesis. It is expected that all these mechanisms accelerate inhibition of MRSA.

MRSA is inherently resistant to oxacillin and fosfomycin. In the conditions tested, vancomycin is also inert to bacterial cells. β-Lactams, such as oxacillin, elicit antibacterial activity by targeting the cell envelope and inhibiting peptidoglycan synthesis by penicillin-binding protein PBP2. Resistance against β-lactams can be expected in MRSA by encoding PBP2a. In this situation, the antibiotic is only able to inhibit PBP2 but not PBP2a, which will take over the biosynthesis process and resists the drug. In addition, the bacteria strain used here is resistant to fosfomycin, which was selected due to its broad-spectrum activity and the lack of toxicity. Its mechanism of action is the inhibition of the initial step of cell wall biosynthesis by inducing product dissociation of MurA enzyme and suppressing the production of PBP.

Finally, glycopeptides, such as vancomycin are potent inhibitors of cell wall synthesis. In this case, the target is the D-Ala-D-Ala dipeptide terminus present in partially cross-linked cell wall and in the Lipid II intermediate. The antibiotic creates five hydrogen bonds with this terminus, which prevents it from attaching to PBPs for transglycosylation and transpeptidation. Thus, vancomycin is expected to be especially antibacterial during highly active cell-wall biosynthesis processes like in cell-division, where the division septum ends up destroyed. In this experimental design, cell division is not expected to occur, as PBS is limited for growth-promoting nutrients. Consistent with this, vancomycin did not reduce the viability of MRSA under the high concentration tested.

Synergy was observed upon exposure to oxacillin, fosfomycin, or the glycopeptide vancomycin, with Ag-BG. The potent inhibition that is demonstrated by the Ag-BG/antibiotic combination cannot be attributed to an additive effect of the two agents, since antibacterial properties were not reported for each of the antibiotics alone (FIGS. 2B, 2C, 2E, 2F, 2H, and 2I). In all cases and similar to Ag-BG delivered alone, the combination of Ag-BG/antibiotic shows time dependent lethality. Synergy is observed after 12 hours of exposure and is enhanced with the culture time. Bactericidal properties are expected for time points longer than 24 hours. A potential mechanism of action based on the byproducts is created during the degradation of Ag-BG particles. The released ions and nanosized pieces can damage the cell envelope, opening nanotunnels/channels for the antibiotic to penetrate and act. As the antibiotics target the cell wall, permeability is further increased, allowing for enhanced exposure to ions and antibiotics.

The synergistic action of Ag-BG with the cell wall targeting antibiotics is only understood if cell-wall biosynthesis is taking place in static cell conditions. After the cell wall gets damaged, biosynthesis will be activated for its reconstruction. As a result, these drugs will penetrate though the wall and will be able to find active targets to inhibit the synthesis process so that the cell structure is unrepairable. This is especially interesting in the case of Ag-BG/oxa, since the mutated PBP2a would now be also exposed to the antibiotic, making the mutated enzyme less effective against the oxacillin.

In agreement with this mechanism are the features observed in MRSA exposed to vancomycin alone versus Ag-BG/vanc. It has been reported that MRSA cells exposed to vancomycin harbor an irregularly thick cell wall lacking a division septum. However, this is not observed here as vancomycin is not activated on cells suspended in PBS (FIGS. 6J, 6K, and 6L). Notably, the combination of Ag-BG/vanc activates vancomycin, allowing this antibiotic to cause pronounced ultrastructural changes leading to decreased viability (FIGS. 6V, 6W, and 6X).

This is also verified by the lack of synergism in the case of Ag-BG/gent. Gentamicin acts on the ribosomes. In particular, it binds the 30S subunit of the bacterial ribosome, interrupting protein synthesis. Thus, there is no benefit from the co-treatment with Ag-BG particles that can damage the cell envelope (FIGS. 4A-4C).

Conclusion

Silver-doped bioactive glass (Ag-BG) is antibacterial to MRSA and also contains bioactive properties in eukaryotic cells. Exposing MRSA to a combination of Ag-BG with antibiotics typically restores the antimicrobial properties of the antibiotic, expanding its spectrum of action. Without being bound by theory, it may be that the mechanism of action is based on the combined action of ions and mainly Ag ions, as well as nanosized pieces that dissociate from the microparticle and corrupt the cell-wall, allowing for increased penetration of antibiotics. Consequently, cells will attempt to repair the cell-wall, but this process potentiates cell wall targeting antibiotics such as oxacillin, fosfomycin, and vancomycin via a penetration process through nanotunnels/channels. The increased permeability caused by nanotunnels/channels supports an additional influx of ions and nanosized pieces that further corrupt the cell. The results indicate that the combined delivery of Ag-BG with cell wall targeting antibiotics advances synergy with strong antibacterial properties that bypass MRSA resistance. This indicates that Ag-BG particles are a powerful tool for healing tissue infected by methicillin-resistant pathogens.

Example 2

This example describes Ag-doped bioactive glass particles for bone tissue regeneration and enhanced MRSA inhibition.

Summary

Infection is a significant risk factor for failed healing of bone and other tissues. A sol-gel derived bioactive glass doped with silver ions (Ag-BG) is developed, tailored to provide non-cytotoxic antibacterial activity while significantly enhancing osteoblast-lineage cell growth in vitro and in vivo. The Ag-BG is a novel material that combats bacterial infection while maintaining the capability to promote bone growth. Ag-BG inhibits bacterial growth and potentiates the efficacy of conventional antibiotic treatment. Ag-BG particles enhance cell proliferation and osteogenic differentiation in human bone marrow stromal cells (hBMSC) in vitro. Moreover, in vivo tests using the calvarial defect model in mice showed the capability of Ag-BG particles to induce bone regeneration. This novel system with dual biological and advanced antibacterial characteristics is a new therapeutic for combating resistant bacteria while triggering new bone formation.

Introduction

Antibiotic resistance is a significant public health concern. The evolution of resistant microbial strains has become a significant threat to regular infection treatments. It represents an enormous economic burden to the health care system with an estimated cost of $20 billion dollars per year in the United States alone. Among the various multi-resistant strains listed by the World Health Organization (WHO), *Staphylococcus aureus* (*S. aureus*) is one of the highest prioritized since it hinders the penetration of antimicrobials by triggering pathological changes in bone. Moreover, it is associated with several implant-related infections causing the failure of almost 35% of the prosthetic joints. Moreover, *S. aureus* is also related to invasive tissue infections like endocarditis and osteomyelitis, underlining the need for novel antibacterial agents. This is a highly prioritized pathogen able to develop resistance against multiple antibiotics. There is a considerable unmet clinical need to develop effective tissue engineering strategies that provide a sustained bactericidal activity to prevent bone infections while mitigating the risk for the development of antibiotic resistance and concurrently promoting bone regeneration.

The use of heavy metal ions against drug-resistant bacteria has appeared as a promising approach for infection treatment. Their release in the body, however, raises a general toxicity concern that prevented their systematic use. In early years, heavy metal ions (e.g., silver, copper, zinc) have been used as such antibacterial agents. Silver ions ($Ag^+$) can act as broad-spectrum biocides against different Gram-negative and Gram-positive bacteria including resistant strains. Over the past decades, research has been done to undercover the working mechanism of $Ag^+$ finding different pathways of interaction that lead to bacteria deathalls. Due to this effect on bacteria, questions about cytotoxic behavior always arise. That is one of the main reasons led to the combination of $Ag^+$ with antibiotics for a dual-action. This pioneering trend aims to optimize the amount of each agent required to treat the infection while minimizing the risks associated with their individual use. Moreover, it has been found that when both agents are delivered together a synergistic effect takes place enhancing the inhibition and expanding the spectrum of action of the antibiotics. However, beyond the advanced antibacterial action, a delivery vehicle with such characteristics and additional regenerative properties is still missing to efficiently target, healing and regenerating infected tissue. Biomaterials able to treat infections and induce tissue regeneration are a promising approach to this problem. However, materials combining both regenerative and antibacterial properties against resistant pathogens are still missing.

This example demonstrates a unique antibacterial action when Ag-doped BG particles that show a controlled ion release process are applied in combination with an antibiotic expanding the spectrum of action of the antibiotic, while the biological and regenerative properties of the bioactive particles are not diminished.

This example aims to address this problem by employing novel bioactive glasses as a delivery platform. Silicate based bioactive glasses are known for the excellent bioactive properties and they have been utilized as delivery vehicles for drugs. The aim is to combat resistance bacteria by means of $Ag^+$ release that acts in combination with a present drug while the released ions from the bioactive and degradable glass stimulate tissue regeneration during the healing process. Here, a sol-gel (solution-gelation) derived bioactive glass in powder form is used with particles in a $SiO_2$ 58.6-CaO 24.9-$P_2O_5$ 7.2-$Al_2O_3$ 4.2-$Na_2O$ 1.5-$K_2O$ 1.5-$Ag_2O$ 2.1 wt. % system. The developed Ag-BG possesses strong and long-term antibacterial properties while maintaining its bioactive behavior required for tissue regeneration. Here, the antibacterial properties of Ag-BG are studied against methicillin-resistant MRSA, a commonly met strain on bone infections.

In this example, the cell-material interaction of Ag-BG in culture with human bone marrow stromal cells (hBMSC) was examined in vitro. The bone regenerative properties of these particles were assessed in vivo. The combination of Ag-BG with antibiotics against methicillin-resistant *Staphylococcus aureus* (MRSA), a commonly met strain on bone infections, demonstrated synergism between the glass and the antibiotic that shows a dependence on the relevant concentrations. In this example, the antibiotic that was selected was vancomycin, which is a common clinical treatment for MRSA. However, MRSA resists vancomycin under growth-arrested conditions, that are relevant to the conditions within the biofilm. The cell viability and differentiation presented the lack of cytotoxicity. Bone growth was also observed in vivo in the calvarial bone model. This example shows the use of Ag-BG particles as advanced therapeutics against MRSA that also promotes bone growth.

Methods

Synthesis of Ag-Doped Bioactive Glass (Ag-BG).

The fabrication of Ag-BG ($SiO_2$ 58.6-CaO 24.9-$P_2O_5$ 7.2-$Al_2O_3$ 4.2-$Na_2O$ 1.5-$K_2O$ 1.5-$Ag_2O$ 2.1 wt. %) microparticles includes a sol-gel acid catalysis. Two systems being in their solution stage (of the 58S sol-gel BG in $SiO_2$ 58-CaO 33-$P_2O_5$ 9 wt. % system with the respective solution stage of the sol-gel porcelain A in $SiO_2$ 60-CaO 6-$P_2O_5$ 3-$Al_2O_3$ 14-$Na_2O$ 7-$K_2O$ 10 wt. % system) were mixed. After stirring, the final solution was aged at 60° C., dried at 180° C. and stabilized up to 700° C. The particles obtained were dry ball-milled to a fine powder and sieved to a particle size below 20 µm.

Antibacterial Activity.

The bactericidal properties of Ag-BG alone, vancomycin alone (vanc) and the combination of Ag-BG with vancomycin (Ag-BG/vanc) were studied against laboratory-derived methicillin-resistant *S. aureus* (MRSA) USA300 JE241. The bacteria cells were prepared by isolation of a single colony, followed by its inoculation in tryptic soy broth overnight at 37° C. A bacterial suspension was prepared by adjusting the concentration of the overnight culture to 108 colony forming units (CFU)/mL in Phosphate Buffered Saline (PBS). Then, the bacterial suspension was mixed 1:1 with the corresponding treatment (Ag-BG, Ag-BG/vanc or vanc) to a final volume of 1 mL. A negative control was prepared by suspending bacteria 1:1 in PBS. After 24 h of incubation at 37° C., 100 mL of suspension were drawn from the mixture for CFU enumeration in tryptic soy agar plates. The effect of the treatments was evaluated based on the decrease of CFU compared to the negative control. Quantification of CFU was performed in biological and technical triplicates.

The inhibition profile of Ag-BG in PBS against MRSA was studied for the same system and experimental conditions as the ones presented here, identifying a minimum inhibitory concentration (MIC) and minimum bacterial concentration (MBC) of 2.5 mg/mL and 6.25 mg/mL, respectively. Vancomycin (molecular formula: $C_{66}H_{75}C_{12}N_9O_{24}$·HCl, Vancomycin hydrochloride) is a cell-wall targeting antibiotic with no effect against MRSA under growth-arrested conditions and was selected for this example. Here, the concentration dependency of this synergism was evaluated by exposing MRSA to different combinations of Ag-BG/vanc. Two experimental set-ups were considered. Initially, 0.5 mg/mL of vancomycin were delivered together with 1.25, 2.5, 3.75 or 6.5 mg/mL of Ag-BG and then, 2.5 mg/mL of Ag-BG were combined with 0.1, 0.3, 0.5 and 1 mg/mL of vancomycin. The Ag-BG powder was sterilized using UV radiation before exposure to bacteria. The antibiotic treatment was prepared by dilution of vancomycin powder at different concentrations in PBS, and the Ag-BG/vanc samples were prepared by mixing Ag-BG powder with the corresponding vancomycin solution.

Proliferation and Differentiation of Human Bone Marrow Stromal Cells (hBMSC).

Primary bone-marrow-derived human mesenchymal stem cells (hBMSC) (line 8013) isolated from 22-year-old healthy male donor was characterized and tested for tri-lineage differentiation (osteoblastic, adipogenic and chondrogenic) potential at the Institute of Regenerative Medicine, Texas A&M University. Frozen vials of cells were thawed and cultured at a density of 3000 cells/$cm^2$ in α-MEM supplemented with 16% fetal bovine serum, 1% Antibiotic-Antimycotic (Gibco 15240062) and 1% L-glutamine (hereafter, growth medium) in a humidified 37° C./5% CO$_2$ incubator. Cells were expanded until 90% confluence to a final passage. At the time of seeding, cells were enzymatically lifted from culture dishes using trypsin and then, centrifuged for 5 min. The pellet was re-suspended in fresh media and cells were plated at a density of 30×103 cells/mL on each well of 24-well plate by pipetting 0.5 mL/well. Seeding was allowed for 24 h. The Ag-BG microparticles were preconditioned for 4 days using α-MEM, centrifuged and dried at 60° C. The powders were sterilized using UV radiation and introduced in inserted porous transwells on the culture plates containing the hBMSC. The effect of Ag-BG in cell proliferation and differentiation was evaluated for different concentrations of Ag-BG and it was compared to a negative control consisting of cells immersed only in culture medium (hereafter, untreated cells). The media was refreshed every other day.

Cell Proliferation.

Figure 11:
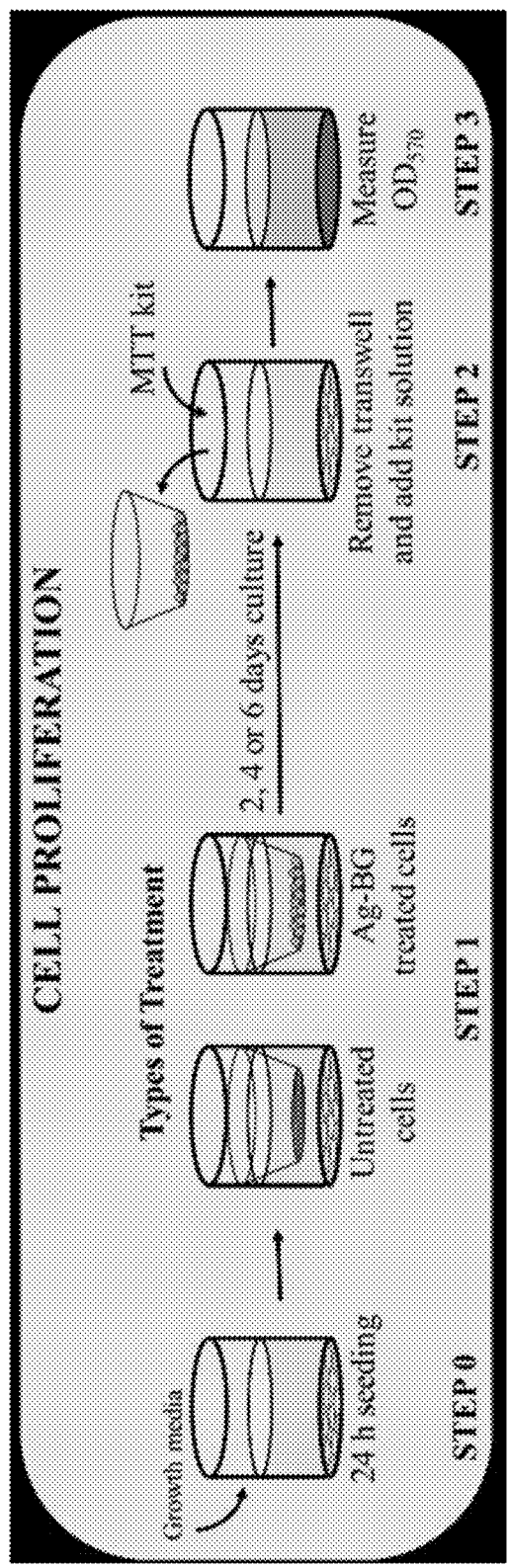
FIG. 11 is an illustration showing a step-by-step experimental design scheme for a cell proliferation assay.

Cell metabolic activity and consequently, cell viability and proliferation were assessed after 2, 4 and 6 days of culture in growth medium using the MTT assay kit (Sigma Aldrich). Cells were exposed to 2.5, 5, 7.5 and 12.5 mg of Ag-BG powder. At the end of each time point, 500 µL of MTT solution was added to each well and incubated for 4 h at 37° C. to allow its cleavages to formazan by enzymes from viable cells. Then, 500 µL of the solubilization solution was added and incubated for 24 h at 37° C. to dissolve the crystals staining the culture solution. The amount of formazan dye formed allowed a correlation to the concentration of metabolically active cells in the untreated vs Ag-BG treated culture. The blue dye was measured using a spectrometer at 570 nm and the results were recorded as optical density values (OD). A schematic illustration of the experimental design is presented in FIG. 11.

Cell Differentiation.

Figure 12:
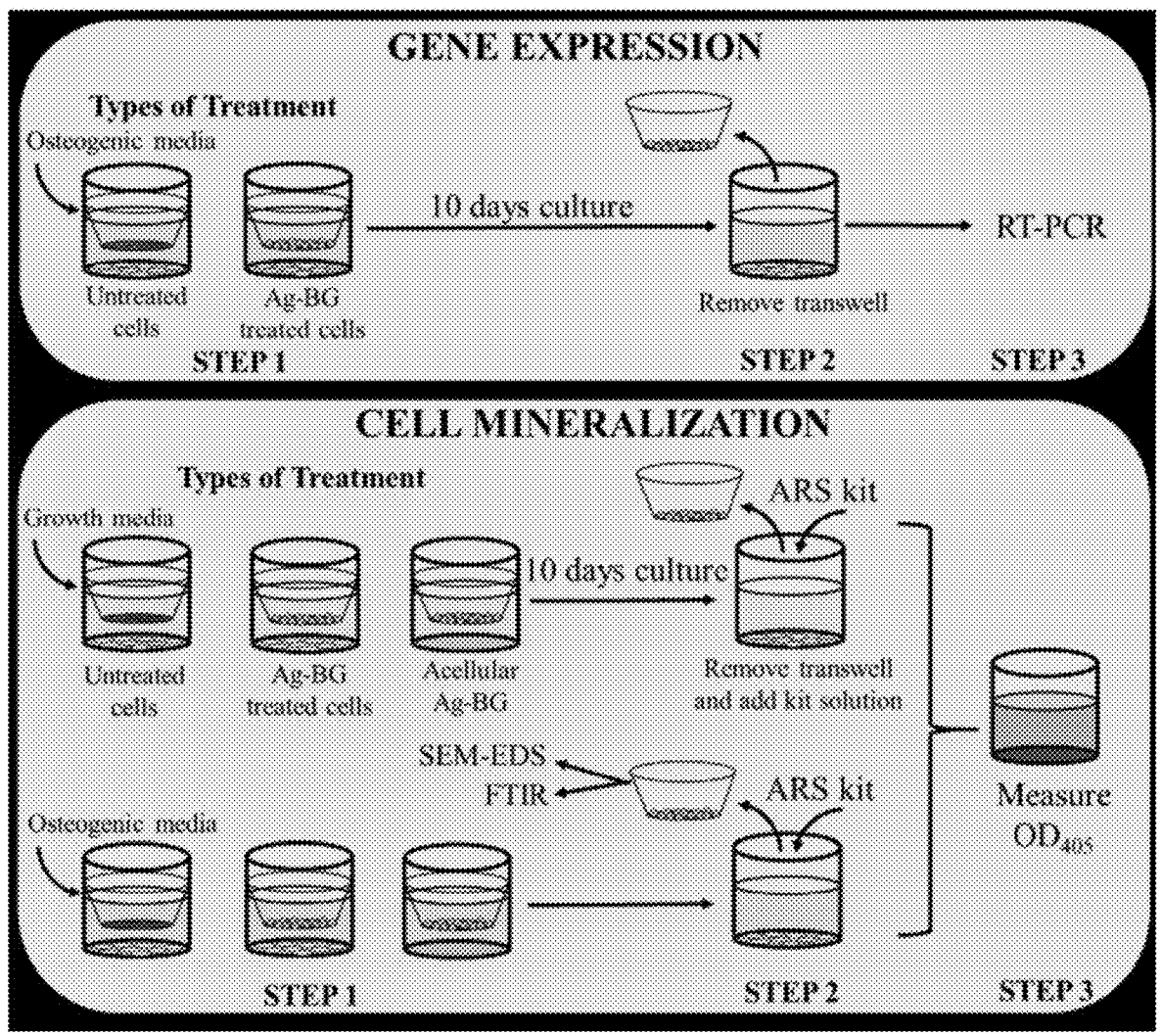
FIG. 12 is an illustration showing a step-by-step experimental design scheme for a cell differentiation test for gene expression and cell mineralization studies.

Cell differentiation to osteoblasts was evaluated in terms of gene expression and cell mineralization after exposure to 5, 7.5 and 12.5 mg of Ag-BG for 10 days (FIG. 12). The expression of specific gene markers, such as bone sialoprotein (BSP) and osteocalcin (OCN), was evaluated using qRT-PCR. Table 1 shows the primers used for qRT-PCR. Cells were maintained in growth medium as described above and additionally supplemented with 25 µg/ml ascorbic-acid-2-phosphate and 5 mM beta-glycerophosphate (hereafter, osteogenic medium). Briefly, 300 ng of total RNA was reverse transcribed using High Capacity cDNA Reverse Transcription Kit (Applied Biosystems) in a 20 µl reaction. One microliter of the resulting cDNA was amplified using Power SYBR® Green PCR Master Mix and gene-specific primers (sequences provided in the table) in a 7500 Fast Real-Time PCR System (Applied Biosystems) following manufacturer's recommendations. The comparison between untreated and Ag-BG treated samples was performed by normalizing to 1 the average value of untreated cells.

TABLE 1

List of primers used for qRT-PCR analysis.

| Primer Name | SEQ ID NO: | Sequence (5'-3') |
|---|---|---|
| hGAPDH_S | 1 | TGGTATCGTGGAAGGACTCATGAC |
| hGAPDH_AS | 2 | ATGCCAGTGAGCTTCCCGTTCAGC |
| hBSP-S | 3 | ACAACACTGGGCTATGGAGA |
| hBSP-AS | 4 | CCTTGTTCGTTTTCATCCAC |
| hOCN_S | 5 | CACCGAGACACCATGAGAGC |
| hOCN_AS | 6 | CGGATTGAGCTCACACACCT |

The capability of Ag-BG to induce cell mineralization was studied under two growth conditions; in growth medium or in osteogenic medium. Alizarin Red Staining (ARS) was used to identify calcium-containing osteocytes in mineralized cells. To make sure that the measured calcium-containing minerals were not formed by depositions induced by Ag-BG particles degradation, acellular wells, containing only Ag-BG particles with medium and without hBMSC, were also taken into consideration for ARS assay. After removing the transwells, 500 µL of 40 mM ARS solution in distilled water (Sigma Aldrich) was mixed with the cells for 30 min. Then, the monolayers were dissolved using 500 µL of 10% acetic acid. The red dye was measured using a spectrometer at 405 nm and the results were recorded as optical density values (OD). The comparison between untreated and Ag-BG treated samples was performed by normalizing to a value of 100 the average of the untreated cell values.

In Vivo Bone Regeneration.

All experiments were conducted under the oversight of the University of Michigan animal care and use committee. Twenty 6-month old mice on a C57B/L6 background were randomly assigned to four groups, each containing five mice (two females and three males). Mice were anesthetized in isoflurane and defect sites aseptically prepared. Bilateral 3 mm defects on the parietal bones of each mouse were created using a Mectron Piezosurgery drill with an OT11 osteotomy bit under saline irrigation. These defects were filled with collagen sponges (Pfizer Gelfoam) loaded with a suspension of 10.5 mg Ag-BG particles in either 40 µl phosphate buffer solution (PBS) or natural extracellular matrix (ECM) hydrogel (from urinary bladder matrix) provided by Professor Badylak. As negative controls, defects were filled with collagen sponge loaded with 40 µl of ECM or PBS. The skin was closed using 3M Vetbond surgical adhesive and, after 30 days, mice were euthanized by CO$_2$ asphyxiation and tissues were collected for analysis. Skulls were scanned in a GE Healthcare eXplore Locus specimen MicroCT and analyzed in Parallax Microview using a 2.9× 2.9×2 mm cylindrical region of interest centered within each defect. The formation of new bone in cranial defects was assessed by microCT analysis (1200 HU as the threshold) and histology.

Mineralization of Ag-BG Microparticles.

The formation of an apatite-like phase on the surface of the Ag-BG microparticles was evaluated after the cell mineralization test in osteogenic media. The particles were collected from the inserted transwells and dried at room temperature before analysis. The surface morphology and elemental composition of Ag-BG before and after cell culture were compared with SEM-EDS. Samples were prepared by spreading a thin layer of powder in carbon tape, followed by metallization in osmium gas for 15 s. Images and spectrum were collected at 15 keV. Structural differences were detected using Fourier-transformed infrared— attenuated total reflectance (FTIR-ATR; Jasco FT/IR-4600) between 400-2000 cm-1 wavenumber directly on the dried powder.

Statistical Analysis.

All the above-mentioned in vitro experiments were repeated three times containing triplicates of each sample. The data was recorded as the representative mean±one SD. The significant difference among in vitro sets was performed using the two-tailed Student's t-test and significance reported when p<0.05. One-way ANOVA followed by Two-stage step-up method of Benjamini, Krieger and Yekutieli was used to analyze microCT data using GraphPad Prism 8.2.1 (GraphPad Software, San Diego, California USA).

Results

Reactivation of Vancomycin at Different Concentrations of Ag-BG Against MRSA.

One of the characteristics of the Ag-BG particles is the antibacterial activity observed against a number of oral bacteria such as Escherichia coli (E. coli), Enterococcus faecalis (E. faecalis), Lactobacillus casei (L. casei), and Streptococcus mutans (S. mutans). The capability of Ag-BG to synergize with cell-wall targeting antibiotics, such as vancomycin, under growth-arrested conditions against MRSA was shown only for the combination of certain concentrations (0.5 mg/ml vancomycin with 2.5 mg/mL of Ag-BG) in Example 1. Here, the concentration dependence of the synergism was analyzed for different combinations of Ag-BG and vancomycin to identify the minimum concentrations required to observe an increase of the synergistic antibacterial effect. FIGS. 13A and 13B present the inhibition of MRSA by increasing concentration of vancomycin and Ag-BG, respectively. Under growth-arrested conditions, MRSA resists vancomycin, demonstrating no reduction of CFU/mL after 24 h treatment. However, high sensitivity was observed for the Ag-BG microparticles treatment with MIC and MBC of 2.5 and 6.25 mg/mL, respectively.

Exposing MRSA to 0.5 mg/mL of vancomycin combined with different concentrations of Ag-BG (1.25-6.25 mg/mL) revealed an increase in the inhibition by increasing Ag-BG concentration (FIG. 13C). A higher concentration of Ag-BG in Ag-BG/vanc leads to increasing inhibition higher than the inhibition of the respective Ag-BG concentration alone. The combination of 0.5 mg/mL of vancomycin with 1.25 mg/mL of Ag-BG was insufficient to reduce bacteria to a statistically significant difference. However, by increasing the concentration of Ag-BG to 2.5 mg/mL in the Ag-BG/vanc system, it inhibits MRSA similarly to the inhibition that observed when MRSA is exposed to 3.75 mg/mL of Ag-BG alone.

Increasing the concentrations of vancomycin (from 0.1 to 1 mg/mL) when combined with 2.5 mg/mL of Ag-BG leads to increase in bacteria inhibition with sterile conditions to occur when 1 mg/mL of vanc is combined with 2.5 mg/mL of Ag-BG (FIG. 13D). The addition of 0.1 mg/mL of vancomycin was insufficient to significantly improve the inhibition provided by 2.5 mg/mL of Ag-BG. However, a vancomycin concentration of 0.3 mg/mL was identified as the minimum required to observe synergism between both antibacterial agents.

Cell Viability and Proliferation.

Experiments were done to test the viability and proliferation of hBMSC cells in a growth medium. Different concentrations of Ag-BG (2.5, 5, 7.5 and 12.5 mg) were co-cultured with cells and proliferation was assessed by OD measurements of dissolved formazan layers. FIG. 14A presents similar cell viability and proliferation for untreated and Ag-BG treated cells at each time point. After 2 days of co-culture cell viability is presented statistically lower for Ag-BG treated cells, slightly decreasing viability as the concentration of Ag-BG increases from 2.5 to 12.5. However, for longer time points there is no significant difference between the treated groups and control. This result shows a nontoxic response of eukaryotic cells to Ag-BG particles of different concentrations. The proliferation rates were also observed by linear fitting the OD values of each group (FIG. 14B) and calculating the slope of the trend for R2>0.9. The proliferation rate of Ag-BG treated cells appears twice faster than in the case of untreated cells. The proliferation rate did not significantly change by increasing the concentration of Ag-BG.

Cell Differentiation.

Moreover, the capability of Ag-BG particles to induce cell differentiation was observed under both growth and osteogenic conditions. RT-PCR for the detection of gene markers was performed after 10 days co-culture (FIG. 15). Bone sialoprotein (BSP) is a significant component of the bone extracellular matrix and was significantly upregulated after treatment with Ag-BG. The expression of osteocalcin (OCN) hormone increases with bone mineral density. Here it was determined that the OCN gene expression also increased after treatment with elevated concentrations of Ag-BG (7.5 and 12.5 mg).

Bone tissue is characterized by its high content of the mineral phase. The differentiation of hBMSC should be also correlated with the secretion of Ca containing minerals by the cells. The mineralization of the cells before and after Ag-BG treatment was studied via Alizarin Red Staining (ARS). In the growth medium, the presence of Ag-BG particles provided a slight increase in the mineral formation compared to untreated cells (FIGS. 16A-16B). A higher mineral formation was detected for higher concentration of Ag-BG treatment. Under osteogenic media, there is a notable mineral phase difference between the untreated and the Ag-BG treated cells with a 400% increase (FIGS. 16C-16D). In this case, different amounts of Ag-BG did not reveal any difference among sets. Optical microscope images of the hBMSC (FIGS. 16B-16D) showed that after 10 days of culture, cells had almost reached confluence. Acellular wells (containing only Ag-BG with media) were also analyzed to confirm that the formation of the observed minerals is not due to depositions from the particles. The lack of red stain in these wells proved that the mineral phase measured in Ag-BG treated cells belonged solely to the differentiation of hBMSC.

Bioactive Response by a Calcium-Phosphate Phase Formation on Ag-BG Particles after Immersion in Cell Culture Media.

The apatite-like phase formed on the surface of the Ag-BG particles after 10 days of co-culture in the osteogenic medium was evaluated using SEM-EDS and FTIR. As synthesized Ag-BG particles present a relatively smooth surface (FIGS. 17A-17B) with the presence of smaller size particles on the surface of the bigger particles. After co-culture, the surface of Ag-BG particles presents the formation of cauliflower deposits with a composition rich in Ca and P with Ca/P ration close to 1.8, indicating the development of an apatite-like phase, as observed by the EDS spectrums FIGS. 17C-17D).

The formation of mineral apatite in the surface of Ag-BG also modified the intensity and features of structural vibration in IR spectra (FIG. 17E). As synthesized, Ag-BG presented a glass-ceramic structure with a weak presence of a calcium-phosphate phase as revealed by the double broad peak of P—O at 575 and 620 cm$^{-1}$. After cell exposure, the intensity of these bands increases, proving the increase in the crystallinity and size of this calcium-phosphate phase at the surface as observed in FIGS. 17C-17D. The region at 900-1200 cm$^{-1}$ also presents slightly different features for Ag-BG as-synthesized and after cell culture. The bands at 900 and 1200 cm$^{-1}$ form stronger and better-defined shoulders after exposure to cells. These features are attributed to a stronger P—O bending vibration in the structure as a consequence of the apatite-like phase deposition.

Bone Regenerative Properties of Ag-BG In Vivo.

Collagen scaffolds were loaded successfully with Ag-BG particles as it is presented in FIGS. 18A-18C. SEM images show that the sponges were fully infiltrated by particles (FIG. 18A). The micro-CT analysis on the harvested calvarial bone tissue (FIGS. 18B-18C) showed a significantly higher fraction of newly formed bone in defects treated with Ag-BG particles in comparison with defects without Ag-BG (as presented in the plot and the representative micro-CT images of FIG. 18C). In the last case, there is only fibrous tissue being formed in the defects and there is no new bone formation as it is obvious from histology images (not shown). However, the treatments with Ag-BG particles show new bone formation for the Ag-BG-PBS and Ag-BG-ECM, as it is has been calculated from histology images (not shown). The treatments with ECM alone show very minimal new bone formation.

Discussion

Ag-BG microparticles were bactericidal to MRSA in agreement with Example 1. The antibacterial activity of Ag-BG is based on a multi-functional mechanism consisting of a simultaneous physicochemical degradation. The degradation is related to the release of nano-sized debris in solution. These nanoparticles were observed to penetrate the cell-wall by creating nano-tunnels and, subsequently, accumulating in the cytoplasm. The ion releasing process from the bioactive glass network as a result of its interaction with the surrounding medium maintains a neutral pH in the solution (7.5-7.7). Although the release of Si, P, Ca, Na and K ions, that make up the glass structure in bioglass, reportedly contributes to a bactericidal osmotic effect, most ionic-based inhibition is probably caused by the presence of the nano-sized debris and the Ag$^+$ ions. Heavy metal ions, such as Ag$^+$, have been reported as strong antibacterial weapons since they provide inhibition through multiple mechanisms, reducing the capability of bacteria to resist the attack. The concentration of Ag$^+$ ions released from Ag-BG after 24 h of immersion in aqueous solution was observed to be approximately 0.4 ppm and sufficient to cause bacterial damage. A similar ion release profile was expected for the concentrations used in this example, with an increase in the concentration of the released Ag ions corresponding to an increase in the concentration of Ag-BG. This mechanism explains the increase in bacterial inhibition by increasing the concentration of Ag-BG as presented in FIG. 13B.

Vancomycin is a potent cell-wall inhibitor during cell division but it remains inactive under growth-arrested conditions at all tested concentrations (FIG. 13A). Supplementing Ag-BG particles with different concentrations (0.3-1 mg/mL) of vancomycin resulted in a synergistic antibacterial effect that increased with increasing concentrations of vancomycin, although under growth-arrested conditions MRSA resisted vancomycin. The ability of Ag-BG to restore vancomycin's antibacterial activity is based on the re-activation of cell-wall biosynthesis due to the nanotunnels created by the Ag-BG nanoproducts. Bacteria attempt to repair the damage caused by the released Ag-BG nano-size debris and Ag$^+$ ions by cell-wall biosynthesis. However, vancomycin binds to the D-Ala-D-Ala dipeptide terminus of bacterial peptidoglycans preventing the creation of new cell-wall.

The steps of this inhibitory process were further confirmed here. The first step of the inhibition comes from the degradation of Ag-BG solely since synergism was not observed in combinations where the concentration of Ag-BG was lower than its MIC (1.25 mg/mL of Ag-BG with 0.5 mg/mL vancomycin) (FIG. 13C). Thus, the initial damage caused by Ag-BG is the driving force for the reactivation of vancomycin under growth-arrested conditions. Increasing the concentration of Ag-BG (2.5-6.25 mg/mL) while maintaining a constant concentration of vancomycin (0.5 mg/mL) allowed stronger bacteria inhibition since the concentrations of the by-products from the physicochemical degradation of Ag-BG particles get increased (FIG. 13C). The concentration of vancomycin in Ag-BG/vanc system was also critical to observe synergism. For example, a concentration of 0.1 mg/mL of vancomycin in Ag-BG/vanc was insufficient to synergize with Ag-BG particles (FIG. 13D). This result was attributed to the limitation of this low concentration of antibiotic molecules to find their target site. Such limitation can be addressed as the concentration of either or both, antibiotic and/or target site, increases. The activation of cell-wall biosynthesis would happen locally near the damaged cell-wall. The synthesis of new cell-wall was significantly low with the treatment of 2.5 mg/mL of Ag-BG since little damage was caused when Ag-BG was delivered in a concentration close to the MIC. Thus, very low numbers of D-Ala-D-Ala dipeptide terminus sites were formed. The increase of the concentration of vancomycin in Ag-BG/vanc increases the potential of the antibiotic to find the terminus as demonstrated when delivering a concentration above 0.3 mg/mL of vancomycin in Ag-BG/vanc. This result also confirmed the second step of the Ag-BG/vanc inhibitory process that is based on the reactivation of cell-wall synthesis to reconstruct the damaged wall and the need for vancomycin to obstruct this process. Under this situation, the combination of low concentrations of vancomycin with a high, yet not completely toxic, the concentration of Ag-BG, would be expected to also synergize; because higher damage on the cell-wall would trigger more cell-wall biosynthesis and consequently an increase on the vancomycin targets.

The antibacterial behavior of Ag-BG did not compromise its bioactive and biological properties when co-cultured with hBMSCs. In fact, Ag-BG was not cytotoxic at any of the tested concentrations (FIG. 14A), similarly to the behavior previously observed in cultures with pulp cells. The release of Si, Ca, P, Na, and K ions from the bioactive glass network enhanced the rate of cell proliferation, while the concentration of the released Ag$^+$ ions is expected to remain constantly below the 1.6 ppm that is nontoxic to eukaryotic cells. The co-cultures of hBMSCs with Ag-BG particles led to an increase in the proliferation rate of the cells compared to untreated cells (FIG. 14B-14G). Measuring the expression level of specific osteogenic markers it was observed enhanced osteogenic gene expression in hBMSCs when co-cultured with Ag-BG (FIG. 15). Bone sialoprotein (BSP) is a significant component of bone extracellular matrix. Osteocalcin (OCN) is a key hormone involved in the binding of calcium to the extracellular matrix and thus, related to bone mineral density. The upregulation of the expression levels of both genes when the concentration of Ag-BG increases in the co-treatment shows the differentiation properties of the Ag-BG particles. BSP and OCN are non-collageneous ligands that play a key role in the mineralization of bone and dentin. In fact, both of these genes appear at high levels in mature osteoblasts, but not in their immature precursors. Thus, the expression of both BSP and OCN serves as an indicator of osteoblastic differentiation of hBMSC. Besides the upregulation of these biomarkers, distinct cell mineralization was identified with ARS (FIGS. 16A-16D). The presence of Ag-BG triggered an enhanced formation of the mineral phase within 10 days of co-treatment. Interestingly, cell mineralization occurs not only in osteogenic medium but also in growth medium without osteogenic supplements. This effect may occur due to the super-saturation of the solution that triggers cell secretion and minerals formation. Because of that, under osteogenic culture conditions, the mineral content was higher than in growth conditions. This super-saturation in the culture medium is also evidenced by the deposition of the apatite-like phase on the surface of the Ag-BG particles (FIGS. 17A-17G). The in vivo regenerative properties of Ag-BG particles are attributed to their physicochemical and microstructural characteristics. Previous in vivo studies showed the capability of these particles to significantly induce pulp dentin regeneration. It is the first time that Ag-BG particles are tested for bone regeneration. The Si and Ca ions that are released from Ag-BG have the most significant role in intracellular and extracellular pathways for osteogenesis. In particular, intracellular Ca ions act as a cell signaling agent during all phases of the cell cycle, triggering various mitogen-activated protein kinases for cell differentiation. The release of Si ions at certain concentrations has also been shown to increase cell proliferation. Extracellular Ca and Si are involved in the upregulation of OCN. Both Si and Ca synergize affecting the metabolism of osteoblastic cells. The effect of these two ions was also evidenced in this work since by increasing the concentration of Ag-BG particles, and consequently the concentration of the released ions, it yielded to a significant upregulation of OCN and higher mineral secretion.

Additionally, the uptake process by cell phagocytosis of the nano-sized debris, that are created during the physicochemical degradation of Ag-BG particles is expected to contribute to the biological response. The intracellular dissolution of the nano-size debris would imply an increased Si and Ca ion content inside the cell, inducing specific signaling for their proliferation and differentiation.

Summarizing, this example unravels the antibacterial mechanisms of Ag-BG particles and the mechanisms that underlie its unique synergism with vancomycin under growth-arrested conditions. Understanding the synergistic mechanism of action underlying the antibacterial activity of Ag-BG and vancomycin significantly impacts the current therapy employed in combating bacteria in biofilm which evade immune and therapeutic response by decreasing bacterial replication. Additionally, the bioactive and regenerative properties of Ag-BG particles were for the first time demonstrated in vitro in co-culture with hBMSCs and in vivo in a calvarial defect model. These properties, combined with the unique antibacterial activity even under growth-arrested conditions, render Ag-BG particles as an excellent regenerative material for the treatment of bone defects, minimizing the risk for infection when MRSA is involved.

Conclusion

Ag-BG microparticles are antibacterial against MRSA. This example demonstrates that the reactivation of vancomycin in Ag-BG/vanc system was possible in scenarios where Ag-BG had already caused sufficient damage to bacteria. Moreover, it was shown that the concentration of vancomycin was key to observe synergism. Ag-BG not only enhanced cell proliferation rate and osteoblastic differentiation in hBMSCs, but also promote bone formation in vivo. These results show that Ag-BG particles are an innovative therapy in bone regenerative applications.

Example 3

This example describes silver-releasing bioactive glass nanoparticles for drug-free infected tissue regeneration against resistant bacteria.

Summary

Ag-doped bioactive glass nanoparticles (Ag-BGNs) of 10 nm size were synthesized by a modified Stöber method. Energy-dispersive X-ray spectroscopy (EDS) results indicated the successful incorporation of P, Ca, Al and Ag in the glass structure at the intended concentration. The nanoparticles were spherical and showed moderate dispersity although they form submicron size aggregates when not in solution. Crystalline hydroxyapatite (HA) started to form on Ag-BGNs upon immersion of the particles in simulated body fluid for 5 days, which indicated that Ag-BGNs maintained high bioactivity. The antibacterial effect was confirmed against MRSA under different experimental conditions showing Ag-BGN was able to sterilize planktonic bacteria without the presence of any type of antibiotic. However, Ag-BGN remained non-cytotoxic. The above results thereby show that the synthesis protocol presented here is a viable alternative to develop potential biomaterials for regeneration of infected tissue.

Introduction

Bacterial infections are one of the main complications in orthopedics. Current treatment procedures comprise the debridement of infected tissue, which generates large bone defects. The implantation of a biomaterial at the surgical site has become one of the most appealing approaches to stimulate bone healing. Ideal bone substitutes are multifunctional and simultaneously provide all the necessary properties for tissue growth such as biocompatibility, biodegradability, osteoconductivity, and angiogenesis. Nevertheless, infections often persist after debridement and need to be further treated with the systematic delivery of antibiotics. Both of these actions significantly increase patient pain and social cost. Additionally, the ability of several bacterial strains to develop antibiotic resistance has raised an interest in alternative antibacterial agents. For example, the incorporation of antiseptic ions (e.g., $Ag^+$) into the biomaterial composition are a valuable alternative to antibiotics since they possess low impact on the resistance acquisition.

Bioactive glasses (BGs) are multifunctional biomaterials having uses for orthopedic and dental grafts. The bone bonding ability of BGs is owed to the deposition of a carbonate hydroxyapatite layer at its surface. BGs release ionic products depending on their chemical composition and dissolution environmental conditions triggering specific biological responses. For example, the release of Si, P and Ca ions from the degradation of a BG structure has shown to increase proliferation and showed genetic control of human cells. BGs also present the advantage of detail compositional design that allows the introduction of antibacterial heavy metal ions (e.g., $Ag^+$ or $Cu^{2+}$) into the glass matrix for their controlled and sustained delivery at the bacterial site. Doping BGs with silver has been achieved by the sol-gel technique as well as by ion exchange processes. The antibacterial behavior was confirmed against *Escherichia coli*, *Pseudomonas aeruginosa*, and *Staphylococcus aureus* when $Ag^+$ were released at a concentration between 0.05-0.20 mg $mL^{-1}$. Moreover, as long as their released concentration remains below cytotoxicity ($Ag^+$<1.6 ppm) the tissue regenerative properties of BG are not compromised. Owed to their advanced bioactive and antibacterial properties, Ag-doped BG has been employed to coat surgical sutures.

It has also been shown that BGs biological and antibacterial properties are greatly enhanced when reducing its particle size to nanoscale. For example, strong antibacterial capabilities of bioactive glass nanoparticles (BGN) lacking heavy metal ions against *E. faecalis*, and *S. aureus* and *E. coli* has been considered. Although the inhibition of both melt-derived nano 45S5 and sol-gel derived nano 58S and 63S were higher than their micro size equivalents, most of the antibacterial effect was attributed to a pH increase of almost three units. Another mechanism has been proposed in which the deposition of hydroxyapatite during BGN degradation encapsulated bacteria around dentin, affecting their viability. However, it has been reported that mineralization had rather little effect on the antimicrobial properties of nano-BG which was mainly caused because of the release of ionic species. Example 1 above shows additional mechanisms such as nanoparticles from the debris of larger size Ag-doped microparticles punctuating the membrane of Methicillin Resistant *S. aureus* (MRSA). Size reduction not only advanced the bactericidal effect but also the biological response. Specifically, BGNs favor localized treatment thanks to intracellular uptake and accelerate the regenerative process owe to their higher surface reactivity. The work presented for antimicrobial ion delivery in BG structures together with the properties observed in nanosized BGs, the combination of both approaches for the development of Ag-doped BGNs (Ag-BGNs) would improve the outcomes in infection treatments.

The sol-gel technique presents several advantages for the fabrication of BGs, although it has often resulted in strongly aggregated nanoparticles. Alternatively, the Stöber method has been modified to control particle size, morphology and distribution. However, this approach has frequently showed poor control over the composition and aggregation due to the addition of salt precursors, such as calcium nitrate. For example, the compositional, morphological and, nanoparticle size and dispersity discrepancies between sol-gel and Stöber derived Ag-BGNs has been described. Although $Ag^+$ was successfully incorporated by both approaches, Stöber-derived Ag-BGNs lack the intended concentration of Ca and P. This result is in agreement with previous reports around the challenges in metallic ion incorporation in BGNs. Surface modification of Stöber-derived silica nanoparticles has been presented as another approach to deliver Ag in BGNs since their high concentration of surface silanol (Si—OH—) groups favor electrostatic adsorption of $Ag^+$ ions. Nevertheless, post-surface modification requires an additional heat treatment to stabilize the structure and usually yields to the incorporation of low metallic ion content. Interestingly, most Stöber-derived Ag-BGN in the literature presented up to date appear in the submicron size (100-300 nm) rather than nanosize (<100 nm) and limit some of the advantages intended with the size reduction.

The aim of this example is to address the challenge on compositional and size control in the synthesis of Ag-BGN using a modified Stöber method. Particles in the nanoscale were developed and characterized to prove successful metallic ion incorporation. An advanced ion-doping approach for BGN is presented since Ag was trapped in its ionic state within the glass structure. Therefore, preventing Ag oxidation and reduction reactions which ensures it is delivered in its optimum state for antibacterial purposes. The bioactivity was assessed in vitro inducing and characterizing the apatite phase deposits after exposure to biological environment. Strong antibacterial capabilities were observed against MRSA, a bacterium responsible for most bone degenerative infections. The release of $Ag^+$ was controlled and maintained at an antibacterial but not cytotoxic level, allowing the Ag-BGN to support eukaryotic cell growth. Overall, this example presents novel multifunctional nanoparticles with attractive properties for regenerative medicine. The synthesized Ag-BGN could be used as bone substitutes in paste form or delivered in other structures such as nanocomposite with biopolymers, injectable gels or coatings on different materials.

Materials and Methods

Materials for Ag-Doped Bioactive Glass Nanoparticles (Ag-BGN).

Analytical grade tetraethyl orthosilicate (TEOS), triethyl phosphate (TEP), aluminum nitrate nonahydrate, silver nitrate and calcium nitrate tetrahydrate and 28-30% ammonium hydroxide ($NH_4OH$) solution from Millipore Sigma. The solvents used were distilled water, 200 proof ethyl alcohol, and methanol. All reagents were used as received without further purification.

Synthesis Approach for Ag-BGN.

The fabrication of Ag-BGN ($SiO_2$ 59.6-CaO 25.5-$P_2O_5$ 5.1-$Al_2O_3$ 7.2-$Ag_2O$ 2.2 wt. %) comprised of a sol-gel one-step basic catalysis. This synthesis approach was based on the modified Stöber-like protocol reported before for the fabrication of 58S BGN (see Example 7). Briefly, two solutions were prepared. In Solution A, methanol was mechanically stirred at room temperature and 500 rpm with the chemical precursors. First, TEOS and TEP were introduced in Solution A and mixed for 24 h. Then, aluminum nitrate, silver nitrate and calcium nitrate were added one by one allowing 24 h stirring in between reagents. Aluminum nitrate was introduced to generate [$Al_2O_4$]—tetrahedra to electrostatically bond to $Ag^+$ to trap $Ag^+$ ion in Ag-doped BG microparticles. Silver nitrate was mortar pulverized to fine powder for a faster dissolution. The photoreduction of silver ions as well as the evaporation of the organic solvent were prevented by conveniently isolating the beaker in a fume hood and covering its mouth with two layers of parafilm and foil. The catalytic reagents—distilled water, 28-30% ammonium hydroxide and ethanol—were mixed in Solution B. After the addition of calcium nitrate, Solution A was homogenized for 24 h before pouring Solution B to induce the condensation reactions for nanoparticle nucleation. The concentrations (in molarity, M) of the reagents (methanol, TEOS, $H_2O$, $NH_4OH$ and ethanol) used are summarized in Table 2. Finally, nanoparticles were collected by centrifugation at 3000 rpm for 3 min and heat treated at 60° C. for 6 h, followed by calcination at 700° C. for 2 h with 2° C./min heating rate and cooling down to room temperature with 5° C./min. The collected powder was additionally mortar pulverized and washed with ethanol twice to remove calcium-rich areas and air-dried before characterization.

TABLE 2

Ratios of reagents based on the concentration of TEOS for the total volume of the reaction, after mixing Solution A and Solution B.

|  | TEOS | MeOH/ TEOS | H$_2$O/ TEOS | NH$_4$OH/ TEOS | EtOH/ TEOS |
|---|---|---|---|---|---|
| Ratios of reagent | 0.23M | 0.02 | 55.96 | 5.3 | 50 |

Morphological and Elemental Evaluation.

The morphology of the Ag-BGN was observed using a ZEISS FIB-SEM operated at 3 kV and the elemental analysis was performed using the same instrument at 15 kV. Powder samples were spread on carbon tape to avoid interference from the substrate in the elemental analysis. All SEM samples were Os coated for 15 s.

Particle Size, Distribution and Surface Charge.

The particle size was investigated using transmission electron microscopy (JEOL100 TEM) operated at 100 kV. Ethanol was used to disperse the Ag-BGN through sonication, and 5 μL of solution was pipetted in a 200 mesh C-coated Cu grid. Particle size, size distribution (dispersity) and surface charge (zeta-potential) were also assessed with a laser dynamic light scattering (DLS) equipped with a laser Doppler electrophoresis (LDE) instrument (Zetasizer-nano series, Malvern Instruments Ltd). The Ag-BGN were dispersed in Mili-Q water at a concentration of 1 mg/mL and sonicated for 10 min before measurements.

Structural Evolution During Apatite Deposition.

The deposition of apatite phase served to evaluate the bioactive response of Ag-BGN. This apatite forming ability was assessed by immersion of Ag-BGN in Kokubo's Simulated Body Fluid at a weight ratio of 3.33:1. Nanoparticles were collected by centrifugation and washed with ethanol after 1, 3, 5, 7 and 14 days of immersion. The structural and morphological evolution of particles were studied with FTIR-ATR for wavenumbers in the range of 400-2000 cm$^{-1}$ and SEM-EDS to calculate the Ca/P ratio. The crystalline apatite formed after 14 days was evaluated using XRD (Rigaku Smartlab XRD) using Cu K$_\alpha$ radiation at 40 kV/40 mA and SAD-TEM. The pH was monitored during the test.

Biological Characterization of Ag-BGN.

The Ag-BGN were preconditioned to allow the initial burst ionic release that causes sudden pH raise for 4 days using α-MEM. Then, Ag-BGN were centrifuged and dried at 60° C. The pellet was mortar pulverized and the powders were sterilized using UV radiation before any biological test.

Antibacterial Activity.

The bactericidal properties of Ag-BGN were studied against laboratory-derived methicillin-resistant *S. aureus* (MRSA) USA300 JE2. The bacteria cells were prepared by isolation of a single colony, followed by its inoculation in tryptic soy broth (TSB) overnight at 37° C. Bacteria were washed with Phosphate Buffered Saline (PBS) twice and suspended to a concentration of 108 colony forming units (CFU)/mL in PBS for growth arrested conditions or TSB to sustain bacterial growth. Then, the bacterial suspension was mixed 1:1 with increasing concentrations of Ag-BGN to a final volume of 1 mL. Under growth arrested conditions, Ag-BGN was used 0.05, 0.1, 0.25, 0.5 and 1 mg/mL while under growth, bacteria were exposed to 2.5, 5, 10, 20 and 30 mg/mL of Ag-BGN. Negative control was prepared by suspending bacteria 1:1 in PBS or TSB and was labeled as 0 mg/mL of Ag-BGN. All solutions were placed in a surface treated 24 well tissue culture plate that prevented bacteria adhesion while maximizing the nanoparticle's surface exposed during treatment. After incubation at 37° C. for 0, 12 and 24 h, 0.03 mL of suspension were drawn from the mixture for CFU enumeration in tryptic soy agar plates. The effect of the treatments was evaluated based on the decrease of CFU compared to the negative control. Quantification of CFU was performed in biological and technical triplicates.

Proliferation of Human Mesenchymal Stem Cells.

Primary bone-marrow derived human mesenchymal stem cells (hBMSC) (line 8013) isolated from 22 years old healthy male donor were obtained from the Institute of Regenerative Medicine, Texas A&M University. Frozen vials of cells were thawed and cultured a in α-MEM supplemented with 16% fetal bovine serum, 1% Antibiotic-Antimycotic and 1% L-glutamine (hereafter, growth medium) in a humidified 37° C./5% CO$_2$ incubator. Cells were expanded until 90% confluence to a final passage. Cells were enzymatically lifted, centrifuged for 5 min and re-suspended fresh media. Cells were seeded at a density of 15×10$^3$ cells/mL on each well of 24-well plate by pipetting 0.5 mL/well. After 24 h, Ag-BGN (5, 10 and 20 mg/mL) were transferred to porous transwells and inside the wells to treat cell for 2, 4, 6, 8 and 10 days. The results were compared to a positive control consisting on cell immersed only in media and a negative control consisting on cells treated with Ag$_2$O exposed using a porous transwell. A single concentration of Ag$_2$O (0.2 mg/mL) was used to represent the total concentration of Ag in 10 mg/mL of Ag-BGN, simulating an environment in which all the Ag concentration was released at once.

After each time point, cell viability and proliferation were assessed introducing a CCK-8 kit solution in the wells after removing the transwells. After 2 h, 100 mL were drawn and placed in a 96 well plate and its optical density was measured at 470 nm wavelength. Then, cells were washed with PBS thrice. Culture media was refreshed and the transwells were transferred back to the plate to treat cells for the next time point. The experiment was performed using triplicate samples.

Results

Morphology, Particle Size, and Distribution.

The particle size and dispersity of the sol-gel derived Ag-BGNs are shown by SEM (FIG. 19A) and TEM (FIG. 19B). Microscopy images indicated an average particle size of 10 nm that aggregated (~300 nm) under dried conditions to reduce their instability. Ag-BGN were consistently dense and spherical throughout the samples. SEM-EDS spectra (FIG. 19C) showed presence of the elements in the Ag-BGN concentration and confirmed the desired concentration was achieved, in agreement with Example 7. Quantitative analysis of particle size by DLS (Table 3) confirmed nanoparticle size (~8.5 nm) with a small deviation from that measured in FIG. 19B. This result was a rough indicator of the ability of Ag-BGN to detach from the aggregates under a favorable environment. The surface charge was evaluated in terms of zeta-potential (Table 3) with an average value of −9 mV.

TABLE 3

Particle size and surface charge of Ag-BGN.

| Particle size and size distribution (nm) | 8.42 ± 0.62 |
|---|---|
| Zeta-potential (mV) | −8.94 ± 3.84 |

Apatite Forming Ability.

The capability of the Ag-BGNs to form an apatite-like phase was evaluated by immersion in SBF at 37° C. under constant agitation to reproduce body conditions. The structural changes were monitored in FTIR (FIG. 20A) over the course of treatment and compared to untreated samples. The IR spectra of the Ag-BGN structure before immersion in SBF showed the typical vibration of an amorphous silicate-based glass. Bending and stretching modes of the Si—O—Si bond were observed at 450, 805 and 1200 cm$^{-1}$. The overlap of the P—O bending and the Si—O—Si stretching mode around 1000-1050 cm$^{-1}$ caused the broadening of the peak. The modification of the silica network, due to the successful incorporation of $Al_2O_4^-$, $Ca_2^+$ and $Ag^+$, was evidenced by the shoulder band at 900 cm$^{-1}$ attributed to Si—O-Non-Bridging Oxygen (NBO) bonds. The immersion of Ag-BGN in SBF induce the development of broad P—O bending peak in the region of 575-620 cm$^{-1}$. This contribution evolved to a double peak after 5 days and sharpen after 7 days, indicating the formation of a crystalline phase. The deposition of a Ca—P phase was also supported by decrease of intensity of the Si—O band at 900 cm$^{-1}$ and 1200 cm$^{-1}$, and the sharpening of the P—O band at 1000 cm$^{-1}$. The crystalline Ca—P phase was further characterized with XRD and TEM (FIG. 20B) after 14 days immersion. FIG. 20B confirmed Ag-BGN were amorphous. After 14 days of immersion, crystalline diffraction peaks (marked at 26, 28, 32, and 46 2θ) confirmed the Ca—P phase formed was hydroxyapatite (PDF No. 9003552) within The International Centre for Diffraction Data (ICCD). Silver-related crystalline phases were not developed after calcination nor after exposure to SBF.

The hydroxyapatite phase developed during Ag-BGN degradation was also characterized using SEM-EDS and, the Ca/P ratio and pH during treatment were recorded (FIGS. 21A-21B). Apatite needles were randomly and very occasionally observed after 1 and 3 days of immersion. The presence of these needles grows with immersion time. FIG. 21A shows needles forming cauliflower structures after 5 and 7 days immersion. Longer exposure to SBF, for up to 14 days caused the densification of the needles into flakes due to crystallization. Before SBF, the Ca/P ratio was ~8 and decreased to ~1.7 after 7 days of immersion, which is the characteristic Ca/P ratio for biological hydroxyapatite. The pH in a simulated biological environment remained within the neutral range over the cause of the experiment.

Antibacterial Behavior.

To determine the antibacterial level of Ag-BGN, increasing concentrations of nanoparticles were incubated with MRSA (FIGS. 22A-22B). Antibacterial behavior was observed after 12 h incubation under both growth arrested and growth conditions, with a minimum inhibitory concentration (MIC) of 0.05 mg/mL and 2.5 mg/mL, respectively. The effect was time dependent as the viability of bacteria significantly decreased after longer exposure period for up to 24 h. Under growth arrested conditions (FIG. 21A), almost linear inhibitory trends were observed, reaching CFUs below the limit of detection (LoD=33 CFU) upon treatment above 0.25 mg/mL of Ag-BGN. The antibacterial effect was also significant when bacteria proliferation was allowed (FIG. 21B). Although the CFUs were reduced compared to untreated MRSA, the lower concentrations of Ag-BGN (2.5 and 5 mg/mL) were not able to bypass the cell growth rate since their CFUs were higher after 24 h than at 12 h exposure. Nevertheless, higher concentrations of Ag-BGN (10 mg/mL and above) surpassed bacterial growth decreasing CFUs below the LoD upon 24 h exposure above 20 mg/m L.

Cell Viability and Proliferation In Vitro.

The cytotoxicity was tested exposing human mesenchymal stem cells to increasing concentrations of Ag-BGN (5, 10 20 mg/mL). The results were compared to the toxicity of $Ag_2O$ to assess the difference in cell viability when $Ag^+$ are delivered at once instead of the gradual release of ions in Ag-BGN. FIG. 23 presents higher cell viability and faster proliferation for Ag-BGN treated cells than the untreated (0 mg/mL) ones at each time point. Fibroblasts exposed to $Ag_2O$ were not viable after 4 days exposure. The increase viability trend observed by $OD_{460}$ measurements was confirmed by the cell confluence in FIG. 24A. After 6 days of Ag-BGN treatment, cells presented an elongated morphology and curvature due to confluence. The proliferation rates were analyzed using linear fitting on the original OD values of each group (FIG. 24B) and calculating the slope of the trend for $R^2>0.9$. The proliferation rate of Ag-BGN treated cells were similar than in the case of untreated cells (0 mg/mL). However, the OD values were significantly higher, indicating that the higher the concentration of Ag-BGN treatment, the faster the cells reached confluence, slowing the overall rate of growth.

Discussion

Biomaterials with enhanced antibacterial and regenerative properties area a valuable choice in orthopedics and dentistry where underlying infections often compromise the success of the prosthetic or treatment. Here, a novel method for the synthesis of Ag-BGN is developed and their potential as an antibacterial and regenerative tool in vitro is evaluated. The Stöber method was conveniently modified from a ternary glass system to a quinary system for the incorporation of the antibacterial agent (i.e., $Ag^+$). A single-step basic catalysis using a combination of ammonium hydroxide and distilled water was used to raise the pH. Thus, accelerating the condensation rate, which is proportional to the concentration of [OH$^-$], and reduced the time for gelation. Mechanical agitation and the use of ethanol as dispersant produced regular shape and size nanoparticles of ~10 nm. Interestingly, although this protocol utilized the same Solution B as Example 7, the particle size obtained was significantly lower. The main difference of the Ag-BGN synthesis approach is the longer total stirring time of the chemical precursors compared to ternary-BGN. This result confirms that the mixing time of reagents is one of the control parameters for particle size. DLS and TEM showed fair nanoparticle dispersity in aqueous medium which suggest their detachment and guarantees properties in the nanoscale. As expected, metallic ion incorporation was achieved following the same mechanism as in ternary BGNs. Briefly, P was incorporated inducing a faster hydrolysis rate using methanol, and Ca was trapped and homogenized in solution before catalysis (see Example 7). Keeping on these facts, Al and Ag were introduced before particle nucleation to allow a similar incorporation process than that observed for Ca. The incorporation of Ag into the structure as $Ag^+$ ions and not in metallic or colloid form was achieved by the presence of $[A_2O_4]^-$ tetrahedra at an ionic ratio of Al/Ag>1. The successful trapping of $Ag^+$ ions was evidenced by the lack of grey or brownish color in the Ag-BGN powder.

The synthesized Ag-BGN were amorphous and presented the typical structure of silicate-based BGs in both FTIR and XRD. The backbone of the glass comprised $SiO_4$ tetrahedral units forming a 3D interconnected network by bonding their corner oxygens. The degree of connectivity was significantly reduced because of the incorporation of $Ca_2^+$, $[A_2O_4]^-$ and $Ag^+$, that opened the silica network forming NBO bonds. It is worth noticing that among these metallic ions, $Ca^{2+}$ is the stronger network modifier since its valency causes 2 NBO for every Ca atom and its concentration on Ag-BGN was significantly higher than that of $[A_2O_4]^-$ and $Ag^+$. The NBO groups facilitate the exchange of ions from BG structure with the $H^+$ in the aqueous solution. Thus, the larger the concentration of NBO bonds, the faster the dissolution rate is, which yields to higher ion release and higher bioactivity. Although the formation of Ag—O bonds was shown to decrease the dissolution rate elsewhere because its bond is highly covalent, the concentration of $Ag^+$ in our Ag-BGN was not enough to significantly delay the degradation of the glass network. In fact, the degradation observed during the apatite-forming experiment in SBF was advanced compared to Ag-BG microparticles. Ag-BGNs were highly reactive and show the development of P—O bonds, associated to Ca—P phase deposition, after only 1 day of exposure. Fully crystallized biological hydroxyapatite was formed after 14 days in SBF as shown by FTIR, XRD, SAD-TEM and SEM-EDS. The faster bioactivity was not only correlated to the low network connectivity but also to the high surface reactivity of small size particle, and the negative zeta-potential value of Ag-BGN in water that allows a favorable deposition.

The antibacterial properties of Ag-BGN were proven against MRSA under growth arrested and growth allowed conditions. The bacterial inhibition cannot be attributed to the pH, since its value was not significantly changed over the course of the experiment. The major mechanisms of inhibition are attributed to both the release of $Ag^+$ ion as well as the ability of nanoparticle to punctuate bacterial membrane similarly to the effect observed from Ag-BG microparticles. Despite Ag-BGN low concentration of $Ag^+$ ion, their MIC under growth arrested conditions was 2% of that in the micrometer counterparts. Thus, proving size reduction was key to advance the antibacterial action. The ability to reduce bacterial viability when their proliferation was allowed suggest the potential of Ag-BGN in a real infected tissue scenario, proving their strong potential as antibacterial tools. More importantly, Ag-BGN were not cytotoxic to eukaryotic cells at any concentration in vitro. The release of Si, Ca, and P from the bioactive glass network benefited the rate of cell proliferation. the results also prove that the systematic delivery $Ag^+$ from Ag-BGNs controlled its toxicity, since direct administration of $Ag_2O$ reduced the viability of human cells.

Conclusion

Ag-doped BG nanoparticles were synthesized using a modified Stöber method in a single-step basic catalysis. This novel fabrication protocol yielded to Ag-BGN of the aimed composition and particle size of 10 nm. The antibacterial properties of Ag-BGN were advanced trapping $Ag^+$ ion within the glass network. The nanosize not only benefited the inhibition of MRSA but also the faster deposition of hydroxyapatite in vitro. Ag-BGN also promoted human cell proliferation. All these properties together point to the value of Ag-BGN for biomedical application, especially for infections while sustaining the regeneration of the surrounding healed tissue.

Example 4

This example describes fabrication and multiscale characterization of 3D silver containing bioactive glass-ceramic scaffolds.

Summary

In this example, bioactive 3D glass-ceramic scaffolds with inherent antibacterial properties is fabricated and characterized. The sol-gel (solution-gelation) technique and the sacrificial template method were applied for the fabrication of 3D highly porous scaffolds in the $58.6SiO_2$-$24.9CaO$-$7.2P_2O_5$-$4.2Al_2O_3$-$1.5Na_2O$-$1.5K_2O$-$2.1Ag_2O$ system (Ag-BG). This system has bioactive and antibacterial properties. The fabrication of 3D scaffolds has applications that impact tissue engineering. The study of the developed scaffolds from macro-characteristics to nano-, revealed a strong correlation between the macroscale properties such as antibacterial action, bioactivity with the microstructural characteristics such as elemental analysis, crystallinity. Elemental homogeneity, morphological, and microstructural characteristics of the scaffolds were studied by scanning electron microscopy associated with energy dispersive spectroscopy (SEM-EDS), transmittance electron microscopy (TEM), X-ray diffraction (XRD), X-ray photoelectron spectroscopy (XPS), Fourier transform infrared spectroscopy (FTIR), and UV-visible spectroscopy methods. The compressive strength of the 3D scaffolds was measured within the range of values for glass-ceramic scaffolds with similar compositions, porosity, and pore size. The capability of the scaffolds to form an apatite-like phase was tested by immersing the scaffolds in simulated body fluid (SBF) and the antibacterial response against methicillin-resistant *Staphylococcus aureus* (MRSA) was studied. The formation of an apatite phase was observed after two weeks of immersion in SBF. The anti-MRSA effect occurs after both direct and indirect exposure.

Introduction

There is a critical need to develop functional biomaterials that stimulate tissue regeneration under a variety of in vivo conditions. Such materials are referred to collectively as "bioactive" materials. The effectiveness of orthopedic devices increases significantly if they are bioactive and capable of developing a natural bone with the surrounding tissue. Many current orthopedic devices are based on metal and metal alloys, given they are readily available, mechanically robust, and biocompatible. However, these metal alloys cannot develop a natural bond with the surrounding tissue and can be prone to wear and corrosion that activates the foreign body reaction mechanism leading to failure. Furthermore, metal and metal alloys are seldom used for treatments requiring complete or partial resorption. For such applications, a 3D scaffold with controllable nano-to macro-scale structure, with degradation rates matching tissue regeneration and controlled release rates of therapeutic/antibacterial agents (e.g., Ag, Cu, Ga), would be considered ideal.

In particular, Ag incorporation into biomaterials has been the subject of studies due to its broad range of antibacterial properties and the lack of bacterial resistance. Therapeutic silver concentration [Ag] ranges from 0.1 to 1.6 ppm killing off bacteria without harming eukaryotic cells. The challenge with silver is that $Ag^+$ ions are the most potent form, which $Ag^+$ ions are notoriously difficult to stabilize. However, successful stabilization of $Ag^+$ was achieved through the use of negatively charged aluminum tetrahedra. The $Ag^+$ stabilization within the glass-ceramic structure further showed that $Ag^+$ ions were released in a controlled manner, making it a suitable approach for $Ag^+$ ions incorporation.

In addition, a 3D open porous scaffold with interconnected porosity can provide the required pathway to the surrounding tissue to migrate and reconstruct the lost or defected tissue throughout the whole volume. It is believed that the chemical, morphological, and microstructural properties of the scaffold need to offer the necessary signals for cell proliferation and differentiation that can lead to the regeneration of functional tissue. Given their potential to satisfy bioactivity and biodegradability, glasses and glass ceramics, particularly those within and based upon the $60SiO_2$-$4P_2O_5$-$36CaO$ (wt. %) compositional system, have garnered attention within the biomaterial community as candidate materials for 3D scaffolds fabrication. It has been shown that the degradation rate of such glasses and glass-ceramic scaffolds can be controlled by tailoring the composition and atomic scale structure of the materials. In addition, the nano-to-macroscale 3D structure of the scaffold is typically controlled through scaffold processing and has a direct effect on scaffold properties.

There are numerous techniques to fabricate 3D scaffolds. Sol-gel based methods are ideal for glass and glass-ceramic scaffold processing, given they afford the realization of scaffolds with (1) a wide range of compositions, (2) controllable nano-to macro-structure, (3) an easy to scale up the approach, and (4) the ability to include therapeutic or antibacterial agents, such as heavy metal ions and antibiotics. Solution based fabrication has been used to fabricate mesoporous 3D scaffolds with surface areas greater than 100 $m^2/g$, as the rate of bioactivity increases when the surface area to volume ratio increases. The sol-gel technique often takes advantage of sacrificial templates for the fabrication of 3D glass or glass-ceramic scaffolds. Polyurethane foams are often used as templates because they can be manipulated to produce a scaffold with optimal three-dimensional networks. The aforementioned characteristics develop the ability to control the multiscale structure of scaffolds, which is paramount as structure-property relationships must be clearly understood. For example, scaffold connectivity, scaffold strut integrity, scaffold matrix structure, and the structural role of any therapeutic/antibacterial agent all affect the bioactivity and therapeutic ion release.

In this example, 3D bioactive glass-ceramic scaffolds containing silver ions for biological and antibacterial applications are fabricated and characterized. These scaffolds are prepared using a sol-gel based sacrificial template method. The structure of these scaffolds was characterized over multiple length scales (500 microns to ~50 nanometers) using a variety of complementary microscopic and spectroscopic techniques. The bioactivity of the scaffolds was confirmed through in vitro exposure to simulated body fluid followed by morphological and chemical examination. This work also examines the micro- and macro-structural characteristics of a novel sol-gel derived Ag-BG 3D scaffold and the resulting bioactive and anti-MRSA properties.

Materials and Methods

Fabrication.

The scaffold composition is based on a silver-containing bioactive glass-ceramic (Ag-BG) in the $58.6SiO_2$-$24.9CaO$-$7.2P_2O_5$-$4.2Al_2O_3$-$1.5Na_2O$-$1.5K_2O$-$2.1Ag_2O$ (wt %) system (Table 4). The glass-ceramic scaffolds were prepared using a sacrificial template method and applying a specific heat treatment to the solution coated polymeric foams. The preparation of the sol-gel glass-ceramic in the solution stage is described above. Briefly, the sol-gel bioactive glass 58S at the solution stage (in the system $58SiO_2$-$33CaO$-$9P_2O_5$ (wt. %)) is mixed with the solution stage of a sol-gel derived glass-ceramic in the system $60SiO_2$-$6CaO$-$3P_2O_5$-$14Al_2O_3$-$7Na_2O$-$10K_2O$ (wt. %), where the fabrication of each solution is described above. After mixing the two sol-gel precursors, the resulting solution was stirred for 17 h to ensure homogeneity. The 3D glass-ceramic scaffolds were prepared by the sacrificial template technique through the calcination of Ag-BG solution coated polyurethane foams. In brief, polyurethane foam (45 pores per inch; United Plastics) was cut into 25.4×25.4×25.4 mm cubes, immersed in ethanol and ultrasonically cleaned for 15 min. The foams were dried at 60° C. for 15 min and soaked in the previously described combined sol-gel solution for approximately 2 min. The foams were then removed from the solution, compressed by 50% in each principal axis for 5 s to release excess sol-gel solution and placed in an oven at 60° C. for 2 min. This process was repeated in each sample six times. The coated foams were allowed to dry at 60° C. for 24 h to ensure the solution was properly gelled. The applied heat treatment (FIG. 25) subjected the coated foams to a temperature of 400° C. with heating rate 2° C. $min^{-1}$ and holding time of 1 h to burn out the polyurethane foam before preceding to 700° C. with the same heating rate and holding time of 5 h. The drying and heat treatment applied to the resultant, coated foams, is shown in FIG. 25. These scaffolds will be referred in the text as "Ag-BG scaffolds", where Ag-BG refers to silver-containing bioactive glass. The heat treatment allowed for the sacrificial template to be removed, leaving behind a 3D glass-ceramic structure with open and interconnected porosity.

TABLE 4

The nominal composition of Ag-BG glass-ceramic scaffolds.

| | Weight % Oxide | Mol % Oxide | | Atom % |
|---|---|---|---|---|
| $SiO_2$ | 58.6 | 61.5 | Si | 20.9 |
| $P_2O_5$ | 7.2 | 4.3 | P | 2.9 |
| $Al_2O_3$ | 4.2 | 2.6 | Al | 1.8 |
| CaO | 24.9 | 28 | Ca | 9.5 |
| $Na_2O$ | 1.5 | 1.5 | Na | 1 |
| K2O | 1.5 | 1 | K | 0.7 |
| AgO | 2.1 | 1.1 | Ag | 0.7 |
| | | | O | 62.4 |

Characterization.

Scaffolds were characterized using a variety of microscopic and spectroscopic techniques. Optical microscopy (OM; VHX-600 E Digital Microscope) and scanning electron microscopy (SEM; Zeiss LS25 EVO/Auriga XB and JEOL JSM-IT500) were utilized to image the scaffolds on the millimeter to nanometer scale respectively. SEM images were collected at accelerating voltages less than or equal to 20 kV. In addition, energy dispersive spectroscopy (EDS; Ametek EDAX Apollo X) was utilized to semi-quantitatively assess the micro-scale chemical homogeneity of the scaffolds. All EDS maps were collected at less than or equal to 20 keV with a step size of 126.2 eV. TEM analysis was performed using a JEOL 100CX microscope using pulverized samples on 200 mesh copper grids with carbon support film (Electron Microscopy Sciences, CF200-CU) under a voltage of 120 kV. Compressive strength was measured using a Rheometric Solids Analyzer (RSA-III) instrument with a load of 2 kg with a crosshead speed of 0.5 mm $min^{-1}$.

X-ray diffraction (XRD; Rigaku Smartlab) was performed on powdered samples to examine the structure and crystallinity of the scaffolds. Diffraction patterns were collected from 10° to 90° 2θ using Cu $K_\alpha$ radiation at 40 kV and 44 mA. Furthermore, the molecular structure of the powdered scaffolds was examined using Fourier transform infrared—attenuated total reflection where samples were placed on top of a diamond crystal and 10,000 psi was applied to ensure the powder had adequate contact with the crystal before performing the measurement (FTIR-ATR; Jasco FT/IR-4600). Absorbance IR spectra were collected from 4000 to 400 cm$^{-1}$ with a resolution 2 cm$^{-1}$. X-ray photoelectron spectroscopy (XPS; PerkinElmer Phi 5400), using non-monochromatic Al Kα radiation X-rays was performed to investigate the chemical structure of the silver within the scaffold. High-resolution $Ag_{3d}$ spectra were collected with a pass energy of 29.35 eV and a step size of 0.125 eV, with peak position normalized to a $C_{1s}$ signal of 284.6 eV. Ultraviolet and visible spectroscopy (UV-VIS; Lambda900) was used to further examine the chemical structure of silver. Absorption spectra were collected from 350 to 600 nm.

The porosity of the 3D scaffolds was calculated using Eq. 1:

$$V_{AIR}/V_{TOTAL}*100=\% \text{ Porosity} \qquad (Eq. 1),$$

where $V_{TOTAL}$ was the dimensions of the scaffold in the three principal directions, $V_{AIR}$ was the empty volume found by subtracting $V_{TOTAL}$ from $V_{GLASS}$, and $V_{GLASS}$ was found by dividing the mass of the scaffold by the density of the glass. The density of Ag-BG glass was measured by $N_2$ pycnometry (AccuPyc II 1340). Ag-BG powder was placed inside the chamber before it was purged 5 times using $N_2$ gas. $N_2$ was added to the chamber at a rate of 0.1 psig min$^{-1}$ to determine the density and repeated 20 times to obtain an average density of the glass.

The capability of the scaffolds to form an apatite-like phase on their surface was studied by immersing the scaffolds in simulated body fluid (SBF) at a pH of 7.26 at 37.5° C., which is a well-established protocol in biomaterials science. SBF was utilized to mimic human plasma with the following ionic concentrations: 142.0 Na$^+$, 5.0 K+, 2.5 $Ca_2^+$, 1.5 $Mg_2^+$, 148.8 Cl$^-$, 1.0 $HPO_4^-$, 4.2 $HCO_3^-$, and 0.5 $SO_4^{2-}$ (mmol dm$^3$) and prepared as known in the art. The scaffolds were exposed to SBF using a mass to volume ratio of 1:1 at 174 RPM and 37.5° C. for 14 days; with SBF replacement every 48 h. SEM and EDS were then used to examine the resulting scaffolds for evidence of CaP formation.

The anti-MRSA effect of the scaffold was studied directly by inoculating bacteria in the nutrient broth and leaving at 37° C. overnight to allow growth. The optical density of the MRSA was measured and adjusted to be 108 cells mL$^{-1}$ in PBS. The MRSA in PBS was exposed to 11.0 mg of the Ag-BG scaffold and incubated for 24 h at 37° C. The supernatant was collected, and serial ten-fold dilutions performed in a 96-well plate. All serial-dilutions were platted on nutrient agar plates and incubated at 37° C. for 24 h. Bacterial growth was assessed by colony forming units (CFU).

The anti-MRSA effect of the scaffold was also indirectly evaluated by placing 50 mg of the Ag-BG scaffold into 8 mL of PBS and leaving at 37° C. for up to 21 days, with 50% of the solution collected every three days while the solution was renewed with an equal volume of fresh PBS. The collected volumes were characterized as extracts and are expected to have incorporated ions that were released from the scaffolds. MRSA in 1 mL of PBS was exposed to an equal volume of the extracts collected at specific times. A culture of MRSA was prepared as previously described which after 24 h of incubation at 37° C., was serial ten-fold diluted in a 96-well plate and plated on nutrient agar plates. The plates were then incubated at 37° C. for 24 h and bacteria growth was assessed by counting the CFU.

The concentration of [Ag$^+$] ions in the extracts was also measured by Inductively Coupled Plasma Optical Emission Spectrometer [(ICPOES)—Perkin Elmer]. All antibacterial tests were performed in biological and technical triplicates.

Results

The surface morphology of the Ag-BG scaffold fracture surfaces was examined from the millimeter to ~50 nm scale using both optical and electron microscopy.

The optical microscopy images (FIGS. 26A-26D) show that the scaffolds exhibit connectivity, with microscale cracks and open pores. The struts and intersections of the scaffolds exhibit heterogeneous color intensities, with dark coloration in the center of the struts and light coloration on the outside of the struts. The struts and intersections of the scaffolds dark colored, less than 10 μm$^{-1}$ μm size circular/oblong features, some of which exhibit a yellow/brown sheen (FIG. 26D). The scaffolds themselves exhibit a microscale distribution of transparent and translucent_sheen (FIGS. 26A-26D). The average strut width is 85±16 μm and the average pore diameter is 504±126 μm (n=20), as measured from SEM back-scattered images (FIG. 26E). The overall scaffold porosity was calculated to be 98% using the value 2.78 g cm$^{-3}$ for Ag-BG density and Eq. 1. The lack of any areas of high atomic number (Z) in the images both in low and high magnification (FIGS. 2E and 2F, respectively) also indicates microscale elemental homogeneity in the Ag-BG scaffolds. FIG. 26F shows cracking on the interior of the struts as well as around the exterior of the overall structure, where porosity is observed with pores less than 10 μm in diameter. The compressive strengths of the Ag– BG scaffolds were measured from the stress-strain curves at 4.4 kPa (FIG. 27).

A secondary electron SEM image and corresponding EDS X-ray maps of a representative Ag-BG fracture surface are shown in FIG. 28. The elemental maps suggest homogeneous distribution of Si, Ca, P, Al, and Ag on the micron scale. Nevertheless, high-resolution SEM back-scattered electron images of the fracture surface of an Ag-BG scaffold shown in FIGS. 29A and 29B feature varying contrast at a scale of <200 nm, suggesting some heterogeneity at the fine scale. EDS X-Ray maps indicate that these lighter areas are aggregates of Ag (FIG. 29C). Further analysis at the nanoscale using TEM presents a clearer perspective of the scaffold's structure (FIG. 31A). Diffraction ring analysis shows that both metallic silver and hydroxyapatite are present (FIG. 31B).

To further analyze the crystalline phases in the Ag-BG scaffolds, the XRD pattern is shown in FIG. 32. All peak positions correspond to crystals within The International Centre for Diffraction Data (ICCD) and indicates that the crystalline components of the scaffolds are a combination of a hydroxyapatite phase (peaks marked with black squares, 26.7, 28.1, 32.3, and 46.8 2θ; PDF No. 9003552), cristobalite (peaks marked with black circles), and metallic silver (peaks marked with black triangles, 37.9, 44.1, 64.3, and 77.1 2θ; PDF No. 01-071-4613). It should be noted that peaks with a lower signal to noise ratio were not matched against the ICCD database. It is worth noting that the background intensity increases with decreasing 28. FTIR-ATR spectra of powdered Ag-BG is shown in FIG. 32. The deconvoluted spectrum displays broad peaks centered at ~1030, ~800, and ~450 cm$^{-1}$, with clear shoulders centered at approximately 1210 and 940 cm$^{-1}$. Dashed lines are shown in FIG. 32 to guide the eye for qualitative peak deconvolution. The characteristic vibration modes of a silicate network are the only features in the IR spectrum of the Ag-BG scaffold.

An XPS survey spectrum of the surface of an Ag-BG fracture surface was collected (not shown) revealing all of the expected, major elements. In addition, a high-resolution scan within the $Ag_{3d}$ region (377-357 eV) was collected and is shown in FIG. 33A. Clear peaks are observed at 367.7 and 373.5 eV, corresponding to $Ag_{3d\ 5/2}$ and $Ag_{3d\ 3/2}$. FIG. 33B shows UV-VIS spectra collected from powdered Ag-BG scaffolds, showing a clear absorbance peak at 428 nm that is correlated with the presence of metallic Ag in the structure.

Secondary electron images of Ag-BG fracture surfaces, before and after soaking in SBF for 14 days, are shown in FIGS. 34A and 34B, respectively. The fracture surface of the scaffold prior to reaction exhibits a relatively featureless surface, with the exception of pores of less than 10 μm in diameter (FIG. 34A). The representative image of a post-reaction fracture surface exhibits a morphology of ~150-500 nm spherical to cylindrical features that are cauliflower-like (FIG. 34B). EDS spectra (not shown) show that these features are composed primarily of Ca and P with Ca/P ratio slightly higher than 1.67, which is the ratio for the stoichiometric hydroxyapatite. The formation rate of this apatite-like layer is under current investigation, while the thickness of this layer is expected to be lower than the EDS interaction volume (<5 μm) as the EDS spectrum identifies also ions from the Ag-BG scaffolds. The Ca—P deposition after the immersion in SBF is also confirmed by the FTIR spectra in FIG. 34C, where the dual-peak at 569-609 cm-1 is assigned to an apatite-like phase (top line). As was expected, the characteristics bands of the Si—O bending and Si—O—Si stretching are still observed in the FTIR spectrum after immersion in SBF, as scaffolds were pulverized and the powder was used for the measurements. Thus, not only the Ca—P deposited phase was identified but the silicate structure as well. This dual peak is not present in the FTIR spectrum of the scaffolds before immersion in SBF (bottom line). The comparison of Ag-BG scaffolds bioactivity to the respect of other BG scaffolds was not the aim of this work.

The antibacterial properties of the Ag-BG scaffolds against MRSA are presented in FIGS. 35A and 35B. The direct test, where the MRSA was exposed to Ag-BG scaffolds, showed a significant decrease in bacteria viability after 24 h of exposure (FIG. 35A). The indirect test, where the MRSA was exposed to the extracts of the scaffold from different time points, showed inhibition that decreased with increasing extract time (FIG. 35B). Likewise, the concentration of Ag in the extracts [Ag] was observed to decrease with increasing time (FIG. 35B, squares). In particular, the concentration of [Ag] was measured at 0.45 ppm on the 3rd day and it was held on cytotoxic for the bacteria concentration (0.18 ppm) for up to the 12th day. When immersions are higher than 15 days there is a decrease in the concentration of silver [Ag] to values lower than 0.1 ppm, which is the minimum required to show significant bactericidal activity. All these values were constantly lower than the upper threshold (1.6 ppm) for cytotoxic behavior to eukaryotic cells. The red dash line in FIG. 35B serves as a guide to the eye showing the decrease in Ag ion concentration with the immersion time.

Discussion

This example presents the fabrication and characterization of 3D scaffolds in a unique composition that incorporates Ag ions within a silicate glass-ceramic structure. The sacrificial template technique was applied, and the structural, chemical, mechanical, bioactive, and antibacterial characteristics were assessed. Structural analysis of the scaffold at scales greater than approximately 100 microns focused primarily on scaffold strut size and geometry, as well as pore size and shape (FIGS. 26A-26F). Using these measurements, the porosity of these scaffolds was determined to be higher than 90%. These highly porous scaffolds are expected to enhance cell migration and spreading when used in in vivo applications. However, the compressive strength of the Ag-BG scaffolds (FIG. 27) was measured to be at the lower end of the range for such highly porous scaffolds with similar compositions, indicating the requirement to use these new scaffolds in small defects or low-load bearing applications.

Optical microscopy (FIGS. 26A-26D) revealed spatial inhomogeneity of the fracture surface sheen and overall translucency, which may be evidence of the presence of both amorphous and crystalline components. In addition, under optical microscopy, the color intensity varies spatially with the "inside" of the struts appearing darker than the outside (FIGS. 26A-6B). This could be the result of surface oxidation and reduction of silver, inhomogeneous distribution of crystalline phases, and/or cracking and pores present on the fracture surface. However, EDS maps (FIG. 28) show homogeneous distribution of all elements on the scale higher than 10 μm, suggesting that the variety in color intensity is primarily the result of surface morphological characteristics. Further, imaging using backscattered electrons (FIGS. 26E-26F) at comparable magnifications to the optical microscope images support this hypothesis.

Fracture surfaces of the scaffold struts clearly exhibit circular to oblong dark areas less than 25 microns in size. Upon further investigation using high-resolution BSE imaging (FIGS. 29A-29C), these areas are shown to be micron to submicron pits in the surface. The circular to oblong pits appear to contain either open space or are partially or completely filled with particulate material. High magnification images (FIG. 29A) of regions with both empty and filled pores suggest that the particulates within the "filled" pores are a material which has a much higher atomic number Z than the surrounding matrix (FIG. 29B). Given the system used here, the bright areas shown in FIG. 29B are silver, or silver dominated, nanoparticles, which is consistent with the TEM images (FIG. 31A). The silver ion localization is most likely a result of the presence of negatively charged aluminum tetrahedra stabilizing Ag ions, thus making Ag agglomeration difficult. This has been shown where Aluminum NMR (nuclear magnetic resonance) showed that the presence of Ag caused an increase in the five-fold coordination of the Al, which was correlated to Ag-stabilized aluminum tetrahedrons. The specific order the reagents when added during the fabrication process, as well as the stirring time, are important. However, the applied heat treatment during the scaffold fabrication process provided conditions to overcome the stabilizing forces localizing silver ions that allowed silver to be reduced to metallic Ag nanoparticles. The TEM diffraction pattern (FIG. 31B) also indicates the presence of hydroxyapatite as an additional crystalline phase. XRD and FTIR were used in combination to further investigate the overall scaffold structure on the atomic to the molecular scale. It is clear from diffraction results the scaffold is composed of crystalline phases. Cristobalite is also observed in the XRD diffraction patterns; the formation of this phase is attributed to the presence of silver and its action as catalyst inducing cristobalite formation at relatively low temperatures. Additionally, FTIR was used to further confirm the presence of the amorphous component and investigate its molecular structure. It is clear from the FTIR data (FIG. 32) that the silicate glass comprises interconnected silicate tetrahedra with both bridging and non-bridging oxygen species.

Matching of the experimental diffraction patterns to standard PDF cards suggests that in addition to silicate glass, the scaffold matrix contains crystalline hydroxyapatite, cristobalite, and metallic silver. However, it is worth noting that the peak at 26.7 2θ (FIG. 30) has been assigned to $Ag_2O_4$ when observed in spectra of similar systems. Therefore, in addition to the other phases, it is also conceivable that silver oxide may also be present. Hydroxyapatite formation, while minimal as evidenced from TEM images (FIG. 31B) and the broad rings in diffraction patterns, can result from the applied heat treatment and the relevant concentrations of the Ca, P ions in the structure. Similarly, the formation of metallic silver indicates that the stabilization of silver ions cannot be preserved under the given processing conditions.

Additional characterization of the metallic silver was performed given its inclusion was to induce therapeutic/antibacterial properties. It has been suggested the overall size, shape, and chemistry of the silver ions and/or particles have a significant effect on the therapeutic/antibacterial performance of Ag-containing biomaterials. Both the XPS and the UV-VIS results suggest silver is primarily in the form of metallic nanoparticles, however, possible contributions from silver oxide and/or ionic silver within the glass structure cannot be ruled out, as a homogeneous distribution of Ag within the scaffolds is observed with the EDS mapping analysis (FIG. 28).

The deposition of an apatite-like phase on the surface of the Ag-BG scaffolds, after 14 days of immersion in SBF, was confirmed by SEM and FTIR analysis (FIGS. 34A-34C). SEM images revealed increased roughness associated with the formation of cauliflower-like structures on the surface. The formation of these morphological features occurred due to deposition during SBF exposure. These deposits were determined to be an apatite-like phase, as evidenced by the dual Ca—P peak at ~570-610 $cm^{-1}$ in the FTIR spectrum. Finally, significant antibacterial properties were observed when MRSA was directly exposed to the novel Ag-BG scaffolds (FIG. 35A). It is very important that Ag-BG scaffolds can inhibit an antibiotic-resistant strain that has been reported as the most common in orthopedic infections. Ag-BG is effective to combat oral bacteria. However, the capability of this system to combat MRSA expands the spectrum of potential applications into orthopedics. This characteristic is primarily attributed to the Ag in the scaffold's structure. The leaching of the ions from the scaffolds is expected to be controlled so that the pH value remains consistently neutral. The scaffold is expected to degrade over time. The degradation of Ag-BG pellets leads to a weight loss of 16% after 45 days of immersion in TRIS buffer. The 3D scaffolds present an increase in the surface to volume ratio that can increase the degradation rate. The degradation profile of these scaffolds immersed in different aqueous solutions seems to affect the indirect antibacterial properties. In particular, the indirect antibacterial test (FIG. 35B) correlates the antibacterial activity with the release of Ag with time. The concentration of Ag in the extracts decreased with time, which agrees with the antibacterial activity of the extracts that also decreased with time.

In summary, this example highlights the microstructural characteristics, bioactive, and antibacterial properties of novel Ag-BG scaffolds. Conditions during the processing led to structural characteristics that significantly affect the overall bioactive and bactericidal behavior of these scaffolds.

Conclusion

The fabrication of 3D scaffolds using a novel bioactive and antibacterial composition (Ag-BG) has been achieved. Structural characteristics from the nano-to-macro-scale affect the overall performance of these scaffolds. Processing has a significant impact on the microstructural characteristics, such as status of Ag in the structure and formation of the specific crystalline phases. The overall bioactive and antibacterial characteristics allow for the use of these scaffolds in biological applications against MRSA and for tissue regeneration.

Example 5

This example describes 3D Ag-doped bioactive glass-ceramic scaffolds.

Summary

Ag-doped sol-gel derived bioactive glass-ceramic particles (Ag-BG) were used in the successful fabrication of highly porous scaffolds exhibiting advanced antibacterial properties and suitable acellular biological response. The applied heat treatments were selected after characterization of the thermal behavior of the as-received Ag-BG particles using differential thermal analysis (DTA), thermal gravimetric analysis (TGA), and hot stage microscopy (HSM). The macro- and microstructural characteristics of the Ag-BG scaffolds were studied using optical microscopy, scanning electron microscopy (SEM), energy dispersive spectroscopy (EDS), micro-computerized tomography (Micro-CT), X-ray diffraction (XRD), Fourier-transformed infrared—attenuated total reflection (FTIR-ATR), and transmission electron microscopy (TEM) to correlate how the differences in the Ag-BG scaffolds hierarchal structure affected their antibacterial and acellular biological response. Planktonic methicillin-resistant *Staphylococcus aureus* (MRSA) was used to evaluate the antibacterial response of the Ag-BG scaffolds and simulated body fluid (SBF) to study their acellular biological behavior. The antibacterial properties, biological response, and structural characteristics make these Ag-BG scaffolds good candidates for bone tissue regenerative applications.

Introduction

The excellent osteogenic, osteoconductive, and osteoinductive properties combined with unparalleled hierarchical structural mimicry make autographs the gold-standard for the regeneration of critically-sized damaged or diseased bone tissue. Despite these characteristics, there is typically a steep cost with utilizing the autograph approach considering the finite amount of healthy bone tissue that can be stolen from the patient and the purposeful induction of additional trauma sites the patient must endure while awaiting spontaneous bone tissue regeneration. The silver standard, allographs, protect the patient against additional trauma at the expense of osteoinduction neutralization, increased risk of disease transmission from the donor, and potential rejection of the donor tissue. Thus, while both treatments are widely used due to their clinical track record, their shortcomings revealed that autographs and allographs are imperfect solutions to the regeneration of critically-sized damaged or diseased bone tissue and investigations into alternative strategies are needed.

Bioactive glasses, such as sol-gel derived 58S ($58SiO_2$-$33CaO$-$9P_2O_5$ (wt. %)) system discussed herein, can easily be transformed into a highly porous 3D scaffold with the potential of delivering the same benefits as autographs without the undesired side effects. The following criteria should be met in order to achieve the ideal scaffold: (1) observable osteoconduction and osteoinduction, (2) support physiological loads, (3) controllable macro- to nanostructure, (4) degradation rate matching new bone tissue formation, (5) provide a bactericidal environment during tissue regeneration to prevent infection-related failure, (6) interconnected highly porous 3D structure, and (7) mean pore diameter greater than 300 µm.

The sol-gel technique is superior for the fabrication of bioactive glasses for its compositional versatility and ability to maintain pores within the micro- and nanostructure increasing the overall surface area, which is expected to improve the biological response of the bioactive glass. Furthermore, the sol-gel technique is the only reported method that has demonstrated the ability to incorporate and stabilize heavy metal ions (e.g., Ag, Cu, Zn) that are released in a controlled and sustainable way. As discussed herein, controlled-sustained release of Ag is achieved by incorporating low levels (<5 wt. %) of Al that favored its tetrahedrally coordinated form ($AlO_4^-$) that was subsequently charge compensated by the Ag ion. This results in a lethal [Ag] towards pathogens (0.1-1.6 ppm) without damaging eukaryotic cells. Example 1 demonstrates that Ag incorporated in this fashion imparted advanced antibacterial properties to the bioactive glass; not only creating bactericidal conditions against methicillin-resistant *Staphylococcus aureus*, but also revealed the ability to resurrect the functionality of antibiotics (e.g., fosfomycin, vancomycin, and oxacillin) that MRSA was known to resist. These compositional factors can address the first, third, fourth, and fifth criteria previously described, but selection of the appropriate scaffold processing technique can address the remaining unfulfilled criteria.

The polymer foam replication technique can be used to produce glass-ceramic scaffolds suitable for load-bearing applications in the range of cancellous bone (0.2-2 MPa). This method provides ease of implementation, ability to mimic the natural microstructure of cancellous bone, and a relatively isotropic distribution of microstructural morphology (i.e., pore and strut distributions). Based on this, the remaining criteria previously described for an ideal scaffold can be fulfilled.

For the first time, Ag-doped sol-gel derived bioactive glass-ceramic particles (Ag-BG) of Example 1 were transformed into highly porous bioactive glass-ceramic scaffolds using the polymer foam replication technique that possessed advanced antibacterial and biological properties. The sintering profile to obtain the Ag-BG scaffolds was determined after studying the thermal behavior of the Ag-BG particles. The Ag-BG scaffolds were characterized from their macro- to nanostructure with particular interest in the microstructural characteristics to describe both their antibacterial and biological properties. The developed Ag-BG scaffolds possessed novel antibacterial properties, an adequate biological response, and sufficient hierarchical structural characteristics making these scaffolds good candidates for bone tissue regenerative applications.

Methods and Materials

Ag-BG Particle Fabrication. The composition of the Ag-BG scaffolds was based on the Ag-containing bioactive glass-ceramic in the $58.6SiO_2$-$26.4CaO$-$7.2P_2O_5$-$4.2Al_2O_3$-$2.1Ag_2O$-$1.5Na_2O$ (wt. %) system. Briefly, two separate sol-gel solutions were fabricated with the first solution containing 58S bioactive glass ($58SiO_2$-$33CaO$-$9P_2O_5$ (wt. %)), and the second solution within the $60SiO_2$-$11CaO$-$3P_2O_5$-$14Al_2O_3$-$7Ag_2O$-$5Na_2O$ (wt. %) system. Both systems were stirred separately for 17 h, mixed, and allowed to stir for another 17 h to ensure adequate dissolution of reagents and solution homogenization. The combined solution was dried at temperatures up to 180° C. and calcined at 700° C. The resulting Ag-BG was ball milled to reduce particle size and sieved to obtain particles smaller than 38 microns. The thermal behavior of the Ag-BG particles was characterized by Differential Scanning calorimetry/Thermal Gravimetric Analysis (DTA/TGA) and hot stage microscopy (HSM).

Scaffold Preparation.

Fully reticulated polyurethane foam (United States Plastic Corporation) having a nominal pore diameter of 569±63.6 µm (45 pores per inch (ppi)) was cut into 12.5×12.5×12.5 mm cubes and ultrasonically cleaned with ethanol (Koptec; 200 proof) before use. The foams were soaked for ~60 s in a slurry consisting of water, poly(vinyl) alcohol (PVA), and Ag-BG particles (<38 µm) at a ratio of 1.67:0.167:1 respectively. Excess slurry was removed by 50% manual compression of the foams three principle axes. The foams were left to dry at ambient conditions for 24 h. The heat treatment to obtain Ag-BG scaffolds followed heating the coated foams to 400° C. at 2° C. $min^{-1}$ where this temperature was maintained for 1 h to allow the organics to vaporize. Sintering of the inorganic Ag-BG constructs occurred either at 900° C. (900-SL) or 1000° C. (1000-SL) with an applied heating rate of 10° C. $min^{-1}$. The sintering temperature was held for 5 h to allow for Ag-BG particle densification before cooling to ambient temperatures at a rate of 5° C. $min^{-1}$.

Structural Characterization: Macrostructural Characterization.

The macrostructure of the Ag-BG scaffolds was analyzed using optical microscopy (VHX-600E Digital Microscope) and Fiji is Just ImageJ (Fiji) used to determine mean pore size, strut thickness, and cross-sectional thickness of struts. Micro-Computerized Tomography (Micro-CT, Rigaku Quantum GX) was additionally used, where the following image acquisition scan parameters were used: scan mode, high resolution; gantry rotation time, 57 minutes; power, 90 kVp/88 µA; Field of View (FOV), 5 mm; number of slices, 512; slice thickness, 10 µm; and voxel resolution, 10 $µm^3$. The acquired micro-CT images were analyzed using MicroView (Parallax Innovations, ON, Canada) to determine porosity (%), strut thickness (µm), and pore diameter (µm). The specific surface area was determined the $N_2$-gas adsorption-desorption isotherms using the Brunauer-Emmett-Teller (BET; ASAP 2020 Micromeritics) method. Samples were degassed at 80° C. under vacuum pressure for 6 h before the measurement. The amount of nitrogen adsorbed was measured volumetrically at −196° C.

Structural Characterization: Microstructural Characterization.

The microstructural morphological characteristics were investigated using Scanning Electron Microscopy (SEM, Tescan MIRA/Auriga XB) with a beam voltage of less than or equal to 10 kV to assess surface morphology and Energy Dispersive Spectroscopy (EDS; Ametek EDAX Apollo X) with a step-size of 126.2 eV to evaluate micro-scale homogeneity. The molecular structure of the powdered Ag-BG scaffolds was examined with Fourier-Transform Infrared—Attenuated Total Reflection (FTIR-ATR, Jasco FT/IR-4600) collecting spectra from 4000-400 $cm^{-1}$ at a resolution of 2 $cm^{-1}$. The structure and crystallinity of the scaffolds was assessed with X-Ray Diffraction (XRD, Rigaku Smartlab X-Ray Diffraction System) utilizing CuKα radiation at 40 kV and 44 mA with diffraction patterns obtained from 10° to 90° 2θ. $^{27}Al$ and $^{29}Si$ magic angle spinning nuclear magnetic resonance (MAS-NMR) spectroscopy was performed on powdered Ag-BG scaffolds to determine the Al coordination within the scaffold structure and to study the different Si structures present. Both spectra were collected using a Varian Infinity—Plus 400 NMR spectrometer using a 6 mm probe and a spin speed of 4 kHz. For the $^{27}$Al, one pulse at 104.16 MHz was applied for 1 µs along with a delay time of 0.2 s. One pulse at 79.41 MHz was applied for 4 µs with a delay time of 100 s to obtain the $^{29}$Si MAS-NMR spectra.

Structural Characterization: Nanoscale Characterization.

The nanostructure of the Ag-BG scaffolds was elucidated with Transmission Electron Microscopy (TEM, JEOL 2010F AEM) under a voltage of 200 kV with pulverized Ag-BG scaffolds placed on 200 mesh copper grids with carbon support film (Electron Microscopy Sciences, CF200-CU).

Scaffold Performance: Antibacterial Characterization.

Laboratory-derived methicillin-resistant *Staphylococcus aureus* (MRSA) USA300JE2 was used for all antibacterial characterization. MRSA cells were streaked onto tryptic soy agar (TSA) from their frozen stock and cultured for 24 h at 37° C. to prepare for isolation. A single MRSA colony was isolated and placed in 5 mL of sterile tryptic soy broth (TSB) that was then placed at 37° C. overnight under a constant agitation rate of 225 RPM. 1 mL solutions of planktonic MRSA in sterile phosphate-buffered saline (PBS) were prepared and normalized to an optical density ($OD_{600\ nm}$) of 1 that equated to a MRSA concentration of $10^8$ colony forming units (CFU) $mL^{-1}$. Untreated controls were prepared using a 1:1 volume ratio of MRSA to PBS. Ag-BG scaffolds were preconditioned in Dulbecco's modified eagle media (DMEM) for 72 h at 37° C. with full replacement of media occurring every 24 h. 11 mg of 900-SL and 1000-SL were UV sterilized for 0.5 h before being inoculated with MRSA and were subsequently placed at 37° C. for either 24 or 48 h. To enumerate the CFUs, the Ag-BG scaffolds were pulverized and a homogenous aliquot extracted for ten-fold serial dilutions. Each dilution was platted onto TSA and incubated at 37° C. for 24 h.

Additionally, 11 mg of 1000-SL were combined with either 0.2 µg $mL^{-1}$ of Fosfomycin or 2 mg $mL^{-1}$ of vancomycin to study the ability of the Ag-BG scaffolds to resurrect antibiotics that MRSA is known to resist. The antibiotics were dissolved in PBS prior to exposure with the 1000-SL scaffolds and combined in a 1:1 volume ratio of MRSA in PBS to antibiotic in PBS. The CFUs were enumerated after 24 and 48 h as previously described. To further investigate the ability of the Ag-BG scaffolds to resurrect antibiotics that MRSA resists, the antibacterial assays were applied as previously described using 2 mg $mL^{-1}$ of vancomycin with 11 mg of Ag-BG powder (as-received) having a particle size below 20 µm and 11 mg of powdered 1000-SL also having a particle size below 20 µm to assess the effect of crystallinity and macro-morphology on antibiotic resurrection.

Scaffold Performance: Biological Characterization.

The capability of the Ag-BG scaffolds to form an apatite-like layer was studied using simulated Body Fluid (SBF) with the following ionic concentrations: $142.0Na^+$, $5.0K^+$, $2.5Ca^{2+}$, $1.5Mg^{2+}$, $148.8Cl^-$, $1.0HPO_4^-$, $4.2HCO_3^-$, and $0.5 SO_4^{2-}$ (mmol $dm^3$), prepared as previously described. Using a mass to volume ratio of 5:1, the Ag-BG scaffolds were immersed in the SBF for up to 21 days at 174 RPM and 37.5° C. with the solution being replaced every 48 h. SEM-EDS, FTIR-ATR, and XRD were used to evaluate the mineralization of a CaP layer on the Ag-BG scaffolds.

Scaffold Performance: Compressive Strength.

Mechanical testing on Ag-BG scaffolds having dimensions of 10 mm×10 mm×10 mm was performed using a Rheometric Solids Analyzer (RSA-III) instrument. Compressive forces were applied to maintain a constant strain rate of 0.5 mm $min^{-1}$. Ag-BG scaffolds were strained to 70% and compressive strength calculated using Eq. 2:

$$\sigma = \frac{F}{A}, \quad \text{(Eq. 2)}$$

where F is the force (N) applied to the scaffold, and A is the initial cross-sectional area ($m^2$).

Statistical Analysis.

The data was expressed in terms of means and standard deviations (error bars). Statistical significance was assessed using the paired Student t-test and indicated if $p<0.05$.

Results

Ag-BG Thermal Analysis.

In order to obtain Ag-BG scaffolds that elicit both an antibacterial and biological response in addition to supporting compressive forces, the thermal behavior of the Ag-BG particles needed to be studied. The Ag-BG particles therefore were characterized using DTA and TGA to determine key characteristics such as its glass-transition temperature ($T_g$), crystallization temperature ($T_c$) and melting temperature ($T_m$). Through an understanding of these transition events, one can control the microstructure which will impact the antibacterial, biological, and mechanical properties. Literature defines the ideal processing window for such bioactive glass-ceramic scaffolds to be between $T_g$ and the onset of $T_c$ with the aim of preserving the amorphous structure of the bioactive glass particles while simultaneously achieving sufficient densification during sintering.

As shown in FIG. 36A, the DTA plot of the as-received Ag-BG particles exhibited a small endothermic peak at ~450° C. that was correlated to the glass-transition temperature of the Ag-BG. As the temperature increased, minimal changes in heat flow were observed until ~700° C., where the heat flow began to steadily increase. This event was noted as the temperature of the onset of crystallization. Therefore, the ideal processing window to fabricate Ag-BG scaffolds is between 450° C. and 700° C.; however, when HSM was performed on the Ag-BG particles (FIG. 36C), notable shrinkage was not observed until temperatures exceeded 800° C. To better describe this observation, the Hruby coefficient for the Ag-BG was calculated as it is a widely established method of determining the glass formability.

The glass formability, as described by the Hruby coefficient, describes the competition of densification that occurs between the viscous sintering mechanism and crystallization, which is compositional dependent. The Hruby coefficient is thus defined as Eq. 3:

$$K_H = \frac{T_X - T_g}{T_m - T_x}, \quad \text{(Eq. 3)}$$

where $T_x$ is the onset of crystallization, $T_g$ is the glass transition temperature, and $T_m$ is the melting temperature. From the DTA (FIG. 36A) $T_x$ was defined at 701° C., $T_g$ at 450° C., and $T_m$ at 1450° C. The second melting temperature was selected as this was the temperature at which the Ag-BG exhibited significant melting behavior. From the previously defined parameters, the Hruby coefficient for the Ag-BG system in this study was 0.34, which can be interpreted as the Ag-BG having a modest glass formability. This would suggest that viscous sintering and crystallization are equitable and therefore the Ag-BG could exhibit notable densification without significant crystallization. This calculation, however, cannot fully explain the thermal behavior of the Ag-BG as densification does not occur without crystallization.

Expanding on the Hruby coefficient and a method has been derived to calculate the sinterability (Sc) of a silicate based-glass that was first applied to bioactive glass systems. The sinterability parameter attempts to describe the independence between viscous sintering and crystallization, where positive values are interpreted to mean viscous sintering and crystallization are independent and vice versa.

Macro and Microscale Characterization and Compressive Strength.

The hierarchal nature of porous 3D scaffolds required characterization on the macroscale, microscale, and nanoscale to understand how the materials characteristics affected the mechanical, antibacterial, and biological performance. The macroscale characteristics can have a significant effect on the mechanical properties, so the Ag-BG scaffolds were studied using optical microscopy, SEM, and micro-CT to determine the porosity, pore diameter, strut thickness, and morphological characteristics (summarized in Table 5) and correlated to the compressive behavior of said scaffolds.

TABLE 5

The porosity, pore diameter, and strut thickness of the as-received polyurethane foam, 900-SL and 1000-SL as determined from optical microscopy and micro-CT analysis.

| Foam Characteristics | 900-SL - Optical | 1000-SL - Optical | 900-SL - Micro-CT | 1000-SL- Micro-CT |
|---|---|---|---|---|
| Porosity (%) 98.4 ± 0.21 | 93.1 ± 2.10 | 88.2 ± 3.63 | 87.1 | 92.4 |
| Pore Diameter (μm) 569 ± 63.6 | 486 ± 101 | 698 ± 157 | 493 ± 14.7 | 722 ± 29.4 |
| Strut Thickness (μm) 99.4 ± 16.7 | 117 ± 25.1 | 80.8 ± 36.3 | 73.2 ± 2.19 | 59.6 ± 2.43 |

The sinterability is defined as Eq. 4:

$$S_c = T_x - T_{MS} \quad \text{(Eq. 4)},$$

where $T_x$ is the onset of crystallization ($T_1$, 701° C.) and TMS (1093° C.) is the temperature at which maximum shrinkage as determined by HSM (FIG. 36B). Given this, the Ag-BG system was found to possess a largely negative sinterability meaning that viscous sintering is suppressed in favor of crystallization. Furthermore, information related to the viscosity and surface tension can be inferred as negative sinterability values indicate that the Ag-BG exhibited low surface tension and high viscosity thus promoting densification by crystallization. The sinterability calculation therefore can better describe the DTA (FIG. 36A) and HSM (FIGS. 36B-36C) of the Ag-BG particles.

Additional temperatures are highlighted in the DTA plot (FIG. 36A) of the Ag-BG particles to examine how the shrinkage correlated with the thermal behavior of the Ag-BG as a function of temperature. As such, the temperature ($T_3$ —764° C.) at which notable shrinkage was observed in HSM (FIG. 36B) corresponded to the lower end of the exothermic peak that spanned from ~700° C. to 1000° C. At the peak crystallization temperature ($T_{c,1}$—917° C. the shrinkage of the Ag-BG was still increasing in a linear fashion (FIG. 36B) before stabilizing out around 964° C., where a shrinkage of 42.4% was observed. The shrinkage remained relatively constant until ~1200° C., where the Ag-BG began to expand. This expansion corresponded with the second crystallization temperature ($T_{c,2}$ — ~1200° C.) that was the result of the phase transformation of hydroxyapatite to β-tricalciumphosphate (β-TCP). This transformation sees the hexagonal crystal structure of hydroxyapatite change into the trigonal crystal structure of β-TCP sees a unit cell volume increase of over 600%, which could explain the expansion observed in the HSM (FIG. 36B).

Given the information provided by performing the DTA and HSM on the Ag-BG particles, it was decided to heat treat the Ag-BG scaffolds at a maximum temperature of 900° C. (900-SL) and 1000° C. (1000-SL) for 5 h with the aim of observing the effect of crystallization on the resulting antibacterial and biological properties of the Ag-BG scaffolds along with how the differences in microstructure affected said properties.

The as-received polyurethane foam was highly porous as expected with a porosity greater than 98%, which unsurprisingly saw the porosity drop to ~90% for both 900-SL and 1000-SL. Maintaining the high degree of porosity was the result of well-maintaining the open porous structure during the fabrication of the Ag-BG scaffolds. This was confirmed when observing the Ag-BG scaffolds with optical microscopic techniques (FIGS. 37A-37B) and verified that the manual compression used to remove the excess slurry during the process was a viable method to maintaining the open porous network. Examining the pore diameters of 900-SL and 1000-SL, it was found that 1000-SL had a pore diameter greater than the as-received polyurethane foam (~700 μm versus ~570 μm) whereas the pore diameter for 900-SL was smaller than the as-received polyurethane foam (~490 μm versus ~570 μm). This discrepancy could be a result of the increased shrinkage of the Ag-BG when sintered at 1000° C. versus 900° C., which is supported by the decrease in strut thickness seen in 1000-SL compared to 900-SL. Interestingly, when observing 900-SL and 1000-SL via micro-CT (FIGS. 37D-37H) the macrostructure for 900-SL was less well-defined, bubbled (FIG. 38C), and slightly less porous, where these were attributed to the shrinkage differences when sintering at 900° C. along with the inherent variability introduced during the manual compression process to remove the excess slurry during fabrication.

The strut thickness saw a ~20% decrease in size for 1000-SL compared to the strut thickness of 900-SL, which was again attributed to the increased densification when sintering at 1000° C. Interestingly, the strut thickness differences as obtained by micro-CT are in good agreement with the differences observed when examining the strut cross-sections (FIGS. 38A-38F). Despite the decrease in strut thickness for 1000-SL, the increased densification is likely to contribute to better mechanical competency of 1000-SL as there should be less free space and thus make crack initiation and propagation more difficult during compression testing. Visual inspection of 900-SL and 1000-SL at various SEM magnifications (FIGS. 37B-37C and 37F-37G) show similar surface morphologies, however 1000-SL appeared to have a minutely smoother surface compared to 900-SL and weakly supports the notion of densification differences between Ag-BG scaffolds whereas the HSM data (FIG. 36B) of the Ag-BG particles provided a more conclusive case in support of shrinkage differences.

Figures 38A, 38B, 38C:
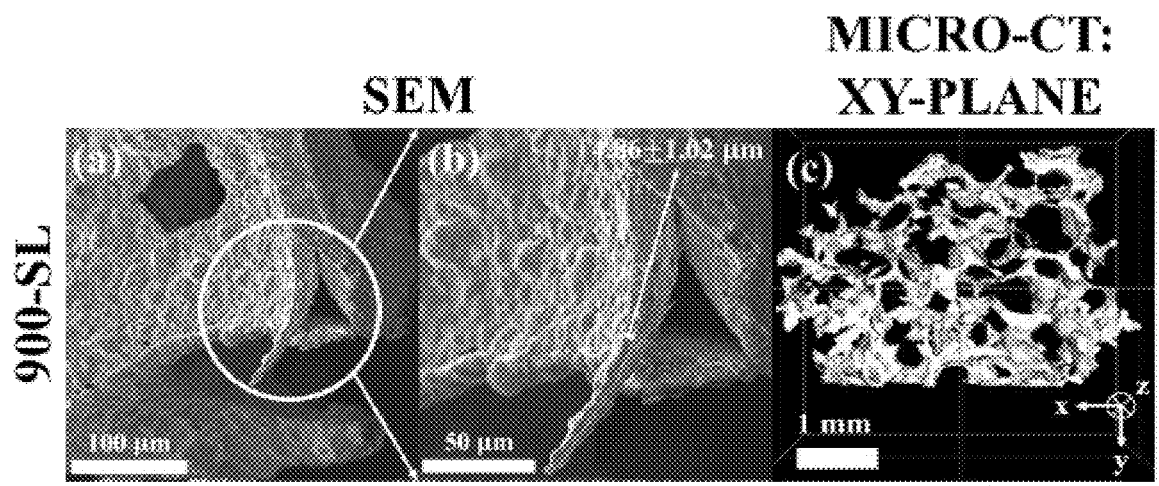
Figures 38D, 38E, 38F:
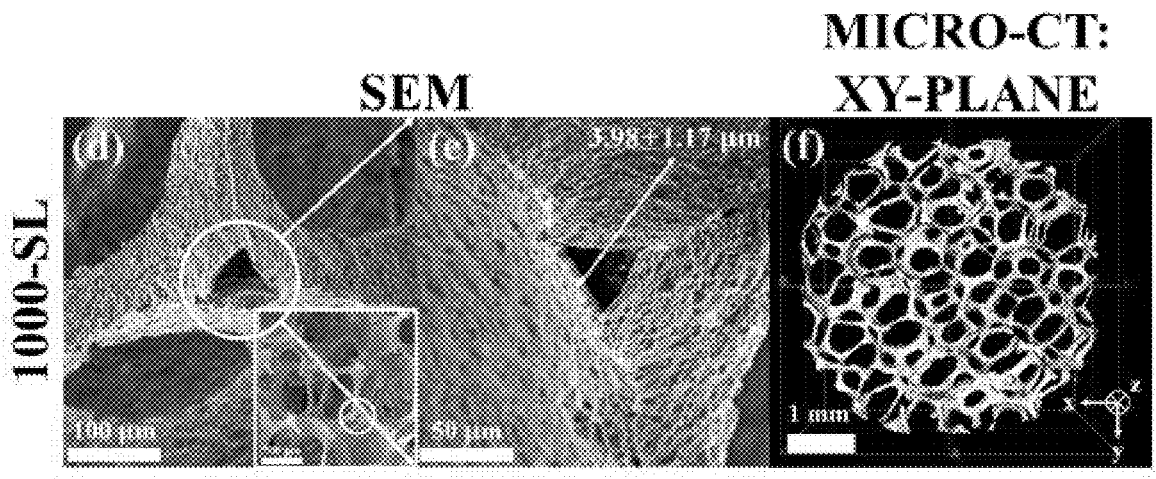

It was found that 900-SL and 1000-SL had similar porosities and it was expected both would behave similarly in compression as it is well-established the strong connection between porosity and compressive strength. Despite this, however, the compressive behavior of 900-SL could not be evaluated as their excessive brittleness from minimal sintering resulted in premature failure. This was not the case for 1000-SL and it was found that its compressive strength was 0.15±0.057 MPa, which is at the lower range of the compressive strength of cancellous bone demonstrating that 1000-SL would be suitable for low-load bearing applications. The low compressive strength of 1000-SL was heavily contributed to the large component of free space present within the internal structure of the Ag-BG scaffolds (FIGS. 38B and 38E).

The compressive behavior of 1000-SL does not follow the typical behavior for glass-ceramics in terms of following a linear increase in stress as a function of strain before catastrophic failure. The compressive stress-strain plot (FIG. 39) depicts a "noisy" pattern with many small breaks as the overall stress increases before failure. The compressive behavior of 1000-SL is, however, typical of porous scaffolds fabricated by the polymer foam replication technique. The breaks observed on the compressive stress-strain plot before catastrophic failure are a result of weaker struts collapsing, which is further compounded by any flaws present within the struts. As the struts break, they release energy causing the compressive force to drop slightly as a function of strain. The overall stress continues to increase as the stronger struts can handle increased compressive forces before they too fail resulting in the catastrophic failure evidenced by the rapid decline in stress when the strain exceeded ~3%.

Micro- and Nano-Scale Characterization of the Antibacterial and Biological Response.

Micro- and nanostructural characteristics can strongly influence the antibacterial and biological response biomaterials, and the Ag-BG scaffolds are no exception. FIGS. 40A-40D show the diffractograms and FTIR-ATR spectra of the Ag-BG particles as-received along with 900-SL and 1000-SL. In both the diffractograms and FTIR-ATR spectra, significant crystallization was observed after processing the Ag-BG particles into highly porous 3D scaffolds. It was shown (FIG. 40A) that the Ag-BG particles as received were glass-ceramic in nature, where poorly crystalline hydroxyapatite (PDF Card No. 00-066-0271) was observed evidenced by the broad peaks overlaid with the amorphous hump noted between ~20 and 35 2θ. The P—O bending (~550 cm$^{-1}$ and ~610 cm$^{-1}$) and stretching (~1030 cm$^{-1}$ and ~1080 cm$^{-1}$) attributed in the FTIR-ATR spectrum of the as-received Ag-BG were in agreement with the included reference spectrum of hydroxyapatite.

For 900-SL and 1000-SL, the observed phases in the diffractograms (FIG. 40A) were hydroxyapatite (HA, PDF Card No. 00-066-0271), cristobalite (PDF Card. No 01-071-3839), Ag (PDF Card No. 01-071-4613), pseudowollastonite (PDF Card No. 01-074-0874) and wollastonite-2M (PDF Card No. 00-066-0271). Both 900-SL and 1000-SL were classified as having a highly crystalline microstructure and as such the respective XRD phases could be identified in their respective FTIR-ATR spectra. To this end, Characteristic Si—O bending peaks were observed at ~450 cm$^{-1}$ and ~800 cm$^{-1}$ consistent with other silicate-based glass systems.

Furthermore, the Si—O bending peaks observed at ~630 cm$^{-1}$ and ~800 cm$^{-1}$ and Si—O stretching at ~1200 cm$^{-1}$ were attributed to the presence of cristobalite. Si—O stretching peaks between 900 cm$^{-1}$ and 1100 cm$^{-1}$ typically result from the presence of network-modifying ions such as Ca$^{2+}$. In the case of the Ag-BG scaffolds, the presence of these Si—O stretching peaks at ~900 cm$^{-1}$, ~1005 cm$^{-1}$ and ~1070 cm$^{-1}$ were attributed to the presence of wollastonite-2M and the peaks at ~930 cm$^{-1}$ and ~990 cm$^{-1}$ to pseudowollastonite. The P—O peaks were attributed towards hydroxyapatite as previously described for the as-received Ag-BG FTIR-ATR spectrum.

Rietveld analysis (FIG. 40B) was performed on the obtained diffractograms and the crystallite size (FIG. 40C) calculated to determine the concentrations of each phase, which is summarized in Table 6, and to determine if the different sintering conditions applied effected crystallite size. The Sherrer equation was used to determine crystallite size and is defined as Eq. 5:

$$t = \frac{0.9\lambda}{B\cos\theta}, \quad (\text{Eq. 5})$$

where λ is the wavelength of the incident X-rays, B is the breadth or full-width half max (FWHM) of the diffraction peak of interest, θ is the angle at which the diffraction peak of interest occurs, and t is the crystallite size. The frequency distribution plot of the crystallite size for 900-SL and 1000-SL (FIG. 40C) saw a Gaussian distribution with a narrower distribution being noted for 1000-SL with an average crystallite size minutely larger than 900-SL. The distribution of crystallite size for 900-SL was likely wider as the decreased sintering temperature resulted in more poorly formed crystallites evidenced by the increased breadth of the diffraction peaks (FIG. 40A) of 900-SL. Examining the phase concentrations noted in Table 6, the most drastic changes in phase concentrations were between wollastonite-2M and pseudowollastonite, where a ~13% increase in pseudowollastonite was observed along with a ~9% decrease in wollastonite-2M. This change was unsurprising as pseudowollastonite is known to be the high temperature stable polymorph of wollastonite. For the remaining phases (i.e., hydroxyapatite, cristobalite, and silver), there was only a minor changes in concentrations (<3%) observed and these small phase concentration changes and minute differences in crystallite size are not expected to affect the antibacterial and biological response of the Ag-BG scaffolds. Interestingly, the unit cell volumes were decreased when sintering occurred at 1000-SL and attributed to an increased number of vacancies that formed during the densification of the Ag-BG particles.

TABLE 6

The phase concentrations that comprised the microstructure of 900-SL and 1000-SL along with how the measured unit cell volume differed from its theoretical value.

| Phases | Phase Oxide (wt. %) | 900-SL | 900-SL Experimental difference in unit cell volume (%) | 1000-SL | 1000-SL Experimental difference in unit cell volume (%) |
| --- | --- | --- | --- | --- | --- |
| Cristobalite | 100SiO2 | 10.50% | −3.67 | 8.93% | −30.5 |
| Hydroxyapatite | 55.8CaO—42.4P2O5 | 39.10% | 2 | 36.60% | −28.7 |
| Wollastonite-2M | 51.7SiO2—48.3CaO | 24.60% | 2.57 | 15.80% | −29.9 |
| Pseudowollastonite | 51.7SiO2—48.3CaO | 25% | 0.47 | 37.90% | −30.2 |
| Silver | 100Ag | 0.86% | −8.52 | 0.81% | −19.4 |

The presence of reduced silver ($Ag^0$) in the diffractograms (FIG. 40A) of 900-SL and 1000-SL was unexpected as it was assumed that the $[AlO_4]^-$ would have maintained the stability of $Ag^+$ ions. The optical images of 900-SL and 1000-SL (FIGS. 37A-37B) show localized regions of dark coloration consistent with a yellow/brown sheen that can be attributed to the presence of Ag particles. EDS mapping (FIGS. 41A-41B) was employed for both 900-SL and 1000-SL to visualize the Ag particles to verify their presence within the diffractograms in addition to identify spatially the location of the other phases. For both 900-SL and 1000-SL a homogenous distribution of Si, Ca, Al, Ag, and Na was observed down to the micron level. The spatial resolution of SEM-EDS is limited to the micron level as a result of the interaction volume between the electron beam and the Ag-BG scaffolds. Since a homogeneous distribution of elements was observed at the micron-level, this is evidence to support that heterogeneity likely exists on the nanoscale and would require TEM (FIGS. 42A-42F) observations to verify.

Low and high-resolution TEM was employed to view the nanostructure of 1000-SL. The low magnification TEM images (FIGS. 42A and 42C) of different 1000-SL particles presented with varying regions of electron contrast with large pockets of minimal electron intensity representing regions of increased thickness resulting from the overlapping of particles. Small circular dark particles (<50 nm) were evidenced randomly dispersed in the lower magnification images that were thought to be nano-sized Ag particles. The high magnification TEM image in FIG. 7d focused on one of these particles where the lattice fringes were measured at 0.235 nm, which was attributed to the (111) of Ag confirming that Ag is present as nanoparticles (AgNPs). It is worth noting that the (111) of Ag was identified in the diffractograms in FIGS. 40A-40D.

Additional investigations at high magnification TEM revealed lattice fringes that were attributable to hydroxyapatite. Indeed, in FIG. 42B, the lattice fringe distance was measured to be 0.185 nm that corresponded to the (213) of hydroxyapatite and the lattice fringe measurement of 0.227 nm in FIG. 42D was attributed to the (130) of hydroxyapatite.

While lattice fringe attribution was successful in identifying Ag and hydroxyapatite, the representative diffraction pattern shown in FIG. 42E contained pseudowollastonite and wollastonite-2M in addition to Ag and hydroxyapatite, thus supporting the phase attributions in the diffractograms (FIG. 40A). Given the diffraction pattern resolved into a spot pattern, each of the attributed phases must be existing as single crystals within close proximity in order to resolve all these phases within the same diffraction pattern. Interestingly, cristobalite was not identified in the diffraction pattern. It is possible that cristobalite was not present in the area of diffraction, however it is more likely that the spots that could be attributed to cristobalite were convoluted by the transmitted beam. Cristobalite can exist in low indexed atomic planes (e.g., (001)) resulting in a large interatomic planar spacing (d-spacing) that translates to a small distance away from the transmitted beam in reciprocal space.

While the presence of the Ag particles was confirmed through TEM investigations, the Rietveld analysis determined the Ag concentration to be less than 1%, which cannot account for all the Ag present within the Ag-BG composition. Since 27Al MAS-NMR can be utilized to identify $Ag^+$ by its effect on the coordination of Al by way of the $[AlO_4]^-$, this was performed on powdered 1000-SL and is shown in FIGS. 43A-43B.

As the amount of Ag was negligibly different between 900-SL and 1000-SL along with similar phase concentrations, only 1000-SL was used for the MAS-NMR investigations. An asymmetric peak was observed around 50 ppm that produced two peaks when deconvoluted: the first at 42.0 ppm attributed as Al in five-fold coordination and the second at 52.4 ppm attributed as Al in four-fold coordination. The presence of five-fold coordinated Al can be correlated to the presence of an $Ag^+$ stabilized by an $[AlO_4]^-$. Indeed, only the presence of $Ag^+$ and $Ag^0$ within 900-SL and 1000-SL could explain the smaller than expected amount of Ag found by the Rietveld analysis (FIG. 40B) and why there was heterogeneous dark coloration observed in the optical images (FIGS. 37A-37B).

$^{29}$Si MAS-NMR was additionally performed on 1000-SL to investigate the Q speciation of Si. The peaks ranging from −96.1 to −112.6 ppm indicates the presence of Q4 species. More specifically, the peak at −112.6 ppm could be attributed to the presence of cristobalite thus supporting the attributions in the diffractograms and FTIR-ATR spectra (FIGS. 40A and 40D). The remaining peaks within this range were correlated to different numbers of four-fold coordinated Al surrounding the Si, where a higher number of Al atoms corresponding to a downward chemical shift towards the $Q^3$ speciation range. The peak at −89.8 ppm was attributed to the presence of $Q^3$ species that was correlated to the presence of wollastonite-2M. At −84.4 ppm, $Q^2$ species are present and was correlated to the presence of pseudowollastonite. The reduction in Q species between wollastonite-2M and pseudowollastonite is explained by the molecular structure of pseudowollastonite, which is comprised of a tricyclic $[Si_3O_9]^{6-}$ molecule that satisfies its charge imbalance by the addition of 3 $Ca^{2+}$ ions, where each Si is thus surrounded by 2 $Ca^{2+}$ atoms resulting in a $Q^2$ species peak in the 29Si MAS-NMR spectrum. A small peak at −73.2 ppm was identified and attributed as $Q^0$ species.

MRSA was used to study the antibacterial properties of 900-SL and 1000-SL as MRSA is a commonly cited cause of bone infection and the CFU method employed to quantify the inhibition induced by the Ag-BG scaffolds. Both 900-SL and 1000-SL (FIGS. 44A-44C) saw a significant reduction in CFU compared to the untreated case, however, the response of both Ag-BG scaffolds were insignificant from one another.

Example 1, using the Ag-BG system, demonstrated that this system can reactivate antibiotics that MRSA resists, thus identifying a novel pathway to combat antibiotic resistance. To investigate whether the highly crystalline Ag-BG scaffolds would possess similar capabilities, 1000-SL was combined with the fosfomycin and vancomycin. Fosfomycin inhibits bacterial growth by targeting peptidoglycan and cell wall synthesis by inhibiting UDP-N-acetylglucosamine-3-enolpyruvyltransferase, MurA and was selected as Example 1 demonstrated that the combination of fosfomycin and Ag-BG micro-sized particles resulted in the strongest synergistic effect. Vancomycin inhibits MRSA growth by disrupting the transport of cell wall precursors from the cytoplasm to the peptidoglycan.

After 24 h of exposure of 1000-SL with either fosfomycin or vancomycin (FIGS. 44B-44C), there was a significant increase in MRSA inhibition compared to 1000-SL alone. Interestingly, however, significant inhibition of the Ag-BG scaffold antibiotic combination after 48 h of exposure did not result in a significant increase in MRSA inhibition compared to 1000-SL alone. It is likely that the initial release of Ag is in sufficient concentrations to allow for a synergistic effect to be observed between the Ag-BG scaffold and antibiotic. This is supported by the fact that after 24 h, the MRSA inhibition of the Ag-BG scaffolds was over 100 times stronger compared to the controls. Furthermore, between 24 h and 48 h, there is only ~10-fold increase in MRSA inhibition demonstrating that the release of Ag is slowed at later time points and could explain why a synergistic effect was observed after 24 h but not 48 h.

To support the above hypothesis, 1000-SL was powderized and sieved to a particle size below 20 μm. The same preparation was used for the as-received Ag-BG particles. Interestingly, the powderized 1000-SL exhibited bactericidal conditions (FIG. 44A) and was approximately 1 million times more potent towards MRSA than the Ag-BG scaffold itself. Example 1 demonstrated that 11 mg of the as-received Ag-BG particles would be bactericidal, which proved to be the case in this study as well. This demonstrated that the differences in crystallinity between the as-received Ag-BG particles and 1000-SL were not limiting the synergistic potential of the material, but rather the morphology of the Ag-BG is the limiting factor. Example 1 shows that the debris from the micro-sized Ag-BG particles played an important role in allowing for a synergistic effect to be observed and this study further highlights the importance of the debris. Furthermore, it is likely as well that the increased surface area of the micro-sized particles allowing for a greater interaction between the material and MRSA. From BET, the surface area of the micro-sized Ag-BG particles was measured to be 90.4±0.57 $m^2$ $g^{-1}$ whereas the surface area of 1000-SL was 0.44±0.01 $m^2$ $g^{-1}$. The surface area of the powderized 1000-SL is assumed to be similar to that of the as-received Ag-BG powder therefore demonstrating that the diminished surface area of 1000-SL and lack of debris supports that the difference in morphological characteristics limits the anti-MRSA effect of the Ag-BG scaffolds in addition to decreasing the synergistic effect the Ag-BG scaffolds can exhibit when combined with antibiotics.

The acellular bioactivity of the Ag-BG scaffolds was assessed on 900-SL and 1000-SL through immersion in SBF for 7, 14, and 21 days. Both Ag-BG scaffolds exhibited similar structural changes seen in their FTIR-ATR spectra and respective diffractograms. The corresponding SEM micrographs (FIGS. 45A-45F and 45K-45V) show similar surface morphological changes after 7 days of soaking in SBF with patchy deposition of the calcium phosphate phase. At 14 days, the surface of both 900-SL and 1000-SL were covered with depositions of the calcium phosphate phase, which were in the process of forming well-defined needle-like crystals as the calcium phosphate phase crystallizes into biological hydroxyapatite. The SEM micrographs after 21 days of soaking in SBF (FIGS. 45A-45B and 45K-45L) presented with a well-crystallized surface of the biological hydroxyapatite for 1000-SL, however for 900-SL the needle-like crystals are less defined.

1000-SL was additionally soaked in SBF at shorter time points (1, 3, 5 days) to investigate the bioactive behavior of the Ag-BG scaffolds at earlier time points. Differences were not expected to be present between 900-SL and 1000-SL at these early time points. After 1 day in SBF, the surface morphology of 1000-SL (FIGS. 45U-45V) saw many small circular features that were representative of the nucleation sites where the calcium phosphate was beginning to deposit. At 3 days, the individual nucleation sites are less visible and are in the process of coalescing together. The layer that is forming is likely not thicker than 500 nm. After 5 days in SBF, crystal-like features were observed on the surface and the formation of spheroid, cauliflower-like structures typical with acellular bioactivity studies were becoming evident.

The rate of bioactivity was found to be faster for 1000-SL, given it reacted faster with SBF to form an apatite-like layer. Well-defined rod-like structures are noted in the SEM micrographs (FIGS. 45K-45L) along with their agglomeration into globular structures suggested the formation of a mature Ca—P layer. 900-SL presented similar features after 21 days in SBF compared to 1000-SL, however, the high magnification SEM micrograph (FIG. 45B) showed that the Ca—P layer did not show a defined rod-like morphology comparatively. For both Ag-BG scaffolds, it was concluded that it took at least 14 days for the depositions to mature into a well-formed apatite layer.

It was unexpected to observe a faster rate of biological hydroxyapatite maturation considering both 900-SL and 1000-SL had similar macrostructures. Therefore, only microstructural differences could account for this difference in the rate of bioactivity. As previously described, both 900-SL and 1000-SL presented with similar concentrations of hydroxyapatite, cristobalite, and Ag with noticeable variations being detected in the wollastonite-2M and pseudowollastonite concentrations. The increased concentration of pseudowollastonite within 1000-SL must account for this difference. Indeed, pseudowollastonite has a unit cell that is approximately 400% greater than that of wollastonite-2M, so there is a greater amount of free space and thus a greater internal lattice energy, resulting in less cohesion and a greater solubility. Using the extended, generalized Kapustinskii equation defined as Eq. 6 and Eq. 7:

$$U_{POT} = AI\left(\frac{2I}{V_m}\right)^{1/3}, \quad \text{(Eq. 6)}$$

$$2I = \sum n_i z_i^2, \quad \text{(Eq. 7)}$$

where A is a constant (121.39 kJ mol-1 nm), I is a constant defined by Eq. 6, $n_i$ is the number of ions with integer charge $z_i$, and $V_m$ the ratio of the number of formula units per unit cell to unit cell volume (0.0663 nm$^{-3}$ for wollastonite), the internal potential lattice energy of Wollastonite-2M was calculated to be 15,234 kJ mol-1 and 32,959 kJ mol-1 for pseudowollastonite thus confirming the aforementioned hypothesis.

Interestingly, even after 21 days of soaking in SBF, peaks corresponding to cristobalite, pseudowollastonite, and wollastonite-2M could still be identified in the diffractograms likely resulting from only a thin layer of biological HA being deposited on the surface. This was further evidenced by EDS spot analysis (not shown), which was employed to elucidate the Ca/P ratio of the surface depositions. The Ca/P ratio for 900-SL never achieved values less than 2, an indication that the material below is still contributing to the EDS. Based on this, it can be said that the biological hydroxyapatite layer that was able to form after 21 d of soaking in SBF for 900-SL was less than 5 microns or the approximate maximum depth of the interaction volume. This was not the case, however for 1000-SL, whose Ca/P ratio did fall below 2. Furthermore, increases in intensity of the P—O bending peaks ~560 cm$^{-1}$ and ~610 cm$^{-1}$ were evident at increasing soaking time on the FTIR-ATR spectra (FIG. 45I) along with the peak broadening noted at ~1030 cm$^{-1}$.

Discussion

The aim of this work was to fabricate highly porous Ag-BG scaffolds, study their antibacterial, biological, and mechanical performance and utilize the structural differences to account for the observed differences in antibacterial and biological performance.

From the thermal analysis of the as-received Ag-BG particles, it was found that the Ag-BG system itself possessed modest glass formability with no clear indication of whether viscous sintering or densification through crystallization would be favored during the densification of Ag-BG particles. Ideally, the Ag-BG would exhibit low viscosity and high surface tension to suppress surface crystallization in favor of viscous sintering. Using the equation of sinterability (Eq. 4), as demonstrated for similar systems, determined that crystallization would occur before observing significant densification, which could further be extrapolated to state that since the sinterability of the Ag-BG system was largely negative that the sintering and crystallization kinetics are highly interdependent supported by the glass-ceramic nature of the as-received Ag-BG (FIG. 40A). It is likely that for the Ag-BG system, the surface tension decreases at a much faster rate than its viscosity as a function of temperature and that considering the time dependence of these parameters would be useful in an effort to decouple the sintering and crystallization kinetics.

The optical images of the Ag-BG scaffolds (FIGS. 37A-37B) exhibited a heterogeneous dispersion of color intensity with regions of a yellow/brown sheen evident. The dark coloration was determined to be the result of the ability of the applied heat treatment to overcome the electrostatic forces between the Ag$^+$ ion that was localized by an [AlO$_4$]$^-$. At sufficiently high temperatures (T >800° C.), the probability is likely that a modifier ion (e.g., Ca or Na) collides with an AgAlO$_4$ complex that could temporarily destabilize the Ag$^+$ ion. The Gibbs free energy ($\Delta G=\Delta H - T\Delta S$) was calculated for AgAlO$_4$, Ca(AlO$_4$)$_2$, and Na(AlO$_4$) at 900° C. and 1000° C., the sintering temperatures used in this study and summarized in Table 7.

TABLE 7

The Gibbs free energy of AgAlO$_4$, Ca(AlO$_4$)$_2$, and NaAlO$_4$ at 900° C. and 1000° C.

| Temperature (° C.) | AgAlO$_4$ (kJ mol$^{-1}$) | Ca(AlO$_4$)$_2$ (kJ mol$^{-1}$) | NaAlO$_4$ (kJ mol$^{-1}$) |
|---|---|---|---|
| 900 | −686.0 | −2049.9 | −643.9 |
| 1000 | −685.7 | −2039.7 | −637.5 |

Based on the free energy calculations, NaAlO$_4$ complexes likely do not exist as the complex is less stable at these temperatures compared to AgAlO$_4$. Therefore, only the collision of Ca$^{2+}$ ions could destabilize the AgAlO$_4$ complex as the Ca(AlO$_4$)$_2$ has a lower free energy. The free Ag$^+$ ion is unstable by itself and reduces to Ag$^0$ to for stability thus resulting in the presence of AgNPs. This supports the identification of Ag$^0$ in the diffractograms where through TEM investigations, the size of the AgNPs was found to be less than 50 nm. Although it should be noted that these collisions are likely not frequent given the presence of five-fold coordinated Al noted in the NMR spectra (FIG. 43A) and the smaller than expected Ag phase concentration identified by the Rietveld analysis (FIG. 40B). The presence of AgNPs within the range of those found in the Ag-BG scaffolds are known to exhibit a surface plasmon resonance effect within the visible light spectrum, thus leading to the yellow/brown sheen whereas the AgAlO$_4$ complex is colorless therefore accounting for the varying colorations observed in the optical images (FIGS. 37A-37B).

Both 900-SL and 1000-SL were identified to contain AgNPs as evidenced by both their respective diffractograms (FIG. 40A) and nanoscale investigations (FIGS. 42A-42F) and demonstrated anti-MRSA capabilities shown by the significant inhibition of MRSA for 900-SL and 1000-SL against the untreated case. The mechanism of MRSA inhibition is related to the status of Ag, which in this case is in both nanoparticle form and ionic form. The AgNPs attach to the cell wall of the MRSA disrupting the cellular functions on the surface which can lead to cell wall perforation and penetration of the AgNP into the cytoplasm. The subsequent release of Ag$^+$ ions from the AgNP within the MRSA and Ag$^+$ ions released from the Ag-BG scaffolds will disrupt protein synthesis and induce DNA damage as a result of the Ag$^+$ ions affinity to complex with electron donor groups such as thiols or phosphates. Interestingly, the size of the AgNPs has a direct effect on their ability to inhibit bacteria, where increasing surface area to volume ratios of the AgNPs correlated to a stronger inhibitory response. Since the difference in MRSA inhibition was insignificantly different, the size of the AgNPs within both 900-SL and 1000-SL are likely similar.

Example 1 demonstrated the ability of Ag-BG microsized particles to reactivate antibiotics that MRSA resists. The example demonstrated that the combination of Ag$^+$ ions released and nanosized debris (a degradation byproduct of the Ag-BG) likely corrupted the cell wall that increased the permeability of the MRSA, thus enhancing the exposure of the antibiotic. When Ag-BG scaffolds were combined with fosfomycin having a concentration of 0.2 μg mL$^{-1}$ or vancomycin having a concentration of 2 mg mL$^{-1}$, a synergistic response in MRSA inhibition was observed after 24 h that could not be from the additive inhibition of the Ag-BG scaffold and antibiotic alone. As previously stated, this synergistic effect was not observed after 48 h and was likely due to the small amount of additional Ag released from the scaffolds considering the inhibition from 24 to 48 h was within an order of magnitude. By studying the effect of crystallinity and morphology, it was found that the morphology was the limiting factor in the expression of MRSA inhibition and that the over 100-fold increase in surface area and the likely presence of debris from the Ag-BG particles as they degraded accounted for the differences shown in MRSA inhibition and supports the mechanism described in Example 1.

Macrostructural and surface morphological investigations (FIGS. 37A-37H) into the Ag-BG scaffolds showed a rough surface with the inability to distinguish individual particles indicative that modest sintering must have occurred during the heat treatment. Additionally, the open porous network is expected to provide a well-suited environment for cell migration and spreading in vivo. Micro-sized cracks, however, were widespread along the surface; a side effect of the polymer foam replication technique reducing the potential compressive strength of the Ag-BG scaffolds since minimal energy would be required for crack initial as many flaws are already present. Furthermore, the strut cross-sections (FIGS. 38A-38F) of 900-SL and 1000-SL revealed the interior of the scaffold was largely hollow contributing to their low compressive strength.

Elucidation of the microstructure of the Ag-BG scaffolds revealed a highly crystalline structure comprised of cristobalite, HA, pseudowollastonite, wollastonite-2M, and Ag. Cristobalite typically appears when temperatures exceed 1400° C., so its presence as a microstructural constituent in the Ag-BG scaffolds was unusual. The presence of Ag resulted in the formation of cristobalite at the sintering temperatures used in this study as a result of the Ag perturbing the Si network and inducing crystallization by acting as a nucleation site. The presence of wollastonite-2M was expected as it is known to crystallize at temperatures exceeding 870° C. Interestingly, pseudowollastonite was present at temperatures as low as 900° C. where its formation is not typically observed until temperatures exceed 1125° C. It is likely that the presence of monovalent modifying ions (e.g., Na or K) act as nucleation sites for the pseudowollastonite and stabilize its presence at temperatures as low as 900° C. Previous studies on the Ag-BG system demonstrated that when the sum total of monovalent ions fell below 1 wt. %, pseudowollastonite could no longer be identified. It is likely then that the Na is trapped within pseudowollastonite thus explaining the absence of any Na containing phases.

Figure 45G:
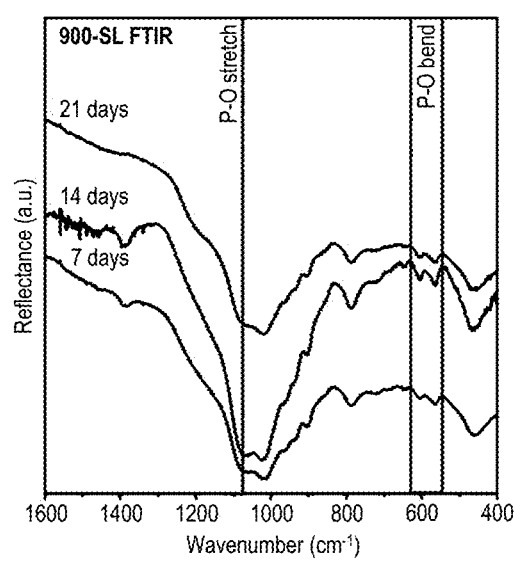
Figure 45H:
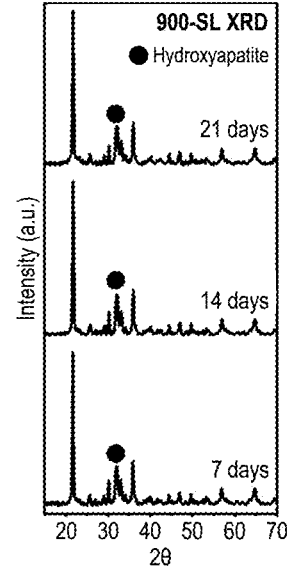

900-SL and 1000-SL both exhibited bioactive behavior under acellular conditions evidenced by the formation of cauliflower-like surface morphological features typical for the deposition and crystallization of biological hydroxyapatite in SBF. Furthermore, at the later time points, structural modifications were observed in the FTIR-ATR spectra (FIGS. 45G and 45I) evidenced by the increased intensity of the P—O bending peaks ~560 cm$^{-1}$ and ~610 cm$^{-1}$ and the P—O stretching peak broadening ~1030 cm$^{-1}$. Modification of the hydroxyapatite diffraction peaks was challenging to observe over the time points measured since the highly crystalline microstructure already contained HA. The high degree of crystallinity retarded the degradation rate of the Ag-BG scaffolds and delayed the appreciable deposition of biological hydroxyapatite given the Ca/P ratio did not begin to converge towards the stoichiometric ratio of 1.67 until after 14 days immersion in SBF. This study also revealed that pseudowollastonite is more reactive in SBF than wollastonite-2M where the differences in unit cell volumes and the potential internal lattice energies accounted for the faster rate of biological hydroxyapatite formation in 1000-SL.

In summary, this example correlated the microstructural characteristics of the Ag-BG scaffolds to their antibacterial, biological, and mechanical properties. Successful fabrication of Ag-BG scaffolds required sintering to temperatures that resulted in a highly crystalline microstructure that formed a biological hydroxyapatite layer after 14 d of immersion in SBF. The Ag-BG scaffolds exhibited unique antibacterial properties, with their ability to not only combat MRSA but also showed an ability to reactivate fosfomycin and vancomycin, which MRSA resists. Morphological differences were able to account for the discrepancies shown in MRSA inhibition. The compressive strength the Ag-BG scaffolds achieved makes them useful for bone tissue regeneration in load-bearing applications.

Conclusion

Ag-BG scaffolds were successfully fabricated exhibiting novel antibacterial properties, biological response, and structural characteristics. The heat treatment was developed from the characterization of the thermal behavior of Ag-BG particles. The nano- to macro-scale characteristics were correlated to the overall performance of the Ag-BG scaffolds. The overall antibacterial and biological characteristics provide a use for the Ag-BG scaffolds in biological applications related to bone regeneration and MRSA prevention.

Example 6

This example describes a 3D printed bioactive and antibacterial silicate glass-ceramic scaffold by fused filament fabrication Summary The fused filament fabrication (FFF) technique was applied for the first time to fabricate novel 3D printed silicate bioactive and antibacterial Ag-doped glass-ceramic (Ag-BG) scaffolds. A novel filament consisting primarily of polyolefin and Ag-BG micro-sized particles was developed and its thermal properties characterized by thermogravimetric analysis (TGA) to define the optimum heat treatment with minimal macrostructural deformation during thermal debinding and sintering. Structural characteristics of the Ag-BG scaffolds were evaluated from macro- to nanoscale using microscopic and spectroscopic techniques. The compressive strength of the Ag-BG scaffolds was found to be in the range of cancellous bone. Bioactivity of the 3D printed Ag-BG scaffolds was evaluated in vitro through immersion in simulated body fluid (SBF) and correlated to the formation of an apatite-like phase. Methicillin-resistant *Staphylococcus aureus* (MRSA) inoculated with the Ag-BG scaffolds exhibited a significant decrease in viability underscoring a potent anti-MRSA effect. This study demonstrates the FFF technique for the fabrication of bioactive 3D silicate scaffolds with characteristics for orthopedic applications.

Introduction

Many processing techniques have been applied to fabricate porous 3D printed bioactive scaffolds for bone tissue engineering applications. The use of 3D printed porous scaffolds is advantageous as they provide a multi-dimensional template that closely mimics the native structure of bone, making them beneficial for creating ideal conditions for bone tissue regeneration. Among the different materials that have been used in 3D printing of scaffolds for tissue regeneration, silicate bioactive glass-ceramics show great promise given their inherent bioconductivity and bioinductivity. To date, no common processing technique is successful in maintaining high porosity while simultaneously achieving compressive strength values close to the range for cortical bone (100-150 MPa). Thus, the implementation of novel strategies is needed.

The application of additive manufacturing (AM) techniques to the fabrication of 3D printed scaffolds from bioactive materials is becoming popular as a result of the superior flexibility in scaffold design. For example, direct ink writing (DIW) involves the creation of a highly viscous paste by combining particles (e.g., bioactive glass) with a polymeric binder. The paste is then extruded through a nozzle and the 3D structure assembled layer-by-layer. Critical to successful printing is the optimization of the rheological properties of the ink, particle size, and maintaining a homogenous distribution of said particles. It is additionally imperative that heat treatment is carefully selected in order to debind and sinter the 3D structure while minimizing macrostructural deformation. When properly optimized, DIW fabricated scaffolds for 45S5 Bioglass® and have demonstrated significant improvement in their compressive strength compared to the more traditional processes. However, the wide range of bioactive glass compositions available makes DIW implementation challenging since each composition will likely require its own ink formulation. Therefore, other processing techniques should be explored.

Fused filament fabrication (FFF) differs from DIW in that a solid filament is used rather than a viscous ink. While thorough consideration of particle size, binder, and viscosity must be considered as before, control of viscosity is primarily accomplished through the printer nozzle temperature, thus minimizing the number of necessary parameters to control (compared to DIW). Furthermore, there is potential to develop a binder system that would be suitable for a wide range of bioactive silicate glass-ceramic systems.

The FFF technique is viable as a processing technique for biomedical applications. This is significantly advantageous as this technique enables the manufacturing of free-standing objects. Moreover, by modifying the filament composition (e.g., varying the thermoplastic polymer concentration between 40-90 vol. % with appropriate adjustment of the incorporated powders and additives) along with modification of the printing temperature (e.g., 150-200° C.), the melt-viscosity can be controlled to produce free-standing bridges (struts) in the 3D scaffolds, creating a considerable increase in scaffold's surface area. This characteristic can have a big impact on scaffolds for bone tissue engineering. Finally, manufacturing and minimal design constraints in FFF is another superior feature versus other printing techniques, such as dispenser-based techniques, which typically require printing the paste onto a substrate, selected based on the solvent within the paste, before curing to allow solidification of the paste.

Overall, the manufacturing capabilities of the FFF technique for printing advanced scaffolds are more attractive compared to other printing techniques. Successful establishment of the FFF technique for fabrication of scaffolds using silicate bioactive glass-ceramic-polyolefin composites will couple the superior geometrical design freedom of the FFF technique with the sintering of novel materials for orthopedic applications. FFF printing and subsequent sintering of Ag-BG scaffolds is a new application that will be explored herein. Not only does FFF produce a polymer glass-ceramic composite (green body), but it can also produce glass-ceramic scaffolds by polymer pyrolysis and subsequent sintering to temperatures of at least 900° C. This makes FFF an innovative and novel manufacturing approach for producing silicate bioactive scaffolds with potential use in orthopedic applications.

In particular, a novel polyolefin-based binder system, primarily consisting of thermoplastic polymers mixed with Ag-BG were used for the development of the filament. Subsequently, the Ag-BG-filament was utilized in the FFF-printer for printing porous, mechanically competent, bioactive, and antibacterial 3D scaffolds. The heat treatment was devised to remove the polyolefin binder and to sinter the Ag-BG particles whilst minimizing macrostructural deformation. 3D printed Ag-BG scaffolds were studied structurally and characterized for their mechanical characteristics, biological response, and antibacterial properties demonstrating the FFF technique as an additive manufacturing approach for silicate bioactive glass-ceramic scaffolds.

Methods and Materials

Ag-BG Fabrication. The fabrication of Ag-BG has previously been described in detail in Example 4. Briefly, the sol-gel derived Ag-doped bioactive glass fabrication is based on the solution stage combination of the sol-gel bioactive glass 58S ($58SiO_2$-$33CaO$-$9P_2O_5$ (wt. %)) and a sol-gel glass in the system $60SiO_2$-$11CaO$-$3P_2O_5$-$14Al_2O_3$-$5Na_2O$-$7Ag_2O$ (wt. %). Both systems were stirred separately for 17 h before mixing and allowed to stir for an additional 17 h to ensure solution homogeneity. The solution was aged at 60° C., dried at 180° C., and stabilized up to 700° C. resulting in the sol-gel derived Ag-doped bioactive glass (Ag-BG) in the system $58.6SiO_2$-$26.4CaO$-$7.2P_2O_5$-$4.2Al_2O_3$-$1.5Na_2O$-$2.1Ag_2O$ (wt %). After the heat treatment, the Ag-BG was dry-milled in a zirconia jar with zirconia beads and sieved to have particles ranging from 20 to 38 µm in size.

FFF and Thermal Treatment.

The FFF technique consists of a powder-filled polymeric binder system that requires proper flexibility and durability to successfully wind on a spool for printing. To satisfy these criteria, a multi-component binder system consisting of polyolefin and elastomer was utilized. To improve the powder-binder homogenization, fatty acids were used as a surfactant in a concentration range from 5-8 vol. %.

The filament fabrication entailed first drying the Ag-BG powder and polymeric resins at 40° C. for 1 h to expel excess water before extrusion. The concentration of Ag-BG powder used ranged between 46.4 vol. % and 48.9 vol. %. The Ag-BG powder and polymeric resins were fed into a modified twin-screw extruder, where the barrel was kept between 170° C. and 210° C. The mixing speed was 50 RPM. The extruded filament was 1.75 mm in diameter and spooled immediately to be used for 3D printing.

A 3D computerized CAD model (FIG. 46A) of the scaffold was designed comprising of cubic unit cells with the central portion voided to achieve an interconnected structure. The 3D scaffolds (termed Ag-BG scaffolds) were printed using a Renkforce RF-1000 3D printer with a nozzle size of 0.40 mm, a printing speed of 1000 mm min$^{-1}$, and a nozzle temperature of 180° C. The green body Ag-BG scaffolds (FIG. 46B) were transferred to a muffle furnace (Carbolite Gero CFW 1305) for thermal debinding (pyrolysis) and sintering.

Thermal, Structural & Morphological Characterization. The thermal behavior of the filament was determined using thermogravimetric analysis (TGA; TA Instruments TGA 500) to optimize the thermal debinding process. The measurement was conducted in $N_2$ atmosphere (50 ml min$^{-1}$) utilizing the dynamic analysis mode in temperatures ranging from 25° C. to 600° C. with a sensitive coefficient at 4. The heating rate in this mode varies automatically according to the weight loss. In particular, a fast heating rate (e.g., 2-6° C. min$^{-1}$) was applied when no significant weight loss (<3%) was detected (e.g. 150-300° C.), while a slow heating rate (e.g., 0.5-1° C. min$^{-1}$) was introduced (from the program automatically) when notable weight loss was detected (e.g. from 300-340° C.). This dynamic analysis was beneficial for the development of the heat treatment of the printed scaffolds. The thermal debinding was carried out according to the dynamic TGA curve and applied heating rates.

The resulting Ag-BG scaffolds were characterized for their macro-, micro-, and nano-structure utilizing a variety of microscopic and spectroscopic techniques. Optical microscopy (OM; VHX-600E Digital Microscope) and micro-computed tomography (micro-CT; Rigaku Quantum GX) were employed to image the macrostructure of the Ag-BG scaffolds both in 2D and 3D space. The micro-CT images were acquired using the following parameters: scan mode, high resolution; gantry rotation time, 57 minutes; power, 90 kVp/88 μA; Field of View (FOV), 5 mm; number of slices, 512; slice thickness, 10 μm; and voxel resolution, 10 μm$^3$. The optical images were evaluated using Fiji is Just ImageJ (Fiji) and the micro-CT images analyzed using MicroView (Parallax Innovations, ON, Canada) to elucidate the porosity (%), mean pore size (μm), mean strut thickness (μm), mean layer spacing (μm), and scaffold surface area to volume ratio (mm$^{-1}$).

The surface morphology of the Ag-BG scaffolds was investigated using scanning electron microscopy (SEM; Tescan MIRA) with a beam voltage of less than or equal to 10 kV. The elemental homogeneity was examined using energy dispersive spectroscopy (EDS; Ametek EDAX Apollo X) with X-ray maps obtained using a beam voltage of less than or equal to 21 kV and a step-size of 126.2 eV. Fourier-transformed infrared—attenuated total reflectance (FTIR-ATR; Jasco FT/IR-4600) spectra of powdered Ag-BG scaffolds were collected in reflectance mode from 4000-400 cm$^{-1}$ at a resolution of 2 cm$^{-1}$ to investigate their molecular structure. The crystallinity and microstructure of powdered Ag-BG scaffolds were evaluated with X-ray diffraction (XRD; Rigaku Smartlab X-Ray Diffraction Systems). The diffraction patterns were collected from 10° to 90° 2θ utilizing Cu K$_\alpha$ radiation at 40 kV and 44 mA. Transmission electron microscopy (TEM; JEOL 1400 Flash) was performed to observe the phases on pulverized Ag-BG scaffolds held on 200 mesh copper grids with carbon support film (Electron Microscopy Sciences, CF200-CU) with images and diffraction patterns acquired under a voltage of 120 kV.

Compressive Strength.

Compression testing was performed to study the mechanical characteristics of the 3D Ag-BG scaffolds using a United SFM electromechanical series universal testing machine having a 4.45 kN load cell. Compressive forces were applied to Ag-BG scaffolds having dimensions of 10 mm×10 mm×5 mm and maintained using a constant strain rate of 0.5 mm min$^{-1}$. The Ag-BG scaffolds were strained to 70% and compressive strength calculated using the Eq. 2:

$$\sigma = \frac{F}{A}, \quad \text{(Eq. 2)}$$

where F is the force (N) applied to the Ag-BG scaffold and A is the initial cross-sectional area (m$^2$).

Bioactive Behavior.

The ability of the Ag-BG scaffolds to form an apatite-like layer was examined using simulated body fluid (SBF), a common technique used to evaluate the acellular bioactivity. The SBF was fabricated to have the following ion concentrations: 142.0Na$^+$, 5.0K$^+$, 2.5Ca$^{2+}$, 1.5Mg$^{2+}$, 148.8Cl$^-$, 1.0HPO$_4^-$, 4.2HCO$_3^-$, and 0.5 SO$_4^{2-}$ (mmol dm$^3$). A mass to volume ratio of 3.33 was used. The Ag-BG scaffolds were immersed in SBF for 14 and 28 days at 175 RPM and 37.5° C. with solution replacement every 48 h. Assessment of the formation of an apatite-like layer on the surface of the acellular Ag-BG scaffolds was investigated using SEM-EDS to observe any distinct morphological modifications in addition to FTIR-ATR and XRD to note any molecular or microstructural changes.

Anti-MRSA Effect.

The anti-MRSA effect of the Ag-BG scaffolds was studied using the laboratory-derived methicillin-resistant *Staphylococcus aureus* USA300 strain JE2. Tryptic soy broth (TSB) was inoculated with a single JE2 colony and cultured overnight at 37° C. with shaking at 225 RPM. A 1 mL suspension of 10$^8$ CFU mL$^{-1}$ JE2 cells was prepared in phosphate-buffered saline (PBS) for exposure to 11 mg of Ag-BG scaffold. The cell-Ag-BG scaffolds mixtures were then incubated at 37° C. for 24 h. The Ag-BG scaffolds were pulverized using a sterilized wooden stick, in solution and homogeneous aliquots removed for ten-fold serial dilutions. Dilutions were plated on tryptic soy agar (TSA) and incubated at 37° C. to enumerate the colony-forming units (CFU) and quantify bacterial viability. The experiment was performed three times in triplicates.

Statistical Analysis.

All data were expressed with their mean values and standard deviation. The statistical analysis was performed using the two-tailed Student's t-test and significance reported when p<0.05.

Results

Thermal Treatment.

The thermal debinding process of the printed green body needed to be optimized carefully in order to minimize the risk of macrostructural deformation caused by the release of the organic vapors. To determine the necessary thermal debinding steps of the 3D printed scaffolds successfully, the debinding and sintering procedure was derived from the dynamic automated thermogravimetric analysis presented in FIG. 47.

In the first stage (300-350° C.), surfactants and low molecular flow additives that support the printing process are decomposed. In the second stage (390-450° C.), higher molecular-weight polyolefins (thermoplastics and elastomers) are decomposed. The polymer binder is fully decomposed when heated up to 500-550° C. The thermal characteristics of Ag-BG particles are described above. It was observed that Ag-BG particles are stable with less than 3% weight loss for heating and sintering up to 1000° C. The total weight loss was slightly higher than 30 wt. % which is assigned mainly to the polymeric components in the Ag-BG filament and only ~2.5 wt. % assigned to the Ag-BG particles. The printed green body Ag-BG scaffolds were treated with the developed sintering profile presented in Table 8.

TABLE 8

Thermal debinding and sintering profile used to obtain Ag-BG scaffolds.

| Step | Temperature (° C.) | Rate (° C. min$^{-1}$) | Holding Time (min) |
|---|---|---|---|
| 1 | 200 | 5 | 0 |
| 2 | 390 | 2 | 30 |

TABLE 8-continued

Thermal debinding and sintering profile
used to obtain Ag-BG scaffolds.

| Step | Temperature (° C.) | Rate (° C. min⁻¹) | Holding Time (min) |
|---|---|---|---|
| 3 | 500 | 1 | 60 |
| 4 | 900 | 2 | 120 |
| 5 | 25° C. | 5 | 0 |

The removal of the fatty acid groups in the first stage created pores that served as channels for the vaporized thermoplastics and elastomers to escape from the scaffold structure at higher temperatures in the second stage. The use of a slower heating rate in the second step was utilized to retard the rate of vaporization to ensure no bloating or macrostructural deformation. After removal of the minor polymer binder fraction in step 1 and 2, a further heating step was applied with a slower heating rate (1° C. min⁻¹) up to 500° C. to ensure no bloating of the scaffold by the creation of gases and to ensure the complete removal of polymers before sintering. At 500-550° C., only the inorganic phase (i.e., Ag-BG particles) is left as a fragile scaffold, which needs to be sintered at higher temperatures for solidification. Ag-BG scaffolds were heated with 2° C. min⁻¹ from 500° C. up to 900° C. and held this temperature for 120 min before furnace cooling to ambient temperatures.

Macrostructural Characteristics.

The optical microscopy images (FIGS. 48A-48D) show a top-down view and a cross-sectional view of the Ag-BG scaffolds. In both cases, circular/oblong features colored light brown to black were observed across the surface in a random distribution. Examining the top-down view (FIGS. 48A and 48C), the cubic unit cell (defined by the pore geometry) was well-maintained during the heat treatment suggesting a successful heat treatment. When viewed from a cross-sectional perspective (FIGS. 48B and 48D), the pores showed signs of deformation primarily in the z-direction as evidenced by their rectangular geometry. The observed deformation was most severe along the z-axis, which was attributed to the vaporization of the organic components from the Ag-BG filament. Interestingly, some of the struts (FIG. 48B) were voided at their center demonstrating that the Ag-BG scaffolds are not fully dense. Micro-CT was utilized to investigate the internal macrostructure of the Ag-BG scaffolds along with elucidation of their porosity, pore size, and strut thickness.

The micro-CT images (FIGS. 49A-49H) expectedly revealed a highly interconnected porous macrostructure. The porosity of the Ag-BG scaffolds (as determined by micro-CT analysis) was 70.0±4.94(%) with an average pore size of 622±139 (μm). The porosity of the Ag-BG scaffolds were within the upper range of trabecular human bone (50-80%) and the large pore size (>300 μm) is expected to be well-suited for cell migration and spreading, thus demonstrating the macrostructural similarities between the Ag-BG scaffolds and the natural structure of bone. Interestingly, some of the interior structure of the struts show empty space (FIG. 49D). It is possible, that the removal of the organic components along with the shrinkage of the Ag-BG particles during sintering could be attributed to the empty space present within the struts.

The individual cross-sections (FIG. 49E) obtained from the micro-CT further demonstrate that voids are pervasive within the internal macrostructure. Furthermore, microcracks are also seen. When two layers are 3D reconstructed and viewed along the y-axis (FIG. 49G), the voids in some cases appear as a channel connecting the distinct layers that when viewed along the z-axis (FIG. 49H) present with open areas within the internal structure. As a result, the compressive strength of the Ag-BG scaffolds is expected to be affected by the presence of these empty areas.

Throughout the internal macrostructure, small circular bright spots of high x-ray attenuation were observed (FIG. 49E, white arrows). These spots are attributed as Ag particles, as their compact face-centered cubic (FCC) structure along with their high Z value makes for these regions of interest to be highly dense compared to other crystalline phases (noted in the XRD pattern, FIGS. 51A-51B), which comprise of the lower Z elements within the Ag-BG. This, along with the circular/oblong features observed in the optical images (FIGS. 48A-48D) supports that the Ag is primarily in particle form within the Ag-BG scaffolds.

Micro- and Nanostructural Characteristics.

The microscale surface morphology and elemental homogeneity were characterized utilizing SEM-EDS and are shown in FIG. 5. The macroscale SEM micrographs (FIGS. 50A-50B) present with rough surface morphologies that were further evidenced at higher magnifications (FIG. 50C). Microcracks were noted when examining the Ag-BG scaffold from a top-down perspective (FIG. 50A); however, this was not apparent when examining the Ag-BG scaffold from its cross-sectional perspective (FIG. 50B). When assessing for elemental homogeneity at the micro-scale (FIGS. 50A-50C), the relevant EDS X-ray mapping revealed that Si, Ca, P, Al, Ag, and Na were homogeneously distributed, while small clusters of more concentrated Ag were also noted (FIGS. 50A-50C), which agrees with the circular/oblong features observed in the optical images (FIGS. 48A-48D) and the small bright circular features noted in the micro-CT (FIG. 49E). To study the microstructure of the Ag-BG scaffolds and observe the developed crystalline phases and molecular structures, XRD patterns and FTIR-ATR spectra were collected.

The FTIR-ATR spectrum and XRD pattern of a powdered Ag-BG scaffold are shown in FIGS. 51A-51B. Multiple well-defined peaks were noted in the FTIR-ATR spectra indicating that the microstructure was highly crystalline. The sharp peaks present in the XRD pattern further support this. All peaks were attributed to crystal phases within the International Centre for Diffraction Data (ICDD) and it was found that five distinct phases were present: cristobalite (PDF No. 01-071-6246), hydroxyapatite (PDF No. 01-074-9776), elemental Ag (PDF No. 01-071-4613), wollastonite-2M (PDF No. 01-075-1396), and pseudowollastonite (PDF No. 01-074-0874).

As expected, Si—O bending peaks were observed at ~450 cm⁻¹ and ~800 cm⁻¹ and are characteristic of other silicate-based glass systems. Additional Si—O bending peaks were attributed at ~650 cm⁻¹ and ~690 cm⁻¹ and were correlated to the presence of wollastonite, however, it is important to note that FTIR cannot distinguish between the two wollastonite phases. Si—O stretching was assigned to the peak at ~900 cm⁻¹ and correlated to the presence of non-bridged oxygens NBOs. An additional Si—O stretching peak was identified at ~1200 cm⁻¹. The P—O bending peaks at ~550 cm⁻¹ and ~610 cm⁻¹ are a key identifier that hydroxyapatite exists within the Ag-BG scaffold microstructure. Additionally, P—O stretching at ~1030 cm⁻¹ and 1080 cm⁻¹ were attributed to hydroxyapatite.

To investigate the nanostructure of the 3D printed Ag-BG scaffolds, TEM was employed and respective micrographs presented in FIGS. 52A-52D. The phase-contrast image (FIG. 52A) was of an isolated Ag-BG scaffold particle ~2-3 μm in diameter. A clear boundary was observed between the interior and exterior of the particle, which indicates the possibility that the particle was multi-phasic. Indeed, when the particle was studied for its selected area diffraction (SAD) pattern (FIG. 52B), wollastonite-2M and hydroxyapatite were identified. The SAD pattern presented as a spot pattern was indicative that the phases were single crystals. The bright field image (FIG. 52C) showed little electron transmission, as evidenced by the black opaque appearance of the particle. Most of the electrons, therefore, are being diffracted, which is confirmed by the widespread illumination of the particle when imaged under dark field conditions (FIG. 52D).

Mechanical Performance, Bioactive Behavior, and Anti-MRSA Effect.

Compression testing was performed on the 3D printed Ag-BG scaffolds to determine their compressive strength (FIG. 53). The compressive strength of the Ag-BG scaffolds was 2.84±0.75 MPa, which is within the range of cancellous bone. The immediate rise in stress and failure at low strain confirm the brittle nature of the Ag-BG scaffolds typical of porous scaffolds fabricated from glass-ceramics.

Assessment of the bioactive behavior of the Ag-BG scaffolds was accomplished by immersion in SBF for 14 and 28 days (FIGS. 54A-F). The SEM micrograph after 14 d in SBF (FIGS. 54B and 54D) resulted in the mineralization of the surface with an apatite-like layer. EDS x-ray spot analysis determined the Ca/P ratio to be ~2.16. Si, Al, Ag, and Na were additionally detected in the EDS x-ray spot analysis indicating that the apatite-like layer that had formed was lower than <5 μm thick. This was further elucidated in the FTIR-ATR spectra and XRD patterns (FIGS. 54A and 54F), where cristobalite and wollastonite phases could still be identified. After 28 d of immersion in SBF (FIGS. 54C and 54E), the surface morphology consisted of well-formed needles consistent with mineralized hydroxyapatite with EDS x-ray spot analysis confirming a Ca/P ratio ~2.04; however, the XRD pattern (FIG. 54F) was still able to detect cristobalite and wollastonite suggesting the new layer that had formed is thinner than 5 μm, which is the expected interaction volume. The FTIR-ATR spectra (FIG. 54A) began to show peak broadening ~1070 $cm^{-1}$ with the peak observed after 14 d in SBF now appearing as a shoulder in the respective spectrum of 28 d in SBF. Additionally, the small peaks observed in the range 900-1000 $cm^{-1}$ after 14 d in SBF can no longer be identified after 28 d in SBF supporting evidence that the deposited apatite-like layer has increased in thickness. Given that the crystalline phases from the substrate structure are still identifiable in the XRD pattern after 28 d of immersion in SBF, the bioactive response of the Ag-BG scaffolds is considered slow due to their high degree of crystallinity diminishing their rate of degradation.

MRSA was selected to study the antibacterial properties of Ag-BG scaffolds as it is the most common cause of bone infections [34, 35]. A significant reduction in CFU was observed compared to untreated MRSA after both 24 h and 48 h of exposure to Ag-BG scaffolds, (FIG. 55). Increasing the time of the exposure resulted in a further enhanced anti-MRA activity as the 48 h of exposure resulted in a significant CFU reduction compared to 24 h. This result demonstrates that the antibacterial activity of the Ag-BG scaffolds is a time-dependent process that is correlated to the degradation profile of the scaffolds (FIG. 55). It is anticipated that a combination of factors is contributing to the anti-MRSA effect as described in Example 1.

The adequate compressive strength, bioactive behavior, and the anti-MRSA activity demonstrate the viability of the 3D printed Ag-BG scaffolds as an effective treatment for orthopedic applications.

Discussion

This example focused on utilizing the fused filament fabrication (FFF) technique to print 3D mechanically competent Ag-BG scaffolds that exhibit bioactive behavior and unique antibacterial properties. Additive manufacturing of porous silicate scaffolds is an attractive processing avenue due to its vast customization capabilities and mechanical superiority over scaffolds fabricated with more traditional techniques (i.e., polymer replication, freeze-casting, foaming). Producing printable filaments from brittle materials with high particle loading remains a challenge due to filament embrittlement and unsuitably high melting temperatures. Using a novel binder system consisting of polyolefin and thermoplastic elastomer allowed for Ag-BG particles to be loaded without compromising the printability of the filament. The Ag-BG filament was characterized to study its thermal behavior to design a heat treatment capable of removing the organic components while minimizing structural deformation. The multiscale structure of the Ag-BG scaffolds was additionally investigated to correlate processing effects to the performance of the Ag-BG scaffolds.

The optical microscopy images (FIG. 47) revealed a multicolored surface that consisted primarily of a colorless matrix that contained light brown to black circular/oblong features. Example 4 showed that Ag-BG scaffolds fabricated through a sol-gel derived polymer replication technique expressed similar surface features that were determined to be Ag nanoparticles (AgNPs). Indeed, the micro-scale elemental heterogeneity of Ag (FIGS. 50A-50C) and the Ag peaks in the XRD pattern (FIGS. 51A-51B) provide further confirmation that these surface features are AgNPs. The formation of the AgNPs is probably the result of the high sintering temperatures (900° C.) that were required to deliver 3D Ag-BG glass-ceramic scaffolds with a robust structure without polymeric residuals. This is reasonable to deduce as the Ag-BG powder that was used to produce the Ag-BG filament was colorless; an indication that Ag maintained in ionic form in the structure. This correlation was demonstrated where Al nuclear magnetic resonance (NMR) was applied to show the increase in Al coordination from four-fold to five-fold when Ag was present, confirming the stabilization of $Ag^+$ ions by Al tetrahedra.

The XRD pattern (FIG. 51B) revealed a highly crystalline microstructure that was further shown to be multi-phasic based on diffraction peak matching with standard PDF cards. The crystalline phases of cristobalite, hydroxyapatite, wollastonite-2M, pseudowollastonite, and Ag were identified. The FTIR-ATR spectrum (FIG. 51A) and TEM images (FIGS. 52A-52D) corroborate this. The presence of cristobalite was interesting considering it typically does not form until temperatures >1400° C. are achieved. Favorable conditions for the precipitation and stabilization of cristobalite at the sintering temperature (900° C.) used in this study were induced by the presence and concentration of Ag and the concentration of Al. It is worth noting that hydroxyapatite and the wollastonite phases are the predominant constituents of the microstructure; however, both are well-known to exhibit bioactive behavior. This was reinforced by the observed new apatite-like phase that is deposited after immersion in SBF as revealed by the SEM images (FIGS. 54A-54F) after both 14 and 28 d. Additionally, the XRD patterns and FTIR-ATR spectra began to demonstrate structural changes after 14 d that were more evident after 28 d of immersion.

The micro-CT images (FIGS. 49A-49H) showed thick struts, including the internal partially empty space assigned to the removal of the organic components that comprised the filament along with the isotropic shrinkage of the Ag-BG particles during sintering. The resulting voids that formed during this process (FIG. 49E) appeared to begin a coalescing process as the atoms continued to diffuse and densify during the sintering process. Efforts to increase the Ag-BG particle loading within the filament should decrease the overall shrinkage and minimize the number of internal voids present leading to denser Ag-BG scaffolds with significantly higher compressive strength. Despite this, however, the compressive strength of the Ag-BG scaffolds within the range of cancellous bone, making the Ag-BG scaffolds viable candidates for load-bearing applications.

The status of Ag has a significant role in the mechanisms of action it will exert on bacteria. $Ag^+$ ions present with potent antibacterial properties resulting from their ability to interfere with a multitude of cellular processes. $Ag^+$ ions have an affinity to complex with electron donor groups such as thiols or phosphates, which disrupts protein synthesis and can cause DNA damage. Furthermore, previous work with the Ag-BG system investigating the mechanisms of action is consistent with this. Since the primary form of Ag in the 3D printed Ag-BG scaffolds is in nanoparticle form, the mechanisms of action for bacterial inhibition are modified. The AgNPs attach to the surface of the bacteria disrupting its function, which can lead to perforation and allow penetration of the AgNPs where the release of $Ag^+$ ions can interact as previously described. The size of the AgNPs has a direct effect on their ability to inhibit bacteria, decreasing size elicits a more potent reduction in bacterial viability resulting from higher surface area to volume ratios. Interestingly, AgNPs <10 nm in diameter demonstrated the strongest reduction of MRSA viability. Notably, AgNPs in the released concentrations do not affect eukaryotic cell function. Thus, the anti-MRSA response exhibited by the Ag-BG scaffolds is likely a result of the previously studied mechanisms of action. Moreover, the anticipated non-cytotoxic effects on eukaryotic cells demonstrate the potential application of Ag-BG scaffolds to repair bone defects while eliminating subsequent MRSA infections.

In summary, this example highlights the structural characteristics and also investigates the mechanical, bioactive, and antibacterial properties of the Ag-BG scaffolds. The optimization of the thermal debinding and sintering led the Ag-BG scaffolds to present with minimal deformation underscoring the reproducibility of scaffolds produced by the FFF technique. Furthermore, the compressive strength of the Ag-BG scaffolds was within the range of cancellous bone allowing for their use in load-bearing applications. The processing did not eliminate the bioactive or antibacterial behavior of the Ag-BG scaffolds demonstrating the efficacy of using the FFF technique for fabricating silicate-based scaffolds for tissue regenerative applications.

Conclusion

The FFF technique was utilized for the fabrication of silicate Ag-doped bioactive glass-ceramic scaffolds with suitable mechanical properties. Additionally, they exhibited bioactive behavior and anti-MRSA capabilities for potential tissue engineering applications in load-bearing areas. The thermal debinding and sintering processes were tailored to minimize the structural deformation of the Ag-BG scaffolds. The sintering temperature used in this study resulted in a highly crystalline microstructure that modified the status of Ag from existing primarily in ionic form to particle form. The FFF technique is effective in preserving bioactive and antibacterial properties of the Ag-BG composition, underscoring its use as a processing technique that can be extended to the fabrication of other silicate-based scaffolds.

Example 7

This example describes sol-gel derived bioactive and antibacterial multi-component thin films prepared by a spin coating technique.

Although metallic alloys commonly used as prosthetics are durable and mechanically strong, they are often bioinert and lack antibacterial properties. Implementing bioactive glass material with antibacterial properties as a coating on a metallic substrate provides mechanical strength, bioactivity, as well as antibacterial properties. Many coating methods have been extensively investigated, however, most of them can be expensive, difficult to scale up, or do not form thin films, which could prevent the translation to the clinical practice. The formation of thin films by spin coating multi-component solution gelation (sol-gel)-derived glass with antibacterial and bioactive properties has not been achieved previously. Here, stainless steel 316L substrates were spin-coated with a sol-gel derived bioactive and antibacterial glass coating in $SiO_2$ 60.7-$P_2O_5$ 6.9-CaO 34.9-$Al_2O_3$ 4.1-$Ag_2O$ 2.0-$Na_2O$ 1.4 wt. % system (Ag-BG). A sol-gel processing condition that avoids elemental separation upon spin coating when sintering happens at lower than the calcination temperature (500° C.) has been developed. This example demonstrates that silver reduction occurs when the concentration of other cations such as $Ca^{2+}$ and $Na^+$ in the solution increases. Increasing the stirring duration time prior to the increase of cations, $Ag^+$ ions are stabilized by aluminum tetrahedra, and their reduction to metallic silver does not occur. This study also shows that large dilution ratios (Water:TEOS) greater than 25:1 accompanied by long stirring durations produce morphologically homogenous coatings. Using this str.-resistant *Staphylococcus aureus* (MRSA) biofilm and biological responses that promote eukaryotic cell adhesion and proliferation. In total, the improved synthesis strategy provides for the development of novel bioactive and antibacterial thin film coatings as it reveals the processing characteristics that control the physicochemical and morphological properties of the formed films.

Introduction

Currently, there are many biomedical approaches focusing on bone tissue replacement, such as the use of autograft, allograft, and inorganic prosthetic implants made of ceramics and/or metal alloys such as stainless steel, cobalt, titanium alloys, etc. Although bone grafts serve as the best candidate for replacement and regeneration of bone, they are not always readily available and are difficult to shape. On the contrary, under certain needs, metal prosthetics are much more abundant, cheap, and mechanically strong. However, they are bioinert (cannot bond to living body tissue) and lack antibacterial properties. After implantation, these materials often become encapsulated by a fibrous membrane and can lead to the loosening of the prosthetic. There is a need for increasing the longevity of prosthetic implants to avoid subsequent surgeries that replace these devices when they become infected or loose from their proper location.

Bioactive glasses have been under recent investigation as implant materials because of their osteogenic properties and their ability to form a strong bond with bone tissue through the formation of a hydroxyapatite layer (HA). Bioactive glasses are amorphous materials composed of a network former, e.g., $SiO_2$, and network modifiers, e.g., CaO and $Na_2O$, in concentrations that allow the material to be bioactive and have osteogenic properties. Their amorphous structure and composition result in degradation in the body, releasing elements that can trigger cell proliferation and differentiation. There are many compositions in the $Na_2O$-CaO-$SiO_2$-$P_2O_5$ system that are considered bioactive. The main methods to fabricate these glasses include a melt-derived process and a chemical alternative in which network forming precursors such as tetraethyl orthosilicate (TEOS) undergo hydrolysis and condensation reactions to create the silicon dioxide network. The advantages of the sol-gel method over the melt derived method include lower processing temperatures, higher porosity in the fabricated bioactive glass, a larger range of silicon dioxide concentration while maintaining bioactivity, and a large range of glass compositions with bioactive properties.

These materials show great potential within the biomedical field as prosthetic implants. However, their use as 3D scaffolds has limitations as these materials are brittle. Studies have investigated the ability to combine the mechanical strength of common metal alloy prosthetics with the bioactivity and antibacterial effects of bioactive glasses through coating techniques, to advance prosthesis performance. Many different coating methods have already been investigated, including plasma spray coating, dip coating, enameling, and many others. However, most of these techniques are expensive, with limited control film thickness, and difficult to scale up.

Spin coating, however, is a low-cost process that is able to produce thin films with consistent properties and exhibits potential for process scale-up. The spin coating technique has already been applied to develop coatings utilizing simple (single-component) systems or suspensions of glass microparticles. However, multicomponent, bioactive coatings have not yet been synthesized via spin coating of complex sol-gel based solution. Although introducing antibacterial properties into bioactive materials is relatively new, such coatings have been made. However, the development of thin-film coatings (few micrometers in thickness) being fabricated by the spin-coating technique, showing antibacterial properties against MRSA biofilm, while maintaining eukaryotic cell growth promotion, has not been achieved. Electrophoretic deposition and dip coating techniques have been the fabrication methods for the formation of coatings on metal substrates in the $SiO_2$-CaO-$P_2O_5$-$Ag_2O$ system with limited success on the development of thin films. In this example, sustainable, homogeneous bioactive and antibacterial, multi-component glass coatings are fabricated on metal substrates via a spin coating technique. It has been previously established that the composition of the solution-gelation (sol-gel) derived glass used in this study shows rapid bioactivity and antibacterial effect Utilizing a spin-coating technique will maintain the bioactive properties of sol-gel derived glass resulting in coated surfaces that inhibit bacterial growth but promote regeneration of mammalian tissues.

This example provides an understanding of effects of processing parameters on morphology, chemical homogeneity, and sustainability of bioactive and antibacterial glass thin films generated through a spin coating technique. It was found that long stirring durations in the solution phase of the sol-gel glass throughout the synthesis process is important for complete homogenization of all elements and the prevention of silver ion reduction to metallic silver. Increasing the duration of stirring ensures incorporation of Ag within the structure in ionic form. Because of this, no burst release of Ag nor cytotoxicity is observed, but on the contrary, long-lasting and controlled antibacterial properties occur. The long stir durations coupled with increased water:TEOS ratio also generated the smoothest and most homogenous surface morphology. These long stir durations avoid the reduction of ionic silver to metallic silver by promoting the formation and stabilization of aluminum tetrahedral ions ($AlO_4$) in solution. The coatings were also shown to be bioactive through the deposition of a calcium phosphate layer when immersed in simulated body fluid (SBF) and the in vitro cell-material interaction. Antibacterial testing on the respective powder samples also displayed bacterial inhibition, with the system that retains Ag in ionic form to present greater antibacterial potential. The viability of both planktonic and biofilm MRSA cells was also studied. Thin films inhibit bacteria growth in biofilm and planktonic. Understanding the processing parameters for developing sol-gel derived thin film coatings by the spin coating technique significantly advances currently available methods that create bioactive and antibacterial prosthetics for biomedical applications.

EXPERIMENTAL

Pre-Treatment of Samples.

The substrates used for this study were 21 mm diameter 316L stainless steel substrates obtained from Swagelok with a composition of 62.18% Fe, 18% Cr, 14% Ni, 3% Mo, 2% Mn, 0.75% Si, 0.04% C, and 0.03% S by weight. Prior to coating, samples were polished to 1200 grit SiC and ultrasonically cleaned in acetone for 20 minutes. Next, each sample was immersed in 0.1M hydrochloric acid for 3 minutes followed by 3 washes in distilled water, rinsing with ethanol, and air drying. The hydrochloric acid serves to remove the passivating oxide layer on the surface of the steel allowing for better adhesion of the coating to the substrate.

Preparation of Solution.

All chemicals were purchased from Sigma-Aldrich™. The bioactive glass was fabricated using an acid-catalyzed sol-gel procedure using distilled water, 2N nitric acid, tetraethyl orthosilicate (TEOS), triethyl phosphate (TEP), aluminum nitrate nonahydrate, silver nitrate, calcium nitrate tetrahydrate, and sodium nitrate in a total molar ratio of 7.30:0.04:1.00:0.10:0.08:0.02:0.50:0.05 respectively for a total water:TEOS ratio (R ratio) of 10:1. However, the fabrication protocol used begins with two separate systems (Sys I and Sys II) that are combined at different time increments depending on which protocol is applied. Also, the molar ratios change slightly for varying R ratios, 10:1 and 25:1. The final composition for each system is shown below in Table 9. The fabrication processes investigated include four different procedures: protocol A, protocol B, protocol C, and protocol D. Each protocol involves mixing the reagents of each separate system on a stirring plate with a stir speed of 400 RPMs with 20-30 minutes between the additions of a new reagent, allowing for the system to stabilize. After the completion of each system, protocol A involves combining Sys II into Sys I, allowing it to stir for one hour, followed by spin coating of the samples. Protocol B combines the two systems just as in protocol A, but allows the combined system to stir for approximately 17 hours before coating samples. Protocol C allows the systems to stir separately for 17 hours followed by the combination of the two systems and an hour of stirring before coating samples. Finally, protocol D follows the same procedure as protocol C but allows for an additional 53 hours of stirring before spinning. The steps for each of these protocols are outlined in FIG. 56.

TABLE 9

Composition of each system in wt. %.

|  | $SiO_2$ | $P_2O_5$ | CaO | $Al_2O_3$ | $Ag_2O$ | $Na_2O$ |
|---|---|---|---|---|---|---|
| Sys I wt. % | 58.7 | 2.9 | 8.7 | 18.0 | 6.8 | 4.9 |
| Sys II wt. % | 58.1 | 8.9 | 33.0 | — | — | — |
| Final Sys wt. % | 58.3 | 7.1 | 25.6 | 5.4 | 2.1 | 1.5 |

Coated Samples.

Samples were placed on the spin coater (Chemat Technology Spin Coater KW-4A) followed by the dropwise application of 0.4 mL of the solution. The sample was spun at 5000 RPMs for 300 seconds with the subsequent removal for heat treatment. FIG. 57 describes this procedure. Spin coating parameters including the volume of solution, spin speed, and spin duration were all downselected from preliminary studies and aimed to create coatings with no cracking. In particular, high spin speed and large spin duration allow for the creation of thin films and was shown to reduce cracking.

Heat Treatment.

Post spinning, the coated substrates were immediately subjected to the heat treatment schedule shown in FIG. 58, resulting in the formation of a glass coating. The process involves first heating to 130° C. at a rate of 5° C./min followed by a 12 hour dwell time. Next, samples were heated to 500° C. at a rate of 1° C./min and held for 4 hours upon which it subsequently cools down to 25° C. at a rate of 5° C./min.

Surface Morphology.

Surface morphology and spatial distribution of elements were studied using a scanning electron microscope (SEM) equipped with energy dispersive spectroscopy (EDS). All imaging and elemental analysis were performed at 20 KV accelerating voltage with a working distance of 8.5 mm. Prior to imaging, samples were sputter-coated with platinum using a Denton sputter coater with an argon plasma for 90 seconds.

Roughness.

The surface roughness of the samples was determined using a Keyence VHX 6000 3-Dimensional optical microscope with magnification ranging from 1000-5000×. Roughness is quantified using two separate parameters, $Z_\alpha$ and $Z_\beta$, which describe the average difference between the highest points and the lowest points as well as describing the highest point in the field of view, respectively.

Microhardness Testing.

Hardness testing was performed using a Clark CM-800 AT microhardness tester using a pyramid diamond indenter with a load of 0.1 N for 25 sec. The indentation marks were measured and averaged to be used in Equation 1 to evaluate the Vickers' hardness of the samples. Ten different areas were measured for each sample type in triplicates to obtain a mean average and standard deviation of the hardness value using Eq. 8:

$$HV = 1.8544 \frac{f}{d^2}. \quad \text{(Eq. 8)}$$

Adhesion Testing.

Tape testing was performed to determine the adhesion of the glass coating to the substrate using Scotch Filament 898 tape with an adhesion strength of 70 oz/in following the testing procedures outlined in ASTM D3359-09 standard testing procedure. The coatings on the samples were cut using a razor blade in a pattern of 11 straight cuts 1 mm apart, with 11 subsequent straight cuts 1 mm apart perpendicular to the previous cuts. The tape was then pressed onto the sample ensuring adhesion to the coating. The tape was removed at a 180° angle to the sample at a consistent speed. The samples were observed both visually for any material removed as well as using a Keyence VHX S15F digital microscope. Following optical imaging, the sample was imaged using SEM/EDS analysis to examine the removal of the coating from the substrate.

Bioactivity.

Samples were soaked in Kokubo's simulated body fluid (SBF) as previously described with a volume to mass ratio of 1 mL/mg. Half of the solution was refreshed, every 2 days to mimic the dynamic environment of the body. Samples were characterized after 1, 2, and 3 weeks. Potential for bioactivity was studied using a Jasco FT/IR—4600 Fourier-transform infrared spectrometer with a transmittance ATR mode with wavenumber range from 400 to 4000 cm$^{-1}$ to encapsulate all possible bond movements. SEM and EDS analysis were also used to study bioactivity of the coatings in determining surface morphology of the deposition as well as elemental composition.

Antibacterial Testing Against Planktonic and Biofilm Bacteria.

Antibacterial testing is described in Example 1 Briefly, bulk powder glass samples were sterilized under UV light for 1 hour and soaked in SBF for 1 hour to remove any residual nitrates that could potentially cause increased growth by nitrate feeding bacteria. The antibacterial experiments were performed against laboratory-derived methicillin-resistant *S. aureus* (MRSA) USA300 JE2. Tryptic soy agar (TSA) was used to streak cells and TSA was used as the growth medium to culture bacterial cells overnight at 37° C. at 225 RPMs. Following the growth period, 1 mL of MRSA was normalized to an optical density (0D600 nm) of 1 in phosphate-buffered saline solution (PBS). The bacterial suspension was combined with a bulk glass powder solution (6.25 mg/mL) in PBS at a 1:1 volume ratio to result in a final bioactive glass concentration of 3.125 mg/mL. A control sample was generated containing PBS and bacterial suspension with the same volume as the samples. The samples were incubated at 37° C. for 24 hours. An aliquot of the samples was removed to enumerate colony forming units (CFU) of the MRSA using serial dilutions and plating on TSA. The plates were incubated at 37° C. with a limit of detection (LOD) of 100 CFU/mL. Experiments were performed in triplicate and statistical analysis was performed using the Student's t-test with 95% confidence.

Fabricated glass coatings were also tested against JE2 biofilm formation. After spin coating, samples were pretreated by soaking in SBF for hour which has shown to remove any residual nitrates that could potentially cause increased bacterial growth by nitrate feeding bacteria. The samples were then sterilized in UV light for 1 hour and transferred to 6-well plates with untreated, non-coated stainless steel samples as controls. The samples were inoculated with 20,000 cells per sample in TSB at a volume to a mass of coating ratio of 4 mL/mg, After incubating for 7 days at 37° C., the samples were washed with 0.85% NaCl wash buffer three times and stained using the LIVE/DEAD™

BacLight™ Bacterial Viability Kit, The samples were then fixed by immersing at room temperature for 2 hours in 2.5% glutaraldehyde, 2.5% paraformaldehyde and 0.1 M cacodylate buffer dissolved in deionized water. After washing with 0.85% NaCl solution, the samples were immediately observed under a Nikon C2 Confocal Laser Scanning Microscope, configured with a Nikon Eclipse NI-U upright microscope using 40× Plan Fluor dry (NA 0.75) and 60× Plan Apo oil (NA 1.40) objectives. Carboxyfluorescence diacetate was excited using 488 nm diode laser, with green fluorescence emission detected using a 500-550 nm bandpass filter. Propidium iodide was excited using a 560 nm diode laser, with red fluorescence emission measured using a 575-625 nm bandpass filter. The percentage of live and dead bacteria in the biofilm formed was quantified by Image J analysis.

Cell Viability and Proliferation In Vitro.

Cell viability and proliferation were measured using human fetal osteoblastic cells (hFOB 1.19) in a manner similar to the biofilm testing. After spin-coating and heat treatment, samples were UV sterilized and transferred to 12-well plates with untreated, non-coated stainless steel discs as control samples. Samples were again soaked in SBF for 1 hour to remove any residual nitrates. Each sample was seeded with 15,000 cells by adding 0.5 mL dropwise of a cell suspension containing 30,000 cells/mL in Dulbecco's modified eagle medium (DMEM) with 10% fetal bovine serum (FBS) and 1% geneticin. This was done to ensure the volume of the suspension did not spill over the sample, allowing for maximum cell adhesion to the sample, and not the tissue culture plate (TCP). The samples were allowed to incubate in a $CO_2$ incubator at 37° C. for 4 hours to allow the cells to adhere to the sample. Following cell adhesion, the samples were carefully given 3.5 mL of media as to not disturb the adhered cells. This was the start of the experiment and began day 0. The samples were incubated at 37° C. for 24 hours. To prevent the assay from reporting a reading from cells adhered to the TCP as opposed to the sample surface, each sample was transferred to new well plates so only the cells adhered to the samples will be measured. The samples were again incubated at 37° C. for various time points including 2, 4, and 6 days. The media was also refreshed at each time point (2, 4, and 6 days) with the same ratio of 4 mL/mg. Cell viability was measured using Dojindo's Cell Counting Kit-8 (CCK-8) at each time point. Before refreshing, 3 mL of media was aspirated off and 100 μL of CCK-8 reagent was added to each sample and well mixed. The samples were incubated in the dark at 37° C. for 2 hours. Following incubation, 100 μL of the media from each sample was transferred to a 96-well plate and the absorbance read at 450 nm. Statistical analysis was performed using the Student's t-test with 95% confidence. Experiments were performed in triplicate.

Results and Discussion

Optimizing Processing: Addressing Silver Reduction, Chemical, and Morphological Heterogeneities.

It has been shown repeatedly that spin coating can be utilized to form crack free spatially homogeneous single-system (e.g., $SiO_2$) glass coatings which exhibit corrosion resistance and bioactivity. However, complications begin to arise when this system is expanded to include additional network modifying ions including calcium and sodium (multi-system glasses). Despite the challenges, fabricating spin coatings of advanced bioactive glasses on metal substrates could be of a significant impact on biomedical applications.

Samples were spin-coated with the solution stage of the 58S glass (58 $SiO_2$, 33 CaO, 9 $P_2O_5$ wt. %) using water: TEOS molar ratio (R ratio) of 10:1. This glass has been well established to be bioactive. The solution was prepared using the protocol A as presented in FIG. 56, followed by the coating process and the heat treatment as shown in FIGS. 57 and 58, respectively. The samples were then observed under SEM and EDS to understand the surface morphology and elemental distribution. As shown in FIG. 59, the silicon and calcium appear to be heterogeneously distributed and possibly separated into two different phases due to the centrifugal forces generated on the surface during spin coating, in addition to the sintering at temperatures lower than the calcination temperature.

The same trend is observed in the more complicated Ag-BG system (Final Sys) with R ratio of 10:1 as outlined in Table 9. The EDS data in FIG. 60 reveals that the calcium and silicon exhibit a similar separation into two distinct phases as was previously observed in the ternary system (58S) FIG. 59. The aluminum also shows separation in the same nature as that of calcium, while oxygen separates as silicon. These data suggest that the system in the solution phase was not completely homogenized upon spin coating. Thus, separation of the phases with different compositions and viscosities occurs due to the forces generated in the spinning process. The resultant chemical and morphological heterogeneity could negatively affect expected biological and antibacterial properties as well as degradation upon implantation, potentially limiting the bonding capability with the surrounding tissue. This elemental and morphological heterogeneity in the solution stage is attributed to the low stirring duration time of the final solution (Final Sys. FIG. 56). Thus, a mixture of two phases with different compositions and potentially different viscosity coexist in the final solution. Because of that silicon-rich areas appear thicker with higher mass and calcium-rich areas appear thinner with lower mass.

The precursors used for Al and Ca ion incorporation into the glass network are both hydrated, having a greater affinity for water, creating a phase separation in the solution, with the aluminum and calcium being attracted to the aqueous phase and becoming separated from the silicon species. A diagram of the proposed mechanism at the molecular level is shown in FIGS. 61A-61C, where the Final Sys consists of two separated phases, one rich to Ca and Al, and the other rich to Si.

Phase separation remains a big challenge in sol-gel science. It concerns multi-component solutions that have been under low stir durations and their final solid materials show elemental heterogeneity regardless of their form (e.g. powders, scaffolds, or coatings). This is attributed to the phase separation at the solution stage, which subsequently results in elementally heterogeneous solid materials. Much research has been done on the behavior and incorporation of calcium within silicate glass networks, however, most of the work has dealt with temperature changes during the heat treatment. It is well known that calcium does not modify the silica network until reaching high temperatures, reportedly above 400° C. Additionally, calcium ions remain within the pore liquid of the glass system and they are not incorporated into the network until reaching high temperatures. Moreover, if the calcium ions are not well distributed within the system prior to applying the heat treatment, their diffusion during the heat treatment will result in a heterogeneous network. This is evidenced in FIGS. 59 and 60, where the elemental heterogeneity after the heat treatment is attributed to phase separation at the solution stage, which is correlated to low stir durations.

Many studies have investigated the issue of phase separation with calcium in bulk material, offering solutions such as alternative calcium precursors including calcium methoxyethoxide. However, this precursor requires a complicated fabrication procedure due to the precursor's instability and reactivity. Also, many studies using calcium nitrate as the precursor with low stir durations have claimed to have complete incorporation of calcium, however, most do not have the supporting EDS data to confirm this. The data show that using low stir durations does not result in homogeneity and fully incorporated calcium compositions even with adequate heat treatment.

As is presented below, this challenge of heterogeneity is addressed by using for the first time calcium nitrate as the calcium precursor in the present work. Understanding how the sol-gel processing parameters affect calcium incorporation is key to developing bioactive glasses with consistent properties. This work will provide a platform for future studies that ensures consistent and accurate calcium composition and bioactivity.

Addressing Chemical Heterogeneity.

To address this problem of heterogeneity, Protocol B was developed with a much longer stir duration (17 hours) for the final system prior to the coating process, aiming to allow for complete homogenization of the elements in solution. The longer stir duration leads to further condensation of the network and greater removal of the aqueous phase, allowing for the increased incorporation of the aluminum and calcium ions. Protocol B was then applied for solution synthesis. Coated samples with the same R ratio of 10:1, were formed applying the same heat treatment. SEM-EDS data of these samples are presented in FIG. 62. A spatially homogeneous distribution of all elements was observed (FIG. 62 EDS mapping images top left), despite the rough morphology and morphological heterogeneity. However, the consistent elemental homogeneity of the glass leads to the conclusion that longer stirring durations are required to completely homogenize hydrated precursors, such as calcium nitrate tetrahydrate, within the glass system and allow homogeneous network modification of the ions, not previously shown. The cross-section of this sample shown in FIG. 62 reveals two distinct coating regions with average thicknesses of 1.5 μm and 0.3 μm respectively. From the cross-section, it can also be seen that the coating appears to well adhere to the surface of the substrate. Although these 2-dimensional roughness plots reveal a much larger difference in depth of up to 6 μm, the average measured over several areas was found to be 1.5 μm for the thicker areas and 0.3 μm for the thinner areas. The data also revealed an average $Z_\alpha$ value of 1.5 μm. From this data and the data presented above, it can be concluded that the elements introduced into the system require longer stirring times to homogenize completely before spin coating to avoid elemental separation. FIG. 62 displays the indents made in both the thicker and thinner areas of the coatings with average hardness values of 403±161 kgf/mm² and 263±69 kgf/mm² respectively. Although these values appear to be within the range for hardness values typical of this material according to the ASTM Standard C730 for the hardness of glass, the vast difference in hardness when comparing the thicker and thinner areas generates a large degree of variability that is not beneficial for load-bearing applications. Looking at the standard deviations for the hardness values, these values are also quite high leading to poor homogeneity in hardness value throughout the coating. The indentation in the thicker areas as shown in FIG. 62 (insert SEM images top right) also has multiple cracks propagating from the indent indicating a system that has poor ductility and increased risk of fracture and spallation upon the application of load.

Moreover, it should be noticed that although the elements were dispersed evenly throughout the coating, the solution of the final system exhibited a distinct, dark grey discoloration before the coating as shown in FIG. 62 (optical image top left), indicative of silver particle formation due to the photosensitive reaction of silver ions with light. Silver ions suspended in solution are photosensitive and will be reduced to metallic silver particles in the presence of light. However, this reaction can still take place in the absence of light, only much slower, but still requires a reducing agent. Possible reducing agents in this system include both water and ethanol produced as a byproduct of the hydrolysis reaction with TEOS. Adding the two half-reactions in the redox couple as shown below leads to a reduction potential of +0.997 V with standard reduction potentials measured at 25° C. and 1 atm pressure using a standard hydrogen electrode.

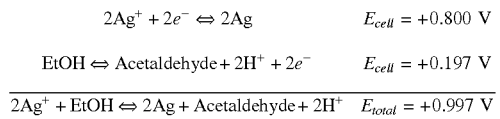

The reduction potential describes the affinity of the compounds to accept or lose electrons in a redox reaction. Adding the two half-reactions as shown previously results in total reduction potential. A positive total reduction potential indicates a spontaneous reaction. This total reduction potential can then be used in a Gibbs free energy derivation of the Nernst equation shown in Eq. 9:

$$\Delta G = -nFE_{cell}^0 \tag{Eq. 9}$$

Utilizing Eq. 9 with the reduction potential of +0.997 V from the silver reduction reaction leads to a Gibbs free energy of −96.2 kJ/mol Ag⁺. The negative Gibbs free energy indicates a spontaneous reaction that has a total change of −96.2 kJ/mol of Ag⁺ reacted. This reduction reaction of silver ions to metallic silver is possible in the solution phase of fabrication due to the large abundance of ethanol produced during the hydrolysis reaction, however, the reaction rate is quite slow in the absence of light as a catalyst. This presence of metallic silver from this redox reaction is the cause of the grey discoloration that metallic silver creates and is apparent in Protocol B in FIG. 62.

It is also known that metallic silver particles exhibit lower antibacterial ability in comparison to silver ions, thus diminishing its potential as an antibacterial glass coating. However, it has been recently shown that the addition of aluminum nitrate in the solution creates ionic aluminum tetrahedral ($AlO_4$) compounds that are able to stabilize the positively charged silver ions ($Ag^+$) in solution, preventing them from reducing to metallic silver. Although this mechanism may be present in this system, it is hypothesized that the much smaller network modifier ions in the system, such as $Ca^{2+}$ or $Na^+$, preferentially bond to the aluminum tetrahedral complexes with time due to their larger abundance, smaller size, and greater electrostatic force. The stabilization of an anion and cation together produces an ionic bond that releases energy in the form of enthalpy, termed the lattice energy. The lattice energy ($\Delta H_L$) is a function of the crystal structure of the ionic bond, the charge of the ions, as well as the radius of the ions in question. The lattice energy of known ionic bonds can be calculated using the Borne-Landé equation is shown in Eq. 10 when the crystal structure is well known:

$$\Delta H_L = -\frac{N_A M z^+ z^- e^2}{4\pi\varepsilon_0 r_0}\left(1 - \frac{1}{B_n}\right). \quad \text{(Eq. 10)}$$

However, for ionic bonding of molecules that do not have well-known crystal structures, Madelung constants (M), or Born exponents ($B_n$) from Eq. 10, the lattice energy can be well estimated using the Kapustinskii equation shown in Eq. 11:

$$\Delta H_L = -K \frac{v z^+ z^-}{r_{sum}}\left(1 - \frac{D}{r_{sum}}\right). \quad \text{(Eq. 11)}$$

The Kapustinskii equation in Eq. 11 can be used with any ionic species that can be stabilized with the $AlO_4^-$ complex such as $Ag^+$, $Ca^{2+}$, or $Na^+$. Using estimated radii of 1.79 Å for the $AlO_4^-$ complex, 1.29 Å for the silver ion, 1.14 Å for the calcium ion and 1.16 Å for the sodium ion, the lattice energy was calculated for each species in generating an ionic bond between the aluminum tetrahedral and the cation species. The lattice energies were found to be −690 kJ/mol, −2170 kJ/mol, and −720 kJ/mol for $Ag(AlO_4)$, $Ca(AlO_4)_2$, and $Na(AlO_4)$ species respectively. This result indicates that each reaction releases energy in the form of enthalpy in increasing order of silver, sodium, and calcium. However, in determining spontaneity, the Gibbs free energy must be determined for each reaction using Eqs. 12-16 below.

$$\Delta G = \Delta H - T\Delta S \quad \text{(Eq. 12)}$$

$$\Delta S = \Sigma S_{products} - S_{reactants} \quad \text{(Eq. 13)}$$

(Eq. 14)

(Eq. 15)

(Eq. 16)

The Gibbs free energy of each ionic bond formed was determined using Eq. 12 in combination with Eq. 13 for each reaction run at approximately 20° C. The Gibbs free energy was calculated to be approximately −689 kJ/mol, −2140 kJ/mol, and −701 kJ/mol for $Ag(AlO_4)$, $Ca(AlO_4)_2$, and $Na(AlO_4)$ respectively. These values are very close to their lattice energies because the reactions have a largely negative enthalpy and are run at low temperatures. These results indicate that each ionic stabilization is spontaneous, however, their reaction rates are not dependent on the magnitude of the Gibbs free energy. Although the $Ca(AlO_4)_2$ species has a larger Gibbs free energy magnitude, this does not mean that it will be a faster reaction. However, because of the spontaneity of each reaction, the silver ions are in competition with the calcium and sodium ions to be stabilized by the negatively charged aluminum tetrahedral being formed. Although the exact reaction rates cannot be determined, it is hypothesized that the stabilization with the calcium and sodium ions is more favorable due to their smaller size and/or their larger electrostatic force. This increased competition between all ionic species makes the silver ions much more susceptible to the reduction reaction as previously outlined. This effect is especially significant after the combination of the two systems due to the much higher calcium ion concentration in Sys. II.

The addition of more ionic species into the final system after the combination of Sys. I with Sys. II also weakens the bond between the silver ions and the alumina tetrahedra. This then allows the free silver ions to reduce to metallic silver over long periods of time even with minimal exposure to light sources. Although the longer stir durations allows the two systems to homogenize elementally, it also generates a detrimental effect on silver ion reduction due to increased competition for stabilization caused by the combination of the two systems. A diagram of this mechanism is shown in FIG. 61B.

Addressing Silver Reduction.

From preliminary experiments (data are not presented), it was determined that Sys. I does not exhibit silver reduction and grey discoloration for stirring duration up to 17 hours, supporting the hypothesis that the much larger abundance of cations in the final system compete for the aluminum tetrahedral species after combination. Since Sys. I contains enough aluminum tetrahedral to compensate for all of the cations in solution, no reduction of silver is present, thus no grey discoloration. Due to this result, protocol C was developed with an R ratio of 10:1 in which the Sys. I and Sys. II were stirred separately for 17 hours, then combined to create the final system, and stirred for only one hour before coating. This protocol was developed with the hypothesis that the longer stirring before combination of the two systems would allow for both the homogeneous incorporation of calcium and aluminum as well as the formation and stabilization of the $AgAlO_4$ complexes, leaving minimal time for other cations to interfere with the stabilization. The SEM and EDS analysis data reveal that although the system avoided silver reduction and elemental separation, the presence of morphological heterogeneity reveals the lack of complete homogeneity into the final system that could be attributed to the short stirring duration of the final system before spin coating, generating two distinct morphologies with thinner and thicker areas on the Ag-BG coatings.

As previously stated, elemental homogeneity of the coatings, as well as morphological, are crucial to ensure consistent and homogeneous physicochemical, biological, and antibacterial properties of the coatings upon implantation. Thus, morphology and consistency in thickness throughout the whole coating are equally important.

Addressing Heterogeneity in Surface Morphology.

The above results collected from Ag-BG coated samples fabricated by protocol C have revealed that long stirring durations of the Sys. I and Sys. II are required to fully incorporate the modifier ions without causing the reduction of silver, however, the stirring duration of the final system must also be increased to fully homogenize the final solution as it is outlined in FIGS. 61A-61B.

To address the limitation that was identified in Protocol C in regards to the morphological heterogeneity, Protocol D was developed. Protocol D exhibits a stir duration of 17 hours for Sys. I and Sys. II separately, with an additional 53 hours of stirring for the final system. Although it was previously stated that the modifier ions such as calcium and sodium compete for stabilization with the aluminum tetrahedra leaving the silver ions to be reduced under longer combined stirring periods, it is hypothesized that the 17 hours separate stir period of the two systems (Sys I and Sys II) will sufficiently stabilize the ions within the first system. Thus, the competition will be less likely after the combination of the two systems and long stirring duration for the final system. However, at an R ratio of 10:1, the final system condenses to a gel during this long stirring period, not allowing the coating process to be applied.

To address this challenge the R ratio was increased to 25:1 to ensure that the systems remained in a more complete hydrolysis phase throughout the stirring, thus avoiding complete gelation before coating. The SEM and EDS data for protocol D shown in FIG. 64 reveal that this protocol resulted in chemical and morphological homogeneity, while not reducing silver and remaining colorless throughout the solution phase, indicative of silver ion stabilization. The coating cross-section presented in FIG. 64 (SEM image bottom insert) reveals an average, approximate thickness of 0.5 μm. The micro-hardness indentation testing revealed an average hardness value of 367 kgf/mm$^2$ with a standard deviation of 50.2 kgf/mm$^2$. An example of indentation is shown in FIG. 64 (SEM image top insert). It is worth noting, the indentations formed on Ag-BG coatings synthesized by protocol D show no cracks propagating from the indent.

The $Z_\alpha$ for this protocol resulted in a consistent 0.06 μm, indicating a much smoother surface compared to the 1.5 μm found in protocol B. The roughness of these coatings appeared significantly lower compared to protocol B (FIG. 62). This is due to the more diluted R ratio, allowing the systems to stay under long stirring duration in an of complete hydrolysis phase upon spin coating.

Due to the much smoother, morphologically consistent, and elementally homogeneous Ag-BG coatings formed by protocol D, it is expected these coatings to reveal consistent and uniform biological and antibacterial properties. Based on the elemental and morphological success of this protocol as well as the inhibition of silver reduction, it can be concluded that the aluminum tetrahedra require longer stirring duration (17 hours) to form and stabilize the cations in Sys. I. The competition from the excess of calcium ions in Sys. II after combination into the final system is then limited due to the aluminum tetrahedral ionic bonds already formed in Sys. I. Although this long stirring time is required to stabilize the free silver ions, an additional prolonged stirring time (53 hours) for the final system is required to completely homogenize the final system. An illustration of the mechanism involved is shown in FIG. 61C.

Next, the adhesion of the coatings on the substrates, their capability to inhibit planktonic MRSA, as well as MRSA biofilm, were evaluated for Ag-BG coatings being synthesized by protocols B and D. Due to the crucial aspect of elemental homogeneity, protocols B and D were considered as the most successful and only samples synthesized by these protocols were further studied. Adhesion, antibacterial ability, and cell-coating interaction were evaluated and observed differences were mainly assigned to the morphological differences between these samples. Samples synthesized by protocol D were the only ones studied for their bioactivity, as preliminary data (not presented here) have previously showed bioactivity for protocol B synthesized samples.

Adhesion Properties.

Ag-BG coated samples using protocols B and D present minimal to no delamination after applying the tape test, as shown by the representative optical images presented in FIG. 65. In both samples, the adhesion strength shows less than 5% removal of the coating from the substrate based on the ASTM (D3359-09) standard. The SEM-EDS images from multiple areas also present the tight, attachment of the coatings synthesized by both protocols to the substrate. The EDS mapping shows coated material adhered up to the edge of the cut. There is no evidence of removed areas, and moreover, the morphological features of the coatings made by protocol B remain even after the tape test. Overall, data shows that both protocols are able to produce well-adhered coatings to the substrate.

Antibacterial Properties.

Planktonic MRSA was exposed to Ag-BG powder (particle size <20 μm) that was fabricated using either protocol B or D while following the heat treatment applied in FIG. 58. Measuring bacterial viability via enumeration of CFUs after exposure (FIG. 66A), Ag-BG produced by both protocols B and D, significantly inhibit MRSA growth compared to the control (untreated MRSA). Moreover, Ag-BG fabricated using protocol D is more potent than Ag-BG fabricated via protocol B. This difference is attributed to the silver reduction to a metallic silver that occurs during fabrication with protocol B. Metallic silver is less antibacterial than silver ions. This result reinforces the conclusion that protocol D is considered more successful in maintaining the ionic status of silver during the fabrication process.

The capacity of Ag-BG thin coatings to inhibit MRSA biofilms was tested using fluorescent dyes that differentiate between live and dead bacteria (Live/Dead). The development of biofilm on Ag-BG coated substrates (protocol B and D) showed significantly more dead bacteria compared to the control (FIG. 66B). Only 45% of dead bacteria were observed in the uncoated samples, while samples coated with Ag-BG applying protocol B and protocol D present ~79% to 83% dead bacteria in the biofilms, respectively (FIG. 66C). This trend was confirmed using SEM. Images of biofilms formed on the surface of the samples after five days of culture demonstrate considerably more bacteria on the surface of the control samples compared to the coated ones (FIG. 66D). Moreover, bacteria present on samples coated with Ag-BG fabricated by protocol D were more sparse, did not form microcolonies, and were smaller in diameter size compared to bacteria observed on the control or protocol B fabricated material.

MRSA biofilm forms on the surface of all samples after seven days of culture. However, due to the ion leaching process and degradation of the Ag-BG coatings, a significant bacteria inhibition is observed by the coated samples that kill more than 80% of the bacteria in biofilm for coatings made by protocol D. Overall, these results demonstrate that Ag-BG coating inhibits both planktonic and the biofilm-associated MRSA, overcoming the advanced resistance mechanisms of the biofilm. Reducing the capacity of pathogenic bacteria to form biofilms is a characteristic that is highly relevant to orthopedic applications.

Bioactivity: Formation of an Apatite Like Phase.

Coatings fabricated using protocol D were considered as the most successful due to its elemental and morphological homogeneity, along with its improved antibacterial efficacy. Only samples coated with Ag-BG using this protocol were fabricated and tested for bioactivity. FTIR spectra of the samples soaked in SBF for up to three weeks are presented in FIG. 67A. The Si—O bending peak at 450 cm$^{-1}$ begins to diminish and have a lower intensity after three weeks while the broad peak in the range 500-600 cm$^{-1}$ is assigned to a Ca—P phase that increases with the soaking time, indicative of a calcium phosphate phase deposition on the surface of the coated samples. The simultaneous decrease of the peak at 450 cm$^{-1}$ by increasing the immersion time is attributed to the increase in the thickness of the new deposited phase that does not allow the detection of the Si—O bonds that are present in the coatings. Moreover, there is a slight shift to higher wavenumbers in the Si—O—Si stretching band at 1050 cm$^{-1}$ towards the 1100 cm$^{-1}$ where P—O bending is also contributing. Finally, SEM images and elemental analysis of the samples before and after SBF is shown in FIG. 67B. This data reveals that there is an increase in the calcium and phosphorous peaks after three weeks in SBF as well as a clearly formed deposition. These data collected from two different characterization techniques support the conclusion that the samples coated with Ag-BG coating fabricated by protocol D are capable of inducing the deposition of a calcium-phosphate phase when immersed in SBF.

Cell Viability and Proliferation.

Cell viability and proliferation were observed. Cell-material interactions for in vitro cultures were studied for up to 6 days (2, 4, and 6 days) and show no statistically significant difference between the different samples (coated and uncoated control) as well as when compared to the TCP (cells cultured on the tissue culture plate) as shown in FIG. 68. This observation confirms the biocompatibility of all samples. As it was expected, the samples coated with Ag-BG do not exhibit cytotoxicity to eukaryotic cells, although they present strong bacterial inhibition in an MRSA biofilm.

Conclusion

This example addresses the challenges of developing multicomponent, bioactive glass coatings on metal substrates using spin coating. For the first time, this example presents the importance of processing parameters such as stirring time duration and the magnitude of R ratio (total water:TEOS) on the elemental and morphological homogeneity as well as retention of Ag in ionic form. Longer stir durations enhance elemental homogeneity. However, this longer stirring duration increases the reduction of silver ions to silver metal due to competition from other ions to be stabilized by negatively charged aluminum tetrahedra. The much smaller, and more abundant calcium and sodium ions in the final solution compete with silver ions to form an ionic bond with the aluminum tetrahedra, increasing the abundance of free silver ions to be reduced to metallic silver. Therefore, increasing the stirring time of the solution systems prior to and after combination allows for maximal stabilization of the silver ions and the homogeneous elemental dispersity within the final network. High R (25:1) ratio allows the implementation of long stirring durations as well as the formation of morphologically homogeneous surfaces. Finally, a tailored synthesis protocol was created that produces a morphologically consistent coating with homogeneous elemental dispersion that also has bioactivity, antibacterial ability, and does not cause eukaryotic cell cytotoxicity, creating a pathway for applications in prosthetics and implants for orthopedic needs.

Symbols: $B_n$—Born exponent determined experimentally by measuring the compressibility of the solid, d—mean average of the diagonals of the indent (mm), D—Kapustinskii constant ($3.45 \times 10^{-11}$ m), e—charge of an electron ($1.6022 \times 10^{-19}$ C), $\varepsilon_0$—vacuum permittivity of space ($8.854 \times 10^{-12}$ F m$^{-1}$), $E^0_{cell}$—reduction potential of a single cell (V), $E^0_{total}$—total reduction potential of entire redox reaction (V), f—force applied to test material (kgf), F—Faraday's constant (96.486 kJ (mol e$^-$)$^{-1}$ V$^{-1}$), HV—Vickers' Hardness value (kgf/mm$^2$), $\Delta H_L$—lattice energy of ionic bond (kJ/mol), K—Kapustinskii constant ($1.202 \times 10^{-7}$ kJ m mol$^{-1}$), M—Madelung constant related to geometry of crystal, n—moles of e$^-$ involved in the redox reaction (mole e$^-$), $N_a$—Avogadro's number ($6.022 \times 10^{23}$ mole$^{-1}$), $r_o$—average radius of ions within an ionic bond (m), $r_{sum}$—sum of the radius of the ions within an ionic bond (m), S—entropy (kJ mol$^{-1}$ K$^{-1}$), T—temperature (K), v—number of ions involved within a single stable ionic bond, $z^+$—charge of cation, $z^-$—charge of anion.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

---

What is claimed is:

1. A bioactive glass-ceramic scaffold comprising:
an interconnected web of struts that define a three dimensional porous structure, the struts comprising a glass-ceramic material system synthesized from $SiO_2$, CaO, $P_2O_5$, $Al_2O_3$, $Na_2O$, $K_2O$, and optionally $Ag_2O$, the glass-ceramic material system including an amorphous phase and at least one crystalline phase, the struts having an average width of greater than or equal to about 50 µm to less than or equal to about 150 µm,
wherein the bioactive glass-ceramic scaffold has antibiotic activity,
wherein the bioactive glass-ceramic scaffold promotes proliferation and differentiation of cells that are in contact with the bioactive glass-ceramic scaffold, and
wherein the bioactive glass-ceramic scaffold has a compressive strength of greater than or equal to about 0.1 MPa to less than or equal to about 2 MPa.

2. The bioactive glass-ceramic scaffold according to claim 1, wherein the bioactive glass-ceramic scaffold has as porosity of greater than or equal to about 60% to less than or equal to about 99% and an average pore size of greater than or equal to about 250 µm to less than or equal to about 750 µm.

3. A method of fabricating the bioactive glass-ceramic scaffold according to claim 1, the method comprising:
obtaining glass-ceramic microparticles particles, the glass-ceramic microparticles optionally doped with silver (Ag);
preparing a polymer slurry by combining and mixing water, a polymer, and the glass-ceramic microparticles particles;
submerging a porous foam having a predetermined three-dimensional shape into the polymer slurry;
drying the polymer slurry in the porous foam to generate a coated foam;
burning out the coated foam to form a scaffold precursor; and
sintering the scaffold precursor to form the bioactive glass-ceramic scaffold.

4. A method of fabricating the bioactive glass-ceramic scaffold according to claim 1, the method comprising:
generating a computer model of a scaffold having a predetermined three-dimensional (3D) structure;
obtaining glass-ceramic microparticles particles, the glass-ceramic microparticles optionally doped with silver (Ag);
adding the glass-ceramic microparticles particles into a binder system comprising a polyolefin, an elastomer, and a fatty acid,
introducing the binder system to an extruder and mixing the glass-ceramic microparticles particles, the polyolefin, and the elastomer in the extruding to form a binder system comprising microparticles;
extruding the binder system as a filament; and
3D printing the computer model from the filament to form the bioactive glass-ceramic scaffold.

5. The method according to claim 4, wherein the polyolefin is selected from the group consisting of poly(methyl methacrylate) (PMMA), polyethylene, polypropylene, acrylonitrile butadiene styrene (ABS), polycarbonate (PC), polylactic acid (PLA), PC/ABS, polyethylene terephthalate (PET), polyphenylsulfone (PPSF), polystyrene, polyether ether ketone (PEEK), polytetrafluoroethylene (PTFE), and combinations thereof; the elastomer is selected from the group consisting of thermoplastic polyurethanes (TPU), ethylene propylene diene monomer (EPDM), thermoplastic polyolefin (TPO), and combinations thereof; and the fatty acid is a saturated fatty acid, an unsaturated fatty acid, or a combination thereof.

6. A method of treating a subject having or at risk of having a bacterial infection, the method comprising:
implanting the bioactive glass-ceramic scaffold according to claim 1 in the subject at a location of the bacterial infection or at a location at risk of developing the bacterial infection.

7. The method according to claim 6, wherein the bioactive glass-ceramic scaffold is doped with silver.

8. The method according to claim 1, wherein the bioactive glass-ceramic scaffold releases a safe and therapeutically effective amount of silver ions over a time period of from about 10 days to about 20 days.

9. The bioactive glass-ceramic scaffold of claim 1, wherein the glass-ceramic material system is synthesized from $SiO_2$, $CaO$, $P_2O_5$, $Al_2O_3$, $Na_2O$, $K_2O$, and $Ag_2O$.

10. The bioactive glass-ceramic scaffold according to claim 1, wherein the bioactive glass-ceramic scaffold is configured to release greater than or equal to about 0.1 ppm to less than or equal to about 1.6 ppm $Ag+$ over a course of from about 10 days to 20 days.

11. The bioactive glass-ceramic scaffold according to claim 1, wherein the glass-ceramic material system is substantially free of silver and silver ions.

12. The bioactive glass-ceramic scaffold according to claim 1, wherein the glass-ceramic material system is substantially free of polyolefin, elastomer, and fatty acid.

13. The bioactive glass-ceramic scaffold according to claim 1, wherein the bioactive glass-ceramic scaffold has a porosity of greater than or equal to about 60% to less than or equal to about 99%.

14. The bioactive glass-ceramic scaffold according to claim 1, wherein the bioactive glass-ceramic scaffold has an average pore size of greater than or equal to about 250 μm to less than or equal to about 750 μm.

15. The bioactive glass-ceramic scaffold according to claim 14, wherein the bioactive glass-ceramic scaffold has an average pore size of greater than or equal to about 400 μm to less than or equal to about 600 μm.

16. The bioactive glass-ceramic scaffold according to claim 1, wherein the at least one crystalline phase includes hydroxyapatite, cristobalite, pseudowollastonite, wollastonite, or a combination thereof.

17. A bioactive glass-ceramic scaffold comprising:
an interconnected web of struts that define a three dimensional porous structure, the struts comprising a glass-ceramic material system synthesized from $SiO_2$, $CaO$, $P_2O_5$, $Al_2O_3$, $Na_2O$, $K_2O$, and optionally $Ag_2O$, the glass-ceramic material system including an amorphous phase and at least one crystalline phase, the struts having an average width of greater than or equal to about 50 μm to less than or equal to about 150 μm, wherein
the bioactive glass-ceramic scaffold has antibiotic activity,
the bioactive glass-ceramic scaffold promotes proliferation and differentiation of cells that are in contact with the bioactive glass-ceramic scaffold, and
the bioactive glass-ceramic scaffold has a compressive strength of greater than or equal to about 0.1 MPa to less than or equal to about 2 MPa, and
the at least one crystalline phase comprises hydroxyapatite, cristobalite, pseudowollastonite, and wollastonite.

18. A bioactive glass-ceramic scaffold comprising:
an interconnected web of struts that define a three dimensional porous structure, the struts comprising a glass-ceramic material system synthesized from $SiO_2$, $CaO$, $P_2O_5$, $Al_2O_3$, $Na_2O$, $K_2O$, and $Ag_2O$, the glass-ceramic material system including an amorphous phase and at least one crystalline phase, the struts having an average width of greater than or equal to about 50 μm to less than or equal to about 150 μm, wherein
the bioactive glass-ceramic scaffold has antibiotic activity,
the bioactive glass-ceramic scaffold promotes proliferation and differentiation of cells that are in contact with the bioactive glass-ceramic scaffold,
the bioactive glass-ceramic scaffold has a compressive strength of greater than or equal to about 0.1 MPa to less than or equal to about 2 MPa,
the bioactive glass-ceramic scaffold has as porosity of greater than or equal to about 60% to less than or equal to about 99%, and
the bioactive glass-ceramic scaffold has an average pore size of greater than or equal to about 400 μm to less than or equal to about 600 μm.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Primer hGAPDH_S

<400> SEQUENCE: 1
tggtatcgtg gaaggactca tgac                                          24

<210> SEQ ID NO 2
<211> LENGTH: 24
<212> TYPE: DNA
<213> ORGANISM: Artificial Sequence
<220> FEATURE:
<223> OTHER INFORMATION: Primer hGAPDH_AS

<400> SEQUENCE: 2
atgccagtga gcttcccgtt cagc                                          24

<210> SEQ ID NO 3
<211> LENGTH: 20
```

```
<212> TYPE: DNA
<213> ORGANISM: Artificial Sequence
<220> FEATURE:
<223> OTHER INFORMATION: Primer hBSP-S

<400> SEQUENCE: 3
acaacactgg gctatggaga                                               20

<210> SEQ ID NO 4
<211> LENGTH: 20
<212> TYPE: DNA
<213> ORGANISM: Artificial Sequence
<220> FEATURE:
<223> OTHER INFORMATION: Primer hBSP-AS

<400> SEQUENCE: 4
ccttgttcgt tttcatccac                                               20

<210> SEQ ID NO 5
<211> LENGTH: 20
<212> TYPE: DNA
<213> ORGANISM: Artificial Sequence
<220> FEATURE:
<223> OTHER INFORMATION: Primer hOCN_S

<400> SEQUENCE: 5
caccgagaca ccatgagagc                                               20

<210> SEQ ID NO 6
<211> LENGTH: 20
<212> TYPE: DNA
<213> ORGANISM: Artificial Sequence
<220> FEATURE:
<223> OTHER INFORMATION: Primer hOCN_AS

<400> SEQUENCE: 6
cggattgagc tcacacacct                                               20
```